(12) United States Patent
Heavner et al.

(10) Patent No.: US 7,718,176 B2
(45) Date of Patent: May 18, 2010

(54) HUMAN EPO MIMETIC HINGE CORE MIMETIBODIES, COMPOSITIONS, METHODS AND USES

(75) Inventors: George A. Heavner, Malvern, PA (US); David M. Knight, Berwyn, PA (US); John Ghrayeb, Downingtown, PA (US); Bernard J. Scallon, Wayne, PA (US); Thomas C. Nesspor, Collegeville, PA (US); Chichi Huang, Berwyn, PA (US)

(73) Assignee: CNA Development LLC PR (US)

( * ) Notice: Subject to any disclaimer, the term of this patent is extended or adjusted under 35 U.S.C. 154(b) by 0 days.

(21) Appl. No.: 12/031,849

(22) Filed: Mar. 27, 2009

(65) Prior Publication Data

US 2009/0220506 A1   Sep. 3, 2009

(51) Int. Cl.
*A61K 39/00* (2006.01)
*A61K 38/00* (2006.01)

(52) U.S. Cl. .......................... 424/134.1; 514/2; 514/12

(58) Field of Classification Search ........................ None
See application file for complete search history.

(56) References Cited

U.S. PATENT DOCUMENTS

| | | |
|---|---|---|
| 3,773,919 A | 11/1973 | Boswell et al. |
| 4,239,754 A | 12/1980 | Sache et al. |
| 4,309,989 A | 1/1982 | Fahim |
| 4,399,216 A | 8/1983 | Axel et al. |
| 4,668,218 A | 5/1987 | Virtanen |
| 4,767,402 A | 8/1988 | Kost et al. |
| 4,873,316 A | 10/1989 | Meade et al. |
| 4,925,673 A | 5/1990 | Steiner et al. |
| 4,946,778 A | 8/1990 | Ladner et al. |
| 4,956,288 A | 9/1990 | Barsoum |
| 5,116,964 A | 5/1992 | Capon |
| 5,122,464 A | 6/1992 | Wilson et al. |
| 5,149,636 A | 9/1992 | Axel et al. |
| 5,155,027 A | 10/1992 | Sledziewski |
| 5,168,062 A | 12/1992 | Stinski |
| 5,179,017 A | 1/1993 | Axel et al. |
| 5,225,538 A | 7/1993 | Capon et al. |
| 5,231,024 A | 7/1993 | Moeller et al. |
| 5,266,491 A | 11/1993 | Nagata et al. |
| 5,304,489 A | 4/1994 | Rosen |
| 5,385,839 A | 1/1995 | Stinski |
| 5,404,871 A | 4/1995 | Goodman et al. |
| 5,428,130 A | 6/1995 | Capon |
| 5,447,851 A | 9/1995 | Beutler et al. |
| 5,458,135 A | 10/1995 | Patton et al. |
| 5,514,670 A | 5/1996 | Friedman et al. |
| 5,565,362 A | 10/1996 | Rosen |
| 5,608,035 A | 3/1997 | Yanofsky et al. |
| 5,770,222 A | 6/1998 | Unger et al. |
| 5,770,359 A | 6/1998 | Wilson et al. |
| 5,773,569 A | 6/1998 | Wrighton |
| 5,786,331 A | 7/1998 | Barrett et al. |
| 5,814,599 A | 9/1998 | Mitragotri et al. |
| 5,827,690 A | 10/1998 | Meade et al. |
| 5,827,739 A | 10/1998 | Wilson et al. |
| 5,839,446 A | 11/1998 | Waner et al. |
| 5,843,725 A | 12/1998 | Sledziewski |
| 5,849,992 A | 12/1998 | Meade et al. |
| 5,851,198 A | 12/1998 | Castellano et al. |
| 5,871,753 A | 2/1999 | Crabtree et al. |
| 5,879,681 A | 3/1999 | Leone-Bay et al. |
| 5,880,096 A | 3/1999 | Barrett et al. |
| 5,994,616 A | 11/1999 | Rosen |
| 6,018,026 A | 1/2000 | Sledziewski |
| 6,153,190 A | 11/2000 | Young et al. |
| 6,165,476 A | 12/2000 | Strom et al. |
| 6,291,212 B1 | 9/2001 | Sledziewski |
| 6,291,646 B1 | 9/2001 | Sledziewski |
| 6,300,099 B1 | 10/2001 | Sledziewski |
| 6,406,697 B1 | 6/2002 | Capon |
| 6,660,843 B1 | 12/2003 | Feige et al. |
| 6,900,292 B2 | 5/2005 | Sun et al. |
| 7,030,226 B2 | 4/2006 | Sunn et al. |
| 7,241,733 B2 | 7/2007 | Heavner et al. |
| 2003/0082749 A1 | 5/2003 | Sun et al. |

FOREIGN PATENT DOCUMENTS

| | | |
|---|---|---|
| CN | 1331701 A | 1/2002 |

(Continued)

OTHER PUBLICATIONS

A.S. Nies and S.P. Spielberg, Principles of Therapeutics. In: J.G. Hardman and L.E. Limbird, Editors, Goodman and Gilman's The Pharmacological Basis of Therapeutics (9*th* Edition), MacGraw Hill, New York, pp. 43-62 (1996).

(Continued)

*Primary Examiner*—Cherie M Woodward
(74) *Attorney, Agent, or Firm*—Brian Carey

(57) ABSTRACT

The present invention relates to at least one human EPO mimetic hinge core mimetibody or specified portion or variant, including isolated nucleic acids that encode at least one EPO mimetic hinge core mimetibody or specified portion or variant, EPO mimetic hinge core mimetibody or specified portion or variants, vectors, host cells, transgenic animals or plants, and methods of making and using thereof, including therapeutic compositions, methods and devices.

5 Claims, 176 Drawing Sheets

FOREIGN PATENT DOCUMENTS

| | | |
|---|---|---|
| EP | 0 288 088 A2 | 10/1988 |
| EP | 0 218 868 A2 | 4/2007 |
| EP | 237507 A1 | 9/2007 |
| WO | WO 91/02078 A1 | 2/1991 |
| WO | WO 92/07076 A1 | 4/1992 |
| WO | WO 92/16221 A1 | 10/1992 |
| WO | WO 94/08552 A2 | 4/1994 |
| WO | WO 94/16970 A1 | 8/1994 |
| WO | WO 96/40772 A2 | 12/1996 |
| WO | WO 97/22376 A1 | 6/1997 |
| WO | WO 97/25086 A2 | 7/1997 |
| WO | WO 98/35888 A1 | 8/1998 |
| WO | WO 98/53847 A1 | 12/1998 |
| WO | WO 00/24782 A2 | 5/2000 |
| WO | WO 02/46238 A2 | 6/2002 |
| WO | WO 2004/050017 A2 | 6/2004 |

OTHER PUBLICATIONS

Bird, R. E. et al., Science:423-426 (1988).
Cramer et al., Curr. Top Microbol. Immunol. 240:95-118 (1999).
Hood et al., Avd. Exp. Med. Biol. 464-127-147 (1999).
Conrad et al., Plant Mol. Biol. 38:101-109 (1998).
Fischer et al., Biotechnol. Appl. Biochem. 30:99-108 (1999).
Ma et al., Trends Biotechnol. 13:522-7 (1995).
Ma et al., Plant Physiol., 109:341-6 (1995).
Whitelam et al., Biochem. Soc. Trans. 22:940-944 (1994).
Berzofsky, et al., "Antibody-Antigen Interactions," In *Fundamental Immunology*, Paul, W. E., Ed., Raven Press: New York, NY (1984).
Kuby, Janis *Immunology*, W. H. Freeman and Company: New York, NY (1992).
Sprague, et al., J. Virol. 45:773-781 (1983).
Bhatnagar et al., J. Med. Chem. 39:3814-9 (1996).
Cuthbertson et al., J. Med. Chem. 40:2876-82 (1997).
Anagnostou et al., Proceedings of the National Academy of Science (USA) 87:5978-82 (1990).
Fandrey J et al., Annals of the New York Academy of Science 628:250-5 (1991).
Geissler K. et al., Contrib. Nephrol. 87:1-10(1990).
Gregory CJ., Journal of Cellular Physiology 89:289-301 (1976).
Jelkman W. et al., Life Sci 50:301-8 (1992).
Kimata H. et al., Clinical and Experimental Immunology 85:151-6 (1991).
Kimata H. et al., Clin. Imunology Immunopathol. 59:495-501(1991).
Kimata H. et al., Clinical and Experimental Immunology 83:487-7 (1991).
Koury et al., Science 248:378-81 (1990).
Lim et al., Kidney International 37:131-6 (1990).
Mitjavila et al., Journal of Clinical Investigation 88:789-97 (1991).
Andre M. et al., Clinical Chemistry 38:758-63 (1992).
Hankins WD et al., Annals of the New York Academy of Science 554: 21-8 (1989).
Kendall RGT et al., Clin. Lab. Haematology 13:189-96 (1991).
Brumvieh D., et al., Dev. Biol. Stand. 69:15-22 (1988).
Ma DD et al., British Journal of Haematology 80:431-6 (1992).
Noe G et al., British Journal of Haematology 80:285-92 (1992).
Pauly JU et al., Behring institute Mitteilungen 90: 112-25 (1991).
Sakata et al., Ann Hematology 64:224-230 (1992).
Sanengen et al., Acta Physiol Scand 135:11-6 (1989).
Widness et al., Journal of Lab. Clin. Med. 119:285-94 (1992).
Katsube, Y., et al., *Int J Mol. Med*, 1(5):863-868 (1998).
Cunningham and Wells, Science 244:1081-1085 (1989).
Smith, et al., J. Mol. Biol. 224:899-904 (1992).
de Vos, et al., Science 255:306-312 (1992).
Fisch et al., *Bioconjugate Chem.*, 3:147-153 (1992).
Werlen et al., *Bioconjugate Chem.*, 5:411-417 (1994).
Kumaran et al., *Protein Sci.* 6(10):2233-2241 (1997).
Itoh et al., *Bioorg. Chem.*, 24(1): 59-68 (1996).
Capellas et al., *Biotechnol. Bioeng.*, 56(4):456-463 (1997).
Evans et al., Bacerial Infections of Humans:Epidemiology and Control, 2d. Ed., pp. 239-254, Plenum Medical Book Co., New York (1991).
Wood et al., FEMS Microbiology Immunology, 76:121-134 (1991).
Marrack et al., Science, 248:705-711 (1990).
Furman et al., Pediatrics, 90:716-728 (1992).
Goldberg Science, 242:1412-1415 (1988).
Paul et al., Ex. Hematol, 12:825-830 (1984).
Erslev et al., Arch Intern Med. 122:230-235 (1968).
Erslev et al, Ann Clin Lab Sci, 10:250-257 (1980).
Jacobs et al., Nature 313:806-810 (1985).
Lin et al, Proc Natl. Acad Sci USA 82-7580-7584 (1985).
Law et al., Proc Natl Acad Sci USA 83:6920-6924 (1986).
Goldwasser et al., J. Biol. Chem 249:4202-4206 (1974).
Eaves et al., Blood 52:1196-1210 (1978).
Sawyer et al., Blood, 74:103-109 (1989).
Winearls et al., Lancet 2:1175-1178 (1986).
Eschbach et al., New England Journal of Medicine, 316:73-78 (1987).
Eschbach et al., Ann Intern Med., 111:992-1000 (1989).
Abels et al., Erythropoietin:evolving clinical applications, Experimental Hematology 19:842-50 (1991).
Graber et al., Erythropoietein:biology and clinical use, Hematology/Oncol. Clin. North Amer. 3:369-400 (1989).
Kelkman, Erythropoietin, Springer, Berlin 1989.
Koury, The Molecular mechanism of erythropoietin action, European Journal of Biochemistry 210:649-63 (1992).
Krantz, Blood 77:419-34 (1991).
Tabbara, Erythropoeitin. Biology and clinical application, Archives of Internal Medine 153:298-304 (1993).
Kozbor et al., Immunol. Today 4:72-79 (1983).
Muller, Meth. Enzymol, 92-589-601 (1983).
Liang et al., Biochem. Biophys Res. Comm. 137:847-854 (1986).
Meager et al. Hybridoma 6:305-511 (1987).
Hirai et al., J. Immunol. Meth. 96:57-62 (1987).
Schall et al., Cell 61:361-370 (1990).
Loetscher et al., Cell 61:351-359 (1990).
Corcoran et al., Eur. J. Biochem. 223:831-840 (1994).
Engelmann et al., J. Biol. Chem.. 265:1531-1536 (1990).
Lesslauer et al., Eur. J. Immunol. 21:2883-2886 (1991).
Ashkenazi et al, Proc. Natl. Acad. Sci USA 88: 10535-10539 (1991).
Peppel et al., J. Exp. Med. 174:1483-1489 (1991).
Kolls et al., Proc Natl. Acad. Sci USA 91:215-219 (1994).
Butler et al., Cytokine 6(6): 616-623 (1994).
Baker et al., Eur. J. Immunol. 4:2040-2048 (1994).
Capon et al., Nature 337:525-531 (1989).
Junginger, et al., Visualization of Drug Transport Across Human Skin and the Influence of Penetration Enhancers, *Drug Permeation*, Hsieh, D. S., Eds., pp. 59-90 Marcel Dekker, Inc. New York 1994.
Murphy, et al., Biochem. J. 227:277-279 (1991).
Bebbington, et al., Bio/Technology 10:169-175 (1992).
Cullen, et al., Molec. Cell. Biol. 5:438-447 (1985).
Boshart, et al., Cell 41:521-530 (1985).
F.W. Alt, et al., J. Biol. Chem. 253:1357-1370 (1978).
J.L. Hamlin and C. Ma, Biochem, et Biophys, Acta 1087(2):107-125 (1990).
M.J. Page and M. A. Sydenham, Biotechnology 9:64-68 (1991).
M. Gossen et al., Proc. Natl. Acad. Sci USA 89:5547-5551 (1992).
Wrighton et al., Science, vol. 273 pp. 458-463 (1996).
Wrighten et al., Nature Biotechnology, vol. 15, pp. 1261-1265 (1997).
Johnson et al., Chem & Bio. vol. 4(12) pp. 939-950 (1997).
Kuai et al. J. Peptide Res., vol. 56, pp. 59-62 (2000).
Sheilds et al, 2001, J. Biol. Chem., vol. 276 (9), 6591-6604.
Komatsu et al., Blood, vol. 82 (2), pp. 456-464 (1993).
Hezereh et al., J. Virol. vol. 75(24) pp. 12161-12168 (2001).
Jefferis et al, Immol. Rev., vol. 163 pp. 50-76 (1998).
Linvah et al., Science, 273(5274), pp. 464-471 Jul. 26, 1996.
Johnson et al., Nephrol Dial Transplant 15:1274-1277 (2000).
Middelton et al., J. Biol. Chem 274(20):14163-14169 (May 14, 1999).

Framework 1

| 1 | 2 | 3 | 4 | 5 | 6 | 7 | 8 | 9 | 10 |
|---|---|---|---|---|---|---|---|---|----|
| E | Q | V | Q | L | V | Q | S | G | A |
| -:1078 | Q:496 | V:587 | Q:600 | L:642 | V:606 | Q:580 | S:672 | G:680 | A:674 |
| E:11 | -:495 | -:460 | -:452 | -:445 | -:429 | -:421 | -:414 | -:401 | -:378 |
| Q:2 | E:61 | Q:17 | L:23 | V:2 | E:28 | E:76 | A:2 | A:7 | P:16 |
|  | V:24 | M:12 | H:9 | M:1 | L:17 | A:7 | F:1 | R:2 | T:10 |
|  | L:6 | K:6 | K:3 | G:1 | Q:6 | T:3 | Y:1 | E:1 | G:4 |
|  | P:3 | E:3 | A:1 |  | R:2 | H:3 | G:1 |  | S:3 |
|  | H:3 | G:3 | X:1 |  | A:1 | V:1 |  |  | L:3 |
|  | N:1 | S:1 | N:1 |  | M:1 |  |  |  | D:2 |
|  | K:1 | A:1 | E:1 |  | G:1 |  |  |  | V:1 |
|  | G:1 | I:1 |  |  |  |  |  |  |  |

Framework 1

| 11 | 12 | 13 | 14 | 15 | 16 | 17 | 18 | 19 | 20 |
|----|----|----|----|----|----|----|----|----|----|
| E | V | K | K | P | G | A | S | V | K |
| E:708 | V:722 | K:703 | K:704 | P:739 | G:784 | A:502 | S:843 | V:869 | K:876 |
| -:372 | -:357 | -:353 | -:348 | -:335 | -:281 | S:275 | -:233 | -:207 | -:179 |
| Q:5 | M:7 | R:19 | R:21 | T:8 | S:22 | -:275 | T:8 | L:6 | R:26 |
| D:2 | L:4 | Q:5 | N:6 | A:3 | V:2 | T:36 | A:3 | S:3 | E:4 |
| X:1 | G:1 | N:4 | E:6 | L:3 | E:1 | V:1 | L:3 | A:3 | T:3 |
| V:1 |  | T:2 | M:3 | S:2 | R:1 | D:1 | P:1 | M:3 | N:2 |
| R:1 |  | E:2 | Q:2 | H:1 |  | L:1 |  |  | Q:1 |
| G:1 |  | X:1 | T:1 |  |  |  |  |  |  |
|  |  | V:1 |  |  |  |  |  |  |  |
|  |  | M:1 |  |  |  |  |  |  |  |

Framework 1

| 21 | 22 | 23 | 24 | 25 | 26 | 27 | 28 | 29 | 30 |
|----|----|----|----|----|----|----|----|----|----|
| V | S | C | K | A | S | G | Y | T | F |
| V:909 | S:937 | C:942 | K:910 | A:884 | S:981 | G:987 | Y:660 | T:892 | F:964 |
| -:155 | -:148 | -:147 | -:146 | -:135 | -:102 | -:94 | G:307 | -:81 | -:80 |
| I:22 | T:4 | S:1 | R:15 | V:30 | F:4 | E:4 | -:84 | S:65 | L:29 |
| G:2 | F:1 | W:1 | E:9 | T:29 | P:2 | S:2 | F:24 | I:22 | Y:6 |
| L:2 | P:1 |  | M:7 | G:6 | A:1 | W:2 | C:3 | M:7 | I:6 |
| F:1 |  |  | T:2 | S:3 | T:1 | A:1 | I:3 | P:6 | V:2 |
|  |  |  | Q:2 | P:2 |  | T:1 | S:2 | A:5 | G:2 |
|  |  |  |  | F:1 |  |  | V:2 | N:4 | S:1 |
|  |  |  |  | X:1 |  |  | H:2 | K:3 | H:1 |
|  |  |  |  |  |  |  | D:2 | V:2 |  |
|  |  |  |  |  |  |  | N:1 | H:2 |  |
|  |  |  |  |  |  |  | L:1 | R:2 |  |

FIG 1A

| | CDR1 | | | | | Framework 2 | | | |
|---|---|---|---|---|---|---|---|---|---|
| 31 | 32 | 33 | 34 | 35 | 36 | 37 | 38 | 39 | 40 |
| T | X | X | X | X | X | W | V | R | Q |
| T:601 | | | | | | W:1080 | V:1066 | R:1066 | Q:1073 |
| S:357 | | | | | | -:5 | L:12 | Q:8 | R:8 |
| -:73 | | | | | | C:3 | -:5 | G:7 | -:4 |
| N:21 | | | | | | F:1 | I:4 | -:4 | L:2 |
| I:19 | | | | | | N:1 | M:2 | L:2 | H:2 |
| A:5 | | | | | | X:1 | F:1 | P:2 | E:1 |
| R:5 | | | | | | | G:1 | S:1 | X:1 |
| K:2 | | | | | | | | H:1 | |
| M:2 | | | | | | | | | |
| G:2 | | | | | | | | | |
| Y:1 | | | | | | | | | |
| V:1 | | | | | | | | | |
| H:1 | | | | | | | | | |
| D:1 | | | | | | | | | |

| Framework 2 | | | | | | | | | |
|---|---|---|---|---|---|---|---|---|---|
| 41 | 42 | 43 | 44 | 45 | 46 | 47 | 48 | 49 | 50 |
| A | P | G | Q | G | L | E | W | M | G |
| A:1078 | P:997 | G:1080 | Q:1031 | G:949 | L:1049 | E:1080 | W:1087 | M:1036 | G:1083 |
| V:4 | T:74 | R:5 | K:33 | R:118 | P:33 | Q:5 | -:2 | V:19 | A:5 |
| -:2 | R:11 | E:3 | E:12 | A:10 | F:5 | V:3 | S:1 | L:19 | S:1 |
| P:2 | A:5 | V:1 | H:8 | S:5 | -:1 | -:1 | N:1 | I:16 | V:1 |
| S:1 | S:2 | -:1 | R:6 | N:3 | X:1 | D:1 | | -:1 | -:1 |
| T:1 | -:2 | D:1 | -:1 | T:1 | R:1 | G:1 | | | |
| X:1 | | | | E:1 | I:1 | | | | |
| D:1 | | | | -:1 | | | | | |
| I:1 | | | | M:1 | | | | | |
| | | | | P:1 | | | | | |
| | | | | H:1 | | | | | |

| CDR2 | | | | | | | | | |
|---|---|---|---|---|---|---|---|---|---|
| 51 | 52 | 53 | 54 | 55 | 56 | 57 | 58 | 59 | 60 |
| X | X | X | X | X | X | X | X | X | X |

FIG 1B

| CDR2 | | | | | | | Framework 3 | | |
|---|---|---|---|---|---|---|---|---|---|
| 61 | 62 | 63 | 64 | 65 | 66 | 67 | 68 | 69 | 70 |
| X | X | X | X | X | X | X | R | V | T |
|   |   |   |   |   |   |   | R:1029 | V:1060 | T:1047 |
|   |   |   |   |   |   |   | W:58 | L:15 | A:16 |
|   |   |   |   |   |   |   | K:1 | I:11 | S:10 |
|   |   |   |   |   |   |   | E:1 | A:4 | I:10 |
|   |   |   |   |   |   |   | I:1 | D:1 | V:3 |
|   |   |   |   |   |   |   | G:1 |   | K:2 |
|   |   |   |   |   |   |   |   |   | N:1 |
|   |   |   |   |   |   |   |   |   | M:1 |
|   |   |   |   |   |   |   |   |   | L:1 |

| Framework 3 | | | | | | | | | |
|---|---|---|---|---|---|---|---|---|---|
| 71 | 72 | 73 | 74 | 75 | 76 | 77 | 78 | 79 | 80 |
| M | T | R | D | T | S | T | S | T | A |
| M:560 | T:1058 | R:552 | D:1008 | T:718 | S:1060 | T:622 | S:926 | T:1075 | A:919 |
| I:468 | S:22 | A:345 | N:71 | E:248 | F:8 | I:312 | N:54 | A:9 | V:130 |
| L:31 | I:6 | T:150 | S:4 | K:75 | A:7 | A:123 | T:50 | I:6 | T:17 |
| F:17 | A:3 | E:23 | Y:2 | M:16 | I:6 | M:11 | D:35 | S:1 | S:16 |
| V:13 | N:1 | S:8 | A:2 | R:12 | P:5 | S:10 | R:13 |   | G:5 |
| S:1 | P:1 | G:4 | H:2 | P:5 | T:2 | V:6 | G:7 |   | F:1 |
| G:1 |   | K:2 | E:1 | S:5 | Y:2 | K:4 | Y:2 |   | -:1 |
|   |   | M:2 | Q:1 | D:4 | L:1 | L:2 | K:1 |   | L:1 |
|   |   | W:2 |   | I:4 |   | Y:1 | E:1 |   | I:1 |
|   |   | V:1 |   | P:3 |   |   | -:1 |   |   |
|   |   | D:1 |   | A:2 |   |   | A:1 |   |   |
|   |   | I:1 |   | V:1 |   |   |   |   |   |
|   |   |   |   | Q:1 |   |   |   |   |   |
|   |   |   |   | L:1 |   |   |   |   |   |
|   |   |   |   | G:1 |   |   |   |   |   |

| Framework 3 | | | | | | | | | |
|---|---|---|---|---|---|---|---|---|---|
| 81 | 82 | 83 | 84 | 85 | 86 | 87 | 88 | 89 | 90 |
| Y | M | E | L | S | S | L | R | S | E |
| Y:1077 | M:1051 | E:1048 | L:1062 | S:843 | S:797 | L:1086 | R:968 | S:1041 | E:626 |
| F:6 | L:33 | D:33 | V:16 | R:166 | R:232 | P:3 | T:73 | Y:18 | D:454 |
| H:3 | V:4 | Q:5 | M:11 | N:44 | N:31 | K:1 | K:24 | F:11 | A:5 |
| S:2 | I:2 | K:1 | P:2 | T:21 | G:21 | X:1 | S:14 | P:11 | G:4 |
| N:1 | T:1 | A:1 |   | I:6 | T:5 |   | I:5 | A:3 | T:1 |
| X:1 |   | X:1 |   | G:4 | I:5 |   | G:4 | L:2 | V:1 |
| D:1 |   | H:1 |   | Y:3 |   |   | E:1 | T:1 |   |
|   |   | G:1 |   | V:1 |   |   | Q:1 | N:1 |   |
|   |   |   |   | A:1 |   |   | A:1 | C:1 |   |
|   |   |   |   | X:1 |   |   |   | H:1 |   |
|   |   |   |   | D:1 |   |   |   | D:1 |   |

FIG 1C

| Framework 3 | | | | | | | | | CDR3 |
|---|---|---|---|---|---|---|---|---|---|
| 91 | 92 | 93 | 94 | 95 | 96 | 97 | 98 | 99 | 100 |
| D | T | A | V | Y | Y | C | A | R | X |
| D:1085 | T:1066 | A:1066 | V:980 | Y:1077 | Y:1036 | C:1079 | A:1046 | R:861 | |
| -:4 | M:12 | G:13 | M:33 | F:6 | F:34 | -:7 | T:14 | -:44 | |
| E:1 | -:4 | -:4 | I:29 | -:5 | T:7 | L:2 | V:10 | S:43 | |
| V:1 | A:4 | T:3 | L:23 | H:1 | -:5 | X:1 | -:7 | T:42 | |
| | S:3 | V:2 | T:8 | D:1 | H:5 | R:1 | S:4 | K:28 | |
| | P:2 | D:2 | -:5 | I:1 | S:3 | G:1 | G:4 | A:21 | |
| | | S:1 | E:4 | | D:1 | | P:2 | G:21 | |
| | | | A:4 | | | | R:2 | N:6 | |
| | | | F:2 | | | | E:1 | V:6 | |
| | | | Q:1 | | | | I:1 | L:6 | |
| | | | W:1 | | | | | I:4 | |
| | | | R:1 | | | | | E:3 | |
| | | | | | | | | C:2 | |
| | | | | | | | | F:1 | |
| | | | | | | | | X:1 | |
| | | | | | | | | P:1 | |
| | | | | | | | | D:1 | |

| CDR3 | | | | | | | | | |
|---|---|---|---|---|---|---|---|---|---|
| 101 | 102 | 103 | 104 | 105 | 106 | 107 | 108 | 109 | 110 |
| X | X | X | X | X | X | X | X | X | X |

| CDR3 | | | | | | | | | |
|---|---|---|---|---|---|---|---|---|---|
| 111 | 112 | 113 | 114 | 115 | 116 | 117 | 118 | 119 | 120 |
| X | X | X | X | X | X | X | X | X | X |

| CDR3 | | | | | | | | | |
|---|---|---|---|---|---|---|---|---|---|
| 121 | 122 | 123 | 124 | 125 | 126 | 127 | 128 | 129 | 130 |
| X | X | X | X | X | X | X | X | X | X |

FIG 1D

| CDR3 | Framework 4 | | | | | | | | |
|---|---|---|---|---|---|---|---|---|---|
| 131 | 132 | 133 | 134 | 135 | 136 | 137 | 138 | 139 | 140 |
| X | X | W | G | Q | G | T | L | V | T |
| | | W:929 | G:781 | Q:625 | G:701 | T:633 | L:418 | V:592 | T:571 |
| | | -:117 | -:266 | -:340 | -:352 | -:392 | -:411 | -:434 | -:455 |
| | | Y:12 | Y:10 | R:41 | D:9 | P:16 | T:133 | S:23 | P:18 |
| | | G:7 | P:8 | K:31 | A:7 | S:10 | M:69 | G:9 | I:14 |
| | | L:6 | A:7 | P:13 | Y:4 | Y:9 | W:19 | D:8 | S:9 |
| | | P:5 | S:5 | G:6 | X:4 | V:6 | P:7 | I:8 | Q:4 |
| | | S:3 | T:4 | F:5 | E:3 | A:4 | F:6 | L:6 | D:4 |
| | | F:3 | D:4 | M:5 | R:3 | N:3 | G:6 | M:4 | R:3 |
| | | V:2 | H:3 | A:5 | S:2 | W:3 | Q:5 | Y:2 | V:2 |
| | | D:2 | F:2 | Y:4 | W:2 | G:3 | R:5 | H:2 | L:2 |
| | | R:2 | I:1 | S:3 | T:1 | F:2 | S:3 | T:1 | A:2 |
| | | T:1 | | E:3 | N:1 | E:2 | V:3 | A:1 | H:2 |
| | | N:1 | | L:3 | P:1 | H:2 | A:3 | R:1 | F:1 |
| | | H:1 | | H:2 | H:1 | K:1 | N:1 | | K:1 |
| | | | | D:2 | | Q:1 | K:1 | | E:1 |
| | | | | T:1 | | C:1 | H:1 | | Y:1 |
| | | | | X:1 | | L:1 | | | G:1 |
| | | | | I:1 | | D:1 | | | |
| | | | | | | I:1 | | | |

| Framework 4 | | | | | | | | | |
|---|---|---|---|---|---|---|---|---|---|
| 141 | 142 | 143 | 144 | 145 | 146 | 147 | 148 | 149 | 150 |
| V | S | S | G | S | T | K | G | P | S |
| V:572 | S:544 | S:532 | -:920 | -:1020 | -:1024 | -:1027 | -:1031 | -:1037 | -:1042 |
| -:479 | -:493 | -:527 | G:115 | S:62 | T:31 | K:31 | G:28 | P:49 | S:27 |
| S:16 | T:15 | T:7 | A:36 | R:3 | A:21 | S:23 | A:24 | H:3 | T:15 |
| W:6 | D:9 | P:7 | Q:5 | T:2 | P:7 | T:5 | S:6 | S:1 | K:4 |
| R:5 | P:7 | G:6 | P:5 | E:1 | S:3 | G:3 | T:1 | T:1 | R:2 |
| D:3 | W:5 | A:4 | R:3 | P:1 | Q:2 | Q:1 | P:1 | | V:1 |
| T:2 | C:4 | L:3 | S:2 | H:1 | R:2 | R:2 | | | |
| C:2 | L:4 | Q:2 | W:2 | G:1 | K:1 | W:1 | | | |
| A:2 | G:4 | F:1 | F:1 | | | | | | |
| G:2 | A:2 | V:1 | N:1 | | | | | | |
| M:1 | F:1 | W:1 | V:1 | | | | | | |
| I:1 | N:1 | | | | | | | | |
| | Y:1 | | | | | | | | |
| | V:1 | | | | | | | | |

| Framework 4 | | | | | | | | | |
|---|---|---|---|---|---|---|---|---|---|
| 151 | 152 | 153 | 154 | 155 | 156 | 157 | 158 | 159 | 160 |
| V | F | P | L | A | P | S | S | K | S |
| -:1045 | -:1061 | -:1062 | -:1064 | -:1065 | -:1067 | -:1076 | -:1076 | -:1076 | -:1076 |
| V:28 | F:27 | P:24 | L:24 | A:12 | P:12 | S:9 | S:9 | K:9 | S:15 |
| L:15 | V:1 | H:2 | S:1 | V:9 | S:7 | C:6 | E:6 | N:6 | |
| S:1 | Q:1 | S:1 | F:1 | S:4 | L:4 | | | | |
| T:1 | P:1 | E:1 | V:1 | C:1 | R:1 | | | | |
| P:1 | | G:1 | | | | | | | |

FIG 1E

| | | | | Framework 4 | | | | | |
|---|---|---|---|---|---|---|---|---|---|
| 161 | 162 | 163 | 164 | 165 | 166 | 167 | 168 | 169 | 170 |
| T | S | G | G | T | A | A | L | G | C |
| -:1076 | -:1076 | -:1076 | -:1076 | -:1076 | -:1076 | -:1076 | -:1076 | -:1076 | -:1076 |
| T:9 | S:15 | G:9 | G:8 | T:9 | A:9 | A:9 | L:9 | G:9 | C:9 |
| P:6 | | D:6 | T:6 | S:6 | S:6 | V:6 | A:6 | V:6 | G:6 |
| | | | D:1 | | | | | | |

| | | | Framework 4 | | | |
|---|---|---|---|---|---|---|
| 171 | 172 | 173 | 174 | 175 | 176 | 177 |
| L | V | K | D | Y | F | P |
| -:1076 | -:1076 | -:1076 | -:1076 | -:1076 | -:1076 | -:1076 |
| L:8 | V:8 | K:8 | D:8 | Y:8 | F:14 | P:9 |
| C:6 | L:6 | A:6 | Q:6 | D:6 | S:1 | L:6 |
| W:1 | S:1 | R:1 | T:1 | T:1 | | |

FIG 1F

| | | | | Framework 1 | | | | | |
|---|---|---|---|---|---|---|---|---|---|
| 1 | 2 | 3 | 4 | 5 | 6 | 7 | 8 | 9 | 10 |
| Q | I | T | L | K | E | S | G | P | A |
| -:120 | -:119 | -:119 | -:119 | -:119 | -:119 | S:83 | G:85 | P:135 | A:82 |
| Q:75 | I:45 | T:78 | L:83 | K:58 | E:83 | -:70 | -:68 | -:67 | -:66 |
| R:4 | V:37 | N:3 | | R:23 | | R:47 | R:48 | | T:53 |
| P:2 | S:1 | S:1 | | Q:2 | | Q:1 | C:1 | | P:1 |
| E:1 | | Q:1 | | | | C:1 | | | |

| | | | | Framework 1 | | | | | |
|---|---|---|---|---|---|---|---|---|---|
| 11 | 12 | 13 | 14 | 15 | 16 | 17 | 18 | 19 | 20 |
| L | V | K | P | T | Q | T | L | T | L |
| L:138 | V:139 | K:154 | P:131 | T:170 | Q:147 | T:174 | L:178 | T:179 | L:179 |
| -:63 | -:63 | -:39 | -:35 | -:31 | -:31 | -:28 | -:24 | -:21 | -:20 |
| V:1 | | N:3 | A:34 | S:1 | P:14 | | | H:1 | S:1 |
| | | R:3 | T:1 | | E:7 | | | K:1 | Q:1 |
| | | T:2 | X:1 | | H:3 | | | | V:1 |
| | | Q:1 | | | | | | | |

| | | | | Framework 1 | | | | | |
|---|---|---|---|---|---|---|---|---|---|
| 21 | 22 | 23 | 24 | 25 | 26 | 27 | 28 | 29 | 30 |
| T | C | T | F | S | G | F | S | L | S |
| T:181 | C:183 | T:173 | F:172 | S:184 | G:190 | F:175 | S:194 | L:178 | S:169 |
| -:19 | -:18 | -:17 | -:14 | -:13 | -:12 | -:12 | -:7 | F:10 | T:14 |
| A:1 | R:1 | S:5 | V:13 | T:3 | | S:10 | X:1 | -:7 | -:7 |
| I:1 | | I:3 | L:3 | Y:2 | | L:5 | | V:5 | N:7 |
| | | A:2 | | | | | | I:2 | D:3 |
| | | D:1 | | | | | | | R:2 |
| | | L:1 | | | | | | | |

| | CDR1 | | | | | | | Framework 2 | |
|---|---|---|---|---|---|---|---|---|---|
| 31 | 32 | 33 | 34 | 35 | 36 | 37 | 38 | 39 | 40 |
| X | X | X | X | X | X | X | W | I | R |
| | | | | | | | W:200 | I:182 | R:199 |
| | | | | | | | -:1 | L:11 | C:2 |
| | | | | | | | R:1 | V:6 | H:1 |
| | | | | | | | | F:2 | |
| | | | | | | | | T:1 | |

FIG 2A

Framework 2

| 41 | 42 | 43 | 44 | 45 | 46 | 47 | 48 | 49 | 50 |
|---|---|---|---|---|---|---|---|---|---|
| Q | P | P | G | K | A | L | E | W | L |
| Q:200 | P:189 | P:199 | G:200 | K:198 | A:198 | L:202 | E:201 | W:200 | L:198 |
| R:1 | S:7 | L:3 | A:1 | R:3 | T:2 | | D:1 | C:1 | I:2 |
| E:1 | T:3 | | E:1 | E:1 | S:1 | | | R:1 | P:1 |
| | R:2 | | | | G:1 | | | | V:1 |
| | X:1 | | | | | | | | |

CDR2

| 51 | 52 | 53 | 54 | 55 | 56 | 57 | 58 | 59 | 60 |
|---|---|---|---|---|---|---|---|---|---|
| A | X | X | X | X | X | X | X | X | X |
| A:200 | | | | | | | | | |
| G:2 | | | | | | | | | |

CDR2 | Framework 3

| 61 | 62 | 63 | 64 | 65 | 66 | 67 | 68 | 69 | 70 |
|---|---|---|---|---|---|---|---|---|---|
| X | X | X | X | X | X | X | R | L | T |
| | | | | | | | R:199 | L:200 | T:193 |
| | | | | | | | S:1 | H:1 | S:8 |
| | | | | | | | W:1 | I:1 | A:1 |
| | | | | | | | T:1 | | |

Framework 3

| 71 | 72 | 73 | 74 | 75 | 76 | 77 | 78 | 79 | 80 |
|---|---|---|---|---|---|---|---|---|---|
| I | T | K | D | T | S | K | N | Q | V |
| I:186 | T:106 | K:196 | D:200 | T:196 | S:201 | K:186 | N:199 | Q:198 | V:201 |
| V:12 | S:93 | R:4 | G:2 | S:2 | F:1 | R:7 | H:2 | R:2 | A:1 |
| G:2 | A:1 | P:1 | | P:2 | | T:3 | S:1 | L:2 | |
| S:1 | M:1 | E:1 | | A:1 | | E:2 | | | |
| L:1 | I:1 | | | I:1 | | Q:2 | | | |
| | | | | | | X:1 | | | |
| | | | | | | I:1 | | | |

Framework 3

| 81 | 82 | 83 | 84 | 85 | 86 | 87 | 88 | 89 | 90 |
|---|---|---|---|---|---|---|---|---|---|
| V | L | T | M | T | N | M | D | P | V |
| V:197 | L:202 | T:183 | M:187 | T:196 | N:193 | M:195 | D:196 | P:200 | V:184 |
| D:2 | | I:6 | L:7 | D:4 | V:2 | E:3 | S:1 | A:8 |
| F:1 | | K:4 | V:5 | S:1 | S:2 | I:2 | S:1 | H:1 | L:4 |
| M:1 | | R:3 | I:2 | A:1 | F:1 | L:2 | N:1 | | I:2 |
| I:1 | | A:2 | -:1 | N:1 | T:1 | T:1 | G:1 | | W:1 |
| | | E:1 | | -:1 | R:1 | | | | P:1 |
| | | V:1 | | | | | | | E:1 |
| | | -:1 | | | | | | | M:1 |
| | | L:1 | | | | | | | |

FIG 2B

| | | | | Framework 3 | | | | | |
|---|---|---|---|---|---|---|---|---|---|
| 91 | 92 | 93 | 94 | 95 | 96 | 97 | 98 | 99 | 100 |
| D | T | A | T | Y | Y | C | A | R | X |
| D:202 | T:199 | A:184 | T:198 | Y:202 | Y:175 | C:201 | A:193 | R:98 | |
| S:2 | G:16 | S:3 | Y:202 | | F:25 | -:1 | V:6 | H:92 | |
| A:1 | F:1 | I:1 | | | H:1 | | T:1 | -:4 | |
| | V:1 | | | | -:1 | | -:1 | Y:3 | |
| | | | | | | | I:1 | Q:2 | |
| | | | | | | | | S:1 | |
| | | | | | | | | T:1 | |
| | | | | | | | | L:1 | |

| | | | | CDR3 | | | | | |
|---|---|---|---|---|---|---|---|---|---|
| 101 | 102 | 103 | 104 | 105 | 106 | 107 | 108 | 109 | 110 |
| X | X | X | X | X | X | X | X | X | X |

| | | | | CDR3 | | | | | |
|---|---|---|---|---|---|---|---|---|---|
| 111 | 112 | 113 | 114 | 115 | 116 | 117 | 118 | 119 | 120 |
| X | X | X | X | X | X | X | X | X | X |

| CDR3 | | | Framework 4 | | | | | | |
|---|---|---|---|---|---|---|---|---|---|
| 121 | 122 | 123 | 124 | 125 | 126 | 127 | 128 | 129 | 130 |
| X | X | X | W | G | Q | G | T | L | V |
| | | | W:169 | G:145 | Q:99 | G:115 | T:81 | -:68 | V:85 |
| | | | -:26 | -:51 | -:61 | -:63 | -:66 | L:59 | -:68 |
| | | | G:2 | A:2 | K:21 | A:11 | P:42 | W:26 | S:41 |
| | | | F:1 | D:2 | R:13 | E:8 | I:5 | R:17 | H:5 |
| | | | Y:1 | M:1 | P:3 | D:2 | S:2 | M:14 | F:1 |
| | | | V:1 | R:1 | V:1 | F:1 | H:2 | P:6 | L:1 |
| | | | L:1 | | M:1 | K:1 | Y:1 | T:4 | R:1 |
| | | | I:1 | | C:1 | C:1 | V:1 | G:4 | |
| | | | | | L:1 | | L:1 | V:2 | |
| | | | | | I:1 | | A:1 | S:1 | |
| | | | | | | | | Y:1 | |

| | | | | Framework 4 | | | | | |
|---|---|---|---|---|---|---|---|---|---|
| 131 | 132 | 133 | 134 | 135 | 136 | 137 | 138 | 139 | 140 |
| T | V | S | S | A | S | P | T | S | P |
| T:78 | V:79 | -:81 | -:123 | -:164 | -:175 | -:175 | -:176 | -:177 | -:179 |
| -:71 | -:76 | S:73 | S:73 | A:21 | S:25 | P:15 | T:15 | S:14 | P:23 |
| P:42 | S:40 | T:38 | Q:3 | G:16 | L:1 | T:6 | K:6 | G:6 | |
| L:3 | R:3 | D:4 | P:2 | S:1 | P:1 | A:4 | S:4 | A:4 | |
| S:2 | Y:1 | L:2 | R:1 | | | V:2 | G:1 | T:1 | |
| I:2 | L:1 | P:2 | | | | | | | |
| R:2 | X:1 | F:1 | | | | | | | |
| C:1 | I:1 | A:1 | | | | | | | |
| D:1 | | | | | | | | | |

FIG 2C

| | | | Framework 4 | | | | | | |
|---|---|---|---|---|---|---|---|---|---|
| 141 | 142 | 143 | 144 | 145 | 146 | 147 | 148 | 149 | 150 |
| K | V | F | P | L | S | L | S | S | K |
| -:181 | -:182 | -:182 | -:182 | -:182 | -:182 | -:182 | -:197 | -:197 | -:197 |
| K:15 | V:20 | F:20 | P:19 | L:20 | S:15 | L:15 | S:3 | S:5 | K:3 |
| S:6 | | | R:1 | | A:5 | P:5 | C:2 | | R:2 |

| | | | Framework 4 | | | | | | |
|---|---|---|---|---|---|---|---|---|---|
| 151 | 152 | 153 | 154 | 155 | 156 | 157 | 158 | 159 | 160 |
| S | T | S | G | G | T | A | A | L | G |
| -:197 | -:197 | -:197 | -:197 | -:197 | -:197 | -:197 | -:197 | -:197 | -:197 |
| S:4 | T:5 | S:5 | G:3 | G:3 | T:5 | A:5 | A:5 | L:5 | G:5 |
| G:1 | | | E:2 | S:2 | | | | | |

| | | | Framework 4 | | | | |
|---|---|---|---|---|---|---|---|
| 161 | 162 | 163 | 164 | 165 | 166 | 167 | 168 |
| C | L | V | K | D | Y | F | P |
| -:197 | -:197 | -:197 | -:197 | -:197 | -:197 | -:197 | -:197 |
| C:4 | L:5 | V:5 | K:5 | D:5 | Y:5 | F:5 | P:5 |
| R:1 | | | | | | | |

FIG 2D

| | | | | Framework 1 | | | | | |
|---|---|---|---|---|---|---|---|---|---|
| 1 | 2 | 3 | 4 | 5 | 6 | 7 | 8 | 9 | 10 |
| E | V | V | Q | L | V | E | S | G | G |
| -:2151 | -:1231 | -:1197 | -:1173 | L:1239 | -:1128 | -:1642 | S:1523 | G:1572 | G:1622 |
| E:427 | V:475 | V:874 | Q:860 | -:1133 | V:879 | E:892 | -:1083 | -:1039 | -:986 |
| Q:35 | E:461 | Q:462 | L:508 | V:211 | E:498 | Q:79 | T:8 | R:7 | E:13 |
| D:6 | Q:413 | E:13 | H:26 | Q:15 | L:56 | D:5 | F:3 | A:4 | R:3 |
| G:2 | L:15 | M:12 | N:15 | E:8 | Q:38 | G:3 | P:3 | W:2 | |
| A:1 | A:7 | K:11 | K:13 | M:7 | D:10 | K:1 | A:2 | | |
| P:1 | P:4 | I:11 | R:10 | S:5 | A:6 | V:1 | X:1 | | |
| V:1 | D:4 | A:10 | V:7 | A:1 | R:6 | R:1 | R:1 | | |
| | M:3 | H:10 | E:4 | F:1 | M:2 | | | | |
| | I:3 | L:9 | M:3 | W:1 | X:1 | | | | |
| | G:3 | R:7 | X:2 | P:1 | | | | | |
| | R:2 | P:3 | P:1 | R:1 | | | | | |
| | S:1 | X:2 | Y:1 | I:1 | | | | | |
| | K:1 | G:2 | I:1 | | | | | | |
| | C:1 | D:1 | | | | | | | |

| | | | | Framework 1 | | | | | |
|---|---|---|---|---|---|---|---|---|---|
| 11 | 12 | 13 | 14 | 15 | 16 | 17 | 18 | 19 | 20 |
| G | L | V | Q | P | G | G | S | L | R |
| G:1540 | L:1173 | V:1704 | Q:1623 | P:1883 | G:1917 | G:1379 | S:2012 | L:2040 | R:2009 |
| -:974 | -:903 | -:821 | -:768 | -:688 | -:675 | -:659 | -:593 | -:570 | -:563 |
| D:54 | V:524 | I:64 | K:175 | V:22 | D:22 | R:538 | P:5 | V:4 | K:32 |
| A:20 | S:11 | A:14 | R:25 | S:17 | E:4 | K:16 | A:4 | Q:3 | T:8 |
| V:12 | F:8 | L:9 | H:10 | T:6 | W:2 | T:11 | F:3 | M:3 | G:6 |
| S:9 | A:1 | G:5 | P:6 | A:4 | R:2 | E:9 | C:3 | R:3 | S:3 |
| N:7 | W:1 | F:3 | T:5 | R:2 | V:1 | W:4 | T:2 | P:1 | I:2 |
| H:4 | M:1 | E:2 | E:4 | H:1 | L:1 | S:2 | Y:2 | | X:1 |
| T:3 | I:1 | S:1 | L:4 | M:1 | | M:2 | | | |
| R:1 | G:1 | T:1 | Z:2 | | | A:1 | | | |
| | | | N:1 | | | N:1 | | | |
| | | | M:1 | | | V:1 | | | |
| | | | | | | D:1 | | | |

FIG 3A

| | | | | Framework 1 | | | | | |
|---|---|---|---|---|---|---|---|---|---|
| 21 | 22 | 23 | 24 | 25 | 26 | 27 | 28 | 29 | 30 |
| L | S | C | A | A | S | G | F | T | F |
| L:2054 | S:2060 | C:2082 | A:1896 | A:1992 | S:2140 | G:2126 | F:2093 | T:1935 | F:2038 |
| -:550 | -:543 | -:536 | -:534 | -:503 | -:458 | -:454 | -:448 | -:437 | -:413 |
| V:14 | C:7 | S:2 | V:67 | V:51 | A:7 | R:17 | L:34 | S:82 | V:90 |
| I:4 | F:5 | R:2 | T:50 | T:28 | Y:5 | E:13 | V:23 | I:68 | L:60 |
| F:1 | T:5 | T:1 | S:29 | G:25 | F:4 | A:4 | I:15 | N:34 | S:10 |
| P:1 | A:4 | Q:1 | E:27 | S:9 | P:4 | D:4 | S:6 | A:21 | I:10 |
| | | | G:13 | P:7 | T:3 | K:3 | Y:4 | P:20 | A:1 |
| | | | I:4 | L:4 | C:1 | S:1 | D:1 | R:10 | Y:1 |
| | | | L:2 | D:2 | R:1 | W:1 | | M:5 | C:1 |
| | | | P:1 | X:1 | L:1 | P:1 | | G:5 | |
| | | | C:1 | K:1 | | | | V:2 | |
| | | | | M:1 | | | | F:1 | |
| | | | | | | | | K:1 | |
| | | | | | | | | E:1 | |
| | | | | | | | | H:1 | |
| | | | | | | | | D:1 | |

| | | CDR1 | | | | | Framework 2 | | |
|---|---|---|---|---|---|---|---|---|---|
| 31 | 32 | 33 | 34 | 35 | 36 | 37 | 38 | 39 | 40 |
| S | X | X | X | X | X | W | V | R | Q |
| S:1842 | | | | | | W:2561 | V:2436 | R:2558 | Q:2573 |
| -:375 | | | | | | -:51 | I:124 | -:36 | -:31 |
| D:123 | | | | | | G:5 | -:41 | L:7 | R:12 |
| R:80 | | | | | | L:4 | A:10 | X:6 | K:5 |
| N:78 | | | | | | C:2 | L:5 | H:6 | H:2 |
| T:60 | | | | | | R:1 | G:5 | P:4 | X:1 |
| G:27 | | | | | | | F:3 | S:2 | |
| K:20 | | | | | | | | A:2 | |
| I:8 | | | | | | | | F:1 | |
| Y:6 | | | | | | | | E:1 | |
| X:1 | | | | | | | | C:1 | |
| P:1 | | | | | | | | | |
| E:1 | | | | | | | | | |
| H:1 | | | | | | | | | |
| L:1 | | | | | | | | | |

FIG 3B

| Framework 2 | | | | | | | | | |
|---|---|---|---|---|---|---|---|---|---|
| 41 | 42 | 43 | 44 | 45 | 46 | 47 | 48 | 49 | 50 |
| A | P | G | K | G | L | E | W | V | S |
| A:2420 | P:2561 | G:2575 | K:2521 | G:2593 | L:2588 | E:2481 | W:2560 | V:2509 | S:1474 |
| T:42 | T:28 | -:16 | R:38 | R:12 | P:24 | V:85 | Y:35 | L:49 | A:1093 |
| V:41 | -:17 | E:10 | E:20 | -:10 | -:9 | D:21 | C:11 | I:37 | T:29 |
| -:29 | S:8 | R:6 | Q:15 | A:6 | S:1 | Q:12 | -:8 | -:8 | -:8 |
| P:29 | A:5 | D:5 | -:10 | S:1 | V:1 | -:11 | R:8 | M:8 | G:6 |
| S:18 | L:3 | A:3 | M:7 | E:1 | Q:1 | M:4 | S:1 | A:7 | L:4 |
| R:18 | Q:2 | X:3 | T:6 | V:1 | | A:3 | L:1 | S:2 | X:4 |
| G:10 | | C:2 | N:3 | | | T:1 | | F:1 | P:4 |
| L:8 | | W:2 | A:2 | | | K:1 | | E:1 | V:2 |
| I:3 | | K:1 | X:1 | | | Y:1 | | X:1 | |
| X:2 | | V:1 | G:1 | | | Z:1 | | G:1 | |
| D:2 | | | | | | L:1 | | | |
| F:1 | | | | | | X:1 | | | |
| C:1 | | | | | | G:1 | | | |

| CDR2 | | | | | | | | | |
|---|---|---|---|---|---|---|---|---|---|
| 51 | 52 | 53 | 54 | 55 | 56 | 57 | 58 | 59 | 60 |
| X | X | X | X | X | X | X | X | X | X |

| CDR2 | | | | | | | | Framework 3 | |
|---|---|---|---|---|---|---|---|---|---|
| 61 | 62 | 63 | 64 | 65 | 66 | 67 | 68 | 69 | 70 |
| X | X | X | X | X | X | X | X | R | F |
| | | | | | | | | R:2616 | F:2553 |
| | | | | | | | | Q:5 | L:44 |
| | | | | | | | | H:2 | S:11 |
| | | | | | | | | G:1 | V:7 |
| | | | | | | | | | Y:4 |
| | | | | | | | | | C:3 |
| | | | | | | | | | I:2 |

| Framework 3 | | | | | | | | | |
|---|---|---|---|---|---|---|---|---|---|
| 71 | 72 | 73 | 74 | 75 | 76 | 77 | 78 | 79 | 80 |
| T | I | S | R | D | N | S | K | N | T |
| T:2473 | I:2499 | S:2601 | R:2568 | D:2564 | N:2513 | S:1560 | K:2393 | N:2461 | T:1619 |
| I:49 | V:84 | F:8 | G:32 | E:38 | D:41 | A:976 | R:79 | K:52 | S:917 |
| S:41 | L:15 | T:4 | K:11 | N:11 | S:19 | T:23 | E:47 | S:42 | L:29 |
| V:25 | T:8 | A:4 | S:7 | G:6 | K:14 | V:15 | N:37 | D:27 | M:19 |
| A:25 | M:7 | Y:3 | T:3 | S:1 | T:12 | G:14 | Q:30 | T:24 | A:18 |
| F:4 | F:3 | C:1 | I:2 | Y:1 | I:8 | P:10 | T:10 | H:6 | I:8 |
| D:2 | S:2 | L:1 | Q:1 | V:1 | R:4 | F:8 | M:9 | Y:3 | P:4 |
| G:2 | N:2 | W:1 | | X:1 | B:3 | D:7 | H:6 | B:3 | R:4 |
| N:1 | A:2 | G:1 | | H:1 | E:2 | Y:4 | L:5 | R:2 | K:2 |
| -:1 | X:1 | | | | V:2 | L:3 | D:3 | Q:1 | Y:2 |
| X:1 | G:1 | | | | Q:2 | N:2 | G:3 | A:1 | F:1 |
| | | | | | C:1 | R:1 | S:1 | X:1 | V:1 |
| | | | | | L:1 | I:1 | -:1 | G:1 | |
| | | | | | H:1 | | | | |

FIG 3C

| Framework 3 | | | | | | | | | |
|---|---|---|---|---|---|---|---|---|---|
| 81 | 82 | 83 | 84 | 85 | 86 | 87 | 88 | 89 | 90 |
| L | Y | L | Q | M | N | S | L | R | A |
| L:2435 | Y:2347 | L:2585 | Q:2523 | M:2536 | N:2353 | S:2473 | L:2601 | R:2497 | A:2098 |
| V:149 | F:162 | V:22 | E:57 | L:29 | S:100 | N:54 | V:14 | T:39 | V:223 |
| M:16 | S:52 | M:12 | H:24 | I:29 | D:81 | G:36 | M:3 | K:28 | D:83 |
| I:7 | H:22 | F:2 | N:5 | V:19 | K:25 | T:28 | R:3 | G:27 | T:70 |
| F:4 | D:14 | I:2 | L:5 | T:9 | T:20 | R:19 | Q:2 | S:19 | P:63 |
| A:4 | C:10 | -:1 | R:5 | K:2 | H:15 | I:4 | P:1 | N:3 | G:39 |
| Q:3 | N:8 | | T:1 | | G:15 | F:3 | | E:3 | S:17 |
| W:2 | L:4 | | K:1 | | Y:5 | D:3 | | -:3 | L:12 |
| P:2 | I:2 | | V:1 | | R:5 | A:2 | | A:2 | E:5 |
| S:1 | T:1 | | Z:1 | | I:3 | Y:1 | | I:2 | I:4 |
| G:1 | E:1 | | D:1 | | E:1 | V:1 | | M:1 | -:3 |
| | V:1 | | | | B:1 | | | | H:3 |
| | | | | | | | | | F:1 |
| | | | | | | | | | N:1 |
| | | | | | | | | | X:1 |
| | | | | | | | | | R:1 |

| Framework 3 | | | | | | | | | |
|---|---|---|---|---|---|---|---|---|---|
| 91 | 92 | 93 | 94 | 95 | 96 | 97 | 98 | 99 | 100 |
| E | D | T | A | V | Y | Y | C | A | R |
| E:2438 | D:2604 | T:2559 | A:2574 | V:2185 | Y:2603 | Y:2456 | C:2607 | A:2357 | R:1369 |
| D:133 | E:6 | S:25 | G:22 | L:255 | F:12 | F:106 | -:5 | V:140 | K:885 |
| G:37 | N:4 | M:21 | S:10 | I:85 | -:4 | H:34 | Y:3 | T:56 | S:85 |
| A:5 | G:4 | A:12 | T:4 | M:42 | H:4 | S:10 | W:3 | G:22 | -:84 |
| V:3 | -:3 | -:4 | -:4 | F:16 | S:1 | -:5 | S:2 | S:14 | T:72 |
| -:3 | B:2 | K:1 | V:3 | A:11 | | L:5 | R:2 | -:11 | N:32 |
| X:2 | Q:1 | P:1 | P:3 | T:7 | | T:3 | F:1 | L:8 | G:29 |
| N:1 | | R:1 | C:1 | -:4 | | N:3 | X:1 | P:4 | A:16 |
| K:1 | | | L:1 | E:3 | | W:1 | | I:4 | I:9 |
| Q:1 | | | X:1 | G:3 | | I:1 | | K:2 | Q:7 |
| | | | D:1 | K:2 | | | | E:2 | E:6 |
| | | | | Y:2 | | | | N:1 | V:6 |
| | | | | Q:2 | | | | Y:1 | L:4 |
| | | | | R:2 | | | | C:1 | P:4 |
| | | | | S:1 | | | | R:1 | D:4 |
| | | | | W:1 | | | | | M:3 |
| | | | | X:1 | | | | | H:3 |
| | | | | H:1 | | | | | C:2 |
| | | | | D:1 | | | | | X:2 |
| | | | | | | | | | F:1 |
| | | | | | | | | | W:1 |

FIG 3D

| | | | | | CDR3 | | | | |
|---|---|---|---|---|---|---|---|---|---|
| 101 | 102 | 103 | 104 | 105 | 106 | 107 | 108 | 109 | 110 |
| X | X | X | X | X | X | X | X | X | X |

| | | | | | CDR3 | | | | |
|---|---|---|---|---|---|---|---|---|---|
| 111 | 112 | 113 | 114 | 115 | 116 | 117 | 118 | 119 | 120 |
| X | X | X | X | X | X | X | X | X | X |

| | | | | | CDR3 | | | | |
|---|---|---|---|---|---|---|---|---|---|
| 121 | 122 | 123 | 124 | 125 | 126 | 127 | 128 | 129 | 130 |
| X | X | X | X | X | X | X | X | X | X |

| | | | CDR3 | | | | Framework 4 | | |
|---|---|---|---|---|---|---|---|---|---|
| 131 | 132 | 133 | 134 | 135 | 136 | 137 | 138 | 139 | 140 |
| X | X | X | X | X | X | X | W | G | Q |

| 138 | 139 | 140 |
|---|---|---|
| W:1497 | -:1406 | -:1188 |
| G:573 | G:1145 | Q:1167 |
| -:445 | D:12 | R:77 |
| Y:15 | S:7 | K:54 |
| L:14 | T:7 | P:28 |
| S:10 | Y:7 | D:16 |
| F:10 | V:7 | G:15 |
| V:10 | W:6 | S:11 |
| D:10 | A:5 | L:11 |
| M:8 | F:4 | H:10 |
| T:7 | P:4 | V:9 |
| R:5 | R:3 | X:8 |
| C:3 | E:2 | Y:7 |
| A:3 | M:2 | T:6 |
| I:3 | C:2 | E:4 |
| N:2 | H:2 | A:4 |
| Q:2 | N:1 | F:3 |
| X:2 | K:1 | W:3 |
| P:2 | Q:1 | M:2 |
| K:1 | | N:1 |

FIG 3E

| | | | | Framework 4 | | | | | |
|---|---|---|---|---|---|---|---|---|---|
| 141 | 142 | 143 | 144 | 145 | 146 | 147 | 148 | 149 | 150 |
| G | T | L | V | T | V | S | S | G | S |
| G:1273 | T:1185 | -:1203 | -:1236 | -:1258 | -:1303 | -:1339 | -:1405 | -:2222 | -:2451 |
| -:1120 | -:1161 | L:826 | V:1168 | T:1130 | V:1123 | S:1071 | S:1152 | G:147 | S:117 |
| Q:139 | G:148 | T:370 | L:134 | V:146 | T:135 | V:136 | T:13 | S:127 | G:16 |
| V:13 | P:22 | M:115 | S:23 | P:24 | S:24 | T:16 | L:12 | A:95 | A:9 |
| R:12 | A:21 | W:17 | M:17 | I:15 | I:7 | G:14 | P:11 | P:8 | P:6 |
| S:8 | S:18 | P:14 | W:9 | S:10 | R:5 | P:10 | A:8 | R:7 | K:5 |
| L:7 | W:12 | A:13 | G:9 | A:10 | F:4 | L:8 | G:6 | T:5 | V:5 |
| A:7 | D:12 | V:12 | I:8 | G:10 | K:4 | W:6 | V:4 | L:4 | E:3 |
| W:7 | N:9 | G:11 | A:5 | L:5 | P:4 | D:6 | Q:4 | K:2 | T:2 |
| E:5 | I:9 | S:8 | Q:4 | W:4 | L:3 | F:4 | R:3 | V:2 | W:2 |
| P:5 | V:7 | D:7 | T:3 | H:4 | A:3 | A:4 | C:2 | Q:2 | H:2 |
| F:4 | Y:6 | R:7 | R:3 | D:3 | G:3 | H:3 | D:2 | M:2 | Y:1 |
| T:4 | F:3 | K:5 | P:2 | Q:2 | Y:2 | R:3 | F:1 | E:1 | Q:1 |
| M:4 | L:3 | Q:5 | Y:1 | M:2 | N:1 | X:2 | K:1 | | C:1 |
| Y:3 | R:3 | I:4 | X:1 | F:1 | Q:1 | K:1 | | | L:1 |
| D:3 | M:2 | X:2 | H:1 | | C:1 | E:1 | | | D:1 |
| I:3 | E:1 | H:2 | | | H:1 | | | | I:1 |
| C:2 | X:1 | F:1 | | | | | | | |
| X:2 | H:1 | E:1 | | | | | | | |
| H:2 | | Y:1 | | | | | | | |
| K:1 | | | | | | | | | |

| | | Framework 4 | | | | |
|---|---|---|---|---|---|---|
| 151 | 152 | 153 | 154 | 155 | 156 | 157 |
| T | K | A | P | S | V | F |
| -:2481 | -:2495 | -:2506 | -:2520 | -:2542 | -:2556 | -:2593 |
| T:82 | K:69 | A:52 | P:71 | S:37 | V:25 | F:17 |
| A:34 | S:40 | G:46 | H:16 | T:24 | L:23 | V:5 |
| S:10 | T:8 | P:6 | S:5 | R:9 | S:6 | Y:4 |
| P:8 | R:5 | K:5 | G:5 | P:5 | D:6 | S:2 |
| R:4 | V:3 | S:3 | T:3 | V:3 | F:5 | P:2 |
| L:2 | Y:1 | V:2 | I:3 | N:1 | G:2 | Q:1 |
| Y:1 | L:1 | L:2 | A:1 | K:1 | R:1 | |
| Q:1 | W:1 | Y:1 | | M:1 | | |
| X:1 | G:1 | X:1 | | H:1 | | |

FIG 3F

| | | | | Framework 1 | | | | | |
|---|---|---|---|---|---|---|---|---|---|
| 1 | 2 | 3 | 4 | 5 | 6 | 7 | 8 | 9 | 10 |
| E | V | Q | L | V | E | S | G | G | G |
| E:150 | V:164 | Q:156 | L:177 | V:174 | E:180 | S:191 | G:193 | G:200 | G:184 |
| -:131 | -:127 | -:126 | -:112 | -:107 | -:104 | -:101 | -:97 | -:93 | -:92 |
| Q:10 | A:1 | H:7 | Q:2 | L:7 | Q:6 | A:1 | A:2 | | D:9 |
| D:1 | E:1 | R:4 | M:2 | Q:4 | D:3 | | R:1 | | A:5 |
| G:1 | | | | A:1 | | | | | N:2 |
| | | | | | | | | | S:1 |

| | | | | Framework 1 | | | | | |
|---|---|---|---|---|---|---|---|---|---|
| 11 | 12 | 13 | 14 | 15 | 16 | 17 | 18 | 19 | 20 |
| L | V | K | P | G | G | S | L | R | L |
| L:182 | V:208 | K:145 | P:226 | G:221 | G:218 | S:233 | L:239 | R:193 | L:239 |
| -:87 | -:74 | -:69 | -:64 | -:65 | -:64 | -:58 | -:54 | -:52 | -:48 |
| S:21 | I:7 | Q:69 | V:2 | E:4 | R:6 | P:2 | | K:39 | V:5 |
| V:2 | A:3 | E:7 | R:1 | D:2 | E:4 | | | T:9 | F:1 |
| F:1 | G:1 | H:2 | | R:1 | Q:1 | | | | |
| | | M:1 | | | | | | | |

| | | | | Framework 1 | | | | | |
|---|---|---|---|---|---|---|---|---|---|
| 21 | 22 | 23 | 24 | 25 | 26 | 27 | 28 | 29 | 30 |
| S | C | A | A | S | G | F | T | F | S |
| S:217 | C:247 | A:197 | A:223 | S:252 | G:248 | F:246 | T:225 | F:251 | S:218 |
| -:48 | -:46 | -:45 | -:43 | -:38 | -:38 | -:35 | -:34 | -:32 | -:31 |
| T:26 | | V:32 | V:16 | A:1 | E:2 | I:5 | I:14 | L:6 | T:16 |
| A:2 | | T:11 | T:5 | F:1 | R:2 | L:5 | S:9 | C:2 | G:9 |
| | | E:5 | G:3 | L:1 | A:1 | S:2 | P:4 | X:1 | N:8 |
| | | S:1 | D:2 | | W:1 | | A:3 | M:1 | R:6 |
| | | G:1 | P:1 | | N:1 | | D:2 | | F:1 |
| | | L:1 | | | | | N:1 | | P:1 |
| | | | | | | | L:1 | | K:1 |
| | | | | | | | | | Q:1 |
| | | | | | | | | | I:1 |

FIG 4A

| CDR1 | | | | | Framework 2 | | | | |
|---|---|---|---|---|---|---|---|---|---|
| 31 | 32 | 33 | 34 | 35 | 36 | 37 | 38 | 39 | 40 |
| X | X | X | X | X | W | V | R | Q | A |
| | | | | | W:286 | V:280 | R:286 | Q:282 | A:276 |
| | | | | | -:6 | F:6 | -:5 | -:5 | -:5 |
| | | | | | X:1 | -:5 | X:1 | L:5 | T:3 |
| | | | | | | A:1 | H:1 | H:1 | V:3 |
| | | | | | | L:1 | | | P:2 |
| | | | | | | | | | S:1 |
| | | | | | | | | | X:1 |
| | | | | | | | | | G:1 |
| | | | | | | | | | L:1 |

| Framework 2 | | | | | | | | | CDR |
|---|---|---|---|---|---|---|---|---|---|
| 41 | 42 | 43 | 44 | 45 | 46 | 47 | 48 | 49 | 50 |
| P | G | K | G | L | E | W | V | G | X |
| P:245 | G:287 | K:287 | G:291 | L:291 | E:287 | W:290 | V:279 | G:277 | |
| S:43 | -:3 | R:5 | E:1 | V:1 | Q:5 | L:2 | L:8 | A:13 | |
| -:3 | A:1 | -:1 | -:1 | -:1 | -:1 | -:1 | I:5 | S:2 | |
| Q:2 | E:1 | | | | | | -:1 | -:1 | |
| | R:1 | | | | | | | | |

| CDR2 | | | | | | | | | |
|---|---|---|---|---|---|---|---|---|---|
| 51 | 52 | 53 | 54 | 55 | 56 | 57 | 58 | 59 | 60 |
| X | X | X | X | X | X | X | X | X | X |

| CDR2 | | | | | | | | | |
|---|---|---|---|---|---|---|---|---|---|
| 61 | 62 | 63 | 64 | 65 | 66 | 67 | 68 | 69 | 70 |
| X | X | X | X | X | X | X | X | X | X |

| Framework 3 | | | | | | | | | |
|---|---|---|---|---|---|---|---|---|---|
| 71 | 72 | 73 | 74 | 75 | 76 | 77 | 78 | 79 | 80 |
| R | F | T | I | S | R | D | D | S | K |
| R:288 | F:285 | T:271 | I:279 | S:292 | R:291 | D:285 | D:289 | S:291 | K:265 |
| K:2 | L:5 | I:10 | V:8 | A:1 | S:1 | E:3 | E:2 | X:1 | E:9 |
| S:1 | V:1 | S:8 | F:2 | | W:1 | N:2 | S:1 | P:1 | Q:9 |
| T:1 | C:1 | A:2 | M:2 | | | H:2 | G:1 | | R:5 |
| G:1 | I:1 | X:1 | X:1 | | | V:1 | | | N:2 |
| | | V:1 | C:1 | | | | | | T:1 |
| | | | | | | | | | M:1 |
| | | | | | | | | | I:1 |

FIG 4B

| | | | | Framework 3 | | | | | |
|---|---|---|---|---|---|---|---|---|---|
| 81 | 82 | 83 | 84 | 85 | 86 | 87 | 88 | 89 | 90 |
| N | T | L | Y | L | Q | M | N | S | L |
| N:252 | T:251 | L:210 | Y:262 | L:293 | Q:278 | M:283 | N:255 | S:271 | L:292 |
| S:25 | S:20 | A:53 | F:12 | | E:10 | I:5 | S:21 | N:7 | V:1 |
| D:7 | M:10 | V:27 | W:12 | | H:2 | L:5 | D:6 | R:5 | |
| K:4 | I:10 | M:2 | S:4 | | T:1 | | I:4 | I:3 | |
| T:3 | A:2 | Q:1 | D:2 | | K:1 | | T:3 | G:3 | |
| Q:1 | | | C:1 | | R:1 | | K:3 | A:1 | |
| R:1 | | | | | | | H:1 | F:1 | |
| | | | | | | | | T:1 | |
| | | | | | | | | H:1 | |

| | | | | Framework 3 | | | | | |
|---|---|---|---|---|---|---|---|---|---|
| 91 | 92 | 93 | 94 | 95 | 96 | 97 | 98 | 99 | 100 |
| K | T | E | D | T | A | V | Y | Y | C |
| K:253 | T:242 | E:284 | D:293 | T:290 | A:276 | V:275 | Y:291 | Y:252 | C:290 |
| E:20 | I:24 | D:7 | | L:2 | G:15 | M:7 | X:1 | S:29 | A:2 |
| R:8 | S:13 | G:2 | | S:1 | T:1 | I:5 | H:1 | F:8 | R:1 |
| Q:6 | A:8 | | | | P:1 | L:2 | | C:3 | |
| T:3 | N:2 | | | | | F:1 | | X:1 | |
| S:1 | P:1 | | | | | A:1 | | | |
| N:1 | V:1 | | | | | T:1 | | | |
| G:1 | D:1 | | | | | E:1 | | | |
| | L:1 | | | | | | | | |

| | | | | | CDR3 | | | | |
|---|---|---|---|---|---|---|---|---|---|
| 101 | 102 | 103 | 104 | 105 | 106 | 107 | 108 | 109 | 110 |
| T | T | X | X | X | X | X | X | X | X |
| T:191 | T:173 | | | | | | | | |
| A:33 | R:62 | | | | | | | | |
| I:27 | S:16 | | | | | | | | |
| V:11 | -:13 | | | | | | | | |
| G:7 | A:8 | | | | | | | | |
| N:6 | G:6 | | | | | | | | |
| S:5 | K:3 | | | | | | | | |
| P:3 | V:3 | | | | | | | | |
| -:3 | P:2 | | | | | | | | |
| L:3 | I:2 | | | | | | | | |
| F:1 | W:1 | | | | | | | | |
| K:1 | N:1 | | | | | | | | |
| Q:1 | Y:1 | | | | | | | | |
| C:1 | E:1 | | | | | | | | |
| | L:1 | | | | | | | | |

| | | | | CDR3 | | | | | |
|---|---|---|---|---|---|---|---|---|---|
| 111 | 112 | 113 | 114 | 115 | 116 | 117 | 118 | 119 | 120 |
| X | X | X | X | X | X | X | X | X | X |

FIG 4D

| CDR3 | | | | | | | | | |
|---|---|---|---|---|---|---|---|---|---|
| 121 | 122 | 123 | 124 | 125 | 126 | 127 | 128 | 129 | 130 |
| X | X | X | X | X | X | X | X | X | X |

| CDR3 | | | | | | Framework 4 | | | |
|---|---|---|---|---|---|---|---|---|---|
| 131 | 132 | 133 | 134 | 135 | 136 | 137 | 138 | 139 | 140 |
| X | X | X | X | X | X | W | G | Q | G |
|  |  |  |  |  |  | W:230 | G:194 | Q:132 | G:169 |
|  |  |  |  |  |  | -:49 | -:89 | -:108 | -:114 |
|  |  |  |  |  |  | L:4 | F:2 | K:31 | W:2 |
|  |  |  |  |  |  | D:2 | T:2 | R:7 | P:2 |
|  |  |  |  |  |  | R:2 | P:2 | D:3 | S:1 |
|  |  |  |  |  |  | T:1 | E:1 | N:2 | E:1 |
|  |  |  |  |  |  | K:1 | M:1 | X:2 | Y:1 |
|  |  |  |  |  |  | Y:1 | L:1 | P:2 | V:1 |
|  |  |  |  |  |  | P:1 | D:1 | S:1 | L:1 |
|  |  |  |  |  |  | I:1 |  | T:1 | R:1 |
|  |  |  |  |  |  | G:1 |  | Y:1 |  |
|  |  |  |  |  |  |  |  | L:1 |  |
|  |  |  |  |  |  |  |  | A:1 |  |
|  |  |  |  |  |  |  |  | H:1 |  |

| Framework 4 | | | | | | | | | |
|---|---|---|---|---|---|---|---|---|---|
| 141 | 142 | 143 | 144 | 145 | 146 | 147 | 148 | 149 | 150 |
| T | L | V | T | V | S | S | A | S | T |
| T:159 | -:124 | V:162 | T:155 | V:156 | S:150 | -:140 | -:272 | -:280 | -:282 |
| -:119 | L:105 | -:126 | -:128 | -:131 | -:136 | S:136 | A:11 | S:13 | T:6 |
| A:3 | T:44 | G:3 | I:5 | S:3 | T:2 | P:14 | G:9 |  | A:3 |
| W:3 | M:9 | S:1 | S:2 | F:1 | V:1 | R:2 | V:1 |  | S:1 |
| S:2 | Q:5 | P:1 | L:1 | L:1 | A:1 | T:1 |  |  | P:1 |
| I:2 | W:2 |  | H:1 | R:1 | D:1 |  |  |  |  |
| F:1 | P:2 |  | R:1 |  | R:1 |  |  |  |  |
| E:1 | V:1 |  |  |  | G:1 |  |  |  |  |
| V:1 | G:1 |  |  |  |  |  |  |  |  |
| H:1 |  |  |  |  |  |  |  |  |  |
| G:1 |  |  |  |  |  |  |  |  |  |

| Framework 4 | | | | | | | | |
|---|---|---|---|---|---|---|---|---|
| 151 | 152 | 153 | 154 | 155 | 156 | 157 | 158 | 159 |
| K | G | P | S | V | F | P | L | A |
| -:283 | -:283 | -:284 | -:285 | -:286 | -:289 | -:290 | -:290 | -:290 |
| K:6 | G:5 | P:8 | S:5 | V:5 | F:4 | P:3 | L:3 | A:2 |
| S:3 | A:4 | H:1 | T:2 | L:2 |  |  |  | G:1 |
| T:1 | S:1 |  | K:1 |  |  |  |  |  |

FIG 4E

| Framework 1 | | | | | | | | | |
|---|---|---|---|---|---|---|---|---|---|
| 1 | 2 | 3 | 4 | 5 | 6 | 7 | 8 | 9 | 10 |
| E | V | Q | L | V | E | S | G | G | G |
| -:26 | -:24 | -:24 | L:25 | -:24 | -:24 | S:33 | G:33 | G:34 | G:24 |
| E:18 | V:24 | Q:23 | -:24 | V:23 | E:23 | -:16 | -:16 | -:15 | -:14 |
| Q:4 | L:1 | H:2 | | Q:2 | Q:2 | | | | A:6 |
| V:1 | | | | | | | | | S:3 |
| | | | | | | | | | D:2 |

| Framework 1 | | | | | | | | | |
|---|---|---|---|---|---|---|---|---|---|
| 11 | 12 | 13 | 14 | 15 | 16 | 17 | 18 | 19 | 20 |
| L | V | Q | P | G | R | S | L | R | L |
| L:33 | V:41 | Q:30 | P:42 | G:42 | R:43 | S:46 | L:47 | R:47 | L:47 |
| -:14 | -:8 | -:8 | -:7 | -:6 | -:5 | -:2 | -:2 | -:2 | -:2 |
| S:2 | | K:6 | | W:1 | P:1 | P:1 | | | |
| | | H:3 | | | | | | | |
| | | E:2 | | | | | | | |

| Framework 1 | | | | | | | | | |
|---|---|---|---|---|---|---|---|---|---|
| 21 | 22 | 23 | 24 | 25 | 26 | 27 | 28 | 29 | 30 |
| S | C | T | A | S | G | F | T | F | G |
| S:47 | C:47 | T:38 | A:34 | S:47 | G:47 | F:46 | T:45 | F:45 | G:47 |
| -:2 | -:2 | S:8 | T:12 | -:2 | -:2 | -:2 | -:2 | -:2 | -:2 |
| | | -:2 | -:2 | | | Y:1 | N:2 | L:1 | |
| | | A:1 | G:1 | | | | | V:1 | |

| CDR1 | | | | | Framework 2 | | | | |
|---|---|---|---|---|---|---|---|---|---|
| 31 | 32 | 33 | 34 | 35 | 36 | 37 | 38 | 39 | 40 |
| X | X | X | X | X | W | V | R | Q | A |
| | | | | | W:49 | V:30 | R:49 | Q:49 | A:46 |
| | | | | | | F:19 | | | P:2 |
| | | | | | | | | | G:1 |

| Framework 2 | | | | | | | | | CDR |
|---|---|---|---|---|---|---|---|---|---|
| 41 | 42 | 43 | 44 | 45 | 46 | 47 | 48 | 49 | 50 |
| P | G | K | G | L | E | W | V | G | X |
| P:49 | G:49 | K:47 | G:49 | L:49 | E:49 | W:49 | V:41 | G:41 | |
| | | R:1 | | | | | I:8 | S:8 | |
| | | T:1 | | | | | | | |

| CDR2 | | | | | | | | | |
|---|---|---|---|---|---|---|---|---|---|
| 51 | 52 | 53 | 54 | 55 | 56 | 57 | 58 | 59 | 60 |
| X | X | X | X | X | X | X | X | X | X |

FIG 5A

| CDR2 | | | | | | | | Framework 3 | |
|---|---|---|---|---|---|---|---|---|---|
| 61 | 62 | 63 | 64 | 65 | 66 | 67 | 68 | 69 | 70 |
| X | X | X | X | X | X | X | X | R | F |
| | | | | | | | | R:49 | F:49 |

| Framework 3 | | | | | | | | | |
|---|---|---|---|---|---|---|---|---|---|
| 71 | 72 | 73 | 74 | 75 | 76 | 77 | 78 | 79 | 80 |
| T | I | S | R | D | D | S | K | S | I |
| T:47 | I:47 | S:49 | R:49 | D:49 | D:48 | S:49 | K:45 | S:45 | I:47 |
| I:2 | V:2 | | | | G:1 | | E:2 | T:2 | V:2 |
| | | | | | | | Q:1 | N:2 | |
| | | | | | | | N:1 | | |

| Framework 3 | | | | | | | | | |
|---|---|---|---|---|---|---|---|---|---|
| 81 | 82 | 83 | 84 | 85 | 86 | 87 | 88 | 89 | 90 |
| A | Y | L | Q | M | N | S | L | K | T |
| A:49 | Y:47 | L:49 | Q:49 | M:48 | N:45 | S:49 | L:49 | K:46 | T:39 |
| | H:2 | | | V:1 | D:2 | | | T:2 | I:8 |
| | | | | | S:1 | | | E:1 | A:1 |
| | | | | | X:1 | | | | S:1 |

| Framework 3 | | | | | | | | | |
|---|---|---|---|---|---|---|---|---|---|
| 91 | 92 | 93 | 94 | 95 | 96 | 97 | 98 | 99 | 100 |
| E | D | T | A | V | Y | Y | C | T | R |
| E:47 | D:49 | T:49 | A:48 | V:34 | Y:49 | Y:37 | C:48 | T:43 | R:29 |
| A:1 | | | G:1 | M:9 | | F:11 | A:1 | S:3 | -:17 |
| D:1 | | | | L:3 | | C:1 | | A:2 | F:1 |
| | | | | A:1 | | | | L:1 | V:1 |
| | | | | I:1 | | | | | G:1 |
| | | | | -:1 | | | | | |

| | CDR3 | | | | | | | | |
|---|---|---|---|---|---|---|---|---|---|
| 101 | 102 | 103 | 104 | 105 | 106 | 107 | 108 | 109 | 110 |
| N | X | X | X | X | X | X | X | X | X |

| CDR3 | | | | | | | | | |
|---|---|---|---|---|---|---|---|---|---|
| 111 | 112 | 113 | 114 | 115 | 116 | 117 | 118 | 119 | 120 |
| X | X | X | X | X | X | X | X | X | W |
| | | | | | | | | | W:25 |
| | | | | | | | | | -:16 |
| | | | | | | | | | V:6 |
| | | | | | | | | | Y:2 |

| Framework 4 | | | | | | | | | |
|---|---|---|---|---|---|---|---|---|---|
| 121 | 122 | 123 | 124 | 125 | 126 | 127 | 128 | 129 | 130 |
| G | Q | G | T | L | V | T | V | S | S |
| G:23 | -:31 | -:35 | -:37 | -:38 | -:38 | -:38 | -:38 | -:38 | -:39 |
| -:19 | Q:12 | G:11 | T:11 | L:9 | V:11 | T:11 | V:9 | S:11 | S:10 |
| S:3 | S:3 | D:2 | V:1 | T:1 | | | S:1 | | |
| T:2 | V:1 | S:1 | | M:1 | | | F:1 | | |
| D:1 | L:1 | | | | | | | | |
| V:1 | M:1 | | | | | | | | |

| Framework 4 | | | | | | | | | |
|---|---|---|---|---|---|---|---|---|---|
| 131 | 132 | 133 | 134 | 135 | 136 | 137 | 138 | 139 | 140 |
| G | S | T | K | G | P | S | V | L | P |
| -:43 | -:46 | -:46 | -:46 | -:46 | -:46 | -:46 | -:46 | -:48 | -:48 |
| G:4 | S:3 | T:2 | K:2 | G:2 | P:3 | S:2 | V:2 | L:1 | P:1 |
| A:2 | | A:1 | S:1 | A:1 | | T:1 | L:1 | | |

FIG 5C

| | | | | | Framework 1 | | | | |
|---|---|---|---|---|---|---|---|---|---|
| 1 | 2 | 3 | 4 | 5 | 6 | 7 | 8 | 9 | 10 |
| Q | V | Q | L | Q | E | S | G | P | G |
| Q:729 | -:673 | Q:733 | L:779 | Q:756 | -:624 | -:621 | G:833 | -:572 | G:866 |
| -:700 | V:660 | -:664 | -:645 | -:629 | E:442 | S:444 | -:595 | P:467 | -:555 |
| E:12 | L:96 | H:20 | Q:12 | L:30 | Q:370 | W:361 | S:13 | A:375 | P:13 |
| R:5 | Q:12 | L:10 | V:8 | H:14 | L:6 | E:13 | Q:2 | G:13 | R:6 |
| L:1 | I:3 | R:7 | S:1 | V:5 | T:1 | Q:3 | D:2 | S:11 | A:3 |
|  | F:1 | E:4 | M:1 | R:4 | K:1 | L:3 | X:1 | T:6 | E:2 |
|  | R:1 | K:3 | I:1 | K:3 | V:1 | R:2 | E:1 | E:1 | V:2 |
|  | G:1 | V:3 |  | T:1 | H:1 |  |  | V:1 |  |
|  |  | P:2 |  | P:1 | R:1 |  |  | R:1 |  |
|  |  | C:1 |  | E:1 |  |  |  |  |  |
|  |  |  |  | Y:1 |  |  |  |  |  |
|  |  |  |  | C:1 |  |  |  |  |  |
|  |  |  |  | D:1 |  |  |  |  |  |

| | | | | | Framework 1 | | | | |
|---|---|---|---|---|---|---|---|---|---|
| 11 | 12 | 13 | 14 | 15 | 16 | 17 | 18 | 19 | 20 |
| L | V | K | P | S | E | T | L | S | L |
| L:874 | V:537 | K:905 | P:891 | S:940 | E:804 | T:1005 | L:1043 | S:1054 | L:1053 |
| -:548 | -:520 | -:499 | -:488 | -:474 | -:449 | -:407 | -:374 | -:355 | -:351 |
| G:13 | L:377 | V:14 | S:34 | P:22 | Q:123 | E:15 | T:17 | L:18 | S:18 |
| P:4 | G:5 | E:6 | K:17 | A:3 | S:30 | S:6 | M:3 | P:6 | T:5 |
| V:3 | A:3 | Q:6 | A:6 | K:3 | G:25 | P:4 | G:3 | F:4 | R:4 |
| Q:2 | P:2 | R:6 | V:4 | T:2 | D:8 | A:3 | V:2 | T:4 | F:3 |
| R:2 | S:1 | S:4 | L:4 | W:2 | L:4 | R:2 | Q:2 | A:3 | P:3 |
| K:1 | X:1 | L:4 | Q:2 | R:1 | A:1 | I:2 | S:1 | E:1 | V:3 |
|  | M:1 | N:2 | T:1 |  | P:1 | Q:1 | P:1 | D:1 | H:2 |
|  |  | M:1 |  |  | K:1 | D:1 | E:1 | C:1 | C:2 |
|  |  |  |  |  | R:1 | G:1 |  |  | I:2 |
|  |  |  |  |  |  |  |  |  | X:1 |

| | | | | | Framework 1 | | | | |
|---|---|---|---|---|---|---|---|---|---|
| 21 | 22 | 23 | 24 | 25 | 26 | 27 | 28 | 29 | 30 |
| T | C | T | V | S | G | G | S | S | I |
| T:1038 | C:1077 | T:549 | V:1095 | S:705 | G:844 | G:788 | S:892 | -:1410 | I:580 |
| -:333 | -:323 | A:448 | -:304 | Y:388 | -:526 | -:523 | G:269 | S:18 | -:485 |
| L:28 | S:12 | -:313 | T:27 | -:295 | S:33 | D:40 | -:254 | G:15 | G:218 |
| S:23 | T:11 | G:59 | C:7 | V:20 | V:14 | Y:36 | D:9 | Y:2 | V:97 |
| I:10 | I:7 | S:26 | A:4 | C:12 | D:8 | V:24 | P:6 | A:1 | S:25 |
| A:3 | L:6 | C:19 | G:4 | F:7 | T:7 | A:17 | Y:4 | I:1 | M:13 |
| N:3 | V:3 | L:9 | F:2 | A:6 | A:5 | S:6 | A:3 |  | F:11 |
| V:3 | R:3 | N:8 | M:1 | H:6 | R:3 | I:6 | F:3 |  | L:8 |
| M:3 | M:2 | V:7 | D:1 | G:3 | N:2 | F:2 | T:3 |  | A:4 |
| P:2 | A:1 | D:5 | I:1 | P:2 | H:2 | E:2 | N:3 |  | E:3 |
| H:1 | W:1 | I:3 | L:1 | L:2 | Y:1 | T:1 | L:1 |  | T:2 |
|  | P:1 | P:1 |  | T:1 | I:1 | W:1 |  |  | D:1 |
|  |  |  |  |  | L:1 | H:1 |  |  |  |

FIG 6A

| Framework 1 | | | CDR1 | | | | | Framework 2 | |
|---|---|---|---|---|---|---|---|---|---|
| 31 | 32 | 33 | 34 | 35 | 36 | 37 | 38 | 39 | 40 |
| S | S | S | X | X | X | X | X | W | I |
| S:920 | S:613 | S:593 | | | | | | W:1419 | I:1335 |
| -:394 | F:463 | -:446 | | | | | | -:23 | V:80 |
| I:41 | -:259 | G:229 | | | | | | C:3 | -:15 |
| G:29 | I:21 | T:99 | | | | | | Y:1 | L:7 |
| N:21 | N:19 | R:20 | | | | | | X:1 | F:3 |
| T:18 | T:18 | N:18 | | | | | | | S:2 |
| R:12 | L:15 | D:14 | | | | | | | X:2 |
| D:3 | R:13 | I:9 | | | | | | | T:1 |
| A:2 | G:10 | V:6 | | | | | | | N:1 |
| P:2 | D:5 | A:4 | | | | | | | M:1 |
| V:2 | V:3 | Y:4 | | | | | | | |
| F:1 | K:2 | F:1 | | | | | | | |
| Y:1 | Y:2 | W:1 | | | | | | | |
| C:1 | Q:2 | K:1 | | | | | | | |
| | A:1 | E:1 | | | | | | | |
| | P:1 | C:1 | | | | | | | |

| Framework 2 | | | | | | | | | |
|---|---|---|---|---|---|---|---|---|---|
| 41 | 42 | 43 | 44 | 45 | 46 | 47 | 48 | 49 | 50 |
| R | Q | P | P | G | K | G | L | E | W |
| R:1431 | Q:1422 | P:1245 | P:1322 | G:1415 | K:1380 | G:1420 | L:1435 | E:1420 | W:1429 |
| -:11 | -:7 | H:107 | A:109 | E:8 | R:35 | A:11 | P:9 | D:8 | C:7 |
| P:2 | R:5 | S:41 | S:7 | -:7 | E:19 | R:10 | V:2 | K:7 | Y:4 |
| Q:1 | H:4 | A:20 | -:7 | R:7 | Q:4 | E:2 | X:1 | Q:7 | X:2 |
| L:1 | L:3 | T:11 | T:1 | A:3 | T:2 | D:2 | | X:2 | F:1 |
| H:1 | K:2 | -:6 | L:1 | K:2 | -:2 | S:1 | | T:1 | L:1 |
| | S:1 | F:5 | | H:2 | M:2 | N:1 | | N:1 | H:1 |
| | T:1 | Y:3 | | V:1 | S:1 | | | A:1 | R:1 |
| | E:1 | L:3 | | W:1 | A:1 | | | | G:1 |
| | P:1 | R:3 | | X:1 | G:1 | | | | |
| | | N:1 | | | | | | | |
| | | V:1 | | | | | | | |
| | | Q:1 | | | | | | | |

FIG 6B

| 51 | 52 | 53 | 54 | 55 | 56 | 57 | 58 | 59 | 60 |
|---|---|---|---|---|---|---|---|---|---|
| I | G | X | X | X | X | X | X | X | X |

I:1418  G:1416
V:12    A:29
L:6     -:1
T:3     X:1
M:3
S:2
X:2
F:1

| 61 | 62 | 63 | 64 | 65 | 66 | 67 | 68 | 69 | 70 |
|---|---|---|---|---|---|---|---|---|---|
| X | X | X | X | X | X | X | X | R | V |

R:1427  V:1364
Q:8     L:40
L:4     I:21
P:3     A:18
G:2     F:2
A:1     X:1
X:1     D:1
H:1

| 71 | 72 | 73 | 74 | 75 | 76 | 77 | 78 | 79 | 80 |
|---|---|---|---|---|---|---|---|---|---|
| T | I | S | V | D | T | S | K | N | Q |

| T:1326 | I:1163 | S:1423 | V:1164 | D:1425 | T:1263 | S:1384 | K:1343 | N:1369 | Q:1364 |
| S:63   | M:191  | L:10   | I:130  | E:6    | K:55   | A:36   | N:56   | K:33   | H:46   |
| I:24   | T:45   | A:5    | L:78   | Y:4    | M:55   | T:14   | E:20   | S:26   | R:13   |
| A:14   | L:21   | Y:3    | A:39   | A:4    | A:35   | P:8    | R:12   | T:8    | E:7    |
| N:8    | V:16   | P:3    | K:9    | G:3    | R:26   | F:2    | T:5    | H:5    | L:6    |
| V:3    | F:7    | F:1    | M:8    | N:2    | S:4    | Y:1    | S:2    | D:3    | K:3    |
| F:2    | A:3    | T:1    | Q:5    | S:1    | P:3    | L:1    | -:2    | M:1    | S:2    |
| K:2    | K:1    | H:1    | G:5    | Q:1    | N:2    | W:1    | Q:2    | X:1    | A:2    |
| M:2    |        |        | E:3    | H:1    | F:1    |        | A:2    | R:1    | N:1    |
| L:2    |        |        | R:3    |        | E:1    |        | M:1    |        | Y:1    |
| X:1    |        |        | X:2    |        | V:1    |        | L:1    |        | M:1    |
|        |        |        | P:1    |        | L:1    |        | H:1    |        | P:1    |

| Framework 3 | | | | | | | | | |
|---|---|---|---|---|---|---|---|---|---|
| 81 | 82 | 83 | 84 | 85 | 86 | 87 | 88 | 89 | 90 |
| F | S | L | K | L | S | S | V | T | A |
| F:1395 | S:1432 | L:1439 | K:1120 | L:1375 | S:1088 | S:1412 | V:1352 | T:1387 | A:1410 |
| L:23 | F:6 | V:3 | R:142 | V:56 | T:184 | A:24 | M:48 | A:36 | V:13 |
| V:11 | Y:3 | Q:3 | N:81 | M:13 | N:81 | F:2 | L:40 | I:11 | P:8 |
| I:11 | A:3 | D:1 | M:34 | S:1 | R:56 | V:2 | A:4 | S:8 | T:5 |
| S:3 | T:1 | R:1 | V:15 | P:1 | I:11 | P:2 | I:2 | R:2 | D:4 |
| Y:3 | V:1 | | S:11 | G:1 | K:9 | G:2 | S:1 | N:1 | G:4 |
| P:1 | P:1 | | Q:11 | | D:6 | N:1 | | P:1 | S:1 |
| | | | T:7 | | G:5 | Y:1 | | D:1 | -:1 |
| | | | A:7 | | A:3 | D:1 | | | X:1 |
| | | | E:6 | | H:3 | | | | |
| | | | I:6 | | Y:1 | | | | |
| | | | Y:2 | | | | | | |
| | | | H:2 | | | | | | |
| | | | L:1 | | | | | | |
| | | | P:1 | | | | | | |
| | | | D:1 | | | | | | |

| Framework 3 | | | | | | | | | CDR3 |
|---|---|---|---|---|---|---|---|---|---|
| 91 | 92 | 93 | 94 | 95 | 96 | 97 | 98 | 99 | 100 |
| A | D | T | A | V | Y | Y | C | A | X |
| A:1422 | D:1426 | T:1434 | A:1425 | V:1286 | Y:1434 | Y:1316 | C:1444 | A:1343 | |
| V:9 | E:10 | A:9 | G:7 | I:34 | F:7 | F:111 | -:1 | V:71 | |
| T:7 | N:6 | S:2 | V:6 | M:29 | C:2 | S:5 | A:1 | T:9 | |
| S:3 | Y:2 | M:2 | S:3 | L:24 | H:2 | C:5 | G:1 | S:6 | |
| G:3 | A:1 | | X:2 | A:20 | D:2 | W:4 | | -:5 | |
| E:2 | X:1 | | D:2 | G:17 | | H:4 | | G:4 | |
| M:1 | G:1 | | T:1 | K:12 | | -:1 | | Q:2 | |
| | | | P:1 | E:10 | | L:1 | | R:2 | |
| | | | | R:5 | | | | E:1 | |
| | | | | T:3 | | | | M:1 | |
| | | | | S:2 | | | | L:1 | |
| | | | | F:1 | | | | X:1 | |
| | | | | W:1 | | | | D:1 | |
| | | | | X:1 | | | | | |
| | | | | H:1 | | | | | |
| | | | | D:1 | | | | | |

| CDR3 | | | | | | | | | |
|---|---|---|---|---|---|---|---|---|---|
| 101 | 102 | 103 | 104 | 105 | 106 | 107 | 108 | 109 | 110 |
| X | X | X | X | X | X | X | X | X | X |

| CDR3 | | | | | | | | | |
|---|---|---|---|---|---|---|---|---|---|
| 111 | 112 | 113 | 114 | 115 | 116 | 117 | 118 | 119 | 120 |
| X | X | X | X | X | X | X | X | X | X |

FIG 6D

| CDR3 | | | | | | | | | |
|---|---|---|---|---|---|---|---|---|---|
| 121 | 122 | 123 | 124 | 125 | 126 | 127 | 128 | 129 | 130 |
| X | X | X | X | X | X | X | X | X | X |

| CDR3 | | | Framework 4 | | | | | | |
|---|---|---|---|---|---|---|---|---|---|
| 131 | 132 | 133 | 134 | 135 | 136 | 137 | 138 | 139 | 140 |
| X | X | X | W | G | Q | G | T | L | V |
| | | | W:1178 | G:949 | Q:725 | G:804 | T:702 | -:618 | V:729 |
| | | | -:190 | -:416 | -:546 | -:565 | -:599 | L:425 | -:630 |
| | | | Y:22 | Y:15 | R:53 | A:13 | A:36 | T:186 | S:16 |
| | | | L:12 | D:12 | K:28 | D:8 | P:23 | M:127 | W:11 |
| | | | S:7 | S:9 | P:16 | Y:7 | G:21 | R:15 | G:9 |
| | | | G:7 | L:9 | Y:14 | M:7 | D:11 | V:13 | T:8 |
| | | | T:4 | W:7 | G:14 | S:6 | S:9 | P:13 | L:8 |
| | | | D:4 | A:5 | L:13 | P:5 | I:9 | W:12 | I:7 |
| | | | V:3 | X:5 | V:7 | E:4 | N:8 | Q:7 | D:6 |
| | | | X:3 | T:3 | H:7 | L:4 | L:6 | G:6 | H:5 |
| | | | R:3 | V:3 | T:6 | W:4 | V:5 | Y:5 | N:3 |
| | | | I:3 | P:3 | A:4 | R:4 | R:5 | D:5 | K:3 |
| | | | F:2 | R:3 | S:3 | F:3 | W:4 | A:4 | A:3 |
| | | | Q:2 | F:2 | W:3 | T:3 | H:4 | S:3 | R:3 |
| | | | M:2 | Q:2 | D:3 | K:3 | Y:2 | E:3 | F:2 |
| | | | K:1 | N:1 | Q:2 | Q:2 | M:2 | K:2 | P:2 |
| | | | E:1 | K:1 | F:2 | C:2 | F:1 | F:1 | Y:1 |
| | | | C:1 | M:1 | M:2 | N:1 | | N:1 | M:1 |
| | | | P:1 | H:1 | X:1 | V:1 | | C:1 | |
| | | | H:1 | | | I:1 | | | |

| Framework 4 | | | | | | | | | |
|---|---|---|---|---|---|---|---|---|---|
| 141 | 142 | 143 | 144 | 145 | 146 | 147 | 148 | 149 | 150 |
| T | V | S | S | A | P | T | K | A | P |
| T:725 | V:701 | S:689 | -:715 | -:1160 | -:1258 | -:1265 | -:1273 | -:1279 | -:1292 |
| -:640 | -:675 | -:685 | S:685 | A:148 | P:123 | T:140 | K:135 | A:136 | P:133 |
| P:23 | S:17 | D:14 | P:16 | G:100 | S:42 | A:17 | S:17 | G:15 | R:6 |
| V:12 | T:10 | T:12 | A:7 | S:9 | G:7 | P:8 | R:7 | L:5 | S:5 |
| G:9 | F:7 | V:12 | T:5 | W:8 | T:4 | S:5 | G:5 | S:4 | H:4 |
| S:7 | L:6 | F:8 | Q:5 | T:7 | V:4 | Q:5 | F:2 | T:2 | L:2 |
| W:7 | P:5 | L:7 | L:4 | H:4 | H:4 | L:2 | V:2 | P:2 | I:2 |
| A:6 | G:5 | P:4 | V:3 | V:3 | W:2 | H:2 | Q:2 | F:1 | F:1 |
| I:4 | A:4 | R:4 | I:2 | L:3 | E:1 | R:2 | T:1 | N:1 | T:1 |
| Q:3 | R:4 | G:4 | G:2 | P:2 | C:1 | V:1 | E:1 | V:1 | D:1 |
| H:3 | Q:3 | C:3 | Y:1 | N:1 | A:1 | | A:1 | Q:1 | |
| R:3 | W:3 | A:2 | M:1 | Y:1 | | | P:1 | | |
| L:2 | D:2 | W:2 | D:1 | X:1 | | | | | |
| E:1 | I:2 | Q:1 | | | | | | | |
| X:1 | N:1 | | | | | | | | |
| D:1 | Y:1 | | | | | | | | |
| | M:1 | | | | | | | | |

FIG 6E

| | | | Framework 4 | | | | | |
|---|---|---|---|---|---|---|---|---|
| 151 | 152 | 153 | 154 | 155 | 156 | 157 | 158 | 159 |
| D | V | F | P | I | I | S | G | C |
| -:1306 | -:1370 | -:1378 | -:1380 | -:1383 | -:1384 | -:1388 | -:1397 | -:1415 |
| D:108 | V:63 | F:61 | P:61 | I:56 | I:54 | S:55 | G:42 | C:25 |
| S:10 | L:5 | L:3 | S:2 | S:2 | G:5 | T:1 | R:6 | V:5 |
| T:8 | G:3 | T:1 | A:2 | N:2 | M:2 | E:1 | N:1 | S:1 |
| V:3 | T:2 | V:1 | T:1 | L:1 | T:1 | L:1 | H:1 | R:1 |
| M:2 | D:2 | P:1 | V:1 | W:1 | C:1 | A:1 | | |
| R:2 | Q:1 | I:1 | | P:1 | | | | |
| I:2 | P:1 | G:1 | | R:1 | | | | |
| G:2 | | | | | | | | |
| F:1 | | | | | | | | |
| Q:1 | | | | | | | | |
| A:1 | | | | | | | | |
| H:1 | | | | | | | | |

FIG 6F

| | | | | Framework 1 | | | | | |
|---|---|---|---|---|---|---|---|---|---|
| 1 | 2 | 3 | 4 | 5 | 6 | 7 | 8 | 9 | 10 |
| E | E | V | Q | L | V | Q | S | G | A |
| -:391 | E:218 | V:239 | Q:245 | L:253 | V:249 | Q:249 | S:275 | G:275 | A:267 |
| E:3 | -:156 | -:145 | -:141 | -:139 | -:120 | -:119 | -:116 | -:111 | -:106 |
| Q:1 | Q:9 | K:2 | L:5 | W:1 | E:13 | E:21 | P:2 | A:8 | V:6 |
| | V:5 | E:2 | H:2 | P:1 | L:8 | H:2 | A:1 | R:1 | T:5 |
| | K:3 | Q:2 | S:1 | V:1 | Q:2 | L:2 | C:1 | | E:5 |
| | A:1 | M:2 | P:1 | | A:1 | A:1 | | | G:4 |
| | X:1 | D:1 | | | W:1 | R:1 | | | P:2 |
| | D:1 | I:1 | | | G:1 | | | | |
| | G:1 | L:1 | | | | | | | |

| | | | | Framework 1 | | | | | |
|---|---|---|---|---|---|---|---|---|---|
| 11 | 12 | 13 | 14 | 15 | 16 | 17 | 18 | 19 | 20 |
| E | V | K | K | P | G | E | S | L | K |
| E:290 | V:286 | K:317 | K:330 | P:331 | G:343 | E:331 | S:349 | L:353 | K:232 |
| -:79 | -:73 | -:56 | -:56 | -:50 | -:50 | -:50 | -:43 | -:41 | R:117 |
| V:23 | D:23 | R:19 | R:5 | A:6 | R:2 | D:8 | F:2 | M:1 | -:39 |
| D:2 | L:4 | Q:3 | E:3 | S:5 | | Q:3 | C:1 | | T:2 |
| K:1 | A:3 | | N:1 | T:2 | | A:1 | | | Q:2 |
| | M:3 | | | L:1 | | K:1 | | | N:1 |
| | R:3 | | | | | G:1 | | | M:1 |
| | | | | | | | | | I:1 |

| | | | | Framework 1 | | | | | |
|---|---|---|---|---|---|---|---|---|---|
| 21 | 22 | 23 | 24 | 25 | 26 | 27 | 28 | 29 | 30 |
| I | S | C | K | G | S | G | Y | S | F |
| I:357 | S:367 | C:369 | K:323 | G:314 | S:350 | G:366 | Y:358 | S:300 | F:372 |
| -:32 | -:26 | -:25 | -:24 | A:25 | -:22 | -:22 | -:17 | R:34 | -:10 |
| T:2 | T:2 | V:1 | Q:21 | -:23 | P:8 | E:3 | F:9 | T:16 | L:6 |
| L:2 | | | E:9 | T:19 | F:7 | A:1 | D:5 | N:13 | I:3 |
| V:1 | | | T:6 | S:5 | A:4 | T:1 | H:3 | -:10 | S:2 |
| M:1 | | | R:5 | D:4 | T:2 | X:1 | N:2 | I:7 | Y:1 |
| | | | M:3 | V:2 | Y:1 | R:1 | C:1 | G:5 | V:1 |
| | | | H:2 | I:2 | L:1 | | | Y:3 | |
| | | | A:1 | E:1 | | | | D:3 | |
| | | | N:1 | | | | | C:2 | |
| | | | | | | | | A:1 | |
| | | | | | | | | K:1 | |

FIG 7A

|  | CDR1 |  |  |  |  | Framework 2 |  |  |  |
|---|---|---|---|---|---|---|---|---|---|
| 31 | 32 | 33 | 34 | 35 | 36 | 37 | 38 | 39 | 40 |
| T | X | X | X | X | X | W | V | R | Q |
| T:318 |  |  |  |  |  | W:395 | V:382 | R:392 | Q:393 |
| S:25 |  |  |  |  |  |  | L:7 | H:2 | X:1 |
| A:13 |  |  |  |  |  |  | A:4 | P:1 | L:1 |
| -:9 |  |  |  |  |  |  |  | M:1 |  |
| N:8 |  |  |  |  |  |  | I:1 |  |  |
| I:8 |  |  |  |  |  |  |  |  |  |
| P:5 |  |  |  |  |  |  |  |  |  |
| V:2 |  |  |  |  |  |  |  |  |  |
| R:2 |  |  |  |  |  |  |  |  |  |
| G:2 |  |  |  |  |  |  |  |  |  |
| K:1 |  |  |  |  |  |  |  |  |  |
| M:1 |  |  |  |  |  |  |  |  |  |
| D:1 |  |  |  |  |  |  |  |  |  |

| Framework 2 | | | | | | | | | |
|---|---|---|---|---|---|---|---|---|---|
| 41 | 42 | 43 | 44 | 45 | 46 | 47 | 48 | 49 | 50 |
| M | P | G | K | G | L | E | W | M | G |
| M:366 | P:389 | G:389 | K:382 | G:388 | L:392 | E:395 | W:383 | M:379 | G:387 |
| V:8 | S:3 | R:3 | E:7 | S:2 | P:2 |  | Y:4 | V:7 | A:4 |
| K:6 | A:2 | E:2 | R:4 | E:2 | Q:1 |  | C:3 | L:5 | R:3 |
| T:5 | T:1 | D:1 | T:2 | D:2 |  |  | F:2 | I:4 | V:1 |
| L:5 |  |  |  | A:1 |  |  | L:2 |  |  |
| I:3 |  |  |  |  |  |  | S:1 |  |  |
| S:1 |  |  |  |  |  |  |  |  |  |
| R:1 |  |  |  |  |  |  |  |  |  |

| CDR2 | | | | | | | | | |
|---|---|---|---|---|---|---|---|---|---|
| 51 | 52 | 53 | 54 | 55 | 56 | 57 | 58 | 59 | 60 |
| X | X | X | X | X | X | X | X | X | X |

| CDR2 |  |  |  |  |  |  | Framework 3 |  |  |
|---|---|---|---|---|---|---|---|---|---|
| 61 | 62 | 63 | 64 | 65 | 66 | 67 | 68 | 69 | 70 |
| X | X | X | X | X | X | X | Q | V | T |
|  |  |  |  |  |  |  | Q:302 | V:387 | T:355 |
|  |  |  |  |  |  |  | H:88 | I:4 | I:20 |
|  |  |  |  |  |  |  | R:4 | A:1 | S:15 |
|  |  |  |  |  |  |  | L:1 | F:1 | F:2 |
|  |  |  |  |  |  |  |  | G:1 | A:1 |
|  |  |  |  |  |  |  |  | L:1 | N:1 |
|  |  |  |  |  |  |  |  |  | Z:1 |

FIG 7B

| Framework 3 | | | | | | | | | |
|---|---|---|---|---|---|---|---|---|---|
| 71 | 72 | 73 | 74 | 75 | 76 | 77 | 78 | 79 | 80 |
| I | S | A | D | K | S | I | S | T | A |
| I:371 | S:390 | A:355 | D:392 | K:363 | S:388 | I:355 | S:295 | T:383 | A:383 |
| F:8 | L:4 | V:31 | A:1 | R:15 | F:3 | T:18 | N:62 | S:7 | T:4 |
| M:8 | P:1 | T:6 | E:1 | E:5 | P:2 | S:6 | T:24 | A:4 | V:4 |
| V:5 | | I:2 | G:1 | T:4 | A:1 | V:6 | G:6 | I:1 | S:3 |
| L:2 | | L:1 | | N:3 | C:1 | L:6 | R:5 | | P:1 |
| T:1 | | | | S:2 | | F:1 | K:1 | | |
| | | | | Q:1 | | N:1 | H:1 | | |
| | | | | M:1 | | M:1 | D:1 | | |
| | | | | I:1 | | G:1 | | | |

| Framework 3 | | | | | | | | | |
|---|---|---|---|---|---|---|---|---|---|
| 81 | 82 | 83 | 84 | 85 | 86 | 87 | 88 | 89 | 90 |
| Y | L | Q | W | S | S | L | K | A | S |
| Y:385 | L:388 | Q:368 | W:390 | S:354 | S:366 | L:391 | K:354 | A:388 | S:389 |
| F:5 | V:6 | K:12 | C:2 | N:16 | N:11 | V:3 | R:19 | T:2 | T:3 |
| H:2 | M:1 | R:7 | L:2 | T:10 | T:8 | K:1 | E:13 | P:2 | P:2 |
| D:2 | | H:6 | R:1 | G:6 | R:4 | | T:4 | D:2 | A:1 |
| C:1 | | E:2 | | R:4 | G:3 | | Q:4 | V:1 | |
| | | | | D:3 | Y:2 | | A:1 | | |
| | | | | X:1 | C:1 | | | | |
| | | | | Y:1 | | | | | |

| Framework 3 | | | | | | | | | CDR3 |
|---|---|---|---|---|---|---|---|---|---|
| 91 | 92 | 93 | 94 | 95 | 96 | 97 | 98 | 99 | 100 |
| D | T | A | M | Y | Y | C | A | R | X |
| D:393 | T:372 | A:387 | M:329 | Y:393 | Y:379 | C:381 | A:360 | R:320 | |
| N:1 | S:16 | G:8 | I:47 | F:1 | F:14 | -:12 | V:12 | S:26 | |
| V:1 | A:3 | | V:6 | C:1 | -:1 | R:2 | -:12 | -:17 | |
| | N:2 | | T:5 | | C:1 | | I:5 | K:8 | |
| | I:2 | | L:4 | | | | T:2 | T:6 | |
| | | | K:2 | | | | G:2 | G:6 | |
| | | | F:1 | | | | F:1 | I:5 | |
| | | | R:1 | | | | S:1 | A:2 | |
| | | | | | | | | N:2 | |
| | | | | | | | | Y:1 | |
| | | | | | | | | Q:1 | |
| | | | | | | | | C:1 | |

| CDR3 | | | | | | | | | |
|---|---|---|---|---|---|---|---|---|---|
| 101 | 102 | 103 | 104 | 105 | 106 | 107 | 108 | 109 | 110 |
| X | X | X | X | X | X | X | X | X | X |

| CDR3 | | | | | | | | | |
|---|---|---|---|---|---|---|---|---|---|
| 111 | 112 | 113 | 114 | 115 | 116 | 117 | 118 | 119 | 120 |
| X | X | X | X | X | X | X | X | X | X |

FIG 7C

| CDR3 | | Framework 4 | | | | | | | |
|---|---|---|---|---|---|---|---|---|---|
| 121 | 122 | 123 | 124 | 125 | 126 | 127 | 128 | 129 | 130 |
| X | X | W | G | Q | G | T | L | V | T |
| | | W:295 | G:257 | Q:199 | G:238 | T:204 | -:171 | V:192 | T:185 |
| | | -:93 | -:127 | -:142 | -:144 | -:165 | L:135 | -:172 | -:178 |
| | | Y:3 | S:3 | R:29 | A:4 | P:18 | T:35 | S:16 | P:15 |
| | | N:1 | Y:2 | K:14 | D:2 | A:2 | M:26 | L:9 | I:11 |
| | | L:1 | A:2 | P:5 | S:1 | I:2 | W:9 | H:2 | R:2 |
| | | D:1 | D:2 | T:1 | T:1 | S:1 | R:9 | I:2 | S:1 |
| | | R:1 | L:1 | E:1 | E:1 | K:1 | V:3 | T:1 | Y:1 |
| | | | P:1 | M:1 | C:1 | V:1 | A:2 | D:1 | V:1 |
| | | | | X:1 | X:1 | R:1 | F:1 | | L:1 |
| | | | | D:1 | P:1 | | K:1 | | |
| | | | | G:1 | H:1 | | C:1 | | |
| | | | | | | | P:1 | | |
| | | | | | | | G:1 | | |

| Framework 4 | | | | | | | | | |
|---|---|---|---|---|---|---|---|---|---|
| 131 | 132 | 133 | 134 | 135 | 136 | 137 | 138 | 139 | 140 |
| V | S | S | A | S | T | K | A | P | S |
| V:192 | -:190 | -:215 | -:350 | -:361 | -:365 | -:367 | -:367 | -:367 | -:372 |
| -:183 | S:175 | S:177 | A:23 | S:32 | T:14 | K:12 | A:12 | P:22 | S:8 |
| S:15 | T:15 | Q:1 | G:22 | T:1 | A:8 | S:8 | G:8 | H:4 | T:8 |
| R:2 | D:8 | L:1 | | P:1 | P:7 | T:6 | S:6 | V:1 | K:6 |
| W:1 | C:4 | A:1 | | | L:1 | V:1 | P:2 | I:1 | R:1 |
| D:1 | P:2 | | | | | R:1 | | | |
| I:1 | G:1 | | | | | | | | |

| Framework 4 | | | | | | | | | |
|---|---|---|---|---|---|---|---|---|---|
| 141 | 142 | 143 | 144 | 145 | 146 | 147 | 148 | 149 | 150 |
| V | F | P | L | V | S | C | E | N | S |
| -:375 | -:376 | -:377 | -:377 | -:377 | -:378 | -:383 | -:383 | -:383 | -:383 |
| V:10 | F:18 | P:17 | L:17 | V:8 | S:8 | C:8 | E:8 | N:8 | S:11 |
| L:9 | G:1 | S:1 | F:1 | S:6 | L:6 | S:3 | S:4 | K:3 | P:1 |
| S:1 | | | | A:3 | P:3 | D:1 | | T:1 | |
| | | | | W:1 | | | | | |

| Framework 4 | | | | | | | | | |
|---|---|---|---|---|---|---|---|---|---|
| 151 | 152 | 153 | 154 | 155 | 156 | 157 | 158 | 159 | 160 |
| P | S | D | T | S | S | V | A | V | G |
| -:383 | -:383 | -:383 | -:383 | -:383 | -:383 | -:383 | -:383 | -:384 | -:384 |
| P:8 | S:11 | D:8 | T:8 | S:8 | S:8 | V:9 | A:9 | V:8 | G:8 |
| T:3 | D:1 | G:4 | G:3 | T:3 | A:3 | A:3 | L:3 | G:3 | C:3 |
| Q:1 | | | N:1 | V:1 | V:1 | | | | |

FIG 7D

| | | | | Framework 4 | | | | | |
|---|---|---|---|---|---|---|---|---|---|
| 161 | 162 | 163 | 164 | 165 | 166 | 167 | 168 | 169 | 170 |
| C | L | A | Q | D | F | L | P | D | S |
| -:384 | -:384 | -:384 | -:384 | -:384 | -:384 | -:384 | -:387 | -:387 | -:387 |
| C:8 | L:8 | A:8 | Q:8 | D:8 | F:11 | L:8 | P:8 | D:8 | S:8 |
| L:3 | V:3 | K:3 | D:3 | Y:3 | | | P:3 | | |

| | | | Framework 4 |
|---|---|---|---|
| 171 | 172 | 173 | 174 |
| I | T | F | S |
| -:387 | -:387 | -:387 | -:387 |
| I:8 | T:8 | F:8 | S:8 |

FIG 7E

| | | | | Framework 1 | | | | | |
|---|---|---|---|---|---|---|---|---|---|
| 1 | 2 | 3 | 4 | 5 | 6 | 7 | 8 | 9 | 10 |
| Q | V | Q | L | Q | Q | S | G | P | G |
| -:143 | -:143 | -:139 | -:138 | -:138 | -:138 | -:136 | -:135 | P:166 | G:167 |
| Q:119 | V:120 | Q:118 | L:124 | Q:120 | Q:117 | S:125 | G:126 | -:94 | -:92 |
| R:1 | | K:4 | V:1 | L:4 | E:6 | P:1 | Q:1 | A:1 | R:2 |
| | | H:1 | | R:1 | L:2 | Q:1 | S:1 | S:1 | P:1 |
| | | L:1 | | | | | | L:1 | E:1 |

| | | | | Framework 1 | | | | | |
|---|---|---|---|---|---|---|---|---|---|
| 11 | 12 | 13 | 14 | 15 | 16 | 17 | 18 | 19 | 20 |
| L | V | K | P | S | Q | T | L | S | L |
| L:174 | V:171 | K:168 | P:208 | S:209 | Q:211 | T:211 | L:211 | S:211 | L:217 |
| -:125 | -:124 | -:123 | -:89 | -:88 | -:88 | -:84 | -:81 | -:85 | -:77 |
| G:1 | L:3 | E:3 | S:1 | P:2 | L:1 | S:4 | T:4 | P:2 | S:5 |
| | A:2 | Q:2 | E:1 | D:1 | | N:1 | V:2 | G:1 | V:1 |
| | | T:2 | V:1 | | | | F:1 | L:1 | |
| | | R:1 | | | | | E:1 | | |
| | | V:1 | | | | | | | |

| | | | | Framework 1 | | | | | |
|---|---|---|---|---|---|---|---|---|---|
| 21 | 22 | 23 | 24 | 25 | 26 | 27 | 28 | 29 | 30 |
| T | C | A | I | S | G | D | S | V | S |
| T:220 | C:278 | A:270 | I:270 | S:284 | G:287 | D:284 | S:278 | V:293 | S:292 |
| -:74 | -:16 | -:17 | -:14 | -:13 | -:13 | -:14 | -:15 | -:5 | F:4 |
| A:3 | W:2 | V:7 | V:11 | F:1 | | N:1 | T:4 | A:1 | -:3 |
| S:1 | Q:1 | G:3 | S:1 | T:1 | | G:1 | D:3 | L:1 | Y:1 |
| D:1 | T:1 | C:2 | H:1 | P:1 | | | | | |
| L:1 | G:1 | T:1 | T:1 | | | | | | |
| | L:1 | | N:1 | | | | | | |
| | | | L:1 | | | | | | |

| CDR1 | | | | | | | Framework 2 | | |
|---|---|---|---|---|---|---|---|---|---|
| 31 | 32 | 33 | 34 | 35 | 36 | 37 | 38 | 39 | 40 |
| X | X | X | X | X | X | X | W | I | R |
| | | | | | | | W:298 | I:287 | R:296 |
| | | | | | | | C:2 | V:8 | G:3 |
| | | | | | | | | F:2 | -:1 |
| | | | | | | | | Y:2 | |
| | | | | | | | | L:1 | |

FIG 8A

| Framework 2 | | | | | | | | | |
|---|---|---|---|---|---|---|---|---|---|
| 41 | 42 | 43 | 44 | 45 | 46 | 47 | 48 | 49 | 50 |
| Q | S | P | S | R | G | L | E | W | L |
| Q:291 | S:299 | P:299 | S:290 | R:297 | G:295 | L:297 | E:300 | W:298 | L:298 |
| L:4 | V:1 | S:1 | W:6 | G:2 | -:3 | P:3 | | S:1 | W:1 |
| S:1 | | | A:2 | K:1 | S:1 | | | -:1 | E:1 |
| P:1 | | | P:2 | | D:1 | | | | |
| K:1 | | | | | | | | | |
| E:1 | | | | | | | | | |
| R:1 | | | | | | | | | |

| | CDR2 | | | | | | | | |
|---|---|---|---|---|---|---|---|---|---|
| 51 | 52 | 53 | 54 | 55 | 56 | 57 | 58 | 59 | 60 |
| G | X | X | X | X | X | X | X | X | X |
| G:299 | | | | | | | | | |
| E:1 | | | | | | | | | |

| CDR2 | | | | | | | | | |
|---|---|---|---|---|---|---|---|---|---|
| 61 | 62 | 63 | 64 | 65 | 66 | 67 | 68 | 69 | 70 |
| X | X | X | X | X | X | X | X | X | R |
| | | | | | | | | | R:299 |
| | | | | | | | | | Q:1 |

| Framework 3 | | | | | | | | | |
|---|---|---|---|---|---|---|---|---|---|
| 71 | 72 | 73 | 74 | 75 | 76 | 77 | 78 | 79 | 80 |
| I | T | I | N | P | D | T | S | K | N |
| I:287 | T:277 | I:293 | N:269 | P:275 | D:298 | T:294 | S:293 | K:280 | N:298 |
| V:6 | S:6 | V:4 | Y:8 | A:11 | G:2 | I:2 | P:3 | E:8 | T:1 |
| L:6 | I:6 | T:2 | D:7 | S:8 | | A:1 | A:2 | M:4 | D:1 |
| M:1 | A:4 | F:1 | S:5 | L:3 | | S:1 | T:2 | T:3 | |
| | N:4 | | K:5 | T:1 | | K:1 | | N:2 | |
| | V:2 | | I:3 | V:1 | | L:1 | | R:2 | |
| | L:1 | | -:2 | Q:1 | | | | G:1 | |
| | | | R:1 | | | | | | |

| Framework 3 | | | | | | | | | |
|---|---|---|---|---|---|---|---|---|---|
| 81 | 82 | 83 | 84 | 85 | 86 | 87 | 88 | 89 | 90 |
| Q | F | S | L | Q | L | N | S | V | T |
| Q:290 | F:288 | S:299 | L:295 | Q:285 | L:295 | N:264 | S:298 | V:291 | T:293 |
| H:6 | V:4 | T:1 | P:4 | H:7 | V:2 | S:14 | F:2 | M:8 | I:3 |
| L:2 | I:4 | | M:1 | R:4 | M:2 | K:11 | | L:1 | S:2 |
| E:1 | L:4 | | | L:2 | P:1 | D:5 | | | N:1 |
| R:1 | | | | E:1 | | T:3 | | | V:1 |
| | | | | D:1 | | H:1 | | | |
| | | | | | | Q:1 | | | |
| | | | | | | R:1 | | | |

FIG 8B

| | | | | Framework 3 | | | | | |
|---|---|---|---|---|---|---|---|---|---|
| 91 | 92 | 93 | 94 | 95 | 96 | 97 | 98 | 99 | 100 |
| P | E | D | T | A | V | Y | Y | C | A |
| P:292 | E:285 | D:299 | T:299 | A:296 | V:282 | Y:298 | Y:283 | C:299 | A:275 |
| S:3 | D:13 | G:1 | A:1 | G:3 | I:7 | T:1 | F:14 | R:1 | V:17 |
| L:2 | A:2 | | | -:1 | M:3 | X:1 | S:1 | | G:3 |
| A:1 | | | | | G:3 | | N:1 | | S:2 |
| -:1 | | | | | L:3 | | C:1 | | T:2 |
| H:1 | | | | | A:1 | | | | F:1 |
| | | | | | E:1 | | | | |

| | CDR3 | | | | | | | | |
|---|---|---|---|---|---|---|---|---|---|
| 101 | 102 | 103 | 104 | 105 | 106 | 107 | 108 | 109 | 110 |
| R | X | X | X | X | X | X | X | X | X |
| R:266 | | | | | | | | | |
| -:16 | | | | | | | | | |
| K:7 | | | | | | | | | |
| S:6 | | | | | | | | | |
| G:4 | | | | | | | | | |
| T:1 | | | | | | | | | |

| CDR3 | | | | | | | | | |
|---|---|---|---|---|---|---|---|---|---|
| 111 | 112 | 113 | 114 | 115 | 116 | 117 | 118 | 119 | 120 |
| X | X | X | X | X | X | X | X | X | X |

| CDR3 | | | Framework 4 | | | | | | |
|---|---|---|---|---|---|---|---|---|---|
| 121 | 122 | 123 | 124 | 125 | 126 | 127 | 128 | 129 | 130 |
| X | X | X | W | G | Q | G | T | L | V |
| | | | W:250 | G:235 | Q:196 | G:216 | T:161 | L:112 | V:202 |
| | | | -:42 | -:57 | -:74 | -:74 | -:76 | -:80 | -:82 |
| | | | R:4 | D:4 | P:8 | E:2 | I:48 | T:60 | S:6 |
| | | | S:1 | S:1 | R:8 | A:2 | P:5 | M:25 | D:4 |
| | | | F:1 | T:1 | K:5 | W:2 | S:3 | W:10 | R:2 |
| | | | K:1 | Q:1 | T:2 | D:2 | W:2 | R:3 | A:1 |
| | | | V:1 | A:1 | X:2 | S:1 | H:2 | F:2 | P:1 |
| | | | | | S:1 | V:1 | N:1 | V:2 | I:1 |
| | | | | | Y:1 | | Q:1 | A:2 | G:1 |
| | | | | | E:1 | | A:1 | S:1 | |
| | | | | | M:1 | | | K:1 | |
| | | | | | H:1 | | | P:1 | |
| | | | | | | | | H:1 | |

FIG 8C

| | | | | Framework 4 | | | | | |
|---|---|---|---|---|---|---|---|---|---|
| 131 | 132 | 133 | 134 | 135 | 136 | 137 | 138 | 139 | 140 |
| T | V | S | S | G | S | A | S | A | P |
| T:141 | V:147 | -:145 | -:156 | -:255 | -:266 | -:266 | -:266 | -:266 | -:266 |
| -:139 | -:142 | S:136 | S:139 | G:31 | S:33 | A:22 | S:21 | A:21 | P:33 |
| I:9 | S:6 | C:6 | T:1 | A:9 | T:1 | T:7 | K:8 | G:8 | V:1 |
| P:4 | R:2 | P:3 | Q:1 | T:3 | | P:4 | T:4 | S:4 | |
| V:3 | W:1 | D:3 | L:1 | R:2 | | L:1 | V:1 | T:1 | |
| S:2 | P:1 | F:2 | P:1 | | | | | | |
| H:1 | D:1 | T:2 | R:1 | | | | | | |
| R:1 | | Q:1 | | | | | | | |
| | | L:1 | | | | | | | |
| | | G:1 | | | | | | | |

| | | | | Framework 4 | | | | | |
|---|---|---|---|---|---|---|---|---|---|
| 141 | 142 | 143 | 144 | 145 | 146 | 147 | 148 | 149 | 150 |
| T | L | F | P | L | V | S | C | E | N |
| -:266 | -:266 | -:267 | -:271 | -:271 | -:271 | -:271 | -:271 | -:271 | -:271 |
| T:21 | L:21 | F:33 | P:28 | L:29 | V:21 | S:21 | C:27 | E:21 | N:21 |
| S:9 | V:12 | | L:1 | | A:8 | P:8 | S:2 | S:8 | R:6 |
| K:4 | S:1 | | | | | | | | K:2 |

| | | | | Framework 4 | | | | | |
|---|---|---|---|---|---|---|---|---|---|
| 151 | 152 | 153 | 154 | 155 | 156 | 157 | 158 | 159 | 160 |
| S | P | S | D | T | S | S | V | A | V |
| -:271 | -:271 | -:271 | -:271 | -:271 | -:279 | -:271 | -:271 | -:271 | -:271 |
| S:29 | P:21 | S:29 | D:21 | T:21 | S:21 | S:21 | V:21 | A:29 | V:21 |
| | T:8 | | E:5 | S:5 | | T:8 | A:8 | | L:8 |
| | | | G:3 | G:3 | | | | | |

| | | | | Framework 4 | | | | |
|---|---|---|---|---|---|---|---|---|
| 161 | 162 | 163 | 164 | 165 | 166 | 167 | 168 | 169 |
| G | C | L | A | Q | D | F | L | P |
| -:271 | -:271 | -:271 | -:271 | -:271 | -:271 | -:271 | -:271 | -:292 |
| G:29 | C:29 | L:29 | A:21 | Q:21 | D:29 | F:21 | L:21 | P:8 |
| | | | V:8 | K:8 | | Y:8 | F:8 | |

FIG 8D

|  | | | | | Framework 1 | | | | |
|---|---|---|---|---|---|---|---|---|---|
| 1 | 2 | 3 | 4 | 5 | 6 | 7 | 8 | 9 | 10 |
| Q | V | Q | L | V | Q | S | G | S | E |
| Q:22 | V:23 | Q:21 | L:23 | V:21 | Q:23 | S:23 | G:24 | S:20 | E:24 |
| -:4 | -:4 | -:4 | -:4 | -:4 | -:4 | -:4 | -:3 | H:3 | -:3 |
| E:1 | | H:2 | | Q:1 | | | | -:3 | |
| | | | | M:1 | | | | A:1 | |

|  | | | | | Framework 1 | | | | |
|---|---|---|---|---|---|---|---|---|---|
| 11 | 12 | 13 | 14 | 15 | 16 | 17 | 18 | 19 | 20 |
| L | K | K | P | G | A | S | V | K | V |
| L:20 | K:25 | K:22 | P:25 | G:27 | A:27 | S:27 | V:27 | K:26 | V:23 |
| V:4 | -:2 | Q:3 | A:1 | | | | | R:1 | I:4 |
| -:2 | | -:2 | -:1 | | | | | | |
| F:1 | | | | | | | | | |

|  | | | | | Framework 1 | | | | |
|---|---|---|---|---|---|---|---|---|---|
| 21 | 22 | 23 | 24 | 25 | 26 | 27 | 28 | 29 | 30 |
| S | C | K | A | S | G | Y | T | F | T |
| S:27 | C:25 | K:27 | A:27 | S:27 | G:27 | Y:27 | T:21 | F:26 | T:25 |
| | R:2 | | | | | | S:5 | L:1 | S:2 |
| | | | | | | | N:1 | | |

| | CDR1 | | | | | Framework 2 | | | |
|---|---|---|---|---|---|---|---|---|---|
| 31 | 32 | 33 | 34 | 35 | 36 | 37 | 38 | 39 | 40 |
| X | X | X | X | X | W | V | R | Q | A |
| | | | | | W:27 | V:27 | R:24 | Q:27 | A:27 |
| | | | | | | | P:3 | | |

| | | | | Framework 2 | | | | | CDR |
|---|---|---|---|---|---|---|---|---|---|
| 41 | 42 | 43 | 44 | 45 | 46 | 47 | 48 | 49 | 50 |
| P | G | Q | G | L | E | W | M | G | X |
| P:27 | G:27 | Q:27 | G:27 | L:27 | E:26 | W:27 | M:27 | G:27 | |
| | | | | | Q:1 | | | | |

| | | | | CDR2 | | | | | |
|---|---|---|---|---|---|---|---|---|---|
| 51 | 52 | 53 | 54 | 55 | 56 | 57 | 58 | 59 | 60 |
| X | X | X | X | X | X | X | X | X | X |

FIG 9A

| CDR2 | | | | | | Framework 3 | | | |
|---|---|---|---|---|---|---|---|---|---|
| 61 | 62 | 63 | 64 | 65 | 66 | 67 | 68 | 69 | 70 |
| X | X | X | X | X | X | R | F | V | F |
| | | | | | | R:27 | F:26<br>L:1 | V:27 | F:26<br>L:1 |

| Framework 3 | | | | | | | | | |
|---|---|---|---|---|---|---|---|---|---|
| 71 | 72 | 73 | 74 | 75 | 76 | 77 | 78 | 79 | 80 |
| S | L | D | T | S | V | S | T | A | Y |
| S:26<br>A:1 | L:24<br>M:3 | D:27 | T:26<br>S:1 | S:27 | V:24<br>A:3 | S:24<br>T:2<br>N:1 | T:27 | A:24<br>T:2<br>S:1 | Y:27 |

| Framework 3 | | | | | | | | | |
|---|---|---|---|---|---|---|---|---|---|
| 81 | 82 | 83 | 84 | 85 | 86 | 87 | 88 | 89 | 90 |
| L | Q | I | S | S | L | K | A | E | D |
| L:26<br>V:1 | Q:25<br>E:1<br>Y:1 | I:27 | S:23<br>N:2<br>T:1<br>C:1 | S:26<br>T:1 | L:27 | K:25<br>T:1<br>E:1 | A:26<br>T:1 | E:22<br>D:3<br>A:2 | D:26<br>-:1 |

| Framework 3 | | | | | | | | CDR3 | |
|---|---|---|---|---|---|---|---|---|---|
| 91 | 92 | 93 | 94 | 95 | 96 | 97 | 98 | 99 | 100 |
| T | A | V | Y | Y | C | A | R | X | X |
| T:24<br>M:2<br>-:1 | A:25<br>-:1<br>G:1 | V:21<br>M:3<br>-:1<br>I:1<br>L:1 | Y:26<br>-:1 | Y:23<br>F:3<br>-:1 | C:26<br>-:1 | A:26<br>-:1 | R:21<br>-:3<br>K:2<br>S:1 | | |

| CDR3 | | | | | | | | | |
|---|---|---|---|---|---|---|---|---|---|
| 101 | 102 | 103 | 104 | 105 | 106 | 107 | 108 | 109 | 110 |
| X | X | X | X | X | X | X | X | X | X |

| | Framework 4 | | | | | | | | |
|---|---|---|---|---|---|---|---|---|---|
| 111 | 112 | 113 | 114 | 115 | 116 | 117 | 118 | 119 | 120 |
| X | W | G | Q | G | T | L | V | T | V |
| | W:11<br>-:11<br>R:2<br>Y:1<br>H:1<br>G:1 | -:11<br>G:10<br>S:1<br>F:1<br>T:1 | -:10<br>Q:10<br>G:2<br>A:1<br>W:1<br>P:1<br>Y:1<br>E:1<br>H:1 | -:10<br>G:10<br>R:2<br>S:1<br>F:1<br>P:1<br>M:1<br>L:1 | T:10<br>-:9<br>D:4<br>S:1<br>N:1<br>Y:1<br>I:1 | L:10<br>-:9<br>Y:3<br>W:2<br>T:1<br>R:1<br>V:1<br>I:1 | V:10<br>-:9<br>W:5<br>F:2<br>S:1<br>V:1 | -:10<br>T:9<br>G:5<br>D:2<br>I:1 | -:13<br>V:10<br>P:2<br>H:1<br>Q:1 |

FIG 9B

```
        ┌─────────────────────┐
        │ ··· Framework·4 ··· │
        └─────────────────────┘
         121       122       123
         S         S         S -:14      -:18      -:25
         S:10      S:8       S:1
         W:3       T:1       G:1
```

FIG 9C

| | | | | Framework 1 | | | | | |
|---|---|---|---|---|---|---|---|---|---|
| 1 | 2 | 3 | 4 | 5 | 6 | 7 | 8 | 9 | 10 |
| D | I | Q | M | T | Q | S | P | S | S |
| -:673 | -:657 | -:623 | -:602 | -:555 | -:541 | -:525 | P:578 | S:530 | S:558 |
| D:307 | I:336 | Q:250 | M:349 | T:487 | Q:500 | S:517 | -:463 | -:404 | -:342 |
| E:27 | A:27 | V:97 | L:84 | A:1 | H:2 | T:1 | A:1 | D:88 | T:83 |
| A:26 | L:21 | E:57 | V:4 | R:1 | K:1 | P:1 | H:1 | F:10 | F:39 |
| V:3 | V:2 | R:8 | I:4 | | | | Q:1 | P:6 | L:6 |
| M:3 | T:1 | L:4 | Q:1 | | | | | T:2 | P:4 |
| N:2 | | W:2 | | | | | | E:2 | I:4 |
| Y:1 | | K:1 | | | | | | A:1 | A:3 |
| B:1 | | Z:1 | | | | | | I:1 | N:3 |
| G:1 | | M:1 | | | | | | | Q:1 |
| | | | | | | | | | C:1 |

| | | | | Framework 1 | | | | | |
|---|---|---|---|---|---|---|---|---|---|
| 11 | 12 | 13 | 14 | 15 | 16 | 17 | 18 | 19 | 20 |
| L | S | A | S | V | G | D | R | R | V |
| L:697 | S:674 | A:677 | S:803 | V:673 | G:852 | D:770 | R:797 | -:909 | V:834 |
| -:293 | -:259 | -:250 | -:229 | -:213 | -:177 | -:248 | E:121 | R:125 | A:132 |
| V:41 | A:97 | V:109 | F:4 | L:109 | R:8 | N:7 | -:103 | V:9 | -:66 |
| F:8 | P:7 | L:3 | Y:2 | I:25 | A:4 | G:6 | T:11 | T:1 | I:9 |
| P:1 | T:2 | T:2 | C:2 | T:17 | S:1 | Y:5 | S:6 | | S:1 |
| Q:1 | Y:1 | H:1 | A:1 | A:3 | K:1 | E:3 | K:2 | | X:1 |
| M:1 | V:1 | C:1 | P:1 | P:1 | C:1 | A:2 | A:1 | | L:1 |
| C:1 | C:1 | D:1 | I:1 | E:1 | | V:2 | N:1 | | |
| G:1 | G:1 | | G:1 | C:1 | | R:1 | Q:1 | | |
| | L:1 | | | D:1 | | | D:1 | | |

| | | | | CDR1 | | | | | |
|---|---|---|---|---|---|---|---|---|---|
| 21 | 22 | 23 | 24 | 25 | 26 | 27 | 28 | 29 | 30 |
| T | I | T | C | X | X | X | X | X | X |
| T:970 | I:992 | T:869 | C:1035 | | | | | | |
| -:43 | -:28 | N:130 | -:6 | | | | | | |
| S:13 | V:7 | S:17 | X:1 | | | | | | |
| I:10 | F:6 | -:15 | R:1 | | | | | | |
| A:3 | M:4 | A:4 | L:1 | | | | | | |
| N:2 | L:4 | P:3 | | | | | | | |
| P:1 | T:1 | H:3 | | | | | | | |
| H:1 | N:1 | I:3 | | | | | | | |
| D:1 | H:1 | | | | | | | | |

| | | | | CDR1 | | | | | |
|---|---|---|---|---|---|---|---|---|---|
| 31 | 32 | 33 | 34 | 35 | 36 | 37 | 38 | 39 | 40 |
| X | X | X | X | X | X | X | X | X | X |

FIG 10A

| | Framework 2 | | | | | | | | |
|---|---|---|---|---|---|---|---|---|---|
| 41 | 42 | 43 | 44 | 45 | 46 | 47 | 48 | 49 | 50 |
| X | W | Y | Q | Q | K | P | G | K | A |
| | W:1043 | Y:973 | Q:1008 | Q:997 | K:995 | P:1017 | G:1022 | K:834 | A:819 |
| | -:1 | F:57 | R:22 | H:23 | R:25 | S:10 | E:11 | Q:146 | P:136 |
| | | -:4 | H:5 | R:7 | T:5 | A:6 | A:7 | E:13 | V:59 |
| | | H:3 | -:3 | K:5 | Q:5 | L:4 | R:2 | T:12 | T:11 |
| | | C:2 | K:2 | Y:2 | I:5 | V:3 | N:1 | R:12 | G:10 |
| | | L:2 | X:2 | -:2 | E:3 | R:2 | -:1 | N:9 | S:9 |
| | | N:1 | L:1 | L:2 | N:2 | T:1 | | S:8 | |
| | | Q:1 | D:1 | X:2 | S:1 | G:1 | | L:3 | |
| | | X:1 | | E:1 | -:1 | | | I:3 | |
| | | | | V:1 | L:1 | | | H:2 | |
| | | | | W:1 | H:1 | | | A:1 | |
| | | | | D:1 | | | | D:1 | |

| | Framework 2 | | | | | CDR2 | | | |
|---|---|---|---|---|---|---|---|---|---|
| 51 | 52 | 53 | 54 | 55 | 56 | 57 | 58 | 59 | 60 |
| P | K | L | L | I | Y | X | X | X | X |
| P:1039 | K:907 | L:887 | L:1028 | I:1013 | Y:964 | | | | |
| L:3 | N:54 | R:48 | F:7 | L:12 | S:34 | | | | |
| S:1 | R:31 | S:46 | R:5 | M:8 | F:25 | | | | |
| A:1 | E:24 | V:41 | V:3 | V:5 | H:11 | | | | |
| | Q:12 | F:12 | I:1 | F:3 | N:4 | | | | |
| | T:11 | H:4 | | T:1 | D:2 | | | | |
| | S:3 | I:3 | | A:1 | K:1 | | | | |
| | V:1 | E:1 | | X:1 | -:1 | | | | |
| | M:1 | C:1 | | | L:1 | | | | |
| | | P:1 | | | X:1 | | | | |

| CDR2 | | | Framework 3 | | | | | | |
|---|---|---|---|---|---|---|---|---|---|
| 61 | 62 | 63 | 64 | 65 | 66 | 67 | 68 | 69 | 70 |
| X | X | X | G | V | P | S | R | F | S |
| | | | G:1037 | V:1027 | P:1024 | S:883 | R:997 | F:1040 | S:1011 |
| | | | T:2 | I:7 | S:13 | D:140 | K:29 | L:2 | R:11 |
| | | | V:2 | A:5 | L:3 | P:8 | T:6 | V:1 | T:8 |
| | | | E:1 | D:2 | T:2 | L:6 | N:6 | I:1 | I:6 |
| | | | A:1 | F:1 | A:2 | A:5 | G:3 | | G:3 |
| | | | D:1 | C:1 | | W:1 | S:2 | | X:2 |
| | | | | G:1 | | I:1 | P:1 | | N:1 |
| | | | | | | | | | V:1 |
| | | | | | | | | | C:1 |

FIG 10B

| | | | | | Framework 3 | | | | |
|---|---|---|---|---|---|---|---|---|---|
| 71 | 72 | 73 | 74 | 75 | 76 | 77 | 78 | 79 | 80 |
| G | S | G | S | G | T | D | F | T | L |
| G:1029 | S:1005 | G:1021 | S:1022 | G:1029 | T:1017 | D:755 | F:1008 | T:1004 | L:909 |
| A:9 | G:16 | R:10 | F:8 | -:8 | A:19 | E:253 | Y:33 | S:13 | F:130 |
| D:6 | T:10 | E:7 | Y:7 | A:3 | S:3 | H:14 | S:1 | N:11 | V:2 |
| | R:9 | V:3 | C:2 | E:2 | R:3 | V:6 | V:1 | A:9 | H:2 |
| | N:1 | A:2 | A:2 | C:1 | P:1 | N:4 | H:1 | I:6 | R:1 |
| | A:1 | D:1 | L:1 | R:1 | I:1 | A:4 | | F:1 | |
| | X:1 | | P:1 | | | I:4 | | | |
| | D:1 | | R:1 | | | G:3 | | | |
| | | | | | | Y:1 | | | |

| | | | | | Framework 3 | | | | |
|---|---|---|---|---|---|---|---|---|---|
| 81 | 82 | 83 | 84 | 85 | 86 | 87 | 88 | 89 | 90 |
| T | I | S | S | L | Q | P | E | D | F |
| T:1029 | I:1034 | S:945 | S:938 | L:1039 | Q:1026 | P:848 | E:873 | D:1034 | F:708 |
| S:5 | V:5 | N:42 | C:30 | V:2 | E:5 | A:147 | D:159 | N:3 | V:203 |
| I:4 | M:3 | T:28 | N:28 | F:1 | R:5 | S:35 | -:5 | -:3 | I:104 |
| A:2 | T:1 | R:11 | G:28 | Q:1 | -:3 | -:5 | G:4 | X:1 | S:11 |
| Y:1 | L:1 | A:6 | R:9 | M:1 | X:2 | L:3 | K:1 | B:1 | L:11 |
| V:1 | | V:3 | T:5 | | Z:1 | T:2 | A:1 | I:1 | -:4 |
| B:1 | | D:3 | D:3 | | L:1 | F:1 | B:1 | G:1 | T:1 |
| R:1 | | Y:2 | K:1 | | H:1 | X:1 | | | A:1 |
| | | I:2 | A:1 | | | H:1 | | | X:1 |
| | | G:2 | X:1 | | | R:1 | | | |

| | | Framework 3 | | | | | CDR3 | | |
|---|---|---|---|---|---|---|---|---|---|
| 91 | 92 | 93 | 94 | 95 | 96 | 97 | 98 | 99 | 100 |
| A | T | Y | Y | C | X | X | X | X | X |
| A:1007 | T:876 | Y:1031 | Y:980 | C:1019 | | | | | |
| G:28 | V:129 | -:4 | F:43 | G:16 | | | | | |
| -:4 | S:10 | S:2 | H:10 | -:4 | | | | | |
| T:2 | I:9 | F:2 | S:4 | S:3 | | | | | |
| P:2 | A:6 | C:2 | -:4 | W:1 | | | | | |
| V:1 | -:5 | X:2 | V:1 | X:1 | | | | | |
| | L:4 | L:1 | Q:1 | | | | | | |
| | G:3 | | X:1 | | | | | | |
| | N:2 | | | | | | | | |

FIG 10C

| CDR3 | | | | | | | | Framework 4 | |
|---|---|---|---|---|---|---|---|---|---|
| 101 | 102 | 103 | 104 | 105 | 106 | 107 | 108 | 109 | 110 |
| X | X | X | X | X | X | X | X | F | G |
| | | | | | | | | F:729 | G:674 |
| | | | | | | | | -:213 | -:299 |
| | | | | | | | | G:22 | F:19 |
| | | | | | | | | T:19 | S:10 |
| | | | | | | | | L:14 | Q:8 |
| | | | | | | | | Q:12 | A:8 |
| | | | | | | | | A:9 | W:8 |
| | | | | | | | | P:7 | R:7 |
| | | | | | | | | R:6 | V:3 |
| | | | | | | | | S:4 | L:2 |
| | | | | | | | | V:4 | P:2 |
| | | | | | | | | H:2 | T:1 |
| | | | | | | | | K:1 | K:1 |
| | | | | | | | | X:1 | X:1 |
| | | | | | | | | D:1 | H:1 |

| Framework 4 | | | | | | | | | |
|---|---|---|---|---|---|---|---|---|---|
| 111 | 112 | 113 | 114 | 115 | 116 | 117 | 118 | 119 | 120 |
| Q | G | T | K | V | E | I | K | R | T |
| -:377 | G:600 | T:589 | K:516 | -:435 | E:462 | I:492 | -:496 | -:634 | -:842 |
| Q:352 | -:409 | -:415 | -:425 | V:391 | -:454 | -:482 | K:488 | R:393 | T:191 |
| G:199 | T:9 | K:8 | R:46 | L:184 | D:79 | V:18 | R:27 | T:5 | V:2 |
| P:76 | K:7 | E:7 | T:16 | K:7 | R:8 | M:12 | N:10 | G:5 | Q:2 |
| A:11 | E:5 | P:4 | V:7 | E:6 | I:8 | K:8 | E:5 | K:2 | R:2 |
| R:10 | D:3 | D:4 | L:6 | I:4 | V:7 | S:6 | T:4 | A:2 | S:1 |
| T:9 | N:2 | G:4 | I:5 | A:3 | Q:5 | T:6 | I:4 | S:1 | N:1 |
| H:2 | Q:2 | S:3 | N:4 | D:3 | G:5 | L:5 | F:2 | L:1 | L:1 |
| S:1 | R:2 | A:3 | D:4 | S:2 | A:4 | N:4 | S:2 | P:1 | A:1 |
| F:1 | S:1 | R:2 | S:3 | W:2 | W:3 | F:3 | L:2 | | W:1 |
| K:1 | L:1 | N:1 | E:2 | G:2 | K:2 | A:3 | V:1 | | |
| E:1 | X:1 | V:1 | Q:2 | Y:1 | M:2 | C:1 | Q:1 | | |
| V:1 | P:1 | L:1 | H:2 | Q:1 | X:2 | H:1 | M:1 | | |
| W:1 | I:1 | X:1 | M:1 | X:1 | T:1 | D:1 | P:1 | | |
| X:1 | | I:1 | A:1 | P:1 | C:1 | R:1 | | | |
| D:1 | | | W:1 | R:1 | H:1 | G:1 | | | |
| | | | X:1 | | | | | | |
| | | | P:1 | | | | | | |
| | | | G:1 | | | | | | |

FIG 10D

| Framework 4 | | | | | | |
|---|---|---|---|---|---|---|
| 121 | 122 | 123 | 124 | 125 | 126 | 127 |
| V | A | A | P | S | V | F |
| -:931 | -:942 | -:957 | -:963 | -:981 | -:996 | -:1002 |
| V:92 | A:84 | A:74 | P:74 | S:51 | V:30 | F:30 |
| G:15 | P:6 | H:7 | H:4 | L:7 | K:5 | S:3 |
| A:3 | L:5 | P:5 | L:2 | T:4 | A:4 | L:3 |
| T:1 | G:3 | N:1 | A:1 | P:1 | X:3 | X:2 |
| W:1 | T:1 | | | | C:2 | E:1 |
| P:1 | V:1 | | | | S:1 | V:1 |
| | Q:1 | | | | M:1 | R:1 |
| | H:1 | | | | L:1 | I:1 |
| | | | | | W:1 | |

FIG 10E

| Framework 1 | | | | | | | | | |
|---|---|---|---|---|---|---|---|---|---|
| 1 | 2 | 3 | 4 | 5 | 6 | 7 | 8 | 9 | 10 |
| D | I | V | M | T | Q | S | P | L | S |
| -:166 | -:165 | -:162 | -:159 | -:157 | -:149 | -:141 | -:136 | L:145 | S:152 |
| D:87 | I:66 | V:87 | M:91 | T:105 | Q:113 | S:87 | P:126 | -:110 | -:109 |
| E:6 | V:23 | E:6 | L:11 | | | T:33 | | P:2 | D:1 |
| A:2 | L:4 | L:6 | V:1 | | | N:1 | | F:1 | |
| Q:1 | E:2 | M:1 | | | | | | S:1 | |
| | A:1 | | | | | | | D:1 | |
| | T:1 | | | | | | | I:1 | |
| | | | | | | | | V:1 | |

| Framework 1 | | | | | | | | | |
|---|---|---|---|---|---|---|---|---|---|
| 11 | 12 | 13 | 14 | 15 | 16 | 17 | 18 | 19 | 20 |
| L | P | V | T | P | G | Q | P | A | S |
| L:163 | P:140 | V:187 | T:186 | P:119 | G:208 | Q:129 | P:217 | A:226 | S:229 |
| -:84 | -:76 | -:74 | -:70 | L:79 | -:54 | E:88 | -:39 | -:36 | -:33 |
| S:15 | S:43 | C:1 | S:2 | -:64 | | -:43 | S:3 | | |
| | T:2 | | N:2 | | | D:2 | Q:2 | | |
| | A:1 | | H:1 | | | | R:1 | | |
| | | | I:1 | | | | | | |

| Framework 1 | | | CDR1 | | | | | | |
|---|---|---|---|---|---|---|---|---|---|
| 21 | 22 | 23 | 24 | 25 | 26 | 27 | 28 | 29 | 30 |
| I | S | C | X | X | X | X | X | X | X |
| I:231 | S:250 | C:252 | | | | | | | |
| -:27 | -:11 | -:8 | | | | | | | |
| F:1 | Y:1 | F:2 | | | | | | | |
| M:1 | | | | | | | | | |
| L:1 | | | | | | | | | |
| V:1 | | | | | | | | | |

| CDR1 | | | | | | | | | |
|---|---|---|---|---|---|---|---|---|---|
| 31 | 32 | 33 | 34 | 35 | 36 | 37 | 38 | 39 | 40 |
| X | X | X | X | X | X | X | X | X | X |

| Framework 2 | | | | | | | | | |
|---|---|---|---|---|---|---|---|---|---|
| 41 | 42 | 43 | 44 | 45 | 46 | 47 | 48 | 49 | 50 |
| W | Y | L | Q | K | P | G | Q | S | P |
| W:257 | Y:159 | L:157 | Q:261 | K:159 | P:259 | G:262 | Q:254 | S:225 | P:260 |
| C:4 | F:81 | Q:98 | Z:1 | R:102 | A:3 | | K:4 | P:32 | -:1 |
| R:1 | L:21 | V:3 | | T:1 | | | Z:1 | T:3 | L:1 |
| | H:1 | X:1 | | | | | -:1 | F:1 | |
| | | P:1 | | | | | H:1 | -:1 | |
| | | H:1 | | | | | R:1 | | |
| | | R:1 | | | | | | | |

FIG 11A

| Framework 2 | | | | | CDR2 | | | | |
|---|---|---|---|---|---|---|---|---|---|
| 51 | 52 | 53 | 54 | 55 | 56 | 57 | 58 | 59 | 60 |
| Q | L | L | I | Y | X | X | X | X | X |
| Q:153 | L:177 | L:261 | I:255 | Y:252 | | | | | |
| R:101 | R:80 | V:1 | L:4 | S:3 | | | | | |
| K:4 | V:3 | | F:2 | F:3 | | | | | |
| W:1 | F:1 | | V:1 | H:3 | | | | | |
| H:1 | I:1 | | | -:1 | | | | | |
| Z:1 | | | | | | | | | |
| L:1 | | | | | | | | | |

| CDR2 | | Framework 3 | | | | | | | |
|---|---|---|---|---|---|---|---|---|---|
| 61 | 62 | 63 | 64 | 65 | 66 | 67 | 68 | 69 | 70 |
| X | X | G | V | P | D | R | F | S | G |
| | | G:262 | V:262 | P:261 | D:258 | R:257 | F:260 | S:260 | G:258 |
| | | | | S:1 | N:3 | S:2 | I:1 | T:2 | A:2 |
| | | | | | H:1 | K:2 | L:1 | | D:2 |
| | | | | | | T:1 | | | |

| Framework 3 | | | | | | | | | |
|---|---|---|---|---|---|---|---|---|---|
| 71 | 72 | 73 | 74 | 75 | 76 | 77 | 78 | 79 | 80 |
| S | G | S | G | T | D | F | T | L | K |
| S:256 | G:260 | S:242 | G:258 | T:256 | D:254 | F:261 | T:261 | L:262 | K:249 |
| G:5 | -:1 | A:19 | -:3 | A:4 | A:2 | V:1 | R:1 | | E:3 |
| T:1 | R:1 | L:1 | D:1 | S:2 | E:2 | | | | R:3 |
| | | | | | S:1 | | | | T:2 |
| | | | | | N:1 | | | | A:1 |
| | | | | | B:1 | | | | N:1 |
| | | | | | H:1 | | | | M:1 |
| | | | | | | | | | I:1 |
| | | | | | | | | | L:1 |

| Framework 3 | | | | | | | | | |
|---|---|---|---|---|---|---|---|---|---|
| 81 | 82 | 83 | 84 | 85 | 86 | 87 | 88 | 89 | 90 |
| I | S | R | V | E | A | E | D | V | G |
| I:260 | S:258 | R:253 | V:256 | E:257 | A:255 | E:252 | D:261 | V:254 | G:261 |
| V:1 | N:3 | K:5 | M:5 | G:2 | T:3 | D:7 | B:1 | A:2 | A:1 |
| M:1 | T:1 | S:2 | A:1 | K:1 | P:2 | A:1 | | D:2 | |
| | | W:2 | | Z:1 | V:2 | Z:1 | | L:2 | |
| | | | | Q:1 | | G:1 | | E:1 | |
| | | | | | | | | I:1 | |

FIG 11B

| Framework 3 | | | | CDR3 | | | | | |
|---|---|---|---|---|---|---|---|---|---|
| 91 | 92 | 93 | 94 | 95 | 96 | 97 | 98 | 99 | 100 |
| V | Y | Y | C | X | X | X | X | X | X |
| V:239 | Y:260 | Y:260 | C:261 | | | | | | |
| I:16 | H:2 | F:2 | -:1 | | | | | | |
| L:4 | | | | | | | | | |
| F:1 | | | | | | | | | |
| T:1 | | | | | | | | | |
| X:1 | | | | | | | | | |

| CDR3 | | | | | | | | | |
|---|---|---|---|---|---|---|---|---|---|
| 101 | 102 | 103 | 104 | 105 | 106 | 107 | 108 | 109 | 110 |
| X | X | X | X | X | X | X | X | X | X |

| Framework 4 | | | | | | | | | |
|---|---|---|---|---|---|---|---|---|---|
| 111 | 112 | 113 | 114 | 115 | 116 | 117 | 118 | 119 | 120 |
| F | G | Q | G | T | K | V | E | I | K |
| F:182 | G:165 | -:102 | G:139 | T:138 | K:119 | -:121 | -:132 | -:139 | -:149 |
| -:43 | -:76 | Q:91 | -:105 | -:108 | -:115 | V:78 | E:98 | I:107 | K:103 |
| A:7 | R:4 | G:29 | F:3 | G:5 | R:14 | L:54 | D:25 | M:4 | R:4 |
| G:7 | Y:3 | P:25 | T:3 | K:3 | N:3 | E:3 | I:2 | K:3 | T:3 |
| R:6 | Q:3 | T:5 | K:2 | Q:2 | V:3 | G:2 | T:1 | S:2 | N:2 |
| L:4 | S:2 | F:2 | L:2 | V:1 | G:3 | A:1 | K:1 | T:2 | Y:1 |
| V:3 | A:2 | A:2 | W:2 | L:1 | S:1 | W:1 | V:1 | V:2 | |
| P:3 | H:2 | R:2 | P:2 | A:1 | E:1 | D:1 | W:1 | F:1 | |
| S:2 | F:1 | S:1 | H:2 | W:1 | W:1 | I:1 | G:1 | Q:1 | |
| Q:2 | K:1 | E:1 | D:2 | P:1 | P:1 | | | R:1 | |
| T:1 | E:1 | V:1 | L:1 | D:1 | H:1 | | | | |
| M:1 | W:1 | L:1 | | | | | | | |
| W:1 | D:1 | | | | | | | | |

| Framework 4 | | | | | | | | |
|---|---|---|---|---|---|---|---|---|
| 121 | 122 | 123 | 124 | 125 | 126 | 127 | 128 | 129 |
| R | T | V | A | A | P | S | V | F |
| -:171 | -:220 | -:244 | -:246 | -:248 | -:249 | -:252 | -:254 | -:255 |
| R:86 | T:39 | V:15 | A:14 | A:12 | P:11 | S:9 | V:8 | F:7 |
| T:2 | L:2 | L:1 | E:1 | P:1 | L:2 | K:1 | | |
| V:1 | G:1 | A:1 | H:1 | H:1 | | | | |
| A:1 | | H:1 | | | | | | |
| G:1 | | | | | | | | |

FIG 11C

| | | | | | | | | | |
|---|---|---|---|---|---|---|---|---|---|
| Framework 1 | | | | | | | | | |
| 1 | 2 | 3 | 4 | 5 | 6 | 7 | 8 | 9 | 10 |
| E | I | V | L | T | Q | S | P | G | T |
| -:503 | -:502 | -:462 | -:457 | -:446 | -:427 | -:413 | P:389 | -:278 | T:506 |
| E:231 | I:224 | V:250 | L:250 | T:314 | Q:341 | S:353 | -:381 | G:258 | -:256 |
| M:19 | A:20 | E:47 | M:59 | I:7 | X:1 | L:2 | | A:204 | S:4 |
| D:9 | L:13 | Q:5 | V:2 | M:1 | R:1 | F:1 | | D:15 | I:2 |
| K:5 | V:7 | I:3 | F:1 | R:1 | | V:1 | | S:6 | H:1 |
| A:1 | F:2 | T:2 | I:1 | V:1 | | | | P:5 | P:1 |
| Q:1 | T:2 | L:1 | | | | | | V:4 | |
| G:1 | | | | | | | | | |

| | | | | | | | | | |
|---|---|---|---|---|---|---|---|---|---|
| Framework 1 | | | | | | | | | |
| 11 | 12 | 13 | 14 | 15 | 16 | 17 | 18 | 19 | 20 |
| L | S | L | S | P | G | E | R | A | T |
| L:522 | S:529 | L:424 | S:545 | P:553 | G:569 | E:563 | R:604 | A:621 | T:667 |
| -:243 | -:235 | -:218 | -:213 | -:209 | -:196 | -:183 | -:130 | -:117 | -:86 |
| M:3 | C:4 | V:119 | T:4 | Q:2 | R:4 | D:18 | K:9 | V:28 | I:7 |
| V:2 | P:1 | F:6 | N:4 | A:1 | A:1 | G:3 | S:8 | S:2 | A:5 |
| | Y:1 | G:2 | F:3 | S:1 | | A:1 | G:7 | C:1 | S:2 |
| | | S:1 | C:1 | T:1 | | K:1 | T:6 | G:1 | P:2 |
| | | | | V:1 | | Q:1 | E:4 | | V:1 |
| | | | | G:1 | | | V:1 | | |
| | | | | L:1 | | | I:1 | | |

| | | | | | | | | | |
|---|---|---|---|---|---|---|---|---|---|
| Framework 1 | | | CDR1 | | | | | | |
| 21 | 22 | 23 | 24 | 25 | 26 | 27 | 28 | 29 | 30 |
| L | S | C | X | X | X | X | X | X | X |
| L:717 | S:725 | C:736 | | | | | | | |
| -:46 | -:38 | -:33 | | | | | | | |
| V:2 | F:2 | Y:1 | | | | | | | |
| I:2 | A:1 | | | | | | | | |
| R:2 | T:1 | | | | | | | | |
| F:1 | P:1 | | | | | | | | |
| | Y:1 | | | | | | | | |
| | L:1 | | | | | | | | |

| | | | | | | | | | |
|---|---|---|---|---|---|---|---|---|---|
| CDR1 | | | | | | Framework 2 | | | |
| 31 | 32 | 33 | 34 | 35 | 36 | 37 | 38 | 39 | 40 |
| X | X | X | X | X | X | W | Y | Q | Q |
| | | | | | | W:769 | Y:735 | Q:762 | Q:732 |
| | | | | | | F:1 | F:31 | R:3 | H:25 |
| | | | | | | | X:2 | L:2 | V:4 |
| | | | | | | | H:2 | K:1 | L:4 |
| | | | | | | | | X:1 | R:2 |
| | | | | | | | | H:1 | K:1 |
| | | | | | | | | | E:1 |
| | | | | | | | | | X:1 |

FIG 12A

| | | | | Framework 2 | | | | | |
|---|---|---|---|---|---|---|---|---|---|
| 41 | 42 | 43 | 44 | 45 | 46 | 47 | 48 | 49 | 50 |
| K | P | G | Q | A | P | R | L | L | I |
| K:711 | P:736 | G:768 | Q:752 | A:730 | P:767 | R:753 | L:746 | L:760 | I:743 |
| R:38 | A:9 | S:2 | L:12 | P:24 | X:2 | K:6 | F:14 | V:9 | M:10 |
| S:4 | S:7 | | R:3 | T:8 | T:1 | S:5 | V:8 | F:1 | V:7 |
| T:4 | R:7 | | H:2 | S:5 | | T:2 | -:1 | | F:4 |
| N:4 | L:6 | | G:1 | V:3 | | N:2 | X:1 | | L:4 |
| I:4 | V:2 | | | | | X:1 | | | T:1 |
| E:2 | T:1 | | | | | G:1 | | | Y:1 |
| Q:2 | H:1 | | | | | | | | |
| H:1 | G:1 | | | | | | | | |

| | | | CDR2 | | | | | Framework 3 | |
|---|---|---|---|---|---|---|---|---|---|
| 51 | 52 | 53 | 54 | 55 | 56 | 57 | 58 | 59 | 60 |
| Y | X | X | X | X | X | X | X | G | I |
| Y:723 | | | | | | | | G:746 | I:729 |
| F:24 | | | | | | | | D:10 | V:31 |
| H:11 | | | | | | | | S:7 | T:4 |
| S:7 | | | | | | | | A:4 | F:2 |
| K:1 | | | | | | | | Y:2 | M:2 |
| Q:1 | | | | | | | | R:1 | -:1 |
| C:1 | | | | | | | | | L:1 |
| W:1 | | | | | | | | | |
| R:1 | | | | | | | | | |

| | | | | Framework 3 | | | | | |
|---|---|---|---|---|---|---|---|---|---|
| 61 | 62 | 63 | 64 | 65 | 66 | 67 | 68 | 69 | 70 |
| P | D | R | F | S | G | S | G | S | G |
| P:763 | D:395 | R:761 | F:758 | S:754 | G:761 | S:751 | G:760 | S:755 | G:743 |
| S:4 | A:350 | K:5 | I:6 | R:5 | A:5 | G:10 | E:3 | P:9 | E:7 |
| T:1 | V:6 | T:4 | L:3 | T:4 | D:2 | R:4 | A:3 | L:2 | A:7 |
| E:1 | G:5 | | V:2 | N:4 | S:1 | T:3 | V:2 | A:2 | V:4 |
| A:1 | S:2 | | S:1 | X:1 | M:1 | N:1 | W:1 | T:1 | -:4 |
| | T:2 | | | I:1 | | I:1 | R:1 | C:1 | R:3 |
| | N:2 | | | G:1 | | | | | W:1 |
| | E:2 | | | | | | | | X:1 |
| | X:2 | | | | | | | | |
| | F:1 | | | | | | | | |
| | Y:1 | | | | | | | | |
| | P:1 | | | | | | | | |
| | H:1 | | | | | | | | |

FIG 12B

| | | | | Framework 3 | | | | | |
|---|---|---|---|---|---|---|---|---|---|
| 71 | 72 | 73 | 74 | 75 | 76 | 77 | 78 | 79 | 80 |
| T | D | F | T | L | T | I | S | R | L |
| T:750 | D:597 | F:766 | T:740 | L:760 | T:743 | I:756 | S:716 | R:393 | L:760 |
| A:7 | E:161 | S:2 | S:15 | F:5 | I:12 | V:12 | T:20 | S:352 | V:6 |
| R:7 | N:4 | C:1 | I:8 | V:2 | S:7 | F:1 | N:20 | G:11 | M:3 |
| S:5 | A:2 | L:1 | A:4 | I:2 | A:5 | N:1 | R:6 | T:5 | P:1 |
| P:1 | G:2 | | N:3 | X:1 | N:3 | | X:2 | K:4 | |
| | Y:1 | | | | | | D:2 | N:3 | |
| | Q:1 | | | | | | G:2 | I:2 | |
| | X:1 | | | | | | F:1 | | |
| | H:1 | | | | | | Y:1 | | |

| | | | | Framework 3 | | | | | |
|---|---|---|---|---|---|---|---|---|---|
| 81 | 82 | 83 | 84 | 85 | 86 | 87 | 88 | 89 | 90 |
| E | P | E | D | F | A | V | Y | Y | C |
| E:587 | P:595 | E:745 | D:759 | F:726 | A:742 | V:703 | Y:760 | Y:738 | C:760 |
| Q:177 | S:170 | -:8 | -:7 | C:13 | -:7 | I:21 | -:7 | F:17 | -:8 |
| A:2 | A:3 | A:5 | G:4 | S:10 | G:7 | L:14 | F:3 | -:7 | S:1 |
| D:2 | T:1 | G:5 | | L:8 | V:6 | M:8 | | S:4 | X:1 |
| K:1 | I:1 | D:4 | | -:7 | D:4 | -:7 | | C:2 | |
| X:1 | | K:1 | | V:2 | T:2 | T:4 | | L:1 | |
| | | Q:1 | | I:2 | R:2 | E:4 | | H:1 | |
| | | X:1 | | Y:1 | | X:3 | | | |
| | | | | X:1 | | F:2 | | | |
| | | | | | | D:2 | | | |
| | | | | | | A:1 | | | |
| | | | | | | H:1 | | | |

| | | | | CDR3 | | | | | |
|---|---|---|---|---|---|---|---|---|---|
| 91 | 92 | 93 | 94 | 95 | 96 | 97 | 98 | 99 | 100 |
| X | X | X | X | X | X | X | X | X | X |

| CDR3 | | | | Framework 4 | | | | | |
|---|---|---|---|---|---|---|---|---|---|
| 101 | 102 | 103 | 104 | 105 | 106 | 107 | 108 | 109 | 110 |
| X | X | X | X | F | G | Q | G | T | K |
| | | | | F:673 | G:600 | Q:337 | G:530 | T:523 | K:453 |
| | | | | -:56 | -:133 | -:201 | -:224 | -:228 | -:232 |
| | | | | L:16 | P:14 | G:126 | D:6 | V:5 | R:53 |
| | | | | V:5 | R:8 | P:85 | K:5 | S:4 | T:7 |
| | | | | R:4 | W:6 | T:5 | Q:2 | A:2 | Q:6 |
| | | | | T:3 | F:3 | F:4 | R:2 | D:2 | N:5 |
| | | | | W:3 | T:2 | A:3 | L:1 | N:1 | E:5 |
| | | | | P:3 | A:2 | R:3 | | Q:1 | D:3 |
| | | | | G:2 | L:1 | H:2 | | L:1 | A:2 |
| | | | | S:1 | X:1 | S:1 | | W:1 | X:2 |
| | | | | K:1 | | K:1 | | P:1 | Y:1 |
| | | | | Q:1 | | Y:1 | | G:1 | M:1 |
| | | | | A:1 | | X:1 | | | |
| | | | | X:1 | | | | | |

FIG 12C

| | | | | Framework 4 | | | | | |
|---|---|---|---|---|---|---|---|---|---|
| 111 | 112 | 113 | 114 | 115 | 116 | 117 | 118 | 119 | 120 |
| V | E | I | K | R | T | V | A | A | P |
| V:350 | E:410 | I:442 | K:458 | -:431 | -:611 | -:725 | -:732 | -:737 | -:741 |
| -:239 | -:250 | -:270 | -:281 | R:323 | T:144 | V:35 | A:31 | A:30 | P:26 |
| L:170 | D:90 | V:21 | R:18 | L:6 | S:6 | G:6 | L:2 | H:2 | T:1 |
| I:3 | K:4 | M:8 | T:4 | T:5 | L:3 | L:2 | P:2 | R:1 | L:1 |
| M:2 | G:4 | L:7 | N:4 | G:2 | F:1 | C:1 | W:1 | | H:1 |
| T:1 | Q:2 | R:6 | Q:2 | S:1 | N:1 | H:1 | H:1 | | |
| K:1 | L:2 | F:5 | M:1 | V:1 | Y:1 | | G:1 | | |
| A:1 | A:2 | N:3 | L:1 | H:1 | C:1 | | | | |
| P:1 | H:2 | S:2 | I:1 | | A:1 | | | | |
| R:1 | T:1 | T:2 | | | I:1 | | | | |
| G:1 | V:1 | K:2 | | | | | | | |
| | W:1 | A:1 | | | | | | | |
| | I:1 | X:1 | | | | | | | |

| 121 | 122 |
|---|---|
| S | V |
| -:755 | -:760 |
| S:11 | V:6 |
| L:3 | Y:1 |
| K:1 | M:1 |
| | L:1 |
| | A:1 |

FIG 12D

| | | | | Framework 1 | | | | | |
|---|---|---|---|---|---|---|---|---|---|
| 1 | 2 | 3 | 4 | 5 | 6 | 7 | 8 | 9 | 10 |
| E | T | T | L | T | Q | S | P | A | F |
| -:21 | -:21 | -:21 | -:21 | -:21 | -:21 | -:18 | P:13 | A:14 | F:18 |
| E:2 | T:2 | T:2 | L:2 | T:2 | Q:2 | S:5 | -:10 | -:9 | -:5 |

| | | | | Framework 1 | | | | | |
|---|---|---|---|---|---|---|---|---|---|
| 11 | 12 | 13 | 14 | 15 | 16 | 17 | 18 | 19 | 20 |
| M | S | A | T | P | G | D | K | V | N |
| M:21 | S:22 | A:22 | T:22 | P:22 | G:22 | D:22 | K:22 | V:23 | N:23 |
| -:2 | -:1 | -:1 | -:1 | -:1 | -:1 | -:1 | -:1 | | |

| Framework 1 | | | CDR1 | | | | | | |
|---|---|---|---|---|---|---|---|---|---|
| 21 | 22 | 23 | 24 | 25 | 26 | 27 | 28 | 29 | 30 |
| I | S | C | X | X | X | X | X | X | X |
| I:23 | S:23 | C:23 | | | | | | | |

| CDR1 | | | | Framework 2 | | | | | |
|---|---|---|---|---|---|---|---|---|---|
| 31 | 32 | 33 | 34 | 35 | 36 | 37 | 38 | 39 | 40 |
| X | X | X | X | W | Y | Q | Q | K | P |
| | | | | W:22 | Y:23 | Q:22 | Q:23 | K:23 | P:23 |
| | | | | C:1 | | R:1 | | | |

| | | | | Framework 2 | | | | | CDR2 |
|---|---|---|---|---|---|---|---|---|---|
| 41 | 42 | 43 | 44 | 45 | 46 | 47 | 48 | 49 | 50 |
| G | E | A | A | I | F | I | I | Q | X |
| G:22 | E:23 | A:22 | A:23 | I:23 | F:23 | I:23 | I:23 | Q:23 | |
| E:1 | | T:1 | | | | | | | |

| | | CDR2 | | | | | Framework 3 | | |
|---|---|---|---|---|---|---|---|---|---|
| 51 | 52 | 53 | 54 | 55 | 56 | 57 | 58 | 59 | 60 |
| X | X | X | X | X | X | G | I | P | P |
| | | | | | | G:23 | I:22 | P:23 | P:23 |
| | | | | | | | F:1 | | |

FIG 13A

| Framework 3 | | | | | | | | | |
|---|---|---|---|---|---|---|---|---|---|
| 61 | 62 | 63 | 64 | 65 | 66 | 67 | 68 | 69 | 70 |
| R | F | S | G | S | G | Y | G | T | D |
| R:23 | F:23 | S:23 | G:23 | S:23 | G:23 | Y:22<br>C:1 | G:23 | T:23 | D:23 |

| Framework 3 | | | | | | | | | |
|---|---|---|---|---|---|---|---|---|---|
| 71 | 72 | 73 | 74 | 75 | 76 | 77 | 78 | 79 | 80 |
| F | T | L | T | I | N | N | I | E | S |
| F:23 | T:23 | L:23 | T:23 | I:23 | N:23 | N:23 | I:23 | E:23 | S:23 |

| Framework 3 | | | | | | | | CDR3 | |
|---|---|---|---|---|---|---|---|---|---|
| 81 | 82 | 83 | 84 | 85 | 86 | 87 | 88 | 89 | 90 |
| E | D | A | A | Y | Y | F | C | X | X |
| E:23 | D:23 | A:23 | A:23 | Y:23 | Y:23 | F:23 | C:23 | | |

| CDR3 | | | | | Framework 4 | | | | |
|---|---|---|---|---|---|---|---|---|---|
| 91 | 92 | 93 | 94 | 95 | 96 | 97 | 98 | 99 | 100 |
| X | X | X | X | X | L | R | H | F | W |
| | | | | | L:12<br>-:6<br>S:2<br>H:1<br>Q:1<br>R:1 | -:5<br>R:4<br>K:3<br>V:3<br>G:3<br>L:2<br>T:1<br>E:1<br>D:1 | H:5<br>-:5<br>T:3<br>V:2<br>D:2<br>L:2<br>S:1<br>A:1<br>Y:1<br>G:1 | F:10<br>-:4<br>T:3<br>T:3<br>H:2<br>L:2<br>V:1<br>R:1 | W:7<br>-:5<br>F:3<br>G:3<br>A:2<br>L:2<br>R:1 |

| Framework 4 | | | | | | |
|---|---|---|---|---|---|---|
| 101 | 102 | 103 | 104 | 105 | 106 | 107 |
| P | G | D | Q | A | A | G |
| -:11<br>P:6<br>W:2<br>L:2<br>Q:1<br>G:1 | -:14<br>G:7<br>A:2 | -:14<br>D:6<br>T:2<br>R:1 | -:16<br>Q:2<br>G:2<br>X:1<br>D:1<br>R:1 | -:16<br>A:4<br>P:2<br>W:1 | -:20<br>A:2<br>G:1 | -:21<br>G:2 |

FIG 13B

| | | | | Framework 1 | | | | | |
|---|---|---|---|---|---|---|---|---|---|
| 1 | 2 | 3 | 4 | 5 | 6 | 7 | 8 | 9 | 10 |
| E | I | V | M | T | Q | S | P | V | N |
| E:7 | I:7 | V:7 | M:7 | T:7 | Q:7 | S:7 | P:7 | V:7 | N:7 |

| | | | | Framework 1 | | | | CDR1 | |
|---|---|---|---|---|---|---|---|---|---|
| 11 | 12 | 13 | 14 | 15 | 16 | 17 | 18 | 19 | 20 |
| L | S | M | S | A | G | E | X | X | X |
| L:7 | S:7 | M:7 | S:7 | A:7 | G:7 | E:7 | | | |

| | | | | CDR1 | | | | | |
|---|---|---|---|---|---|---|---|---|---|
| 21 | 22 | 23 | 24 | 25 | 26 | 27 | 28 | 29 | 30 |
| X | X | X | X | X | X | X | X | X | X |

| | CDR1 | | | | | Framework 2 | | | |
|---|---|---|---|---|---|---|---|---|---|
| 31 | 32 | 33 | 34 | 35 | 36 | 37 | 38 | 39 | 40 |
| X | X | X | X | W | Y | Q | Q | K | P |
| | | | | W:7 | Y:7 | Q:7 | Q:7 | K:7 | P:7 |

| | | | | Framework 2 | | | | | CDR2 |
|---|---|---|---|---|---|---|---|---|---|
| 41 | 42 | 43 | 44 | 45 | 46 | 47 | 48 | 49 | 50 |
| G | Q | A | P | R | L | F | I | Y | X |
| G:7 | Q:7 | A:7 | P:7 | R:7 | L:7 | F:7 | I:7 | Y:7 | |

| | | CDR2 | | | | | Framework 3 | | |
|---|---|---|---|---|---|---|---|---|---|
| 51 | 52 | 53 | 54 | 55 | 56 | 57 | 58 | 59 | 60 |
| X | X | X | X | X | X | G | I | S | A |
| | | | | | | G:7 | I:7 | S:7 | A:7 |

| | | | | Framework 3 | | | | | |
|---|---|---|---|---|---|---|---|---|---|
| 61 | 62 | 63 | 64 | 65 | 66 | 67 | 68 | 69 | 70 |
| R | F | S | G | S | G | S | G | T | D |
| R:7 | F:7 | S:6<br>N:1 | G:7 | S:7 | G:7 | S:7 | G:7 | T:7 | D:7 |

FIG 14A

| | | | | Framework 3 | | | | | |
|---|---|---|---|---|---|---|---|---|---|
| 71 | 72 | 73 | 74 | 75 | 76 | 77 | 78 | 79 | 80 |
| F | T | L | T | I | T | S | L | Q | S |
| F:7 | T:6<br>N:1 | L:6<br>F:1 | T:5<br>I:1<br>N:1 | I:7 | T:6<br>S:1 | S:7 | L:7 | Q:7 | S:7 |

| | | | Framework 3 | | | | | CDR3 | |
|---|---|---|---|---|---|---|---|---|---|
| 81 | 82 | 83 | 84 | 85 | 86 | 87 | 88 | 89 | 90 |
| E | D | F | A | V | Y | Y | C | X | X |
| E:7 | D:7 | F:7 | A:7 | V:7 | Y:7 | Y:7 | C:7 | | |

| | | | CDR3 | | | | | Framework 4 | |
|---|---|---|---|---|---|---|---|---|---|
| 91 | 92 | 93 | 94 | 95 | 96 | 97 | 98 | 99 | 100 |
| X | X | X | X | X | X | X | F | G | Q |
| | | | | | | | F:7 | G:7 | Q:7 |

| | | | | Framework 4 | | | | |
|---|---|---|---|---|---|---|---|---|
| 101 | 102 | 103 | 104 | 105 | 106 | 107 | 108 | 109 |
| G | T | K | L | D | I | K | R | T |
| G:7 | T:7 | K:7 | L:7 | D:7 | I:7 | K:7 | R:7 | -:6<br>T:1 |

FIG 14B

| | | | | Framework 1 | | | | | |
|---|---|---|---|---|---|---|---|---|---|
| 1 | 2 | 3 | 4 | 5 | 6 | 7 | 8 | 9 | 10 |
| E | L | T | Q | S | P | G | T | L | S |
| E:5 | L:5 | T:5 | Q:5 | S:3<br>A:2 | P:5 | G:5 | T:5 | L:5 | S:5 |

| | Framework 1 | | | | | CDR1 | | | |
|---|---|---|---|---|---|---|---|---|---|
| 11 | 12 | 13 | 14 | 15 | 16 | 17 | 18 | 19 | 20 |
| L | S | P | G | E | X | X | X | X | X |
| L:5 | S:5 | P:5 | G:5 | E:3<br>D:2 | | | | | |

| | | | | CDR1 | | | | | |
|---|---|---|---|---|---|---|---|---|---|
| 21 | 22 | 23 | 24 | 25 | 26 | 27 | 28 | 29 | 30 |
| X | X | X | X | X | X | X | X | X | X |

| | CDR1 | | | | Framework 2 | | | | |
|---|---|---|---|---|---|---|---|---|---|
| 31 | 32 | 33 | 34 | 35 | 36 | 37 | 38 | 39 | 40 |
| X | X | X | W | Y | Q | H | K | P | G |
| | | | W:5 | Y:5 | Q:5 | H:5 | K:5 | P:5 | G:5 |

| | | | Framework 2 | | | | | CDR2 | |
|---|---|---|---|---|---|---|---|---|---|
| 41 | 42 | 43 | 44 | 45 | 46 | 47 | 48 | 49 | 50 |
| Q | A | P | R | L | V | I | H | X | X |
| Q:5 | A:5 | P:5 | R:5 | L:5 | V:5 | I:5 | H:5 | | |

| | CDR2 | | | | Framework 3 | | | | |
|---|---|---|---|---|---|---|---|---|---|
| 51 | 52 | 53 | 54 | 55 | 56 | 57 | 58 | 59 | 60 |
| X | X | X | X | X | G | I | S | D | R |
| | | | | | G:5 | I:5 | S:5 | D:5 | R:5 |

| | | | | Framework 3 | | | | | |
|---|---|---|---|---|---|---|---|---|---|
| 61 | 62 | 63 | 64 | 65 | 66 | 67 | 68 | 69 | 70 |
| F | S | G | S | G | S | G | T | D | F |
| F:5 | S:5 | G:5 | S:5 | G:5 | S:5 | G:5 | T:5 | D:5 | F:5 |

FIG 15A

| | | | | | Framework 3 | | | | |
|---|---|---|---|---|---|---|---|---|---|
| 71 | 72 | 73 | 74 | 75 | 76 | 77 | 78 | 79 | 80 |
| T | L | T | I | T | R | L | E | P | E |
| T:5 | L:5 | T:5 | I:5 | T:5 | R:5 | L:3<br>V:2 | E:5 | P:5 | E:5 |

| | | | Framework 3 | | | | | CDR3 | |
|---|---|---|---|---|---|---|---|---|---|
| 81 | 82 | 83 | 84 | 85 | 86 | 87 | 88 | 89 | 90 |
| D | F | A | L | Y | Y | C | X | X | X |
| D:5 | F:5 | A:5 | L:5 | Y:5 | Y:5 | C:5 | | | |

| | | CDR3 | | | | | Framework 4 | | |
|---|---|---|---|---|---|---|---|---|---|
| 91 | 92 | 93 | 94 | 95 | 96 | 97 | 98 | 99 | 100 |
| X | X | X | X | X | X | F | G | Q | G |
| | | | | | | F:5 | G:5 | Q:5 | G:5 |

| | | | | Framework 4 | | | |
|---|---|---|---|---|---|---|---|
| 101 | 102 | 103 | 104 | 105 | 106 | 107 | 108 |
| T | K | L | D | F | K | R | T |
| T:5 | K:5 | L:5 | D:3<br>E:2 | F:3<br>R:2 | K:5 | R:5 | -:3<br>T:2 |

FIG 15B

| | | | | | Framework 1 | | | | |
|---|---|---|---|---|---|---|---|---|---|
| 1 | 2 | 3 | 4 | 5 | 6 | 7 | 8 | 9 | 10 |
| D | I | V | M | T | Q | S | P | D | S |
| -:32 | -:32 | -:32 | -:32 | -:32 | -:32 | -:29 | -:29 | -:29 | -:28 |
| D:4 | I:4 | V:5 | M:5 | T:5 | Q:5 | S:8 | P:8 | D:7 | S:8 |
| E:1 | L:1 | | | | | | | E:1 | D:1 |

| | | | | | Framework 1 | | | | |
|---|---|---|---|---|---|---|---|---|---|
| 11 | 12 | 13 | 14 | 15 | 16 | 17 | 18 | 19 | 20 |
| L | A | V | S | L | G | G | R | R | A |
| -:22 | -:19 | -:19 | -:19 | -:20 | -:19 | -:19 | -:19 | -:24 | -:19 |
| L:11 | A:9 | V:9 | S:9 | L:8 | G:7 | G:10 | R:10 | R:7 | A:12 |
| S:3 | L:6 | A:6 | V:6 | S:6 | L:7 | E:7 | E:7 | A:3 | T:3 |
| T:1 | P:3 | G:3 | Y:2 | V:3 | S:3 | D:1 | T:1 | E:3 | G:3 |
| | | | C:1 | | D:1 | | | | |

| | Framework 1 | | | | | CDR1 | | | |
|---|---|---|---|---|---|---|---|---|---|
| 21 | 22 | 23 | 24 | 25 | 26 | 27 | 28 | 29 | 30 |
| T | I | N | C | X | X | X | X | X | X |
| -:19 | I:20 | N:23 | C:27 | | | | | | |
| T:14 | -:16 | -:13 | -:10 | | | | | | |
| P:3 | M:1 | S:1 | | | | | | | |
| S:1 | | | | | | | | | |

| | | | | | CDR1 | | | | |
|---|---|---|---|---|---|---|---|---|---|
| 31 | 32 | 33 | 34 | 35 | 36 | 37 | 38 | 39 | 40 |
| X | X | X | X | X | X | X | X | X | X |

| | | | | | Framework 2 | | | | |
|---|---|---|---|---|---|---|---|---|---|
| 41 | 42 | 43 | 44 | 45 | 46 | 47 | 48 | 49 | 50 |
| X | W | Y | Q | Q | K | P | G | Q | P |
| | W:37 | Y:35 | Q:37 | Q:34 | K:36 | P:35 | G:34 | Q:37 | P:36 |
| | | F:2 | | H:3 | R:1 | A:1 | R:2 | | S:1 |
| | | | | | | V:1 | K:1 | | |

| | | Framework 2 | | | | | CDR2 | | |
|---|---|---|---|---|---|---|---|---|---|
| 51 | 52 | 53 | 54 | 55 | 56 | 57 | 58 | 59 | 60 |
| P | K | L | L | I | Y | X | X | X | X |
| P:37 | K:32 | L:36 | L:36 | I:35 | Y:36 | | | | |
| | N:2 | Q:1 | V:1 | F:1 | H:1 | | | | |
| | R:2 | | | T:1 | | | | | |
| | E:1 | | | | | | | | |

FIG 16A

| CDR2 | | | Framework 3 | | | | | | |
|---|---|---|---|---|---|---|---|---|---|
| 61 | 62 | 63 | 64 | 65 | 66 | 67 | 68 | 69 | 70 |
| X | X | X | G | V | P | D | R | F | S |
| | | | G:37 | V:37 | P:37 | D:37 | R:37 | F:37 | S:36 |
| | | | | | | | | | G:1 |

| Framework 3 | | | | | | | | | |
|---|---|---|---|---|---|---|---|---|---|
| 71 | 72 | 73 | 74 | 75 | 76 | 77 | 78 | 79 | 80 |
| G | S | G | S | G | T | D | F | T | L |
| G:37 | S:36 | G:37 | S:37 | G:35 | T:37 | D:35 | F:37 | T:37 | L:37 |
| | G:1 | | | A:1 | | N:1 | | | |
| | | | | E:1 | | V:1 | | | |

| Framework 3 | | | | | | | | | |
|---|---|---|---|---|---|---|---|---|---|
| 81 | 82 | 83 | 84 | 85 | 86 | 87 | 88 | 89 | 90 |
| T | I | S | S | L | Q | A | E | D | V |
| T:37 | I:37 | S:36 | S:36 | L:37 | Q:35 | A:35 | E:36 | D:37 | V:36 |
| | | T:1 | N:1 | | H:2 | T:1 | D:1 | | A:1 |
| | | | | | | V:1 | | | |

| Framework 3 | | | | | CDR3 | | | | |
|---|---|---|---|---|---|---|---|---|---|
| 91 | 92 | 93 | 94 | 95 | 96 | 97 | 98 | 99 | 100 |
| A | V | Y | Y | C | X | X | X | X | X |
| A:37 | V:35 | Y:37 | Y:37 | C:37 | | | | | |
| | I:1 | | | | | | | | |
| | L:1 | | | | | | | | |

| CDR3 | | | | | Framework 3 | | | | |
|---|---|---|---|---|---|---|---|---|---|
| 101 | 102 | 103 | 104 | 105 | 106 | 107 | 108 | 109 | 110 |
| X | X | X | X | X | F | G | G | G | T |
| | | | | | F:24 | -:22 | -:27 | -:30 | -:30 |
| | | | | | -:8 | G:12 | G:5 | G:7 | T:7 |
| | | | | | S:1 | A:1 | Q:4 | | |
| | | | | | A:1 | F:1 | A:1 | | |
| | | | | | T:1 | L:1 | | | |
| | | | | | W:1 | | | | |
| | | | | | L:1 | | | | |

FIG 16B

| | | | | Framework 4 | | | | | |
|---|---|---|---|---|---|---|---|---|---|
| 111 | 112 | 113 | 114 | 115 | 116 | 117 | 118 | 119 | 120 |
| K | V | E | I | K | R | T | V | A | A |
| -:30 | -:30 | -:31 | -:31 | -:31 | -:33 | -:33 | -:33 | -:33 | -:33 |
| K:6 | V:5 | E:6 | I:5 | K:6 | R:4 | T:4 | V:4 | A:4 | A:4 |
| N:1 | L:2 | | L:1 | | | | | | |

| | | Framework 4 | | | |
|---|---|---|---|---|---|
| 121 | 122 | 123 | 124 | 125 | 126 |
| P | S | V | F | K | F |
| -:33 | -:33 | -:33 | -:33 | -:35 | -:36 |
| P:4 | S:4 | V:3 | F:2 | K:1 | F:1 |
| | | G:1 | X:2 | I:1 | |

FIG 16C

| | | | | | Framework 1 | | | | |
|---|---|---|---|---|---|---|---|---|---|
| 1 | 2 | 3 | 4 | 5 | 6 | 7 | 8 | 9 | 10 |
| Q | S | V | L | T | Q | P | P | S | V |
| -:265 | -:254 | -:249 | -:241 | T:254 | Q:266 | P:269 | P:277 | S:307 | V:170 |
| Q:189 | S:195 | V:199 | L:222 | -:230 | -:224 | -:218 | -:199 | -:184 | A:163 |
| S:18 | Y:19 | E:28 | V:23 | L:4 | H:2 | S:2 | A:8 | X:1 | -:155 |
| P:10 | A:13 | A:13 | E:4 | I:2 | L:1 | E:2 | S:3 | P:1 | L:2 |
| E:8 | L:8 | M:2 | A:1 | A:1 | | T:1 | G:2 | | P:1 |
| H:1 | M:2 | Q:1 | H:1 | N:1 | | X:1 | T:1 | | M:1 |
| N:1 | P:2 | L:1 | Q:1 | E:1 | | | H:1 | | G:1 |
| R:1 | F:1 | | | | | | Q:1 | | |
| | M:1 | | | | | | R:1 | | |

| | | | | | Framework 1 | | | | |
|---|---|---|---|---|---|---|---|---|---|
| 11 | 12 | 13 | 14 | 15 | 16 | 17 | 18 | 19 | 20 |
| S | G | A | P | G | Q | R | V | T | I |
| S:364 | G:322 | A:203 | P:418 | G:420 | Q:435 | R:367 | V:459 | T:452 | I:474 |
| -:126 | -:108 | T:196 | -:71 | -:60 | -:52 | K:63 | -:24 | -:18 | -:9 |
| T:1 | A:50 | -:83 | S:2 | R:12 | H:2 | -:42 | I:6 | S:10 | V:5 |
| P:1 | E:12 | P:6 | A:2 | E:1 | R:2 | T:6 | A:2 | I:7 | F:2 |
| Y:1 | R:1 | S:2 | | | K:1 | G:6 | G:2 | A:5 | T:1 |
| | | I:2 | | | L:1 | P:3 | | P:1 | M:1 |
| | | V:1 | | | | S:2 | | | L:1 |
| | | | | | | N:2 | | | |
| | | | | | | W:1 | | | |
| | | | | | | M:1 | | | |

| | | | | CDR1 | | | | | |
|---|---|---|---|---|---|---|---|---|---|
| 21 | 22 | 23 | 24 | 25 | 26 | 27 | 28 | 29 | 30 |
| S | C | X | X | X | X | X | X | X | X |
| S:483 | C:486 | | | | | | | | |
| -:7 | -:5 | | | | | | | | |
| A:1 | S:1 | | | | | | | | |
| F:1 | G:1 | | | | | | | | |
| T:1 | | | | | | | | | |

| | | CDR1 | | | | | | Framework 2 | |
|---|---|---|---|---|---|---|---|---|---|
| 31 | 32 | 33 | 34 | 35 | 36 | 37 | 38 | 39 | 40 |
| X | X | X | X | X | X | W | Y | Q | Q |
| | | | | | | W:493 | Y:487 | Q:476 | Q:439 |
| | | | | | | | F:3 | H:6 | H:44 |
| | | | | | | | H:2 | L:4 | L:4 |
| | | | | | | | C:1 | R:4 | K:3 |
| | | | | | | | | K:2 | V:1 |
| | | | | | | | | Y:1 | D:1 |
| | | | | | | | | | R:1 |

FIG 17A

| | | | | Framework 2 | | | | | |
|---|---|---|---|---|---|---|---|---|---|
| 41 | 42 | 43 | 44 | 45 | 46 | 47 | 48 | 49 | 50 |
| L | P | G | T | A | P | K | L | L | I |
| L:425 | P:489 | G:484 | T:442 | A:483 | P:490 | K:471 | L:468 | L:469 | I:475 |
| F:41 | S:1 | R:4 | A:16 | S:5 | L:1 | R:13 | V:16 | V:16 | M:8 |
| V:16 | T:1 | K:1 | K:15 | V:3 | A:1 | Q:3 | F:4 | I:5 | V:6 |
| R:4 | Q:1 | E:1 | S:5 | T:2 | H:1 | I:2 | I:3 | F:3 | T:2 |
| P:3 | R:1 | A:1 | M:5 | | | T:1 | Q:1 | P:1 | N:1 |
| I:3 | | X:1 | I:3 | | | E:1 | P:1 | | L:1 |
| Y:1 | | D:1 | V:2 | | | A:1 | | | |
| | | | Q:2 | | | P:1 | | | |
| | | | R:2 | | | | | | |
| | | | E:1 | | | | | | |

| | CDR2 | | | | | | | Framework 3 | |
|---|---|---|---|---|---|---|---|---|---|
| 51 | 52 | 53 | 54 | 55 | 56 | 57 | 58 | 59 | 60 |
| Y | X | X | X | X | X | X | X | G | V |
| Y:444 | | | | | | | | G:490 | V:416 |
| S:15 | | | | | | | | W:1 | I:73 |
| F:14 | | | | | | | | X:1 | A:3 |
| H:11 | | | | | | | | D:1 | L:1 |
| C:3 | | | | | | | | | |
| N:2 | | | | | | | | | |
| E:1 | | | | | | | | | |
| W:1 | | | | | | | | | |
| X:1 | | | | | | | | | |
| D:1 | | | | | | | | | |

| | | | | Framework 3 | | | | | |
|---|---|---|---|---|---|---|---|---|---|
| 61 | 62 | 63 | 64 | 65 | 66 | 67 | 68 | 69 | 70 |
| P | D | R | F | S | G | S | K | S | G |
| P:471 | D:484 | R:490 | F:476 | S:491 | G:476 | S:490 | K:468 | S:490 | G:472 |
| S:19 | G:4 | Q:2 | I:10 | L:1 | A:15 | T:2 | R:14 | A:1 | D:18 |
| A:2 | E:2 | G:1 | V:3 | P:1 | V:1 | Y:1 | Q:5 | W:1 | V:2 |
| R:1 | A:2 | | L:3 | | D:1 | | T:4 | P:1 | A:1 |
| | H:1 | | S:1 | | | | N:1 | | |
| | | | | | | | E:1 | | |

| | | | | Framework 3 | | | | | |
|---|---|---|---|---|---|---|---|---|---|
| 71 | 72 | 73 | 74 | 75 | 76 | 77 | 78 | 79 | 80 |
| T | S | A | S | L | A | I | S | G | L |
| T:467 | S:491 | A:484 | S:418 | L:493 | A:418 | I:485 | S:267 | G:487 | L:492 |
| A:17 | T:1 | T:4 | T:71 | | G:60 | V:7 | T:212 | E:3 | P:1 |
| I:5 | P:1 | G:2 | F:1 | | V:10 | F:1 | A:6 | R:3 | |
| S:3 | | S:1 | C:1 | | D:4 | | G:3 | | |
| N:1 | | V:1 | A:1 | | T:1 | | N:2 | | |
| | | X:1 | P:1 | | | | X:1 | | |
| | | | | | | | I:1 | | |
| | | | | | | | R:1 | | |

FIG 17B

| Framework 3 | | | | | | | | | |
|---|---|---|---|---|---|---|---|---|---|
| 81 | 82 | 83 | 84 | 85 | 86 | 87 | 88 | 89 | 90 |
| Q | S | E | D | E | A | D | Y | Y | C |
| Q:390 | S:271 | E:394 | D:487 | E:488 | A:468 | D:463 | Y:484 | Y:468 | C:487 |
| R:100 | A:149 | G:75 | N:2 | D:3 | S:13 | H:7 | F:8 | F:13 | S:2 |
| H:2 | T:68 | D:20 | V:2 | N:1 | T:5 | E:6 | S:1 | H:7 | W:2 |
| L:1 | P:4 | V:2 | A:2 | A:1 | G:5 | N:3 | | S:5 | R:2 |
| | V:1 | K:1 | | | D:2 | V:3 | | | |
| | | Q:1 | | | | Q:3 | | | |
| | | | | | | T:2 | | | |
| | | | | | | A:2 | | | |
| | | | | | | I:2 | | | |
| | | | | | | Y:1 | | | |
| | | | | | | R:1 | | | |

| CDR3 | | | | | | | | | |
|---|---|---|---|---|---|---|---|---|---|
| 91 | 92 | 93 | 94 | 95 | 96 | 97 | 98 | 99 | 100 |
| X | X | X | X | X | X | X | X | X | X |

| CDR3 | | | | Framework 4 | | | | | |
|---|---|---|---|---|---|---|---|---|---|
| 101 | 102 | 103 | 104 | 105 | 106 | 107 | 108 | 109 | 110 |
| X | X | X | X | F | G | G | G | T | K |
| | | | | F:395 | G:369 | G:236 | G:287 | T:274 | K:230 |
| | | | | -:57 | -:98 | -:188 | -:196 | -:208 | -:211 |
| | | | | V:11 | S:8 | T:51 | R:3 | A:4 | Q:22 |
| | | | | S:5 | F:4 | R:4 | X:2 | S:1 | R:16 |
| | | | | Y:5 | R:4 | S:3 | T:1 | K:1 | T:4 |
| | | | | C:4 | A:3 | A:3 | E:1 | E:1 | X:3 |
| | | | | I:4 | V:2 | F:2 | A:1 | L:1 | E:2 |
| | | | | G:4 | T:1 | L:2 | P:1 | P:1 | P:2 |
| | | | | L:3 | Y:1 | K:1 | H:1 | H:1 | N:1 |
| | | | | R:2 | C:1 | E:1 | | I:1 | V:1 |
| | | | | E:1 | X:1 | X:1 | | | G:1 |
| | | | | M:1 | P:1 | P:1 | | | |
| | | | | W:1 | | | | | |

| Framework 4 | | | | | | | | | |
|---|---|---|---|---|---|---|---|---|---|
| 111 | 112 | 113 | 114 | 115 | 116 | 117 | 118 | 119 | 120 |
| L | T | V | L | G | Q | P | K | A | A |
| L:218 | T:246 | V:244 | -:234 | -:284 | -:340 | -:341 | -:421 | -:423 | -:425 |
| -:215 | -:216 | -:230 | L:233 | G:156 | Q:150 | P:151 | K:72 | A:69 | A:56 |
| V:52 | E:11 | I:14 | K:15 | R:27 | G:2 | G:1 | | V:1 | N:9 |
| T:2 | D:8 | S:1 | V:5 | S:25 | R:1 | | | | G:2 |
| S:1 | S:4 | K:1 | G:3 | C:1 | | | | | P:1 |
| A:1 | A:3 | M:1 | Q:1 | | | | | | |
| W:1 | G:2 | L:1 | P:1 | | | | | | |
| X:1 | N:1 | P:1 | I:1 | | | | | | |
| P:1 | V:1 | | | | | | | | |
| G:1 | I:1 | | | | | | | | |

FIG 17C

| | | | | Framework 4 | | | | | |
|---|---|---|---|---|---|---|---|---|---|
| 121 | 122 | 123 | 124 | 125 | 126 | 127 | 128 | 129 | 130 |
| P | S | V | T | L | F | P | P | S | S |
| -:434 | -:447 | -:454 | -:459 | -:462 | -:463 | -:463 | -:463 | -:463 | -:463 |
| P:56 | S:37 | V:37 | T:32 | L:30 | F:29 | P:30 | P:30 | S:29 | S:29 |
| Q:1 | T:5 | L:1 | M:1 | R:1 | S:1 | | | X:1 | L:1 |
| L:1 | F:1 | G:1 | I:1 | | | | | | |
| H:1 | K:1 | | | | | | | | |
| | L:1 | | | | | | | | |
| | R:1 | | | | | | | | |

FIG 17D

| Framework 1 | | | | | | | | | |
|---|---|---|---|---|---|---|---|---|---|
| 1 | 2 | 3 | 4 | 5 | 6 | 7 | 8 | 9 | 10 |
| A | Q | S | V | L | T | Q | P | P | S |
| -:71 | Q:55 | S:62 | V:62 | L:62 | T:64 | Q:68 | P:69 | P:69 | S:70 |
| A:1 | -:8 | -:5 | -:5 | -:5 | L:5 | -:3 | -:3 | -:3 | -:2 |
| | P:5 | A:2 | A:2 | E:3 | -:3 | V:1 | | | |
| | L:2 | L:2 | E:2 | V:2 | | | | | |
| | E:2 | M:1 | L:1 | | | | | | |

| Framework 1 | | | | | | | | | |
|---|---|---|---|---|---|---|---|---|---|
| 11 | 12 | 13 | 14 | 15 | 16 | 17 | 18 | 19 | 20 |
| V | S | A | A | P | G | Q | K | V | T |
| V:67 | S:68 | A:72 | A:72 | P:71 | G:71 | Q:70 | K:58 | V:72 | T:70 |
| -:2 | -:2 | | | L:1 | V:1 | E:2 | T:5 | | A:1 |
| I:1 | Y:1 | | | | | | E:4 | | S:1 |
| L:1 | T:1 | | | | | | R:3 | | |
| M:1 | | | | | | | S:1 | | |
| | | | | | | | N:1 | | |

| Framework 1 | | | CDR1 | | | | | | |
|---|---|---|---|---|---|---|---|---|---|
| 21 | 22 | 23 | 24 | 25 | 26 | 27 | 28 | 29 | 30 |
| I | S | C | X | X | X | X | X | X | X |
| I:72 | S:70 | C:72 | | | | | | | |
| | P:2 | | | | | | | | |

| CDR1 | | | | | | Framework 2 | | | |
|---|---|---|---|---|---|---|---|---|---|
| 31 | 32 | 33 | 34 | 35 | 36 | 37 | 38 | 39 | 40 |
| X | X | X | X | X | X | W | Y | Q | Q |
| | | | | | | W:72 | Y:70 | Q:64 | Q:63 |
| | | | | | | H:1 | H:4 | H:8 | |
| | | | | | | F:1 | R:2 | L:1 | |
| | | | | | | | L:2 | | |

| Framework 2 | | | | | | | | | |
|---|---|---|---|---|---|---|---|---|---|
| 41 | 42 | 43 | 44 | 45 | 46 | 47 | 48 | 49 | 50 |
| L | P | G | T | A | P | K | L | L | I |
| L:52 | P:72 | G:70 | T:63 | A:71 | P:71 | K:68 | L:69 | L:72 | I:70 |
| F:17 | | P:1 | A:4 | P:1 | K:1 | E:2 | T:1 | | T:2 |
| V:2 | | R:1 | S:3 | | | R:1 | V:1 | | |
| T:1 | | | R:1 | | | N:1 | F:1 | | |
| | | | K:1 | | | | | | |

FIG 18A

| | CDR2 | | | | | | | Framework 3 | |
|---|---|---|---|---|---|---|---|---|---|
| 51 | 52 | 53 | 54 | 55 | 56 | 57 | 58 | 59 | 60 |
| Y | X | X | X | X | X | X | X | G | I |
| Y:71 | | | | | | | | G:70 | I:69 |
| F:1 | | | | | | | | R:1 | V:2 |
| | | | | | | | | S:1 | L:1 |

| Framework 3 | | | | | | | | | |
|---|---|---|---|---|---|---|---|---|---|
| 61 | 62 | 63 | 64 | 65 | 66 | 67 | 68 | 69 | 70 |
| P | D | R | F | S | G | S | K | S | G |
| P:68 | D:68 | R:71 | F:71 | S:72 | G:67 | S:72 | K:68 | S:71 | G:68 |
| S:3 | E:2 | Q:1 | I:1 | | A:5 | | Q:1 | F:1 | A:3 |
| L:1 | V:1 | | | | | | R:1 | | D:1 |
| | G:1 | | | | | | T:1 | | |
| | | | | | | | N:1 | | |

| Framework 3 | | | | | | | | | |
|---|---|---|---|---|---|---|---|---|---|
| 71 | 72 | 73 | 74 | 75 | 76 | 77 | 78 | 79 | 80 |
| T | S | A | T | L | G | I | T | G | L |
| T:70 | S:72 | A:71 | T:71 | L:72 | G:54 | I:72 | T:71 | G:71 | L:72 |
| A:1 | | V:1 | N:1 | | A:6 | | A:1 | R:1 | |
| S:1 | | | | | D:6 | | | | |
| | | | | | V:5 | | | | |
| | | | | | S:1 | | | | |

| Framework 3 | | | | | | | | | |
|---|---|---|---|---|---|---|---|---|---|
| 81 | 82 | 83 | 84 | 85 | 86 | 87 | 88 | 89 | 90 |
| Q | T | G | D | E | A | D | Y | Y | C |
| Q:66 | T:69 | G:67 | D:71 | E:72 | A:71 | D:67 | Y:71 | Y:59 | C:72 |
| W:3 | P:3 | E:3 | Y:1 | | S:1 | H:2 | C:1 | F:11 | |
| R:2 | | W:2 | | | | E:2 | | C:1 | |
| H:1 | | | | | | Y:1 | | L:1 | |

| CDR3 | | | | | | | | | |
|---|---|---|---|---|---|---|---|---|---|
| 91 | 92 | 93 | 94 | 95 | 96 | 97 | 98 | 99 | 100 |
| X | X | X | X | X | X | X | X | X | X |

FIG 18B

| CDR3 | | | | | Framework 4 | | | | |
|---|---|---|---|---|---|---|---|---|---|
| 101 | 102 | 103 | 104 | 105 | 106 | 107 | 108 | 109 | 110 |
| X | X | X | X | X | F | G | G | G | T |
|  |  |  |  |  | F:63 | G:63 | G:56 | G:61 | T:61 |
|  |  |  |  |  | -:9 | -:9 | -:9 | -:9 | -:10 |
|  |  |  |  |  |  |  | A:2 | A:2 | S:1 |
|  |  |  |  |  |  |  | T:2 |  |  |
|  |  |  |  |  |  |  | V:1 |  |  |
|  |  |  |  |  |  |  | S:1 |  |  |
|  |  |  |  |  |  |  | E:1 |  |  |

| Framework 4 | | | | | | | | | |
|---|---|---|---|---|---|---|---|---|---|
| 111 | 112 | 113 | 114 | 115 | 116 | 117 | 118 | 119 | 120 |
| K | L | T | V | L | G | Q | P | K | A |
| K:52 | L:50 | T:60 | V:60 | L:60 | G:36 | -:48 | -:48 | -:70 | -:70 |
| -:10 | V:12 | -:10 | -:10 | -:10 | -:29 | Q:22 | P:21 | K:2 | A:2 |
| Q:4 | -:10 | E:2 | I:2 | K:2 | S:5 | P:1 | A:1 |  |  |
| E:2 |  |  |  |  | R:1 | A:1 | S:1 |  |  |
| R:2 |  |  |  |  | W:1 |  | K:1 |  |  |
| M:1 |  |  |  |  |  |  |  |  |  |
| T:1 |  |  |  |  |  |  |  |  |  |

| Framework 4 | | | | | | | | | |
|---|---|---|---|---|---|---|---|---|---|
| 121 | 122 | 123 | 124 | 125 | 126 | 127 | 128 | 129 | 130 |
| A | P | S | V | T | L | F | P | P | S |
| -:70 | -:70 | -:70 | -:70 | -:70 | -:70 | -:70 | -:70 | -:70 | -:70 |
| A:2 | P:2 | S:2 | V:2 | T:2 | L:2 | F:2 | P:2 | P:2 | S:2 |

| | | | | Framework 1 | | | | | |
|---|---|---|---|---|---|---|---|---|---|
| 1 | 2 | 3 | 4 | 5 | 6 | 7 | 8 | 9 | 10 |
| Q | S | A | L | T | Q | P | A | S | V |
| Q:283 | S:311 | A:290 | L:313 | T:327 | Q:335 | P:346 | A:238 | S:364 | V:285 |
| -:264 | -:253 | -:251 | -:250 | -:241 | -:239 | -:230 | -:223 | -:211 | -:201 |
| P:12 | L:9 | V:20 | V:11 | L:4 | R:3 | A:1 | P:94 | A:2 | A:83 |
| E:10 | A:3 | E:11 | E:3 | S:2 | S:1 | F:1 | R:20 | P:2 | M:7 |
| H:3 | F:1 | Q:6 | X:2 | A:2 | H:1 | S:1 | S:2 | T:1 | E:2 |
| X:2 | P:1 | P:1 | P:1 | D:2 | Z:1 | R:1 | D:2 | | W:1 |
| K:2 | Y:1 | I:1 | | I:2 | | | C:1 | | T:1 |
| A:1 | V:1 | | | | | | | | |
| S:1 | | | | | | | | | |
| R:1 | | | | | | | | | |
| L:1 | | | | | | | | | |

| | | | | Framework 1 | | | | | |
|---|---|---|---|---|---|---|---|---|---|
| 11 | 12 | 13 | 14 | 15 | 16 | 17 | 18 | 19 | 20 |
| S | G | S | P | G | Q | S | I | T | I |
| S:397 | G:406 | S:416 | P:420 | G:441 | Q:455 | S:490 | I:333 | T:543 | I:550 |
| -:174 | -:167 | -:158 | -:149 | -:137 | -:120 | -:87 | V:183 | -:26 | -:16 |
| C:5 | A:4 | A:3 | L:6 | W:1 | T:1 | K:1 | -:61 | A:4 | V:5 |
| F:1 | W:1 | F:2 | R:3 | D:1 | P:1 | P:1 | A:1 | I:3 | F:3 |
| T:1 | E:1 | V:1 | S:1 | | H:1 | V:1 | S:1 | S:2 | L:3 |
| P:1 | R:1 | | G:1 | | R:1 | | D:1 | V:1 | M:2 |
| V:1 | | | | | L:1 | | | H:1 | H:1 |

| | | CDR1 | | | | | | | |
|---|---|---|---|---|---|---|---|---|---|
| 21 | 22 | 23 | 24 | 25 | 26 | 27 | 28 | 29 | 30 |
| S | C | X | X | X | X | X | X | X | X |
| S:561 | C:573 | | | | | | | | |
| -:12 | -:6 | | | | | | | | |
| P:5 | X:1 | | | | | | | | |
| F:1 | | | | | | | | | |
| T:1 | | | | | | | | | |

FIG 19A

| CDR1 | | | | | | Framework 2 | | | |
|---|---|---|---|---|---|---|---|---|---|
| 31 | 32 | 33 | 34 | 35 | 36 | 37 | 38 | 39 | 40 |
| X | X | X | X | X | X | W | Y | Q | Q |
| | | | | | | W:580 | Y:566 | Q:567 | Q:531 |
| | | | | | | F:13 | R:6 | H:34 |
| | | | | | | C:1 | L:5 | Y:5 |
| | | | | | | | E:1 | R:4 |
| | | | | | | | Z:1 | L:2 |
| | | | | | | | | N:1 |
| | | | | | | | | K:1 |
| | | | | | | | | Z:1 |
| | | | | | | | | C:1 |

| Framework 2 | | | | | | | | | |
|---|---|---|---|---|---|---|---|---|---|
| 41 | 42 | 43 | 44 | 45 | 46 | 47 | 48 | 49 | 50 |
| H | P | G | K | A | P | K | L | M | I |
| H:500 | P:571 | G:553 | K:518 | A:556 | P:579 | K:551 | L:514 | M:445 | I:568 |
| Y:25 | S:6 | D:12 | T:39 | V:18 | L:1 | Q:13 | V:33 | I:95 | V:4 |
| P:23 | A:1 | A:10 | R:14 | T:2 | | R:10 | F:22 | L:25 | L:4 |
| R:10 | T:1 | T:2 | E:7 | X:1 | | N:2 | P:4 | V:12 | T:2 |
| Q:9 | Q:1 | V:2 | N:1 | P:1 | | E:2 | I:3 | T:2 | M:2 |
| N:6 | | S:1 | Q:1 | D:1 | | T:1 | A:2 | K:1 | |
| L:4 | | | | G:1 | | X:1 | H:1 | | |
| S:2 | | | | | | | M:1 | | |
| A:1 | | | | | | | | | |

| | CDR2 | | | | | | | Framework 3 | |
|---|---|---|---|---|---|---|---|---|---|
| 51 | 52 | 53 | 54 | 55 | 56 | 57 | 58 | 59 | 60 |
| Y | X | X | X | X | X | X | X | G | V |
| Y:524 | | | | | | | | G:573 | V:548 |
| F:34 | | | | | | | | R:6 | I:27 |
| S:8 | | | | | | | | E:1 | L:2 |
| C:7 | | | | | | | | | A:1 |
| H:4 | | | | | | | | | T:1 |
| N:1 | | | | | | | | | G:1 |
| X:1 | | | | | | | | | |
| L:1 | | | | | | | | | |

FIG 19B

| Framework 3 | | | | | | | | | |
|---|---|---|---|---|---|---|---|---|---|
| 61 | 62 | 63 | 64 | 65 | 66 | 67 | 68 | 69 | 70 |
| S | N | R | F | S | G | S | K | S | G |
| S:355 | N:306 | R:579 | F:573 | S:575 | G:565 | S:574 | K:565 | S:572 | G:557 |
| P:220 | D:233 | P:1 | L:3 | F:2 | A:12 | C:2 | R:10 | F:3 | D:15 |
| X:2 | S:12 | | S:2 | T:1 | F:1 | F:1 | Q:2 | P:2 | A:6 |
| F:1 | Y:8 | | X:1 | P:1 | S:1 | A:1 | S:1 | X:1 | S:1 |
| H:1 | T:7 | | Y:1 | Y:1 | D:1 | P:1 | E:1 | Y:1 | H:1 |
| C:1 | H:6 | | | | L:1 | Y:1 | G:1 | -:1 | |
| | E:2 | | | | | | | | |
| | G:2 | | | | | | | | |
| | F:1 | | | | | | | | |
| | P:1 | | | | | | | | |
| | R:1 | | | | | | | | |
| | I:1 | | | | | | | | |

| Framework 3 | | | | | | | | | |
|---|---|---|---|---|---|---|---|---|---|
| 71 | 72 | 73 | 74 | 75 | 76 | 77 | 78 | 79 | 80 |
| N | T | A | S | L | T | I | S | G | L |
| N:560 | T:574 | A:579 | S:572 | L:578 | T:577 | I:446 | S:573 | G:576 | L:579 |
| S:8 | S:3 | G:1 | F:5 | P:2 | A:2 | V:133 | C:3 | R:3 | V:1 |
| D:6 | A:2 | | H:2 | | I:1 | T:1 | T:2 | E:1 | |
| K:3 | M:1 | | P:1 | | | | F:1 | | |
| T:1 | | | | | | | X:1 | | |
| B:1 | | | | | | | | | |
| H:1 | | | | | | | | | |

| Framework 3 | | | | | | | | | |
|---|---|---|---|---|---|---|---|---|---|
| 81 | 82 | 83 | 84 | 85 | 86 | 87 | 88 | 89 | 90 |
| Q | A | E | D | E | A | D | Y | Y | C |
| Q:559 | A:520 | E:557 | D:578 | E:562 | A:572 | D:547 | Y:573 | Y:553 | C:578 |
| R:11 | P:28 | D:19 | N:1 | G:7 | G:7 | E:9 | F:2 | F:14 | P:1 |
| L:7 | T:19 | Q:2 | G:1 | D:5 | S:1 | H:4 | H:2 | H:8 | R:1 |
| H:2 | S:6 | A:1 | | A:3 | | G:4 | C:2 | S:3 | |
| T:1 | V:5 | G:1 | | K:1 | | N:3 | N:1 | C:2 | |
| | G:2 | | | V:1 | | Y:3 | | | |
| | | | | Q:1 | | V:3 | | | |
| | | | | | | T:2 | | | |
| | | | | | | F:1 | | | |
| | | | | | | A:1 | | | |
| | | | | | | B:1 | | | |
| | | | | | | Q:1 | | | |
| | | | | | | L:1 | | | |

FIG 19C

| CDR3 | | | | | | | | | |
|---|---|---|---|---|---|---|---|---|---|
| 91 | 92 | 93 | 94 | 95 | 96 | 97 | 98 | 99 | 100 |
| X | X | X | X | X | X | X | X | X | X |

| CDR3 | | | | | Framework 4 | | | | |
|---|---|---|---|---|---|---|---|---|---|
| 101 | 102 | 103 | 104 | 105 | 106 | 107 | 108 | 109 | 110 |
| X | X | X | X | X | F | G | G | G | T |
|  |  |  |  |  | F:408 | G:407 | G:297 | G:359 | -:565 |
|  |  |  |  |  | -:101 | -:129 | -:182 | -:203 | T:12 |
|  |  |  |  |  | V:18 | F:20 | T:66 | T:5 | X:1 |
|  |  |  |  |  | S:13 | V:15 | F:14 | A:5 | P:1 |
|  |  |  |  |  | G:13 | A:4 | R:7 | R:3 | G:1 |
|  |  |  |  |  | P:8 | R:2 | S:4 | E:1 |  |
|  |  |  |  |  | W:5 | C:1 | E:4 | V:1 |  |
|  |  |  |  |  | R:4 | X:1 | P:2 | Q:1 |  |
|  |  |  |  |  | L:3 | P:1 | I:2 | X:1 |  |
|  |  |  |  |  | I:3 |  | V:1 | H:1 |  |
|  |  |  |  |  | K:1 |  | A:1 |  |  |

| Framework 4 | | | | | | | | | |
|---|---|---|---|---|---|---|---|---|---|
| 111 | 112 | 113 | 114 | 115 | 116 | 117 | 118 | 119 | 120 |
| T | K | L | T | V | L | G | Q | P | K |
| T:331 | K:273 | -:239 | T:289 | V:286 | -:276 | -:405 | -:441 | -:448 | -:518 |
| -:214 | -:228 | L:210 | -:243 | -:259 | L:272 | G:136 | Q:122 | P:127 | K:54 |
| K:15 | Q:22 | V:102 | V:14 | R:12 | R:10 | S:17 | P:6 | A:2 | Q:2 |
| G:8 | L:14 | T:18 | D:7 | L:11 | F:5 | R:11 | L:3 | G:2 | A:2 |
| P:5 | R:10 | Q:3 | A:5 | T:3 | V:5 | Q:5 | S:1 | D:1 | R:2 |
| A:2 | G:7 | R:2 | S:3 | I:3 | G:5 | V:3 | T:1 |  | X:1 |
| N:1 | T:6 | N:1 | N:3 | S:2 | T:2 | H:2 | K:1 |  | D:1 |
| L:1 | X:5 | K:1 | Q:3 | Q:2 | K:2 | L:1 | Z:1 |  |  |
| X:1 | S:3 | W:1 | L:3 | K:1 | Q:1 |  | A:1 |  |  |
| H:1 | N:3 | P:1 | R:3 | D:1 | W:1 |  | X:1 |  |  |
| R:1 | E:3 | H:1 | K:2 |  | I:1 |  | D:1 |  |  |
|  | M:2 | D:1 | E:2 |  |  |  | G:1 |  |  |
|  | A:2 |  | X:1 |  |  |  |  |  |  |
|  | V:1 |  | P:1 |  |  |  |  |  |  |
|  | D:1 |  | I:1 |  |  |  |  |  |  |

| Framework 4 | | | | | | | | | |
|---|---|---|---|---|---|---|---|---|---|
| 121 | 122 | 123 | 124 | 125 | 126 | 127 | 128 | 129 | 130 |
| A | A | P | S | V | T | L | F | P | P |
| -:522 | -:532 | -:537 | -:540 | -:548 | -:552 | -:555 | -:557 | -:557 | -:557 |
| A:51 | A:36 | P:41 | S:29 | V:28 | T:26 | L:24 | F:23 | P:23 | P:23 |
| P:3 | N:10 | H:2 | T:10 | D:2 | S:1 | G:1 |  |  |  |
| Q:2 | P:2 |  | R:1 | S:1 | M:1 |  |  |  |  |
| L:1 |  |  |  | L:1 |  |  |  |  |  |
| D:1 |  |  |  |  |  |  |  |  |  |

FIG 19D

```
         ┌─────────────────┐
         │   Framework 4   │
         └─────────────────┘
           131       132
           S         S -:557     -:557
           S:23      S:20
                     L:2
                     X:1
```

FIG 19E

| Framework 1 | | | | | | | | | |
|---|---|---|---|---|---|---|---|---|---|
| 1 | 2 | 3 | 4 | 5 | 6 | 7 | 8 | 9 | 10 |
| S | Y | E | L | T | Q | P | P | S | V |
| S:168 | Y:164 | E:169 | L:177 | T:176 | Q:183 | P:176 | P:180 | S:186 | V:185 |
| -:66 | -:63 | -:61 | -:59 | -:59 | -:58 | -:56 | -:55 | -:53 | -:51 |
| Q:3 | S:4 | D:4 | E:3 | M:2 | | A:3 | S:4 | A:1 | A:2 |
| P:2 | H:3 | V:4 | Q:1 | L:2 | | S:2 | A:1 | L:1 | L:2 |
| N:1 | F:3 | Q:3 | M:1 | K:1 | | L:2 | H:1 | | E:1 |
| L:1 | D:3 | | | I:1 | | Q:1 | | | |
| | N:1 | | | | | T:1 | | | |

| Framework 1 | | | | | | | | | |
|---|---|---|---|---|---|---|---|---|---|
| 11 | 12 | 13 | 14 | 15 | 16 | 17 | 18 | 19 | 20 |
| S | V | S | P | G | Q | T | A | R | I |
| S:188 | V:193 | S:193 | P:187 | G:197 | Q:194 | T:193 | A:192 | R:158 | I:209 |
| -:49 | -:48 | -:46 | -:45 | -:42 | -:40 | -:39 | -:37 | S:39 | -:28 |
| A:2 | | P:1 | L:7 | R:1 | H:6 | M:6 | V:5 | -:31 | F:2 |
| T:2 | | Y:1 | S:1 | L:1 | R:1 | R:2 | S:4 | T:8 | T:1 |
| | | | Q:1 | | | S:1 | T:2 | G:4 | L:1 |
| | | | | | | | G:1 | K:1 | |

| | CDR1 | | | | | | | | |
|---|---|---|---|---|---|---|---|---|---|
| 21 | 22 | 23 | 24 | 25 | 26 | 27 | 28 | 29 | 30 |
| T | C | X | X | X | X | X | X | X | X |
| T:225 | C:227 | | | | | | | | |
| -:13 | -:12 | | | | | | | | |
| S:1 | R:2 | | | | | | | | |
| P:1 | | | | | | | | | |
| I:1 | | | | | | | | | |

| CDR1 | | | Framework 2 | | | | | | |
|---|---|---|---|---|---|---|---|---|---|
| 31 | 32 | 33 | 34 | 35 | 36 | 37 | 38 | 39 | 40 |
| X | X | X | W | Y | Q | Q | K | P | G |
| | | | W:241 | Y:234 | Q:237 | Q:228 | K:227 | P:137 | G:237 |
| | | | F:6 | H:2 | R:4 | R:12 | S:93 | S:3 | |
| | | | H:1 | K:1 | L:4 | E:1 | A:8 | D:1 | |
| | | | | R:1 | H:2 | M:1 | T:2 | | |
| | | | | | S:1 | | L:1 | | |
| | | | | | K:1 | | | | |
| | | | | | E:1 | | | | |

FIG 20A

| Framework 2 | | | | | | | | CDR2 | |
|---|---|---|---|---|---|---|---|---|---|
| 41 | 42 | 43 | 44 | 45 | 46 | 47 | 48 | 49 | 50 |
| Q | A | P | V | L | V | I | Y | X | X |
| Q:235 | A:178 | P:240 | V:225 | L:211 | V:224 | I:224 | Y:225 | | |
| L:4 | S:58 | L:1 | M:6 | V:14 | I:8 | M:15 | F:12 | | |
| V:1 | F:5 | | L:5 | M:8 | L:6 | V:2 | S:1 | | |
| R:1 | | | I:4 | Q:4 | A:1 | | T:1 | | |
| | | | A:1 | R:2 | X:1 | | K:1 | | |
| | | | | S:1 | -:1 | | H:1 | | |
| | | | | T:1 | | | | | |

| CDR2 | | | | | Framework 3 | | | | |
|---|---|---|---|---|---|---|---|---|---|
| 51 | 52 | 53 | 54 | 55 | 56 | 57 | 58 | 59 | 60 |
| X | X | X | X | X | G | I | P | E | R |
| | | | | | G:233 | I:240 | P:239 | E:229 | R:237 |
| | | | | | E:6 | V:1 | L:2 | D:5 | Q:3 |
| | | | | | K:1 | | | A:3 | K:1 |
| | | | | | V:1 | | | Q:2 | |
| | | | | | | | | V:1 | |
| | | | | | | | | G:1 | |

| Framework 3 | | | | | | | | | |
|---|---|---|---|---|---|---|---|---|---|
| 61 | 62 | 63 | 64 | 65 | 66 | 67 | 68 | 69 | 70 |
| F | S | G | S | S | S | G | T | T | A |
| F:231 | S:237 | G:235 | S:236 | S:161 | S:234 | G:240 | T:179 | T:140 | A:151 |
| I:4 | I:2 | A:3 | A:3 | N:56 | T:3 | E:1 | N:56 | M:73 | V:89 |
| S:3 | Y:1 | P:2 | F:1 | T:14 | C:2 | | A:2 | V:10 | L:1 |
| L:2 | C:1 | S:1 | P:1 | R:3 | A:1 | | S:1 | I:10 | |
| V:1 | | | | Y:2 | F:1 | | K:1 | A:3 | |
| | | | | I:2 | | | D:1 | K:3 | |
| | | | | A:1 | | | R:1 | S:1 | |
| | | | | H:1 | | | | R:1 | |
| | | | | G:1 | | | | | |

FIG 20B

| | | | | Framework 3 | | | | | |
|---|---|---|---|---|---|---|---|---|---|
| 71 | 72 | 73 | 74 | 75 | 76 | 77 | 78 | 79 | 80 |
| T | L | T | I | S | G | V | Q | A | E |
| T:240 | L:238 | T:230 | I:240 | S:228 | G:235 | V:90 | Q:233 | A:141 | E:177 |
| A:1 | S:2 | I:9 | N:1 | T:9 | E:2 | A:89 | H:4 | V:86 | M:51 |
| | Q:1 | N:1 | | I:2 | R:2 | T:59 | R:3 | T:6 | D:3 |
| | | K:1 | | A:1 | A:1 | P:2 | L:1 | M:3 | L:3 |
| | | | | G:1 | D:1 | I:1 | | L:3 | T:2 |
| | | | | | | | | S:1 | V:2 |
| | | | | | | | | P:1 | G:2 |
| | | | | | | | | | I:1 |

| | | | Framework 3 | | | | CDR3 | |
|---|---|---|---|---|---|---|---|---|
| 81 | 82 | 83 | 84 | 85 | 86 | 87 | 88 | 89 | 90 |
| D | E | A | D | Y | Y | C | X | X | X |
| D:238 | E:233 | A:228 | D:231 | Y:241 | Y:234 | C:238 | | | |
| G:3 | D:5 | G:6 | E:5 | | F:4 | Y:1 | | | |
| | G:2 | S:4 | A:1 | | H:2 | -:1 | | | |
| | A:1 | D:2 | Y:1 | | N:1 | R:1 | | | |
| | | V:1 | V:1 | | | | | | |
| | | | I:1 | | | | | | |
| | | | G:1 | | | | | | |

| | | | | CDR3 | | | | | |
|---|---|---|---|---|---|---|---|---|---|
| 91 | 92 | 93 | 94 | 95 | 96 | 97 | 98 | 99 | 100 |
| X | X | X | X | X | X | X | X | X | X |

| | | | | Framework 4 | | | | | |
|---|---|---|---|---|---|---|---|---|---|
| 101 | 102 | 103 | 104 | 105 | 106 | 107 | 108 | 109 | 110 |
| F | G | G | G | T | K | L | T | V | L |
| F:218 | G:215 | G:143 | G:177 | T:171 | K:153 | L:139 | T:169 | V:174 | L:171 |
| -:20 | -:25 | -:63 | -:64 | -:64 | -:65 | -:65 | -:65 | -:65 | -:67 |
| S:1 | D:1 | T:25 | | S:2 | R:12 | V:35 | S:4 | M:1 | T:1 |
| V:1 | | P:3 | | A:2 | T:5 | M:1 | A:2 | I:1 | V:1 |
| L:1 | | R:3 | | I:2 | E:2 | X:1 | P:1 | | R:1 |
| | | S:2 | | | Q:2 | | | | |
| | | L:1 | | | M:1 | | | | |
| | | I:1 | | | H:1 | | | | |

FIG 20C

| Framework 4 | | | | | | | | | |
|---|---|---|---|---|---|---|---|---|---|
| 111 | 112 | 113 | 114 | 115 | 116 | 117 | 118 | 119 | 120 |
| G | Q | P | K | A | A | P | S | V | T |
| -:173 | -:182 | -:182 | -:219 | -:219 | -:220 | -:221 | -:222 | -:222 | -:223 |
| G:57 | Q:59 | P:59 | K:22 | A:22 | A:16 | P:20 | S:13 | V:18 | T:17 |
| R:5 | | | | | N:5 | | T:5 | R:1 | S:1 |
| S:4 | | | | | | | L:1 | | |
| K:1 | | | | | | | | | |
| C:1 | | | | | | | | | |

| Framework 4 | | | | | | | | | |
|---|---|---|---|---|---|---|---|---|---|
| 121 | 122 | 123 | 124 | 125 | 126 | 127 | 128 | 129 | 130 |
| L | F | P | P | S | S | E | E | L | Q |
| -:224 | -:224 | -:224 | -:224 | -:225 | -:225 | -:233 | -:234 | -:234 | -:234 |
| L:17 | F:15 | P:16 | P:16 | S:14 | S:11 | E:7 | E:7 | L:7 | Q:7 |
| | Y:1 | S:1 | H:1 | L:1 | L:3 | G:1 | | | |
| | C:1 | | | P:1 | K:1 | | | | |
| | | | | | P:1 | | | | |

| Framework 4 | | | | |
|---|---|---|---|---|
| 131 | 132 | 133 | 134 | 135 |
| A | N | K | A | T |
| -:234 | -:234 | -:234 | -:234 | -:234 |
| A:7 | N:7 | K:7 | A:7 | T:7 |

FIG 20D

| | | | | Framework 1 | | | | | |
|---|---|---|---|---|---|---|---|---|---|
| 1 | 2 | 3 | 4 | 5 | 6 | 7 | 8 | 9 | 10 |
| S | Y | V | L | T | Q | P | P | S | V |
| -:97 | Y:94 | V:94 | L:110 | T:110 | Q:115 | P:117 | P:120 | S:124 | V:128 |
| S:95 | -:87 | -:87 | -:86 | -:85 | -:84 | -:80 | -:72 | -:71 | -:67 |
| Q:5 | S:13 | E:12 | V:4 | S:2 | H:2 | S:2 | L:6 | A:4 | L:4 |
| E:3 | D:3 | D:4 | E:1 | N:1 | | A:1 | H:2 | P:1 | A:1 |
| F:1 | L:3 | Q:2 | | I:1 | | T:1 | R:1 | L:1 | E:1 |
| | C:1 | I:1 | | P:1 | | | | | |
| | | L:1 | | L:1 | | | | | |

| | | | | Framework 1 | | | | | |
|---|---|---|---|---|---|---|---|---|---|
| 11 | 12 | 13 | 14 | 15 | 16 | 17 | 18 | 19 | 20 |
| S | V | A | P | G | Q | T | A | R | I |
| S:138 | V:135 | A:143 | P:129 | G:151 | Q:113 | T:159 | A:168 | R:154 | I:177 |
| -:62 | -:61 | -:56 | -:52 | -:45 | K:43 | -:37 | -:30 | -:25 | -:18 |
| X:1 | E:2 | P:1 | L:14 | A:4 | -:40 | M:5 | D:1 | T:10 | F:3 |
| | A:1 | V:1 | T:5 | E:1 | M:2 | | G:1 | S:9 | L:2 |
| | P:1 | | X:1 | | T:1 | | V:1 | W:1 | V:1 |
| | L:1 | | | | R:1 | | | I:1 | |
| | | | | | L:1 | | | K:1 | |

| | | | CDR1 | | | | | | |
|---|---|---|---|---|---|---|---|---|---|
| 21 | 22 | 23 | 24 | 25 | 26 | 27 | 28 | 29 | 30 |
| T | C | X | X | X | X | X | X | X | X |
| T:173 | C:195 | | | | | | | | |
| -:10 | -:6 | | | | | | | | |
| S:6 | | | | | | | | | |
| A:5 | | | | | | | | | |
| P:4 | | | | | | | | | |
| N:2 | | | | | | | | | |
| I:1 | | | | | | | | | |

| CDR1 | | | Framework 2 | | | | | | |
|---|---|---|---|---|---|---|---|---|---|
| 31 | 32 | 33 | 34 | 35 | 36 | 37 | 38 | 39 | 40 |
| X | X | X | W | Y | Q | Q | K | P | G |
| | | | W:201 | Y:199 | Q:198 | Q:197 | K:187 | P:190 | G:199 |
| | | | | F:2 | Y:1 | R:2 | R:11 | S:5 | A:1 |
| | | | | | H:1 | K:1 | E:1 | A:3 | D:1 |
| | | | | | R:1 | H:1 | Q:1 | T:3 | |
| | | | | | | | M:1 | | |

FIG 21A

| | | | | Framework 2 | | | | | CDR2 |
|---|---|---|---|---|---|---|---|---|---|
| 41 | 42 | 43 | 44 | 45 | 46 | 47 | 48 | 49 | 50 |
| Q | A | P | V | L | V | V | Y | D | X |
| Q:199 | A:197 | P:200 | V:186 | L:187 | V:198 | V:129 | Y:174 | D:128 | |
| R:1 | D:4 | S:1 | L:5 | V:8 | I:3 | I:68 | F:17 | Y:38 | |
| L:1 | | | E:4 | M:4 | | M:3 | H:7 | R:15 | |
| | | | A:3 | P:2 | | L:1 | S:1 | S:6 | |
| | | | I:2 | | | | Q:1 | E:4 | |
| | | | K:1 | | | | C:1 | H:3 | |
| | | | | | | | | G:3 | |
| | | | | | | | | F:2 | |
| | | | | | | | | A:1 | |
| | | | | | | | | C:1 | |

| | CDR2 | | | | | Framework 3 | | | |
|---|---|---|---|---|---|---|---|---|---|
| 51 | 52 | 53 | 54 | 55 | 56 | 57 | 58 | 59 | 60 |
| X | X | X | X | X | G | I | P | E | R |
| | | | | | G:196 | I:196 | P:200 | E:193 | R:201 |
| | | | | | R:2 | T:2 | S:1 | D:5 | |
| | | | | | A:1 | F:1 | | A:2 | |
| | | | | | X:1 | V:1 | | K:1 | |
| | | | | | E:1 | L:1 | | | |

| | | | | Framework 3 | | | | | |
|---|---|---|---|---|---|---|---|---|---|
| 61 | 62 | 63 | 64 | 65 | 66 | 67 | 68 | 69 | 70 |
| F | S | G | S | N | S | G | N | T | A |
| F:198 | S:201 | G:201 | S:201 | N:181 | S:192 | G:193 | N:192 | T:194 | A:198 |
| V:2 | | | | K:8 | P:5 | E:4 | D:4 | A:2 | T:2 |
| L:1 | | | | I:5 | L:3 | R:3 | S:2 | M:2 | V:1 |
| | | | | T:3 | X:1 | D:1 | H:2 | R:2 | |
| | | | | H:3 | | | T:1 | P:1 | |
| | | | | D:1 | | | | | |

| | | | | Framework 3 | | | | | |
|---|---|---|---|---|---|---|---|---|---|
| 71 | 72 | 73 | 74 | 75 | 76 | 77 | 78 | 79 | 80 |
| T | L | T | I | S | R | V | E | A | G |
| T:198 | L:201 | T:198 | I:198 | S:185 | R:188 | V:182 | E:178 | A:187 | G:201 |
| S:1 | | I:2 | S:1 | T:8 | G:7 | A:15 | Q:16 | S:5 | |
| A:1 | | A:1 | N:1 | N:5 | W:2 | I:4 | A:3 | V:5 | |
| I:1 | | | V:1 | R:2 | S:1 | | G:2 | G:2 | |
| | | | | I:1 | T:1 | | X:1 | P:1 | |
| | | | | | X:1 | | D:1 | D:1 | |
| | | | | | M:1 | | | | |

FIG 21B

| Framework 3 | | | | | | | CDR3 | | |
|---|---|---|---|---|---|---|---|---|---|
| 81 | 82 | 83 | 84 | 85 | 86 | 87 | 88 | 89 | 90 |
| D | E | A | D | Y | Y | C | X | X | X |
| D:201 | E:198 | A:198 | D:193 | Y:195 | Y:193 | C:201 | | | |
| | A:1 | V:2 | A:4 | F:6 | F:3 | | | | |
| | Q:1 | G:1 | G:2 | | H:3 | | | | |
| | G:1 | | E:1 | | S:1 | | | | |
| | | | V:1 | | C:1 | | | | |

| CDR3 | | | | | | | | | |
|---|---|---|---|---|---|---|---|---|---|
| 91 | 92 | 93 | 94 | 95 | 96 | 97 | 98 | 99 | 100 |
| X | X | X | X | X | X | X | X | X | X |

| Framework 4 | | | | | | | | | |
|---|---|---|---|---|---|---|---|---|---|
| 101 | 102 | 103 | 104 | 105 | 106 | 107 | 108 | 109 | 110 |
| F | G | G | G | T | K | L | T | V | L |
| F:145 | G:147 | G:99 | G:122 | T:116 | K:100 | -:80 | T:105 | V:105 | L:105 |
| -:25 | -:36 | -:59 | -:66 | -:73 | -:75 | L:72 | -:82 | -:82 | -:86 |
| G:11 | R:6 | T:28 | T:6 | K:5 | L:5 | V:38 | V:5 | L:4 | V:3 |
| V:7 | F:5 | F:5 | S:2 | G:2 | E:4 | T:5 | N:4 | A:3 | P:3 |
| S:5 | V:5 | S:3 | A:2 | L:1 | Q:4 | D:2 | A:2 | G:2 | T:1 |
| W:3 | S:1 | R:3 | H:2 | X:1 | T:3 | K:1 | S:1 | S:1 | D:1 |
| R:3 | X:1 | A:2 | E:1 | P:1 | A:3 | Y:1 | L:1 | T:1 | I:1 |
| A:1 | | E:1 | | H:1 | R:2 | P:1 | R:1 | N:1 | G:1 |
| I:1 | | P:1 | | D:1 | S:1 | I:1 | | E:1 | |
| | | | | | N:1 | | | X:1 | |
| | | | | | M:1 | | | | |
| | | | | | P:1 | | | | |
| | | | | | H:1 | | | | |

| Framework 4 | | | | | | | | | |
|---|---|---|---|---|---|---|---|---|---|
| 111 | 112 | 113 | 114 | 115 | 116 | 117 | 118 | 119 | 120 |
| G | Q | P | K | A | A | P | T | V | T |
| -:134 | -:147 | -:151 | -:182 | -:182 | -:182 | -:190 | -:194 | -:196 | -:197 |
| G:55 | Q:48 | P:48 | K:19 | A:19 | A:15 | P:11 | T:3 | V:5 | T:3 |
| R:4 | G:4 | G:2 | | | N:4 | | S:2 | | I:1 |
| S:3 | M:1 | | | | | | K:1 | | |
| N:1 | A:1 | | | | | | L:1 | | |
| E:1 | | | | | | | | | |
| M:1 | | | | | | | | | |
| L:1 | | | | | | | | | |
| I:1 | | | | | | | | | |

FIG 21C

|  |  |  |  | Framework 1 |  |  |  |  |  |
|---|---|---|---|---|---|---|---|---|---|
| 1 | 2 | 3 | 4 | 5 | 6 | 7 | 8 | 9 | 10 |
| S | Y | E | L | T | Q | P | P | S | V |
| S:55 | Y:62 | E:58 | L:68 | T:67 | Q:73 | P:71 | P:70 | S:73 | V:70 |
| -:21 | -:12 | -:9 | -:6 | -:6 | -:6 | -:5 | -:5 | -:5 | -:5 |
| Q:3 | S:4 | D:7 | V:3 | A:2 |  | T:2 | A:3 | A:1 | L:3 |
|  | F:1 | Q:3 | E:2 | L:2 |  | S:1 | T:1 |  | M:1 |
|  |  | V:1 |  | S:1 |  |  |  |  |  |
|  |  | G:1 |  | F:1 |  |  |  |  |  |

|  |  |  |  | Framework 1 |  |  |  |  |  |
|---|---|---|---|---|---|---|---|---|---|
| 11 | 12 | 13 | 14 | 15 | 16 | 17 | 18 | 19 | 20 |
| S | V | S | P | G | Q | T | A | S | I |
| S:74 | V:74 | S:72 | P:75 | G:75 | Q:74 | T:74 | A:73 | S:65 | I:76 |
| -:5 | -:3 | -:3 | -:3 | -:3 | -:3 | -:3 | P:2 | T:7 | -:1 |
|  | Q:1 | F:2 | Q:1 | D:1 | R:1 | Q:1 | V:2 | R:3 | F:1 |
|  | C:1 | P:1 |  |  | E:1 | S:1 | -:1 | N:3 | V:1 |
|  |  | A:1 |  |  |  |  | G:1 | -:1 |  |

|  |  | CDR1 |  |  |  |  |  |  |  |
|---|---|---|---|---|---|---|---|---|---|
| 21 | 22 | 23 | 24 | 25 | 26 | 27 | 28 | 29 | 30 |
| T | C | X | X | X | X | X | X | X | X |
| T:71 | C:78 |  |  |  |  |  |  |  |  |
| S:4 | -:1 |  |  |  |  |  |  |  |  |
| P:1 |  |  |  |  |  |  |  |  |  |
| A:1 |  |  |  |  |  |  |  |  |  |
| I:1 |  |  |  |  |  |  |  |  |  |
| -:1 |  |  |  |  |  |  |  |  |  |

| CDR1 |  |  | Framework 2 |  |  |  |  |  |  |
|---|---|---|---|---|---|---|---|---|---|
| 31 | 32 | 33 | 34 | 35 | 36 | 37 | 38 | 39 | 40 |
| X | X | X | W | Y | Q | Q | K | P | G |
|  |  |  | W:78 | Y:78 | Q:78 | Q:75 | K:72 | P:75 | G:79 |
|  |  |  | -:1 | F:1 | R:1 | L:2 | R:6 | S:2 |  |
|  |  |  |  |  |  | R:1 | Q:1 | T:1 |  |
|  |  |  |  |  |  | K:1 |  | L:1 |  |

FIG 22A

| Framework 2 | | | | | | | | CDR2 | |
|---|---|---|---|---|---|---|---|---|---|
| 41 | 42 | 43 | 44 | 45 | 46 | 47 | 48 | 49 | 50 |
| Q | S | P | V | L | V | I | Y | X | X |
| Q:77 | S:76 | P:79 | V:74 | L:70 | V:70 | I:76 | Y:69 | | |
| P:1 | P:1 | | I:2 | V:5 | L:5 | L:2 | F:4 | | |
| H:1 | A:1 | | L:2 | R:3 | I:4 | M:1 | H:2 | | |
| | V:1 | | M:1 | M:1 | | | C:2 | | |
| | | | | | | | S:2 | | |

| CDR2 | | | | | Framework 3 | | | | |
|---|---|---|---|---|---|---|---|---|---|
| 51 | 52 | 53 | 54 | 55 | 56 | 57 | 58 | 59 | 60 |
| X | X | X | X | X | G | I | P | E | R |
| | | | | | G:78 | I:77 | P:78 | E:74 | R:79 |
| | | | | | W:1 | T:1 | S:1 | G:3 | |
| | | | | | | V:1 | | P:1 | |
| | | | | | | | | D:1 | |

| Framework 3 | | | | | | | | | |
|---|---|---|---|---|---|---|---|---|---|
| 61 | 62 | 63 | 64 | 65 | 66 | 67 | 68 | 69 | 70 |
| F | S | G | S | N | S | G | N | T | A |
| F:79 | S:76 | G:77 | S:78 | N:74 | S:78 | G:79 | N:70 | T:79 | A:78 |
| | A:3 | A:2 | A:1 | T:2 | F:1 | | D:4 | | V:1 |
| | | | | H:1 | | | S:2 | | |
| | | | | S:1 | | | K:2 | | |
| | | | | K:1 | | | T:1 | | |

| Framework 3 | | | | | | | | | |
|---|---|---|---|---|---|---|---|---|---|
| 71 | 72 | 73 | 74 | 75 | 76 | 77 | 78 | 79 | 80 |
| T | L | T | I | S | G | T | Q | A | M |
| T:76 | L:79 | T:77 | I:79 | S:73 | G:78 | T:76 | Q:78 | A:73 | M:71 |
| I:1 | | I:1 | | T:4 | V:1 | A:1 | V:1 | T:3 | L:5 |
| A:1 | | S:1 | | I:1 | | S:1 | | S:2 | V:3 |
| S:1 | | | | V:1 | | N:1 | | V:1 | |

FIG 22B

| | Framework 3 | | | | | | CDR3 | | |
|---|---|---|---|---|---|---|---|---|---|
| 81 | 82 | 83 | 84 | 85 | 86 | 87 | 88 | 89 | 90 |
| D | E | A | D | Y | Y | C | X | X | X |
| D:79 | E:79 | A:78 G:1 | D:79 | Y:79 | Y:76 F:3 | C:79 | | | |

| | | | CDR3 | | | | | Framework 4 | |
|---|---|---|---|---|---|---|---|---|---|
| 91 | 92 | 93 | 94 | 95 | 96 | 97 | 98 | 99 | 100 |
| X | X | X | X | X | X | X | X | F | G |
| | | | | | | | | F:67 -:10 L:2 | G:68 -:10 L:1 |

| | | | | Framework 4 | | | | | |
|---|---|---|---|---|---|---|---|---|---|
| 101 | 102 | 103 | 104 | 105 | 106 | 107 | 108 | 109 | 110 |
| G | G | T | K | L | T | V | L | G | Q |
| G:47 T:19 -:10 P:1 Q:1 S:1 | G:68 -:10 P:1 | T:68 -:11 | K:62 -:12 R:2 Q:1 E:1 Y:1 | L:43 V:22 -:14 | T:65 -:14 | V:64 -:14 I:1 | L:64 -:14 P:1 | -:49 G:29 S:1 | -:61 Q:18 |

| | | | | Framework 4 | | | | | |
|---|---|---|---|---|---|---|---|---|---|
| 111 | 112 | 113 | 114 | 115 | 116 | 117 | 118 | 119 | 120 |
| P | K | A | A | P | S | R | S | L | C |
| -:61 P:18 | -:77 K:2 | -:77 A:2 | -:77 A:2 | -:77 P:2 | -:77 S:1 L:1 | -:77 R:1 V:1 | -:77 S:1 T:1 | -:77 L:2 | -:77 C:1 F:1 |

| | Framework 4 | | |
|---|---|---|---|
| 121 | 122 | 123 | 124 |
| P | P | P | P |
| -:77 P:1 S:1 | -:77 P:1 H:1 | -:77 P:1 S:1 | -:77 P:1 S:1 |

FIG 22C

Framework 1

| 1 | 2 | 3 | 4 | 5 | 6 | 7 | 8 | 9 | 10 |
|---|---|---|---|---|---|---|---|---|---|
| S | S | E | L | T | Q | D | P | A | V |
| S:80 | S:96 | E:98 | L:101 | T:100 | Q:114 | D:117 | P:116 | A:93 | V:118 |
| -:58 | -:42 | -:37 | -:29 | -:27 | -:26 | -:25 | -:25 | -:24 | -:24 |
| A:2 | Y:2 | A:4 | E:12 | L:15 | K:2 | | S:1 | V:23 | |
| Q:1 | A:1 | M:1 | | | | | | P:1 | |
| N:1 | F:1 | D:1 | | | | | | G:1 | |
| | | V:1 | | | | | | | |

Framework 1

| 11 | 12 | 13 | 14 | 15 | 16 | 17 | 18 | 19 | 20 |
|---|---|---|---|---|---|---|---|---|---|
| S | V | A | L | G | Q | T | V | R | I |
| S:120 | V:121 | A:120 | L:128 | G:130 | Q:134 | T:133 | V:135 | R:136 | I:136 |
| -:21 | -:20 | -:17 | -:13 | -:12 | -:7 | -:7 | -:5 | K:3 | T:2 |
| P:1 | M:1 | G:5 | F:1 | | E:1 | A:1 | A:1 | -:2 | -:1 |
| | | | | | | K:1 | I:1 | T:1 | F:1 |

CDR1

| 21 | 22 | 23 | 24 | 25 | 26 | 27 | 28 | 29 | 30 |
|---|---|---|---|---|---|---|---|---|---|
| T | C | X | X | X | X | X | X | X | X |
| T:141 | C:142 | | | | | | | | |
| P:1 | | | | | | | | | |

CDR1 / Framework 2

| 31 | 32 | 33 | 34 | 35 | 36 | 37 | 38 | 39 | 40 |
|---|---|---|---|---|---|---|---|---|---|
| X | X | X | W | Y | Q | Q | K | P | G |
| | | | W:142 | Y:140 | Q:141 | Q:138 | K:140 | P:142 | G:139 |
| | | | | S:1 | H:1 | K:1 | S:1 | | R:3 |
| | | | | F:1 | | E:1 | R:1 | | |
| | | | | | | V:1 | | | |
| | | | | | | R:1 | | | |

Framework 2 / CDR2

| 41 | 42 | 43 | 44 | 45 | 46 | 47 | 48 | 49 | 50 |
|---|---|---|---|---|---|---|---|---|---|
| Q | A | P | V | L | V | I | Y | X | X |
| Q:141 | A:142 | P:142 | V:115 | L:137 | V:139 | I:121 | Y:137 | | |
| K:1 | | | I:11 | F:3 | L:2 | M:11 | F:3 | | |
| | | | L:9 | V:2 | F:1 | V:5 | S:1 | | |
| | | | A:3 | | | F:2 | R:1 | | |
| | | | T:2 | | | T:2 | | | |
| | | | K:2 | | | L:1 | | | |

FIG 23A

| CDR2 | | | | | Framework 3 | | | | |
|---|---|---|---|---|---|---|---|---|---|
| 51 | 52 | 53 | 54 | 55 | 56 | 57 | 58 | 59 | 60 |
| X | X | X | X | X | G | I | P | D | R |
| | | | | | G:141 | I:140 | P:142 | D:134 | R:142 |
| | | | | | R:1 | T:1 | | Y:4 | |
| | | | | | | V:1 | | A:2 | |
| | | | | | | | | B:1 | |
| | | | | | | | | G:1 | |

| Framework 3 | | | | | | | | | |
|---|---|---|---|---|---|---|---|---|---|
| 61 | 62 | 63 | 64 | 65 | 66 | 67 | 68 | 69 | 70 |
| F | S | G | S | S | S | G | N | T | A |
| F:142 | S:141 | G:141 | S:142 | S:118 | S:141 | G:139 | N:127 | T:140 | A:135 |
| | F:1 | A:1 | | N:10 | P:1 | A:1 | D:7 | M:1 | D:3 |
| | | | | T:6 | | E:1 | T:3 | I:1 | G:2 |
| | | | | I:3 | | R:1 | S:2 | | S:1 |
| | | | | R:2 | | | Q:2 | | V:1 |
| | | | | G:2 | | | H:1 | | |
| | | | | Y:1 | | | | | |

| Framework 3 | | | | | | | | | |
|---|---|---|---|---|---|---|---|---|---|
| 71 | 72 | 73 | 74 | 75 | 76 | 77 | 78 | 79 | 80 |
| S | L | T | I | T | G | A | Q | A | E |
| S:139 | L:140 | T:141 | I:141 | T:137 | G:141 | A:134 | Q:138 | A:142 | E:140 |
| A:2 | T:1 | G:1 | V:1 | A:2 | T:1 | T:6 | R:3 | | D:1 |
| T:1 | W:1 | | | S:1 | | S:1 | E:1 | | G:1 |
| | | | | N:1 | | V:1 | | | |
| | | | | I:1 | | | | | |

| Framework 3 | | | | | | | CDR3 | | |
|---|---|---|---|---|---|---|---|---|---|
| 81 | 82 | 83 | 84 | 85 | 86 | 87 | 88 | 89 | 90 |
| D | E | A | D | Y | Y | C | X | X | X |
| D:140 | E:140 | A:141 | D:141 | Y:141 | Y:139 | C:142 | | | |
| E:2 | K:1 | G:1 | A:1 | F:1 | S:1 | | | | |
| | G:1 | | | | F:1 | | | | |
| | | | | | H:1 | | | | |

| CDR3 | | | | | | | | | |
|---|---|---|---|---|---|---|---|---|---|
| 91 | 92 | 93 | 94 | 95 | 96 | 97 | 98 | 99 | 100 |
| X | X | X | X | X | X | X | X | X | X |

FIG 23B

| | Framework 4 | | | | | | | | |
|---|---|---|---|---|---|---|---|---|---|
| 101 | 102 | 103 | 104 | 105 | 106 | 107 | 108 | 109 | 110 |
| X | F | G | G | G | T | K | L | T | V |
| | F:126 | G:121 | G:101 | G:115 | T:113 | K:108 | L:98 | T:111 | V:108 |
| | -:12 | -:21 | -:27 | -:27 | -:27 | -:29 | -:30 | -:30 | -:31 |
| | L:2 | | T:7 | | I:2 | R:2 | V:14 | D:1 | H:1 |
| | S:1 | | S:3 | | | T:1 | | | I:1 |
| | Y:1 | | I:2 | | | X:1 | | | R:1 |
| | | | H:1 | | | Q:1 | | | |
| | | | C:1 | | | | | | |

| | Framework 4 | | | | | | | | |
|---|---|---|---|---|---|---|---|---|---|
| 111 | 112 | 113 | 114 | 115 | 116 | 117 | 118 | 119 | 120 |
| L | G | Q | P | K | A | A | P | S | V |
| L:106 | -:94 | -:124 | -:124 | -:136 | -:136 | -:136 | -:136 | -:136 | -:137 |
| -:33 | G:44 | Q:18 | P:18 | K:6 | A:6 | A:6 | P:6 | S:6 | V:5 |
| P:1 | S:3 | | | | | | | | |
| D:1 | R:1 | | | | | | | | |
| G:1 | | | | | | | | | |

| | Framework 4 | | | | | |
|---|---|---|---|---|---|---|
| 121 | 122 | 123 | 124 | 125 | 126 | 127 |
| T | L | F | P | P | S | S |
| -:138 | -:138 | -:138 | -:138 | -:138 | -:138 | -:138 |
| T:4 | L:4 | F:4 | P:4 | P:4 | S:4 | S:4 |

FIG 23C

| | | | | Framework 1 | | | | | |
|---|---|---|---|---|---|---|---|---|---|
| 1 | 2 | 3 | 4 | 5 | 6 | 7 | 8 | 9 | 10 |
| Q | P | V | L | T | Q | S | S | S | A |
| Q:20 | P:20 | V:20 | L:20 | T:20 | Q:20 | S:20 | S:20 | S:20 | A:20 |
| -:4 | -:4 | -:4 | -:4 | -:4 | -:4 | -:4 | -:4 | -:4 | -:4 |

| | | | | Framework 1 | | | | | |
|---|---|---|---|---|---|---|---|---|---|
| 11 | 12 | 13 | 14 | 15 | 16 | 17 | 18 | 19 | 20 |
| S | A | S | L | G | S | S | V | K | L |
| S:20 | A:20 | S:20 | L:20 | G:20 | S:21 | S:20 | V:21 | K:20 | L:21 |
| -:4 | -:4 | -:4 | -:4 | -:4 | -:3 | -:3 | -:3 | -:2 | -:2 |
| | | | | | | L:1 | | R:1 | V:1 |
| | | | | | | | | E:1 | |

| | | | | | | CDR1 | | | |
|---|---|---|---|---|---|---|---|---|---|
| 21 | 22 | 23 | 24 | 25 | 26 | 27 | 28 | 29 | 30 |
| T | C | X | X | X | X | X | X | X | X |
| T:23 | C:23 | | | | | | | | |
| -:1 | -:1 | | | | | | | | |

| CDR1 | | | | Framework 2 | | | | | |
|---|---|---|---|---|---|---|---|---|---|
| 31 | 32 | 33 | 34 | 35 | 36 | 37 | 38 | 39 | 40 |
| X | X | X | X | W | H | Q | Q | Q | P |
| | | | | W:24 | H:24 | Q:24 | Q:22 | Q:24 | P:24 |
| | | | | | | | H:1 | | |
| | | | | | | | R:1 | | |

| | | | | Framework 2 | | | | | CDR2 |
|---|---|---|---|---|---|---|---|---|---|
| 41 | 42 | 43 | 44 | 45 | 46 | 47 | 48 | 49 | 50 |
| G | K | A | P | R | Y | L | M | K | X |
| G:24 | K:24 | A:23 | P:24 | R:24 | Y:23 | L:24 | M:24 | K:24 | |
| | | G:1 | | | F:1 | | | | |

| | | | | CDR2 | | | | | |
|---|---|---|---|---|---|---|---|---|---|
| 51 | 52 | 53 | 54 | 55 | 56 | 57 | 58 | 59 | 60 |
| X | X | X | X | X | X | X | X | X | X |

| | | | | Framework 3 | | | | | |
|---|---|---|---|---|---|---|---|---|---|
| 61 | 62 | 63 | 64 | 65 | 66 | 67 | 68 | 69 | 70 |
| G | V | P | D | R | F | S | G | S | S |
| G:18 | V:21 | P:23 | D:22 | R:24 | F:24 | S:24 | G:24 | S:24 | S:24 |
| -:6 | D:2 | S:1 | N:2 | | | | | | |
| | -:1 | | | | | | | | |

FIG 24A

| | | | | | Framework 3 | | | | |
|---|---|---|---|---|---|---|---|---|---|
| 71 | 72 | 73 | 74 | 75 | 76 | 77 | 78 | 79 | 80 |
| S | G | A | D | R | Y | L | T | I | S |
| S:24 | G:24 | A:24 | D:24 | R:24 | Y:24 | L:24 | T:24 | I:24 | S:24 |

| | | | | | Framework 3 | | | | |
|---|---|---|---|---|---|---|---|---|---|
| 81 | 82 | 83 | 84 | 85 | 86 | 87 | 88 | 89 | 90 |
| N | L | Q | S | E | D | E | A | D | Y |
| N:24 | L:24 | Q:24 | S:18 | E:20 | D:24 | E:22 | A:24 | D:24 | Y:21 |
| | | | F:4 | D:4 | | Q:2 | | | H:3 |
| | | | L:2 | | | | | | |

| | | | | | CDR3 | | | | |
|---|---|---|---|---|---|---|---|---|---|
| 91 | 92 | 93 | 94 | 95 | 96 | 97 | 98 | 99 | 100 |
| Y | C | X | X | X | X | X | X | X | X |
| Y:24 | C:24 | | | | | | | | |

| CDR3 | | | | | Framework 4 | | | | |
|---|---|---|---|---|---|---|---|---|---|
| 101 | 102 | 103 | 104 | 105 | 106 | 107 | 108 | 109 | 110 |
| X | X | F | G | G | G | T | K | L | T |
| | | F:15 | G:17 | G:16 | G:14 | T:17 | K:16 | L:14 | T:12 |
| | | -:7 | -:7 | -:7 | -:9 | -:7 | -:7 | -:7 | -:12 |
| | | G:2 | | S:1 | D:1 | | T:1 | V:3 | |

| | | | | | Framework 4 | | | | |
|---|---|---|---|---|---|---|---|---|---|
| 111 | 112 | 113 | 114 | 115 | 116 | 117 | 118 | 119 | 120 |
| V | L | G | Q | P | K | A | A | P | S |
| -:13 | -:14 | -:16 | -:17 | -:17 | -:20 | -:22 | -:23 | -:23 | -:23 |
| V:11 | L:10 | G:8 | Q:7 | P:7 | K:4 | A:2 | A:1 | P:1 | S:1 |

| Framework 4 | | | |
|---|---|---|---|
| 121 | 122 | 123 | 124 |
| V | T | L | F |
| -:23 | -:23 | -:23 | -:23 |
| V:1 | T:1 | L:1 | F:1 |

FIG 24B

| | | | | Framework 1 | | | | | |
|---|---|---|---|---|---|---|---|---|---|
| 1 | 2 | 3 | 4 | 5 | 6 | 7 | 8 | 9 | 10 |
| Q | L | V | L | T | Q | S | P | S | A |
| Q:41 | L:40 | V:37 | L:59 | T:61 | Q:61 | S:61 | P:61 | S:61 | A:61 |
| -:22 | -:22 | A:17 | -:3 | -:3 | -:3 | -:3 | -:3 | -:3 | -:2 |
| H:1 | I:2 | -:3 | V:2 | | | | | | C:1 |
| | | Q:3 | | | | | | | |
| | | L:2 | | | | | | | |
| | | E:2 | | | | | | | |

| | | | | Framework 1 | | | | | |
|---|---|---|---|---|---|---|---|---|---|
| 11 | 12 | 13 | 14 | 15 | 16 | 17 | 18 | 19 | 20 |
| S | A | S | L | G | A | S | V | K | L |
| S:60 | A:61 | S:57 | L:62 | G:62 | A:59 | S:62 | V:62 | K:53 | L:56 |
| -:2 | -:2 | F:4 | -:2 | -:2 | -:2 | -:2 | -:2 | N:8 | F:3 |
| R:1 | P:1 | -:2 | | | T:2 | | | -:2 | V:2 |
| Y:1 | | P:1 | | | D:1 | | | T:1 | -:1 |
| | | | | | | | | | I:1 |
| | | | | | | | | | P:1 |

| | CDR1 | | | | | | | | |
|---|---|---|---|---|---|---|---|---|---|
| 21 | 22 | 23 | 24 | 25 | 26 | 27 | 28 | 29 | 30 |
| T | C | X | X | X | X | X | X | X | X |
| T:63 | C:64 | | | | | | | | |
| -:1 | | | | | | | | | |

| CDR1 | | | | Framework 2 | | | | | |
|---|---|---|---|---|---|---|---|---|---|
| 31 | 32 | 33 | 34 | 35 | 36 | 37 | 38 | 39 | 40 |
| X | X | X | X | W | H | Q | Q | Q | P |
| | | | | W:64 | H:60 | Q:64 | Q:61 | Q:57 | P:59 |
| | | | | | Y:3 | | H:3 | H:3 | S:3 |
| | | | | | L:1 | | | L:3 | A:2 |
| | | | | | | | | R:1 | |

| | | | Framework 2 | | | | | | CDR2 |
|---|---|---|---|---|---|---|---|---|---|
| 41 | 42 | 43 | 44 | 45 | 46 | 47 | 48 | 49 | 50 |
| E | K | G | P | R | Y | L | M | K | X |
| E:53 | K:58 | G:63 | P:63 | R:63 | Y:51 | L:64 | M:64 | K:57 | |
| Q:4 | R:3 | A:1 | L:1 | Q:1 | F:10 | | | T:4 | |
| A:2 | T:2 | | | | H:2 | | | N:2 | |
| D:2 | N:1 | | | | C:1 | | | I:1 | |
| G:2 | | | | | | | | | |
| H:1 | | | | | | | | | |

FIG 25A

| | | | | CDR2 | | | | | |
|---|---|---|---|---|---|---|---|---|---|
| 51 | 52 | 53 | 54 | 55 | 56 | 57 | 58 | 59 | 60 |
| X | X | X | X | X | X | X | X | X | X |

| | | | | Framework 3 | | | | | |
|---|---|---|---|---|---|---|---|---|---|
| 61 | 62 | 63 | 64 | 65 | 66 | 67 | 68 | 69 | 70 |
| G | I | P | D | R | F | S | G | S | S |
| G:35 | I:62 | P:64 | D:63 | R:64 | F:64 | S:63 | G:64 | S:64 | S:60 |
| -:28 | -:1 | | A:1 | | | L:1 | | | R:2 |
| V:1 | T:1 | | | | | | | | T:1 |
| | | | | | | | | | G:1 |

| | | | | Framework 3 | | | | | |
|---|---|---|---|---|---|---|---|---|---|
| 71 | 72 | 73 | 74 | 75 | 76 | 77 | 78 | 79 | 80 |
| S | G | A | E | R | Y | L | T | I | S |
| S:63 | G:64 | A:62 | E:63 | R:62 | Y:63 | L:62 | T:61 | I:64 | S:64 |
| F:1 | | T:2 | D:1 | L:1 | W:1 | P:2 | I:2 | | |
| | | | | Y:1 | | | S:1 | | |

| | | | | Framework 3 | | | | | |
|---|---|---|---|---|---|---|---|---|---|
| 81 | 82 | 83 | 84 | 85 | 86 | 87 | 88 | 89 | 90 |
| S | L | Q | S | E | D | E | A | D | Y |
| S:63 | L:64 | Q:64 | S:64 | E:60 | D:64 | E:64 | A:63 | D:64 | Y:64 |
| T:1 | | | | D:3 | | | V:1 | | |
| | | | | A:1 | | | | | |

| | | | | | | CDR3 | | | |
|---|---|---|---|---|---|---|---|---|---|
| 91 | 92 | 93 | 94 | 95 | 96 | 97 | 98 | 99 | 100 |
| Y | C | X | X | X | X | X | X | X | X |
| Y:63 | C:64 | | | | | | | | |
| F:1 | | | | | | | | | |

| CDR3 | | | | Framework 4 | | | | | |
|---|---|---|---|---|---|---|---|---|---|
| 101 | 102 | 103 | 104 | 105 | 106 | 107 | 108 | 109 | 110 |
| X | X | F | G | G | I | G | G | G | T |
| | | F:45 | G:55 | G:54 | -:63 | -:63 | -:63 | G:50 | T:51 |
| | | -:15 | -:9 | -:9 | I:1 | G:1 | G:1 | -:14 | -:13 |
| | | C:1 | | R:1 | | | | | |

FIG 25B

| | | | | Framework 4 | | | | | |
|---|---|---|---|---|---|---|---|---|---|
| 111 | 112 | 113 | 114 | 115 | 116 | 117 | 118 | 119 | 120 |
| K | L | T | V | L | G | Q | P | K | A |
| K:43 | L:49 | T:49 | V:48 | L:40 | -:28 | -:33 | -:42 | -:45 | -:47 |
| -:14 | -:14 | -:15 | -:15 | -:20 | G:28 | Q:31 | P:22 | K:19 | A:14 |
| T:2 | V:1 | | S:1 | X:2 | S:4 | | | | V:3 |
| Q:2 | | | | V:1 | R:3 | | | | |
| R:2 | | | | R:1 | W:1 | | | | |
| S:1 | | | | | | | | | |

| | Framework 4 | | | |
|---|---|---|---|---|
| 121 | 122 | 123 | 124 | 125 |
| A | P | S | V | S |
| -:51 | -:55 | -:60 | -:61 | -:63 |
| A:12 | P:9 | S:4 | V:3 | S:1 |
| P:1 | | | | |

FIG 25C

| Framework 1 | | | | | | | | | |
|---|---|---|---|---|---|---|---|---|---|
| 1 | 2 | 3 | 4 | 5 | 6 | 7 | 8 | 9 | 10 |
| Q | A | V | L | T | Q | P | S | S | L |
| Q:53 | A:41 | V:53 | L:51 | T:55 | Q:55 | P:55 | S:25 | S:54 | L:48 |
| -:15 | -:15 | -:13 | -:13 | -:13 | -:13 | -:13 | A:18 | -:13 | -:12 |
|  | P:12 | E:2 | V:4 |  |  |  | -:13 | P:1 | S:6 |
|  |  |  |  |  |  |  | P:7 |  | H:1 |
|  |  |  |  |  |  |  | T:5 |  | P:1 |

| Framework 1 | | | | | | | | | |
|---|---|---|---|---|---|---|---|---|---|
| 11 | 12 | 13 | 14 | 15 | 16 | 17 | 18 | 19 | 20 |
| S | A | S | P | G | A | S | A | S | L |
| S:59 | A:60 | S:60 | P:63 | G:65 | A:54 | S:66 | A:67 | S:50 | L:62 |
| -:9 | -:8 | -:6 | -:5 | -:3 | E:8 | -:2 | -:1 | R:17 | F:4 |
|  |  | H:2 |  |  | -:3 |  |  | -:1 | -:1 |
|  |  |  |  |  | T:2 |  |  |  | I:1 |
|  |  |  |  |  | S:1 |  |  |  |  |

|  | | CDR1 | | | | | | | |
|---|---|---|---|---|---|---|---|---|---|
| 21 | 22 | 23 | 24 | 25 | 26 | 27 | 28 | 29 | 30 |
| T | C | X | X | X | X | X | X | X | X |
| T:65 | C:68 |  |  |  |  |  |  |  |  |
| S:3 |  |  |  |  |  |  |  |  |  |

| CDR1 | | | | | | Framework 2 | | | |
|---|---|---|---|---|---|---|---|---|---|
| 31 | 32 | 33 | 34 | 35 | 36 | 37 | 38 | 39 | 40 |
| X | X | X | X | X | X | W | Y | Q | Q |
|  |  |  |  |  |  | W:67 | Y:63 | Q:67 | Q:67 |
|  |  |  |  |  |  | C:1 | F:5 | R:1 | R:1 |

| Framework 2 | | | | | | | | | |
|---|---|---|---|---|---|---|---|---|---|
| 41 | 42 | 43 | 44 | 45 | 46 | 47 | 48 | 49 | 50 |
| K | P | G | S | P | P | Q | Y | L | L |
| K:55 | P:66 | G:66 | S:68 | P:61 | P:68 | Q:49 | Y:66 | L:67 | L:68 |
| R:12 | A:2 | E:2 |  | L:5 |  | R:17 | F:2 | V:1 |  |
| N:1 |  |  |  | S:2 |  | L:2 |  |  |  |

FIG 26A

| | CDR2 | | | | | | | | |
|---|---|---|---|---|---|---|---|---|---|
| 51 | 52 | 53 | 54 | 55 | 56 | 57 | 58 | 59 | 60 |
| R | Y | X | X | X | X | X | X | X | X |
| R:53 | Y:68 | | | | | | | | |
| Y:9 | | | | | | | | | |
| S:4 | | | | | | | | | |
| N:1 | | | | | | | | | |
| G:1 | | | | | | | | | |

| CDR2 | | Framework 3 | | | | | | | |
|---|---|---|---|---|---|---|---|---|---|
| 61 | 62 | 63 | 64 | 65 | 66 | 67 | 68 | 69 | 70 |
| X | X | G | V | P | S | R | F | S | G |
| | | G:35 | V:35 | P:35 | S:60 | R:68 | F:68 | S:68 | G:68 |
| | | -:33 | -:33 | -:33 | -:6 | | | | |
| | | | | | X:2 | | | | |

| Framework 3 | | | | | | | | | |
|---|---|---|---|---|---|---|---|---|---|
| 71 | 72 | 73 | 74 | 75 | 76 | 77 | 78 | 79 | 80 |
| S | K | D | A | S | A | N | A | G | I |
| S:67 | K:66 | D:67 | A:64 | S:68 | A:58 | N:67 | A:59 | G:62 | I:55 |
| F:1 | I:2 | A:1 | I:2 | | T:6 | K:1 | T:9 | X:6 | -:6 |
| | | D:1 | | | S:4 | | | | L:6 |
| | | V:1 | | | | | | | F:1 |

| Framework 3 | | | | | | | | | |
|---|---|---|---|---|---|---|---|---|---|
| 81 | 82 | 83 | 84 | 85 | 86 | 87 | 88 | 89 | 90 |
| L | L | I | S | G | L | Q | S | E | D |
| L:61 | L:57 | I:62 | S:62 | G:61 | L:66 | Q:67 | S:68 | E:67 | D:68 |
| -:6 | -:6 | -:6 | -:6 | -:6 | V:2 | L:1 | | D:1 | |
| I:1 | V:4 | | | W:1 | | | | | |
| | H:1 | | | | | | | | |

| Framework 3 | | | | | | CDR3 | | | |
|---|---|---|---|---|---|---|---|---|---|
| 91 | 92 | 93 | 94 | 95 | 96 | 97 | 98 | 99 | 100 |
| E | A | D | Y | Y | C | X | X | X | X |
| E:68 | A:68 | D:68 | Y:68 | Y:65 | C:64 | | | | |
| | | | | F:2 | -:1 | | | | |
| | | | | -:1 | S:1 | | | | |
| | | | | | W:1 | | | | |
| | | | | | R:1 | | | | |

FIG 26B

| CDR3 | | | | | Framework 4 | | | | |
|---|---|---|---|---|---|---|---|---|---|
| 101 | 102 | 103 | 104 | 105 | 106 | 107 | 108 | 109 | 110 |
| X | X | X | X | X | F | G | G | G | T |
| | | | | | F:46 | G:41 | G:34 | G:39 | T:40 |
| | | | | | -:15 | -:22 | -:26 | -:27 | -:27 |
| | | | | | S:2 | V:2 | T:8 | E:1 | P:1 |
| | | | | | Y:2 | F:1 | | H:1 | |
| | | | | | G:2 | S:1 | | | |
| | | | | | V:1 | D:1 | | | |

| Framework 4 | | | | | | | |
|---|---|---|---|---|---|---|---|
| 111 | 112 | 113 | 114 | 115 | 116 | 117 | 118 |
| K | L | T | V | L | S | Q | P |
| K:38 | -:31 | T:36 | V:36 | L:36 | -:43 | -:47 | -:48 |
| -:27 | L:28 | -:31 | -:31 | -:31 | S:13 | Q:19 | P:20 |
| W:1 | V:7 | S:1 | R:1 | Q:1 | G:10 | P:1 | |
| T:1 | P:1 | | | | K:1 | L:1 | |

FIG 26C

| | | | | Framework 1 | | | | | |
|---|---|---|---|---|---|---|---|---|---|
| 1 | 2 | 3 | 4 | 5 | 6 | 7 | 8 | 9 | 10 |
| N | F | M | L | T | Q | P | H | S | V |
| N:50 | F:66 | M:62 | L:68 | T:68 | Q:68 | P:68 | H:70 | S:79 | V:81 |
| -:24 | -:24 | -:23 | -:23 | -:23 | -:23 | -:22 | -:16 | -:12 | -:10 |
| D:12 | S:1 | I:2 | | | | | H:1 | R:2 | |
| S:2 | | A:1 | | | | | | A:1 | |
| T:2 | | K:1 | | | | | | Y:1 | |
| Q:1 | | L:1 | | | | | | L:1 | |
| | | E:1 | | | | | | | |

| | | | | Framework 1 | | | | | |
|---|---|---|---|---|---|---|---|---|---|
| 11 | 12 | 13 | 14 | 15 | 16 | 17 | 18 | 19 | 20 |
| S | E | S | P | G | K | T | V | T | I |
| S:83 | E:81 | S:83 | P:87 | G:87 | K:83 | T:86 | V:85 | T:80 | I:87 |
| -:8 | -:7 | -:6 | -:4 | -:3 | -:3 | -:3 | -:3 | -:3 | -:3 |
| | G:3 | F:2 | | E:1 | T:2 | S:2 | A:1 | I:3 | F:1 |
| | | | | | E:2 | | N:1 | V:2 | |
| | | | | | R:1 | | I:1 | S:1 | |
| | | | | | | | | Q:1 | |
| | | | | | | | | N:1 | |

| | | | | CDR1 | | | | | |
|---|---|---|---|---|---|---|---|---|---|
| 21 | 22 | 23 | 24 | 25 | 26 | 27 | 28 | 29 | 30 |
| S | C | X | X | X | X | X | X | X | X |
| S:87 | C:88 | | | | | | | | |
| -:3 | -:3 | | | | | | | | |
| P:1 | | | | | | | | | |

| | CDR1 | | | | | Framework 2 | | | |
|---|---|---|---|---|---|---|---|---|---|
| 31 | 32 | 33 | 34 | 35 | 36 | 37 | 38 | 39 | 40 |
| X | X | X | X | X | W | Y | Q | Q | R |
| | | | | | W:90 | Y:87 | Q:90 | Q:88 | R:91 |
| | | | | | G:1 | F:2 | H:1 | L:3 | |
| | | | | | | S:1 | | | |
| | | | | | | N:1 | | | |

FIG 27A

| | | | | | Framework 2 | | | | |
|---|---|---|---|---|---|---|---|---|---|
| 41 | 42 | 43 | 44 | 45 | 46 | 47 | 48 | 49 | 50 |
| P | G | S | A | P | T | T | V | I | Y |
| P:88 | G:88 | S:82 | A:69 | P:91 | T:79 | T:75 | V:80 | I:91 | Y:81 |
| S:2 | A:2 | R:6 | S:21 | | S:4 | I:5 | L:5 | | F:7 |
| R:1 | V:1 | N:2 | V:1 | | I:4 | A:4 | I:4 | | S:2 |
| | | X:1 | | | A:1 | N:4 | M:2 | | H:1 |
| | | | | | F:1 | S:3 | | | |
| | | | | | N:1 | | | | |
| | | | | | M:1 | | | | |

| | | CDR2 | | | | | | Framework 3 | |
|---|---|---|---|---|---|---|---|---|---|
| 51 | 52 | 53 | 54 | 55 | 56 | 57 | 58 | 59 | 60 |
| X | X | X | X | X | X | X | G | V | P |
| | | | | | | | G:83 | V:82 | P:82 |
| | | | | | | | -:6 | -:6 | X:6 |
| | | | | | | | E:1 | I:2 | A:2 |
| | | | | | | | R:1 | X:1 | T:1 |

| | | | | | Framework 3 | | | | |
|---|---|---|---|---|---|---|---|---|---|
| 61 | 62 | 63 | 64 | 65 | 66 | 67 | 68 | 69 | 70 |
| D | R | F | S | G | S | I | D | S | S |
| D:87 | R:91 | F:91 | S:88 | G:89 | S:89 | I:63 | D:65 | S:54 | S:88 |
| N:2 | | | F:2 | V:2 | -:2 | X:20 | -:25 | -:23 | -:2 |
| T:1 | | | A:1 | | | V:3 | G:1 | T:7 | T:1 |
| Y:1 | | | | | | -:3 | | R:5 | |
| | | | | | | S:2 | | N:1 | |
| | | | | | | | | C:1 | |

| | | | | | Framework 3 | | | | |
|---|---|---|---|---|---|---|---|---|---|
| 71 | 72 | 73 | 74 | 75 | 76 | 77 | 78 | 79 | 80 |
| S | N | S | A | S | L | T | I | S | G |
| S:90 | N:90 | S:86 | A:91 | S:89 | L:91 | T:86 | I:90 | S:90 | G:85 |
| A:1 | K:1 | A:2 | | A:2 | | N:2 | V:1 | F:1 | R:4 |
| | | C:2 | | | | I:2 | | | E:2 |
| | | F:1 | | | | S:1 | | | |

FIG 27B

| | | | | Framework 3 | | | | | |
|---|---|---|---|---|---|---|---|---|---|
| 81 | 82 | 83 | 84 | 85 | 86 | 87 | 88 | 89 | 90 |
| L | K | T | E | D | E | A | D | Y | Y |
| L:91 | K:75 | T:82 | E:89 | D:91 | E:89 | A:90 | D:88 | Y:91 | Y:88 |
| | R:9 | A:5 | D:2 | | K:1 | G:1 | N:2 | | F:3 |
| | E:2 | S:2 | | | D:1 | | G:1 | | |
| | Q:2 | F:1 | | | | | | | |
| | M:2 | P:1 | | | | | | | |
| | T:1 | | | | | | | | |

| | | | | CDR3 | | | | | |
|---|---|---|---|---|---|---|---|---|---|
| 91 | 92 | 93 | 94 | 95 | 96 | 97 | 98 | 99 | 100 |
| C | X | X | X | X | X | X | X | X | X |
| C:91 | | | | | | | | | |

| | | | | Framework 4 | | | | | |
|---|---|---|---|---|---|---|---|---|---|
| 101 | 102 | 103 | 104 | 105 | 106 | 107 | 108 | 109 | 110 |
| X | X | F | G | G | G | T | K | L | T |
| | | F:72 | G:76 | G:72 | G:74 | T:73 | K:57 | L:67 | T:72 |
| | | -:8 | -:11 | -:16 | -:17 | -:18 | -:19 | -:19 | -:19 |
| | | S:4 | F:4 | T:2 | | | R:8 | V:5 | |
| | | V:4 | | A:1 | | | Q:5 | | |
| | | X:1 | | | | | T:2 | | |
| | | I:1 | | | | | | | |
| | | L:1 | | | | | | | |

| | | | | Framework 4 | | | | | |
|---|---|---|---|---|---|---|---|---|---|
| 111 | 112 | 113 | 114 | 115 | 116 | 117 | 118 | 119 | 120 |
| V | L | G | Q | P | K | A | A | P | S |
| V:66 | L:68 | G:49 | Q:48 | P:48 | -:59 | -:60 | -:60 | -:60 | -:61 |
| -:23 | -:23 | -:36 | -:43 | -:43 | K:32 | A:30 | A:31 | P:31 | S:30 |
| A:2 | | S:4 | | | | D:1 | | | |
| | | R:2 | | | | | | | |

| | | | | Framework 4 | | | | | |
|---|---|---|---|---|---|---|---|---|---|
| 121 | 122 | 123 | 124 | 125 | 126 | 127 | 128 | 129 | |
| V | T | L | F | P | P | S | S | S | |
| -:61 | -:62 | -:62 | -:62 | -:62 | -:62 | -:62 | -:62 | -:88 | |
| V:30 | T:29 | L:28 | F:28 | P:28 | P:29 | S:27 | S:25 | S:2 | |
| | | C:1 | S:1 | Q:1 | | P:2 | L:3 | X:1 | |
| | | | | | | | F:1 | | |

FIG 27C

| | | | | | Framework 1 | | | | |
|---|---|---|---|---|---|---|---|---|---|
| 1 | 2 | 3 | 4 | 5 | 6 | 7 | 8 | 9 | 10 |
| Q | A | V | V | T | Q | E | P | S | L |
| Q:30 | -:21 | V:31 | V:31 | T:33 | Q:33 | E:31 | P:34 | S:35 | L:39 |
| -:23 | A:14 | -:20 | -:20 | -:20 | -:20 | -:20 | -:19 | -:18 | -:14 |
| | T:14 | E:2 | L:2 | | | Q:1 | | | |
| | V:3 | | | | | P:1 | | | |
| | I:1 | | | | | | | | |

| | | | | | Framework 1 | | | | |
|---|---|---|---|---|---|---|---|---|---|
| 11 | 12 | 13 | 14 | 15 | 16 | 17 | 18 | 19 | 20 |
| T | V | S | P | G | G | T | V | T | L |
| T:47 | V:51 | S:51 | P:51 | G:52 | G:51 | T:51 | V:52 | T:50 | L:52 |
| -:5 | -:2 | -:2 | -:2 | -:1 | -:1 | -:1 | -:1 | S:2 | F:1 |
| S:1 | | | | | E:1 | A:1 | | A:1 | |

| | | | | | CDR1 | | | | |
|---|---|---|---|---|---|---|---|---|---|
| 21 | 22 | 23 | 24 | 25 | 26 | 27 | 28 | 29 | 30 |
| T | C | X | X | X | X | X | X | X | X |
| T:53 | C:52 | | | | | | | | |
| | P:1 | | | | | | | | |

| | CDR1 | | | | | | Framework 2 | | |
|---|---|---|---|---|---|---|---|---|---|
| 31 | 32 | 33 | 34 | 35 | 36 | 37 | 38 | 39 | 40 |
| X | X | X | X | X | X | W | F | Q | Q |
| | | | | | | W:53 | F:50 | Q:53 | Q:53 |
| | | | | | | | L:2 | | |
| | | | | | | | V:1 | | |

| | | | | | Framework 2 | | | | |
|---|---|---|---|---|---|---|---|---|---|
| 41 | 42 | 43 | 44 | 45 | 46 | 47 | 48 | 49 | 50 |
| K | P | G | Q | A | P | R | A | L | I |
| K:50 | P:53 | G:52 | Q:53 | A:50 | P:52 | R:53 | A:26 | L:53 | I:50 |
| R:2 | | S:1 | | T:1 | S:1 | | T:23 | | T:2 |
| I:1 | | | | G:1 | | | P:4 | | V:1 |
| | | | | V:1 | | | | | |

| | CDR2 | | | | | | | Framework 3 | |
|---|---|---|---|---|---|---|---|---|---|
| 51 | 52 | 53 | 54 | 55 | 56 | 57 | 58 | 59 | 60 |
| Y | X | X | X | X | X | X | X | W | T |
| Y:51 | | | | | | | | W:53 | T:53 |
| F:2 | | | | | | | | | |

FIG 28A

| | | | | Framework 3 | | | | | |
|---|---|---|---|---|---|---|---|---|---|
| 61 | 62 | 63 | 64 | 65 | 66 | 67 | 68 | 69 | 70 |
| P | A | R | F | S | G | S | L | L | G |
| P:52 | A:52 | R:53 | F:53 | S:53 | G:53 | S:53 | L:53 | L:51 | G:53 |
| R:1 | V:1 | | | | | | | F:1 | |
| | | | | | | | | I:1 | |

| | | | | Framework 3 | | | | | |
|---|---|---|---|---|---|---|---|---|---|
| 71 | 72 | 73 | 74 | 75 | 76 | 77 | 78 | 79 | 80 |
| G | K | A | A | L | T | L | S | G | V |
| G:52 | K:53 | A:52 | A:49 | L:53 | T:52 | L:53 | S:51 | G:52 | V:31 |
| D:1 | | T:1 | V:3 | | I:1 | | W:1 | H:1 | A:22 |
| | | | T:1 | | | | L:1 | | |

| | | | | Framework 3 | | | | | |
|---|---|---|---|---|---|---|---|---|---|
| 81 | 82 | 83 | 84 | 85 | 86 | 87 | 88 | 89 | 90 |
| Q | P | E | D | E | A | E | Y | Y | C |
| Q:50 | P:53 | E:53 | D:53 | E:53 | A:52 | E:42 | Y:53 | Y:49 | C:53 |
| H:1 | | | | | T:1 | D:10 | | F:4 | |
| L:1 | | | | | | K:1 | | | |
| E:1 | | | | | | | | | |

| | | | | CDR3 | | | | | |
|---|---|---|---|---|---|---|---|---|---|
| 91 | 92 | 93 | 94 | 95 | 96 | 97 | 98 | 99 | 100 |
| X | X | X | X | X | X | X | X | X | X |

| CDR3 | | | | Framework 4 | | | | | |
|---|---|---|---|---|---|---|---|---|---|
| 101 | 102 | 103 | 104 | 105 | 106 | 107 | 108 | 109 | 110 |
| X | X | F | G | G | G | T | K | L | T |
| | | F:46 | G:44 | G:42 | G:46 | T:42 | K:26 | L:33 | T:35 |
| | | -:7 | -:9 | -:10 | -:6 | -:6 | Q:16 | -:17 | -:17 |
| | | | | T:1 | W:1 | A:4 | -:8 | V:3 | F:1 |
| | | | | | | D:1 | R:2 | | |
| | | | | | | | E:1 | | |

| | | | | Framework 4 | | | | | |
|---|---|---|---|---|---|---|---|---|---|
| 111 | 112 | 113 | 114 | 115 | 116 | 117 | 118 | 119 | |
| V | L | G | Q | P | K | A | A | P | |
| V:27 | L:26 | -:32 | -:34 | -:35 | -:52 | -:52 | -:52 | -:52 | |
| -:23 | -:25 | G:14 | Q:18 | P:18 | K:1 | A:1 | A:1 | P:1 | |
| T:1 | P:1 | S:6 | Y:1 | | | | | | |
| X:1 | V:1 | R:1 | | | | | | | |
| N:1 | | | | | | | | | |

FIG 28B

Framework 1

| 1 | 2 | 3 | 4 | 5 | 6 | 7 | 8 | 9 | 10 |
|---|---|---|---|---|---|---|---|---|---|
| Q | T | V | V | T | Q | E | P | S | F |
| Q:24 | T:23 | V:25 | V:40 | T:42 | Q:42 | E:43 | P:42 | S:43 | F:43 |
| -:22 | -:22 | -:22 | -:6 | -:5 | -:5 | -:4 | -:4 | -:4 | -:3 |
| R:1 | A:2 |  | A:1 |  |  |  | A:1 |  | L:1 |

Framework 1

| 11 | 12 | 13 | 14 | 15 | 16 | 17 | 18 | 19 | 20 |
|---|---|---|---|---|---|---|---|---|---|
| S | V | S | P | G | G | T | V | T | L |
| S:45 | V:47 | S:41 | P:47 | G:47 | G:42 | T:47 | V:47 | T:47 | L:45 |
| -:1 |  | A:5 |  |  | E:5 |  |  |  | F:2 |
| L:1 |  | P:1 |  |  |  |  |  |  |  |

CDR1

| 21 | 22 | 23 | 24 | 25 | 26 | 27 | 28 | 29 | 30 |
|---|---|---|---|---|---|---|---|---|---|
| T | C | X | X | X | X | X | X | X | X |
| T:47 | C:47 |  |  |  |  |  |  |  |  |

CDR1 / Framework 2

| 31 | 32 | 33 | 34 | 35 | 36 | 37 | 38 | 39 | 40 |
|---|---|---|---|---|---|---|---|---|---|
| X | X | X | X | X | X | W | Y | Q | Q |
|  |  |  |  |  |  | W:47 | Y:45 | Q:43 | Q:47 |
|  |  |  |  |  |  | T:1 |  | N:4 |  |
|  |  |  |  |  |  | L:1 |  |  |  |

Framework 2

| 41 | 42 | 43 | 44 | 45 | 46 | 47 | 48 | 49 | 50 |
|---|---|---|---|---|---|---|---|---|---|
| T | P | G | Q | A | P | R | T | L | I |
| T:42 | P:47 | G:47 | Q:47 | A:39 | P:47 | R:46 | T:47 | L:46 | I:47 |
| A:5 |  |  |  | T:2 |  | H:1 |  | V:1 |  |
|  |  |  |  | P:2 |  |  |  |  |  |
|  |  |  |  | G:2 |  |  |  |  |  |
|  |  |  |  | S:1 |  |  |  |  |  |
|  |  |  |  | V:1 |  |  |  |  |  |

CDR2 / Framework 3

| 51 | 52 | 53 | 54 | 55 | 56 | 57 | 58 | 59 | 60 |
|---|---|---|---|---|---|---|---|---|---|
| Y | X | X | X | X | X | X | X | G | V |
| Y:38 |  |  |  |  |  |  |  | G:47 | V:47 |
| H:9 |  |  |  |  |  |  |  |  |  |

FIG 29A

| Framework 3 | | | | | | | | | |
|---|---|---|---|---|---|---|---|---|---|
| 61 | 62 | 63 | 64 | 65 | 66 | 67 | 68 | 69 | 70 |
| P | D | R | F | S | G | S | I | L | G |
| P:47 | D:46 | R:45 | F:47 | S:45 | G:47 | S:45 | I:46 | L:46 | G:47 |
|  | E:1 | C:2 |  | F:2 |  | T:2 | L:1 | A:1 |  |

| Framework 3 | | | | | | | | | |
|---|---|---|---|---|---|---|---|---|---|
| 71 | 72 | 73 | 74 | 75 | 76 | 77 | 78 | 79 | 80 |
| N | K | A | A | L | T | I | T | G | A |
| N:40 | K:46 | A:47 | A:46 | L:47 | T:47 | I:47 | T:46 | G:45 | A:46 |
| H:5 | R:1 |  | G:1 |  |  |  | M:1 | W:1 | G:1 |
| S:1 |  |  |  |  |  |  |  | R:1 |  |
| D:1 |  |  |  |  |  |  |  |  |  |

| Framework 3 | | | | | | | | | |
|---|---|---|---|---|---|---|---|---|---|
| 81 | 82 | 83 | 84 | 85 | 86 | 87 | 88 | 89 | 90 |
| Q | A | D | D | E | S | D | Y | Y | C |
| Q:47 | A:46 | D:45 | D:47 | E:43 | S:36 | D:28 | Y:30 | Y:30 | C:30 |
|  | V:1 | E:2 |  | -:3 | -:5 | -:17 | -:17 | -:17 | -:17 |
|  |  |  |  | D:1 | C:5 | H:1 |  |  |  |
|  |  |  |  |  | A:1 | V:1 |  |  |  |

| CDR3 | | | | | | | | | |
|---|---|---|---|---|---|---|---|---|---|
| 91 | 92 | 93 | 94 | 95 | 96 | 97 | 98 | 99 | 100 |
| X | X | X | X | X | X | X | X | X | X |

| CDR3 | | Framework 4 | | | | | | | |
|---|---|---|---|---|---|---|---|---|---|
| 101 | 102 | 103 | 104 | 105 | 106 | 107 | 108 | 109 | 110 |
| X | X | F | G | G | G | T | K | L | T |
|  |  | F:24 | G:24 | G:24 | G:25 | T:25 | -:23 | -:23 | T:24 |
|  |  | -:22 | -:23 | -:21 | -:21 | -:21 | K:22 | L:22 | -:23 |
|  |  | C:1 |  | S:2 | R:1 | I:1 | Q:1 | V:2 |  |
|  |  |  |  |  |  |  | R:1 |  |  |

| Framework 4 | | | | | | | | | |
|---|---|---|---|---|---|---|---|---|---|
| 111 | 112 | 113 | 114 | 115 | 116 | 117 | 118 | 119 | |
| V | L | G | Q | P | K | A | A | P | |
| -:23 | -:24 | -:26 | -:28 | -:29 | -:44 | -:44 | -:44 | -:44 | |
| V:23 | L:23 | G:15 | Q:18 | P:18 | K:3 | A:3 | A:3 | P:3 | |
| R:1 |  | S:6 | R:1 |  |  |  |  |  | |

FIG 29B

| | | | | Framework 1 | | | | | |
|---|---|---|---|---|---|---|---|---|---|
| 1 | 2 | 3 | 4 | 5 | 6 | 7 | 8 | 9 | 10 |
| Q | P | V | L | T | Q | P | P | S | A |
| Q:10 | P:10 | V:10 | L:10 | T:10 | Q:10 | P:10 | P:10 | S:10 | A:10 |
| -:3 | -:3 | -:3 | -:3 | -:3 | -:3 | -:3 | -:3 | -:3 | -:3 |

| | | | | Framework 1 | | | | | |
|---|---|---|---|---|---|---|---|---|---|
| 11 | 12 | 13 | 14 | 15 | 16 | 17 | 18 | 19 | 20 |
| S | A | S | L | G | A | S | V | T | L |
| S:11 | A:11 | S:11 | L:11 | G:12 | A:12 | S:12 | V:12 | T:13 | L:13 |
| -:2 | -:2 | -:2 | -:2 | -:1 | -:1 | -:1 | -:1 | | |

| | | CDR1 | | | | | | | |
|---|---|---|---|---|---|---|---|---|---|
| 21 | 22 | 23 | 24 | 25 | 26 | 27 | 28 | 29 | 30 |
| T | C | X | X | X | X | X | X | X | X |
| T:13 | C:13 | | | | | | | | |

| | CDR1 | | | | Framework 2 | | | | |
|---|---|---|---|---|---|---|---|---|---|
| 31 | 32 | 33 | 34 | 35 | 36 | 37 | 38 | 39 | 40 |
| X | X | X | X | W | Y | Q | Q | R | P |
| | | | | W:13 | Y:13 | Q:13 | Q:13 | R:13 | P:13 |

| | | | | Framework 2 | | | | | CDR2 |
|---|---|---|---|---|---|---|---|---|---|
| 41 | 42 | 43 | 44 | 45 | 46 | 47 | 48 | 49 | 50 |
| G | K | G | P | R | F | V | M | R | X |
| G:12 | K:13 | G:13 | P:13 | R:13 | F:13 | V:12 | M:13 | R:13 | |
| E:1 | | | | | | A:1 | | | |

| | | | | CDR2 | | | | | |
|---|---|---|---|---|---|---|---|---|---|
| 51 | 52 | 53 | 54 | 55 | 56 | 57 | 58 | 59 | 60 |
| X | X | X | X | X | X | X | X | X | X |

| | | | | Framework 3 | | | | | |
|---|---|---|---|---|---|---|---|---|---|
| 61 | 62 | 63 | 64 | 65 | 66 | 67 | 68 | 69 | 70 |
| X | G | I | P | D | R | F | S | V | L |
| | -:8 | I:12 | P:13 | D:13 | R:13 | F:13 | S:12 | V:13 | L:13 |
| | G:5 | X:1 | | | | | L:1 | | |

FIG 30A

| | | | | Framework 3 | | | | | |
|---|---|---|---|---|---|---|---|---|---|
| 71 | 72 | 73 | 74 | 75 | 76 | 77 | 78 | 79 | 80 |
| G | S | G | L | N | R | Y | L | T | I |
| G:13 | S:13 | G:13 | L:13 | N:12<br>D:1 | R:13 | Y:11<br>S:1<br>N:1 | L:13 | T:13 | I:13 |

| | | | | Framework 3 | | | | | |
|---|---|---|---|---|---|---|---|---|---|
| 81 | 82 | 83 | 84 | 85 | 86 | 87 | 88 | 89 | 90 |
| K | N | I | Q | E | E | D | E | S | D |
| K:13 | N:13 | I:12<br>L:1 | Q:13 | E:13 | E:13 | D:13 | E:13 | S:13 | D:12<br>V:1 |

| | Framework 3 | | | | CDR3 | | | | |
|---|---|---|---|---|---|---|---|---|---|
| 91 | 92 | 93 | 94 | 95 | 96 | 97 | 98 | 99 | 100 |
| Y | H | C | X | X | X | X | X | X | X |
| Y:13 | H:13 | C:13 | | | | | | | |

| | | | CDR3 | | | | | Framework 4 | |
|---|---|---|---|---|---|---|---|---|---|
| 101 | 102 | 103 | 104 | 105 | 106 | 107 | 108 | 109 | 110 |
| X | X | X | X | X | X | X | X | F | G |
| | | | | | | | | -:9<br>F:3<br>G:1 | -:10<br>G:3 |

| | | | | Framework 4 | | | | | |
|---|---|---|---|---|---|---|---|---|---|
| 111 | 112 | 113 | 114 | 115 | 116 | 117 | 118 | 119 | 120 |
| G | G | T | K | L | T | V | L | G | Q |
| -:10<br>G:2<br>A:1 | -:9<br>G:4 | -:9<br>T:4 | -:9<br>K:3<br>R:1 | -:9<br>L:3<br>V:1 | -:9<br>T:4 | -:9<br>V:4 | -:9<br>L:4 | -:9<br>G:4 | -:9<br>Q:4 |

| | | | Framework 4 | | | |
|---|---|---|---|---|---|---|
| 121 | 122 | 123 | 124 | 125 | 126 | 127 |
| P | K | A | A | P | S | V |
| -:9<br>P:4 | -:12<br>K:1 | -:12<br>A:1 | -:12<br>A:1 | -:12<br>P:1 | -:12<br>S:1 | -:12<br>V:1 |

FIG 30B

| | | | | | Framework 1 | | | | |
|---|---|---|---|---|---|---|---|---|---|
| 1 | 2 | 3 | 4 | 5 | 6 | 7 | 8 | 9 | 10 |
| Q | A | G | L | T | Q | P | P | S | V |
| Q:13 | A:13 | G:14 | L:15 | T:15 | Q:15 | P:15 | P:15 | S:15 | V:16 |
| -:10 | -:10 | -:9 | -:9 | -:9 | -:9 | -:9 | -:9 | -:9 | -:8 |
| R:1 | S:1 | E:1 | | | | | | | |

| | | | | | Framework 1 | | | | |
|---|---|---|---|---|---|---|---|---|---|
| 11 | 12 | 13 | 14 | 15 | 16 | 17 | 18 | 19 | 20 |
| S | K | G | L | R | Q | T | A | T | L |
| S:16 | K:16 | G:15 | L:16 | R:22 | Q:23 | T:23 | A:23 | T:22 | L:22 |
| -:8 | -:8 | -:7 | -:7 | -:1 | -:1 | -:1 | -:1 | -:1 | -:1 |
| | | D:2 | M:1 | G:1 | | | | S:1 | F:1 |

| | | CDR1 | | | | | | | |
|---|---|---|---|---|---|---|---|---|---|
| 21 | 22 | 23 | 24 | 25 | 26 | 27 | 28 | 29 | 30 |
| T | C | X | X | X | X | X | X | X | X |
| T:24 | C:24 | | | | | | | | |

| CDR1 | | | | | Framework 2 | | | | |
|---|---|---|---|---|---|---|---|---|---|
| 31 | 32 | 33 | 34 | 35 | 36 | 37 | 38 | 39 | 40 |
| X | X | X | X | X | W | L | Q | Q | H |
| | | | | | W:24 | L:22 | Q:22 | Q:22 | H:24 |
| | | | | | | P:2 | E:2 | H:1 | |
| | | | | | | | | E:1 | |

| | | | | | Framework 2 | | | | |
|---|---|---|---|---|---|---|---|---|---|
| 41 | 42 | 43 | 44 | 45 | 46 | 47 | 48 | 49 | 50 |
| Q | G | H | P | P | K | L | L | S | Y |
| Q:24 | G:24 | H:20 | P:23 | P:24 | K:22 | L:24 | L:24 | S:24 | Y:21 |
| | | R:2 | S:1 | | R:2 | | | | F:1 |
| | | Q:1 | | | | | | | H:1 |
| | | Y:1 | | | | | | | S:1 |

| | | CDR2 | | | | | Framework 3 | | |
|---|---|---|---|---|---|---|---|---|---|
| 51 | 52 | 53 | 54 | 55 | 56 | 57 | 58 | 59 | 60 |
| X | X | X | X | X | X | X | G | I | S |
| | | | | | | | G:19 | I:20 | S:20 |
| | | | | | | | -:4 | -:4 | -:4 |
| | | | | | | | E:1 | | |

FIG 31A

| | | | | Framework 3 | | | | | |
|---|---|---|---|---|---|---|---|---|---|
| 61 | 62 | 63 | 64 | 65 | 66 | 67 | 68 | 69 | 70 |
| E | R | F | S | A | S | R | S | G | N |
| E:20 | R:24 | F:13 | S:24 | A:20 | S:24 | R:24 | S:24 | G:24 | N:23 |
| X:4 | | L:10 | | S:3 | | | | | D:1 |
| | | S:1 | | T:1 | | | | | |

| | | | | Framework 3 | | | | | |
|---|---|---|---|---|---|---|---|---|---|
| 71 | 72 | 73 | 74 | 75 | 76 | 77 | 78 | 79 | 80 |
| T | A | S | L | T | I | T | G | L | Q |
| T:24 | A:22 | S:24 | L:24 | T:24 | I:24 | T:21 | G:23 | L:24 | Q:23 |
| | S:1 | | | | | A:1 | R:1 | | L:1 |
| | T:1 | | | | | S:1 | | | |
| | | | | | | I:1 | | | |

| | | | | Framework 3 | | | | | CDR3 |
|---|---|---|---|---|---|---|---|---|---|
| 81 | 82 | 83 | 84 | 85 | 86 | 87 | 88 | 89 | 90 |
| P | E | D | E | A | D | Y | Y | C | X |
| P:24 | E:24 | D:24 | E:24 | A:24 | D:24 | Y:24 | Y:23 | C:24 | |
| | | | | | | | F:1 | | |

| CDR3 | | | | | | | | | |
|---|---|---|---|---|---|---|---|---|---|
| 91 | 92 | 93 | 94 | 95 | 96 | 97 | 98 | 99 | 100 |
| X | X | X | X | X | X | X | X | X | X |

| | | | | Framework 4 | | | | | |
|---|---|---|---|---|---|---|---|---|---|
| 101 | 102 | 103 | 104 | 105 | 106 | 107 | 108 | 109 | 110 |
| X | F | G | G | G | T | K | L | T | V |
| | F:13 | G:14 | G:10 | G:12 | -:12 | -:12 | -:12 | -:12 | -:14 |
| | -:8 | -:9 | -:9 | -:10 | T:11 | K:9 | L:9 | T:10 | V:9 |
| | I:1 | R:1 | A:2 | T:1 | H:1 | T:2 | V:2 | W:1 | G:1 |
| | R:1 | | R:2 | P:1 | | Q:1 | X:1 | X:1 | |
| | L:1 | | T:1 | | | | | | |

| | | Framework 4 | | | |
|---|---|---|---|---|---|
| 111 | 112 | 113 | 114 | 115 | 116 |
| L | G | Q | P | K | A |
| -:15 | -:14 | -:16 | -:16 | -:22 | -:23 |
| L:9 | G:10 | Q:8 | P:8 | K:2 | A:1 |

FIG 31B

| | | | | C$_H$1 | | | | | |
|---|---|---|---|---|---|---|---|---|---|
| 1 | 2 | 3 | 4 | 5 | 6 | 7 | 8 | 9 | 10 |
| A | S | P | T | S | P | K | V | F | P |
| A:4<br>-:1 | S:5 | P:5 | T:5 | S:5 | P:5 | K:5 | V:5 | F:5 | P:5 |

| | | | | C$_H$1 | | | | | |
|---|---|---|---|---|---|---|---|---|---|
| 11 | 12 | 13 | 14 | 15 | 16 | 17 | 18 | 19 | 20 |
| L | S | L | C | S | T | Q | P | D | G |
| L:5 | S:5 | L:5 | C:5 | S:5 | T:5 | Q:4<br>Z:1 | P:5 | D:4<br>B:1 | G:5 |

| | | | | C$_H$1 | | | | | |
|---|---|---|---|---|---|---|---|---|---|
| 21 | 22 | 23 | 24 | 25 | 26 | 27 | 28 | 29 | 30 |
| N | V | V | I | A | C | L | V | Q | G |
| N:4<br>B:1 | V:5 | V:5 | I:5 | A:5 | C:5 | L:5 | V:5 | Q:5 | G:5 |

| | | | | C$_H$1 | | | | | |
|---|---|---|---|---|---|---|---|---|---|
| 31 | 32 | 33 | 34 | 35 | 36 | 37 | 38 | 39 | 40 |
| F | F | P | Q | E | P | L | S | V | T |
| F:5 | F:5 | P:5 | Q:5 | E:3<br>Q:2 | P:5 | L:5 | S:5 | V:5 | T:5 |

| | | | | C$_H$1 | | | | | |
|---|---|---|---|---|---|---|---|---|---|
| 41 | 42 | 43 | 44 | 45 | 46 | 47 | 48 | 49 | 50 |
| W | S | E | S | G | Q | G | V | T | A |
| W:5 | S:5 | E:5 | S:5 | G:5 | Q:4<br>Z:1 | G:5 | V:5 | T:5 | A:5 |

| | | | | C$_H$1 | | | | | |
|---|---|---|---|---|---|---|---|---|---|
| 51 | 52 | 53 | 54 | 55 | 56 | 57 | 58 | 59 | 60 |
| R | N | F | P | P | S | Q | D | A | S |
| R:5 | N:4<br>B:1 | F:5 | P:5 | P:5 | S:5 | Q:4<br>Z:1 | D:3<br>B:1<br>N:1 | A:5 | S:5 |

| | | | | C$_H$1 | | | | | |
|---|---|---|---|---|---|---|---|---|---|
| 61 | 62 | 63 | 64 | 65 | 66 | 67 | 68 | 69 | 70 |
| G | D | L | Y | T | T | S | S | Q | L |
| G:5 | D:3<br>B:1<br>N:1 | L:5 | Y:5 | T:5 | T:5 | S:5 | S:5 | Q:5 | L:5 |

FIG 32A

| C$_H$1 | | | | | | | | | |
|---|---|---|---|---|---|---|---|---|---|
| 71 | 72 | 73 | 74 | 75 | 76 | 77 | 78 | 79 | 80 |
| T | L | P | A | T | Q | C | L | A | G |
| T:5 | L:5 | P:5 | A:5 | T:5 | Q:4<br>Z:1 | C:5 | L:5 | A:5 | G:5 |

| C$_H$1 | | | | | | | | | |
|---|---|---|---|---|---|---|---|---|---|
| 81 | 82 | 83 | 84 | 85 | 86 | 87 | 88 | 89 | 90 |
| K | S | V | T | C | H | V | K | H | Y |
| K:5 | S:5 | V:5 | T:5 | C:5 | H:5 | V:5 | K:5 | H:5 | Y:5 |

| C$_H$1 | | | | | | | | | |
|---|---|---|---|---|---|---|---|---|---|
| 91 | 92 | 93 | 94 | 95 | 96 | 97 | 98 | 99 | 100 |
| T | N | P | S | Q | D | V | T | V | P |
| T:5 | N:5 | P:5 | S:5 | Q:5 | D:4<br>B:1 | V:5 | T:5 | V:5 | P:5 |

| C$_H$1 | | HINGE | | | | | | | |
|---|---|---|---|---|---|---|---|---|---|
| 101 | 102 | 103 | 104 | 105 | 106 | 107 | 108 | 109 | 110 |
| C | P | V | P | S | T | P | P | T | P |
| C:5 | P:5 | V:5 | P:5 | S:5 | T:5 | P:5 | P:5 | T:5 | P:5 |

| HINGE | | | | | | | | | |
|---|---|---|---|---|---|---|---|---|---|
| 111 | 112 | 113 | 114 | 115 | 116 | 117 | 118 | 119 | 120 |
| S | P | S | T | P | P | T | P | S | P |
| S:5 | P:5 | S:5 | T:5 | P:5 | P:5 | T:5 | P:5 | S:5 | P:5 |

| | C$_H$2 | | | | | | | | |
|---|---|---|---|---|---|---|---|---|---|
| 121 | 122 | 123 | 124 | 125 | 126 | 127 | 128 | 129 | 130 |
| S | C | C | H | P | R | L | S | L | H |
| S:5 | C:5 | C:5 | H:5 | P:5 | R:5 | L:5 | S:5 | L:5 | H:5 |

| C$_H$2 | | | | | | | | | |
|---|---|---|---|---|---|---|---|---|---|
| 131 | 132 | 133 | 134 | 135 | 136 | 137 | 138 | 139 | 140 |
| R | P | A | L | E | D | L | L | L | G |
| R:5 | P:5 | A:5 | L:5 | E:3<br>Q:2 | D:4<br>N:1 | L:5 | L:5 | L:5 | G:5 |

FIG 32B

| | | | | C_H2 | | | | | |
|---|---|---|---|---|---|---|---|---|---|
| 141 | 142 | 143 | 144 | 145 | 146 | 147 | 148 | 149 | 150 |
| S | E | A | N | L | T | C | T | L | T |
| S:5 | E:4 Q:1 | A:5 | N:5 | L:5 | T:5 | C:5 | T:5 | L:5 | T:5 |

| | | | | C_H2 | | | | | |
|---|---|---|---|---|---|---|---|---|---|
| 151 | 152 | 153 | 154 | 155 | 156 | 157 | 158 | 159 | 160 |
| G | L | R | D | A | S | G | V | T | F |
| G:5 | L:5 | R:5 | D:5 | A:5 | S:5 | G:5 | V:5 | T:5 | F:5 |

| | | | | C_H2 | | | | | |
|---|---|---|---|---|---|---|---|---|---|
| 161 | 162 | 163 | 164 | 165 | 166 | 167 | 168 | 169 | 170 |
| T | W | T | P | S | S | G | K | S | A |
| T:5 | W:5 | T:4 P:1 | P:4 S:1 | S:4 T:1 | S:5 | G:5 | K:5 | S:5 | A:5 |

| | | | | C_H2 | | | | | |
|---|---|---|---|---|---|---|---|---|---|
| 171 | 172 | 173 | 174 | 175 | 176 | 177 | 178 | 179 | 180 |
| V | Q | G | P | P | E | R | D | L | C |
| V:5 | Q:5 | G:5 | P:5 | P:5 | E:4 D:1 | R:5 | D:5 | L:5 | C:5 |

| | | | | C_H2 | | | | | |
|---|---|---|---|---|---|---|---|---|---|
| 181 | 182 | 183 | 184 | 185 | 186 | 187 | 188 | 189 | 190 |
| G | C | Y | S | V | S | S | V | L | P |
| G:5 | C:5 | Y:5 | S:5 | V:5 | S:5 | S:5 | V:5 | L:5 | P:4 S:1 |

| | | | | C_H2 | | | | | |
|---|---|---|---|---|---|---|---|---|---|
| 191 | 192 | 193 | 194 | 195 | 196 | 197 | 198 | 199 | 200 |
| G | C | A | E | P | W | N | H | G | K |
| G:5 | C:5 | A:5 | E:4 Q:1 | P:5 | W:5 | N:4 D:1 | H:5 | G:5 | K:4 E:1 |

| | | | | C_H2 | | | | | |
|---|---|---|---|---|---|---|---|---|---|
| 201 | 202 | 203 | 204 | 205 | 206 | 207 | 208 | 209 | 210 |
| T | F | T | C | T | A | A | Y | P | E |
| T:5 | F:5 | T:5 | C:5 | T:5 | A:5 | A:5 | Y:4 H:1 | P:5 | E:5 |

FIG 32C

| | | | | C$_H$2 | | | | | |
|---|---|---|---|---|---|---|---|---|---|
| 211 | 212 | 213 | 214 | 215 | 216 | 217 | 218 | 219 | 220 |
| S | K | T | P | L | T | A | T | L | S |
| S:4 L:1 | K:5 | T:5 | P:5 | L:5 | T:5 | A:5 | T:4 N:1 | L:4 I:1 | S:4 T:1 |

| C$_H$2 | | | | C$_H$3 | | | | | |
|---|---|---|---|---|---|---|---|---|---|
| 221 | 222 | 223 | 224 | 225 | 226 | 227 | 228 | 229 | 230 |
| K | S | G | N | T | F | R | P | E | V |
| K:5 | S:5 | G:5 | N:5 | T:5 | F:5 | R:5 | P:5 | E:4 Q:1 | V:5 |

| | | | | C$_H$3 | | | | | |
|---|---|---|---|---|---|---|---|---|---|
| 231 | 232 | 233 | 234 | 235 | 236 | 237 | 238 | 239 | 240 |
| H | L | L | P | P | P | S | Z | E | E |
| H:5 | L:5 | L:5 | P:5 | P:5 | P:5 | S:5 | -:4 Z:1 | E:3 Q:1 Z:1 | E:3 Q:1 Z:1 |

| | | | | C$_H$3 | | | | | |
|---|---|---|---|---|---|---|---|---|---|
| 241 | 242 | 243 | 244 | 245 | 246 | 247 | 248 | 249 | 250 |
| L | A | L | N | E | L | V | T | L | T |
| L:5 | A:5 | L:5 | N:4 B:1 | E:3 Q:1 Z:1 | L:5 | V:5 | T:5 | L:5 | T:5 |

| | | | | C$_H$3 | | | | | |
|---|---|---|---|---|---|---|---|---|---|
| 251 | 252 | 253 | 254 | 255 | 256 | 257 | 258 | 259 | 260 |
| C | L | A | R | G | F | S | P | K | D |
| C:5 | L:5 | A:5 | R:5 | G:5 | F:5 | S:5 | P:5 | K:5 | D:5 |

| | | | | C$_H$3 | | | | | |
|---|---|---|---|---|---|---|---|---|---|
| 261 | 262 | 263 | 264 | 265 | 266 | 267 | 268 | 269 | 270 |
| V | L | V | R | W | L | Q | G | S | Q |
| V:5 | L:5 | V:5 | R:5 | W:5 | L:5 | Q:5 | G:5 | S:5 | Q:5 |

| | | | | C$_H$3 | | | | | |
|---|---|---|---|---|---|---|---|---|---|
| 271 | 272 | 273 | 274 | 275 | 276 | 277 | 278 | 279 | 280 |
| E | L | P | R | E | K | Y | L | T | W |
| E:5 | L:5 | P:5 | R:5 | E:5 | K:5 | Y:5 | L:5 | T:5 | W:5 |

FIG 32D

| C$_H$3 | | | | | | | | | |
|---|---|---|---|---|---|---|---|---|---|
| 281 A | 282 S | 283 R | 284 Q | 285 E | 286 P | 287 S | 288 Q | 289 G | 290 T |
| A:5 | S:5 | R:5 | Q:5 | E:4 Q:1 | P:5 | S:5 | Q:5 | G:5 | T:5 |

| C$_H$3 | | | | | | | | | |
|---|---|---|---|---|---|---|---|---|---|
| 291 T | 292 T | 293 F | 294 A | 295 V | 296 T | 297 S | 298 I | 299 L | 300 R |
| T:5 | T:5 | F:5 | A:5 | V:5 | T:5 | S:5 | I:5 | L:5 | R:5 |

| C$_H$3 | | | | | | | | | |
|---|---|---|---|---|---|---|---|---|---|
| 301 V | 302 A | 303 A | 304 E | 305 D | 306 W | 307 K | 308 K | 309 G | 310 D |
| V:5 | A:5 | A:5 | E:5 | D:5 | W:5 | K:5 | K:5 | G:5 | D:5 |

| C$_H$3 | | | | | | | | | |
|---|---|---|---|---|---|---|---|---|---|
| 311 T | 312 F | 313 S | 314 C | 315 M | 316 V | 317 G | 318 H | 319 E | 320 A |
| T:5 | F:5 | S:5 | C:5 | M:5 | V:5 | G:5 | H:5 | E:5 | A:5 |

| C$_H$3 | | | | | | | | | |
|---|---|---|---|---|---|---|---|---|---|
| 321 L | 322 P | 323 L | 324 A | 325 F | 326 T | 327 Q | 328 K | 329 T | 330 I |
| L:5 | P:5 | L:5 | A:5 | F:5 | T:5 | Q:5 | K:5 | T:5 | I:5 |

| C$_H$3 | | | | | | | | | |
|---|---|---|---|---|---|---|---|---|---|
| 331 D | 332 R | 333 L | 334 A | 335 G | 336 K | 337 P | 338 T | 339 H | 340 V |
| D:5 | R:5 | L:5 | A:5 | G:5 | K:5 | P:5 | T:5 | H:5 | V:5 |

| C$_H$3 | | | | | | | | | |
|---|---|---|---|---|---|---|---|---|---|
| 341 N | 342 V | 343 S | 344 V | 345 V | 346 M | 347 A | 348 E | 349 V | 350 D |
| N:5 | V:5 | S:5 | V:5 | V:5 | M:5 | A:5 | E:5 | V:5 | D:5 |

| C$_H$3 | | | | |
|---|---|---|---|---|
| 351 G | 352 T | 353 C | 354 Y | |
| G:5 | T:5 | C:5 | Y:5 | |

FIG 32E

|  |  |  |  | C_H1 |  |  |  |  |  |
|---|---|---|---|---|---|---|---|---|---|
| 1 | 2 | 3 | 4 | 5 | 6 | 7 | 8 | 9 | 10 |
| A | S | P | T | S | P | K | V | F | P |
| A:5 | S:6 | P:6 | T:6 | S:6 | P:6 | K:6 | V:6 | F:6 | P:6 |
| -:2 | -:1 | -:1 | -:1 | -:1 | -:1 | -:1 | -:1 | -:1 | -:1 |

|  |  |  |  | C_H1 |  |  |  |  |  |
|---|---|---|---|---|---|---|---|---|---|
| 11 | 12 | 13 | 14 | 15 | 16 | 17 | 18 | 19 | 20 |
| L | S | L | D | S | T | P | Q | D | G |
| L:6 | S:6 | L:6 | D:6 | S:6 | T:6 | P:6 | Q:6 | D:6 | G:6 |
| -:1 | -:1 | -:1 | -:1 | -:1 | -:1 | -:1 | -:1 | -:1 | -:1 |

|  |  |  |  | C_H1 |  |  |  |  |  |
|---|---|---|---|---|---|---|---|---|---|
| 21 | 22 | 23 | 24 | 25 | 26 | 27 | 28 | 29 | 30 |
| N | V | V | V | A | C | L | V | Q | G |
| N:6 | V:6 | V:5 | V:5 | A:5 | C:5 | L:5 | V:5 | Q:5 | G:5 |
| -:1 | -:1 | -:2 | -:2 | -:2 | -:2 | -:2 | -:2 | -:2 | -:2 |

|  |  |  |  | C_H1 |  |  |  |  |  |
|---|---|---|---|---|---|---|---|---|---|
| 31 | 32 | 33 | 34 | 35 | 36 | 37 | 38 | 39 | 40 |
| F | F | P | Q | E | P | L | S | V | T |
| F:5 | F:5 | P:5 | Q:5 | E:3 | P:5 | L:5 | S:5 | V:5 | T:5 |
| -:2 | -:2 | -:2 | -:2 | Z:2 | -:2 | -:2 | -:2 | -:2 | -:2 |
|  |  |  |  | -:2 |  |  |  |  |  |

|  |  |  |  | C_H1 |  |  |  |  |  |
|---|---|---|---|---|---|---|---|---|---|
| 41 | 42 | 43 | 44 | 45 | 46 | 47 | 48 | 49 | 50 |
| W | S | E | S | G | Q | N | V | T | A |
| W:5 | S:5 | E:5 | S:5 | G:5 | Q:3 | N:5 | V:5 | T:5 | A:5 |
| -:2 | -:2 | -:2 | -:2 | -:2 | Z:2 | -:2 | -:2 | -:2 | -:2 |
|  |  |  |  |  | -:2 |  |  |  |  |

FIG 33A

| | | | | | C_H1 | | | | |
|---|---|---|---|---|---|---|---|---|---|
| 51 | 52 | 53 | 54 | 55 | 56 | 57 | 58 | 59 | 60 |
| R | N | F | P | P | S | Q | D | A | S |
| R:5 | N:5 | F:5 | P:5 | P:5 | S:5 | Q:5 | D:3 | A:5 | S:5 |
| -:2 | -:2 | -:2 | -:2 | -:2 | -:2 | -:2 | B:2 | -:2 | -:2 |
| | | | | | | | -:2 | | |

| | | | | | C_H1 | | | | |
|---|---|---|---|---|---|---|---|---|---|
| 61 | 62 | 63 | 64 | 65 | 66 | 67 | 68 | 69 | 70 |
| G | D | L | Y | T | T | S | S | Q | L |
| G:5 | D:5 | L:5 | Y:5 | T:5 | T:5 | S:5 | S:5 | Q:5 | L:5 |
| -:2 | -:2 | -:2 | -:2 | -:2 | -:2 | -:2 | -:2 | -:2 | -:2 |

| | | | | | C_H1 | | | | |
|---|---|---|---|---|---|---|---|---|---|
| 71 | 72 | 73 | 74 | 75 | 76 | 77 | 78 | 79 | 80 |
| T | L | P | A | T | Q | C | P | D | G |
| T:5 | L:5 | P:5 | A:5 | T:5 | Q:3 | C:5 | P:5 | D:5 | G:5 |
| -:2 | -:2 | -:2 | -:2 | -:2 | -:2 | -:2 | -:2 | -:2 | -:2 |
| | | | | | Z:1 | | | | |
| | | | | | B:1 | | | | |

| | | | | | C_H1 | | | | |
|---|---|---|---|---|---|---|---|---|---|
| 81 | 82 | 83 | 84 | 85 | 86 | 87 | 88 | 89 | 90 |
| K | S | V | T | C | H | V | K | H | Y |
| K:5 | S:5 | V:5 | T:5 | C:5 | H:6 | V:6 | K:6 | H:6 | Y:6 |
| -:2 | -:2 | -:2 | -:2 | -:2 | -:1 | -:1 | -:1 | -:1 | -:1 |

| | | | | | C_H1 | | | | |
|---|---|---|---|---|---|---|---|---|---|
| 91 | 92 | 93 | 94 | 95 | 96 | 97 | 98 | 99 | 100 |
| T | N | P | S | Q | D | V | T | V | P |
| T:6 | N:6 | P:4 | S:6 | Q:6 | D:6 | V:6 | T:6 | V:6 | P:6 |
| -:1 | -:1 | S:2 | -:1 | -:1 | -:1 | -:1 | -:1 | -:1 | -:1 |
| | | -:1 | | | | | | | |

FIG 33B

| C_H1 | | HINGE | | | | | | C_H2 | |
|---|---|---|---|---|---|---|---|---|---|
| 101 | 102 | 103 | 104 | 105 | 106 | 107 | 108 | 109 | 110 |
| C | P | V | P | P | P | P | P | C | C |
| C:6 | P:5 | V:5 | P:5 | P:5 | P:5 | P:5 | P:5 | C:5 | C:5 |
| -:1 | R:1 | -:2 | -:2 | -:2 | -:2 | -:2 | -:2 | -:2 | -:2 |
|  | -:1 |  |  |  |  |  |  |  |  |

| C_H2 | | | | | | | | | |
|---|---|---|---|---|---|---|---|---|---|
| 111 | 112 | 113 | 114 | 115 | 116 | 117 | 118 | 119 | 120 |
| H | P | R | L | S | L | H | R | P | A |
| H:5 | P:5 | R:5 | L:5 | S:5 | L:5 | H:5 | R:5 | P:5 | A:5 |
| -:2 | -:2 | -:2 | -:2 | -:2 | -:2 | -:2 | -:2 | -:2 | -:2 |

| C_H2 | | | | | | | | | |
|---|---|---|---|---|---|---|---|---|---|
| 121 | 122 | 123 | 124 | 125 | 126 | 127 | 128 | 129 | 130 |
| L | E | D | L | L | L | G | S | E | A |
| L:7 | E:7 | D:7 | L:7 | L:7 | L:7 | G:7 | S:7 | E:7 | A:7 |

| C_H2 | | | | | | | | | |
|---|---|---|---|---|---|---|---|---|---|
| 131 | 132 | 133 | 134 | 135 | 136 | 137 | 138 | 139 | 140 |
| N | L | T | C | T | L | T | G | L | R |
| N:7 | L:7 | T:7 | C:7 | T:7 | L:7 | T:7 | G:7 | L:7 | R:7 |

| C_H2 | | | | | | | | | |
|---|---|---|---|---|---|---|---|---|---|
| 141 | 142 | 143 | 144 | 145 | 146 | 147 | 148 | 149 | 150 |
| D | A | S | G | A | T | F | T | W | T |
| D:7 | A:7 | S:7 | G:7 | A:7 | T:7 | F:7 | T:7 | W:7 | T:5 |
|  |  |  |  |  |  |  |  |  | -:2 |

FIG 33C

| | | | | | | | | | |
|---|---|---|---|---|---|---|---|---|---|
| C$_H$2 | | | | | | | | | |
| 151 | 152 | 153 | 154 | 155 | 156 | 157 | 158 | 159 | 160 |
| P | S | S | G | K | S | A | V | Q | G |
| P:7 | S:7 | S:7 | G:7 | K:7 | S:7 | A:7 | V:7 | Q:5 E:2 | G:7 |

| | | | | | | | | | |
|---|---|---|---|---|---|---|---|---|---|
| C$_H$2 | | | | | | | | | |
| 161 | 162 | 163 | 164 | 165 | 166 | 167 | 168 | 169 | 170 |
| P | P | E | R | D | L | C | G | C | Y |
| P:7 | P:7 | E:7 | R:7 | D:7 | L:7 | C:7 | G:7 | C:7 | Y:7 |

| | | | | | | | | | |
|---|---|---|---|---|---|---|---|---|---|
| C$_H$2 | | | | | | | | | |
| 171 | 172 | 173 | 174 | 175 | 176 | 177 | 178 | 179 | 180 |
| S | V | S | S | V | L | P | G | C | A |
| S:7 | V:7 | S:7 | S:7 | V:7 | L:7 | P:7 | G:7 | C:7 | A:7 |

| | | | | | | | | | |
|---|---|---|---|---|---|---|---|---|---|
| C$_H$2 | | | | | | | | | |
| 181 | 182 | 183 | 184 | 185 | 186 | 187 | 188 | 189 | 190 |
| Q | P | W | N | H | G | E | T | F | T |
| Q:5 Z:2 | P:7 | W:7 | N:7 | H:7 | G:7 | E:7 | T:7 | F:7 | T:7 |

| | | | | | | | | | |
|---|---|---|---|---|---|---|---|---|---|
| C$_H$2 | | | | | | | | | |
| 191 | 192 | 193 | 194 | 195 | 196 | 197 | 198 | 199 | 200 |
| C | T | A | A | H | P | E | L | K | T |
| C:7 | T:7 | A:7 | A:7 | H:7 | P:7 | E:7 | L:7 | K:7 | T:7 |

| | | | | | | | | | |
|---|---|---|---|---|---|---|---|---|---|
| C$_H$2 | | | | | | | | | C$_H$ |
| 201 | 202 | 203 | 204 | 205 | 206 | 207 | 208 | 209 | 210 |
| P | L | T | A | N | I | T | K | S | G |
| P:7 | L:7 | T:7 | A:7 | N:7 | I:7 | T:7 | K:7 | S:7 | G:6 -:1 |

FIG 33D

| | | | | C$_H$3 | | | | | |
|---|---|---|---|---|---|---|---|---|---|
| 211 | 212 | 213 | 214 | 215 | 216 | 217 | 218 | 219 | 220 |
| N | T | F | R | P | E | V | H | L | L |
| N:4 | T:6 | F:6 | R:6 | P:6 | E:6 | V:6 | H:6 | L:6 | L:6 |
| B:2 | -:1 | -:1 | -:1 | -:1 | -:1 | -:1 | -:1 | -:1 | -:1 |
| -:1 | | | | | | | | | |

| | | | | C$_H$3 | | | | | |
|---|---|---|---|---|---|---|---|---|---|
| 221 | 222 | 223 | 224 | 225 | 226 | 227 | 228 | 229 | 230 |
| P | P | P | S | E | E | L | A | L | N |
| P:6 | P:6 | P:6 | S:6 | E:6 | E:6 | L:6 | A:6 | L:6 | N:4 |
| -:1 | -:1 | -:1 | -:1 | -:1 | -:1 | -:1 | -:1 | -:1 | B:2 |
| | | | | | | | | | -:1 |

| | | | | C$_H$3 | | | | | |
|---|---|---|---|---|---|---|---|---|---|
| 231 | 232 | 233 | 234 | 235 | 236 | 237 | 238 | 239 | 240 |
| E | L | V | T | L | T | C | L | A | R |
| E:4 | L:6 | V:6 | T:6 | L:6 | T:6 | C:6 | L:6 | A:6 | R:6 |
| Z:2 | -:1 | -:1 | -:1 | -:1 | -:1 | -:1 | -:1 | -:1 | -:1 |
| -:1 | | | | | | | | | |

| | | | | C$_H$3 | | | | | |
|---|---|---|---|---|---|---|---|---|---|
| 241 | 242 | 243 | 244 | 245 | 246 | 247 | 248 | 249 | 250 |
| G | F | S | P | K | D | V | L | V | R |
| G:6 | F:6 | S:6 | P:6 | K:6 | D:4 | V:6 | L:6 | V:6 | R:6 |
| -:1 | -:1 | -:1 | -:1 | -:1 | B:2 | -:1 | -:1 | -:1 | -:1 |
| | | | | | -:1 | | | | |

| | | | | C$_H$3 | | | | | |
|---|---|---|---|---|---|---|---|---|---|
| 251 | 252 | 253 | 254 | 255 | 256 | 257 | 258 | 259 | 260 |
| W | L | Q | G | S | Q | E | L | P | R |
| W:6 | L:6 | Q:6 | G:6 | S:6 | Q:6 | E:6 | L:6 | P:6 | R:6 |
| -:1 | -:1 | -:1 | -:1 | -:1 | -:1 | -:1 | -:1 | -:1 | -:1 |

FIG 33E

| | | | | C$_H$3 | | | | | |
|---|---|---|---|---|---|---|---|---|---|
| 261 | 262 | 263 | 264 | 265 | 266 | 267 | 268 | 269 | 270 |
| E | K | Y | L | T | W | A | S | R | Q |
| E:6 | K:6 | Y:6 | L:6 | T:6 | W:6 | A:6 | S:6 | R:6 | Q:6 |
| -:1 | -:1 | -:1 | -:1 | -:1 | -:1 | -:1 | -:1 | -:1 | -:1 |

| | | | | C$_H$3 | | | | | |
|---|---|---|---|---|---|---|---|---|---|
| 271 | 272 | 273 | 274 | 275 | 276 | 277 | 278 | 279 | 280 |
| E | P | S | Q | G | T | T | T | F | A |
| E:4 | P:6 | S:6 | Q:5 | G:6 | T:6 | T:6 | T:6 | F:4 | A:6 |
| Z:2 | -:1 | -:1 | Z:1 | -:1 | -:1 | -:1 | -:1 | Y:2 | -:1 |
| -:1 | | | -:1 | | | | | -:1 | |

| | | | | C$_H$3 | | | | | |
|---|---|---|---|---|---|---|---|---|---|
| 281 | 282 | 283 | 284 | 285 | 286 | 287 | 288 | 289 | 290 |
| V | T | S | I | L | R | V | A | A | E |
| V:6 | T:6 | S:6 | I:6 | L:6 | R:6 | V:6 | A:6 | A:6 | E:4 |
| -:1 | -:1 | -:1 | -:1 | -:1 | -:1 | -:1 | -:1 | -:1 | Z:2 |
| | | | | | | | | | -:1 |

| | | | | C$_H$3 | | | | | |
|---|---|---|---|---|---|---|---|---|---|
| 291 | 292 | 293 | 294 | 295 | 296 | 297 | 298 | 299 | 300 |
| D | W | K | K | G | D | T | F | S | C |
| D:4 | W:6 | K:6 | K:6 | G:6 | D:4 | T:6 | F:6 | S:6 | C:6 |
| B:2 | -:1 | -:1 | -:1 | -:1 | E:2 | -:1 | -:1 | -:1 | -:1 |
| -:1 | | | | | -:1 | | | | |

| | | | | C$_H$3 | | | | | |
|---|---|---|---|---|---|---|---|---|---|
| 301 | 302 | 303 | 304 | 305 | 306 | 307 | 308 | 309 | 310 |
| M | V | G | H | E | A | L | P | L | A |
| M:6 | V:6 | G:6 | H:6 | E:6 | A:6 | L:6 | P:6 | L:6 | A:6 |
| -:1 | -:1 | -:1 | -:1 | -:1 | -:1 | -:1 | -:1 | -:1 | -:1 |

FIG 33F

| | | | | C$_H$3 | | | | | |
|---|---|---|---|---|---|---|---|---|---|
| 311 | 312 | 313 | 314 | 315 | 316 | 317 | 318 | 319 | 320 |
| F | T | Q | K | T | I | D | R | L | A |
| F:6 | T:6 | Q:6 | K:6 | T:6 | I:6 | D:6 | R:6 | L:5 | A:6 |
| -:1 | -:1 | -:1 | -:1 | -:1 | -:1 | -:1 | -:1 | M:1 | -:1 |
| | | | | | | | | -:1 | |

| | | | | C$_H$3 | | | | | |
|---|---|---|---|---|---|---|---|---|---|
| 321 | 322 | 323 | 324 | 325 | 326 | 327 | 328 | 329 | 330 |
| G | K | P | T | H | V | N | V | S | V |
| G:6 | K:6 | P:6 | T:6 | H:6 | V:4 | N:6 | V:6 | S:6 | V:6 |
| -:1 | -:1 | -:1 | -:1 | -:1 | I:2 | -:1 | -:1 | -:1 | -:1 |
| | | | | | -:1 | | | | |

| | | | | C$_H$3 | | | | | |
|---|---|---|---|---|---|---|---|---|---|
| 331 | 332 | 333 | 334 | 335 | 336 | 337 | 338 | 339 | 340 |
| V | M | A | E | V | D | G | T | C | Y |
| V:6 | M:6 | A:6 | E:6 | V:4 | D:4 | G:6 | T:6 | C:6 | Y:6 |
| -:1 | -:1 | -:1 | -:1 | A:2 | B:2 | -:1 | -:1 | -:1 | -:1 |
| | | | | -:1 | -:1 | | | | |

FIG 33G

| | | | | | C_H1 | | | | |
|---|---|---|---|---|---|---|---|---|---|
| 1 | 2 | 3 | 4 | 5 | 6 | 7 | 8 | 9 | 10 |
| A | P | T | K | A | P | D | V | F | P |
| A:2 | P:3 | T:3 | K:3 | A:3 | P:3 | D:3 | V:3 | F:3 | P:3 |
| -:2 | -:1 | -:1 | -:1 | -:1 | -:1 | -:1 | -:1 | -:1 | -:1 |

| | | | | | C_H1 | | | | |
|---|---|---|---|---|---|---|---|---|---|
| 11 | 12 | 13 | 14 | 15 | 16 | 17 | 18 | 19 | 20 |
| I | I | S | G | C | R | H | P | K | D |
| I:3 | I:3 | S:3 | G:3 | C:3 | R:3 | H:3 | P:3 | K:3 | D:3 |
| -:1 | -:1 | -:1 | -:1 | -:1 | -:1 | -:1 | -:1 | -:1 | -:1 |

| | | | | | C_H1 | | | | |
|---|---|---|---|---|---|---|---|---|---|
| 21 | 22 | 23 | 24 | 25 | 26 | 27 | 28 | 29 | 30 |
| N | S | P | V | V | L | A | C | L | I |
| N:3 | S:3 | P:3 | V:3 | V:3 | L:3 | A:3 | C:3 | L:3 | I:3 |
| -:1 | -:1 | -:1 | -:1 | -:1 | -:1 | -:1 | -:1' | -:1 | -:1 |

| | | | | | C_H1 | | | | |
|---|---|---|---|---|---|---|---|---|---|
| 31 | 32 | 33 | 34 | 35 | 36 | 37 | 38 | 39 | 40 |
| T | G | Y | H | P | T | S | V | T | V |
| T:3 | G:3 | Y:3 | H:3 | P:3 | T:3 | S:3 | V:3 | T:3 | V:3 |
| -:1 | -:1 | -:1 | -:1 | -:1 | -:1 | -:1 | -:1 | -:1 | -:1 |

| | | | | | C_H1 | | | | |
|---|---|---|---|---|---|---|---|---|---|
| 41 | 42 | 43 | 44 | 45 | 46 | 47 | 48 | 49 | 50 |
| T | W | Y | M | G | T | Q | S | Q | P |
| T:3 | W:3 | Y:3 | M:3 | G:3 | T:3 | Q:3 | S:3 | Q:3 | P:3 |
| -:1 | -:1 | -:1 | -:1 | -:1 | -:1 | -:1 | -:1 | -:1 | -:1 |

FIG 34A

| | | | | | C$_H$1 | | | | |
|---|---|---|---|---|---|---|---|---|---|
| 51 | 52 | 53 | 54 | 55 | 56 | 57 | 58 | 59 | 60 |
| Q | R | T | F | P | E | I | Q | R | R |
| Q:3 | R:3 | T:3 | F:3 | P:3 | E:3 | I:3 | Q:3 | R:3 | R:3 |
| -:1 | -:1 | -:1 | -:1 | -:1 | -:1 | -:1 | -:1 | -:1 | -:1 |

| | | | | | C$_H$1 | | | | |
|---|---|---|---|---|---|---|---|---|---|
| 61 | 62 | 63 | 64 | 65 | 66 | 67 | 68 | 69 | 70 |
| D | S | Y | Y | M | T | S | S | Q | L |
| D:3 | S:3 | Y:3 | Y:3 | M:3 | T:3 | S:3 | S:3 | Q:3 | L:3 |
| -:1 | -:1 | -:1 | -:1 | -:1 | -:1 | -:1 | -:1 | -:1 | -:1 |

| | | | | | C$_H$1 | | | | |
|---|---|---|---|---|---|---|---|---|---|
| 71 | 72 | 73 | 74 | 75 | 76 | 77 | 78 | 79 | 80 |
| S | T | P | L | Q | Q | W | R | Q | G |
| S:3 | T:3 | P:3 | L:3 | Q:3 | Q:3 | W:3 | R:3 | Q:3 | G:3 |
| -:1 | -:1 | -:1 | -:1 | -:1 | -:1 | -:1 | -:1 | -:1 | -:1 |

| | | | | | C$_H$1 | | | | |
|---|---|---|---|---|---|---|---|---|---|
| 81 | 82 | 83 | 84 | 85 | 86 | 87 | 88 | 89 | 90 |
| E | Y | K | C | V | V | Q | H | T | A |
| E:3 | Y:3 | K:3 | C:3 | V:3 | V:3 | Q:3 | H:3 | T:3 | A:3 |
| -:1 | -:1 | -:1 | -:1 | -:1 | -:1 | -:1 | -:1 | -:1 | -:1 |

| | | | | | C$_H$1 | | | | |
|---|---|---|---|---|---|---|---|---|---|
| 91 | 92 | 93 | 94 | 95 | 96 | 97 | 98 | 99 | 100 |
| S | K | S | K | K | E | I | F | R | W |
| S:3 | K:3 | S:3 | K:3 | K:3 | E:3 | I:3 | F:3 | R:3 | W:3 |
| -:1 | -:1 | -:1 | -:1 | -:1 | -:1 | -:1 | -:1 | -:1 | -:1 |

FIG 34B

| C_H | Hinge 1 | | | | | | | | |
|---|---|---|---|---|---|---|---|---|---|
| 101 P | 102 E | 103 S | 104 P | 105 K | 106 A | 107 Q | 108 A | 109 S | 110 S |
| P:3 -:1 | E:3 -:1 | S:3 -:1 | P:3 -:1 | K:3 -:1 | A:3 -:1 | Q:3 -:1 | A:3 -:1 | S:3 -:1 | S:3 -:1 |

| Hinge 1 | | | | | | | | | |
|---|---|---|---|---|---|---|---|---|---|
| 111 V | 112 P | 113 T | 114 A | 115 Q | 116 P | 117 Q | 118 A | 119 E | 120 G |
| V:3 -:1 | P:3 -:1 | T:3 -:1 | A:3 -:1 | Q:3 -:1 | P:3 -:1 | Q:3 -:1 | A:3 -:1 | E:3 -:1 | G:3 -:1 |

| Hinge 1 | | | | | | | | | |
|---|---|---|---|---|---|---|---|---|---|
| 121 S | 122 L | 123 A | 124 K | 125 A | 126 T | 127 T | 128 A | 129 P | 130 A |
| S:3 -:1 | L:3 -:1 | A:3 -:1 | K:3 -:1 | A:3 -:1 | T:3 -:1 | T:3 -:1 | A:3 -:1 | P:3 -:1 | A:3 -:1 |

| Hinge 1 | | | | | Hinge 2 | | | | |
|---|---|---|---|---|---|---|---|---|---|
| 131 T | 132 T | 133 R | 134 N | 135 T | 136 G | 137 R | 138 G | 139 G | 140 E |
| T:3 -:1 | T:3 -:1 | R:3 -:1 | N:3 -:1 | T:3 -:1 | G:3 -:1 | R:3 -:1 | G:3 -:1 | G:3 -:1 | E:3 -:1 |

| Hinge 2 | | | | | | | | | |
|---|---|---|---|---|---|---|---|---|---|
| 141 E | 142 K | 143 K | 144 K | 145 E | 146 K | 147 E | 148 K | 149 E | 150 E |
| E:3 -:1 | K:3 -:1 | K:3 -:1 | K:3 -:1 | E:3 -:1 | K:3 -:1 | E:3 -:1 | K:3 -:1 | E:3 -:1 | E:3 -:1 |

FIG 34C

| | | | | Hinge 2 | | | | | C_H |
|---|---|---|---|---|---|---|---|---|---|
| 151 | 152 | 153 | 154 | 155 | 156 | 157 | 158 | 159 | 160 |
| Q | E | E | R | E | T | K | T | P | E |
| Q:3 | E:3 | E:3 | R:3 | E:3 | T:3 | K:3 | T:4 | P:4 | E:4 |
| -:1 | -:1 | -:1 | -:1 | -:1 | -:1 | -:1 | | | |

| | | | | $C_H2$ | | | | | |
|---|---|---|---|---|---|---|---|---|---|
| 161 | 162 | 163 | 164 | 165 | 166 | 167 | 168 | 169 | 170 |
| C | P | S | H | T | Q | P | L | G | V |
| C:4 | P:4 | S:4 | H:4 | T:4 | Q:4 | P:4 | L:4 | G:4 | V:4 |

| | | | | $C_H2$ | | | | | |
|---|---|---|---|---|---|---|---|---|---|
| 171 | 172 | 173 | 174 | 175 | 176 | 177 | 178 | 179 | 180 |
| Y | L | L | T | P | A | V | Q | D | L |
| Y:4 | L:4 | L:4 | T:4 | P:4 | A:4 | V:4 | Q:4 | D:4 | L:4 |

| | | | | $C_H2$ | | | | | |
|---|---|---|---|---|---|---|---|---|---|
| 181 | 182 | 183 | 184 | 185 | 186 | 187 | 188 | 189 | 190 |
| W | L | R | D | K | A | T | F | T | C |
| W:4 | L:4 | R:4 | D:4 | K:4 | A:4 | T:4 | F:4 | T:4 | C:4 |

| | | | | $C_H2$ | | | | | |
|---|---|---|---|---|---|---|---|---|---|
| 191 | 192 | 193 | 194 | 195 | 196 | 197 | 198 | 199 | 200 |
| F | V | V | G | S | D | L | K | D | A |
| F:4 | V:4 | V:4 | G:4 | S:4 | D:4 | L:4 | K:4 | D:4 | A:4 |

| | | | | $C_H2$ | | | | | |
|---|---|---|---|---|---|---|---|---|---|
| 201 | 202 | 203 | 204 | 205 | 206 | 207 | 208 | 209 | 210 |
| H | L | T | W | E | V | A | G | K | V |
| H:4 | L:4 | T:4 | W:4 | E:4 | V:4 | A:4 | G:4 | K:4 | V:4 |

FIG 34D

| | | | | C_H2 | | | | | |
|---|---|---|---|---|---|---|---|---|---|
| 211 | 212 | 213 | 214 | 215 | 216 | 217 | 218 | 219 | 220 |
| P | T | G | G | V | E | E | G | L | L |
| P:4 | T:4 | G:4 | G:4 | V:4 | E:4 | E:4 | G:4 | L:4 | L:4 |

| | | | | C_H2 | | | | | |
|---|---|---|---|---|---|---|---|---|---|
| 221 | 222 | 223 | 224 | 225 | 226 | 227 | 228 | 229 | 230 |
| E | R | H | S | N | G | S | Q | S | Q |
| E:4 | R:4 | H:4 | S:4 | N:4 | G:4 | S:4 | Q:4 | S:4 | Q:4 |

| | | | | C_H2 | | | | | |
|---|---|---|---|---|---|---|---|---|---|
| 231 | 232 | 233 | 234 | 235 | 236 | 237 | 238 | 239 | 240 |
| H | S | R | L | T | L | P | R | S | L |
| H:4 | S:4 | R:4 | L:4 | T:4 | L:4 | P:4 | R:4 | S:4 | L:4 |

| | | | | C_H2 | | | | | |
|---|---|---|---|---|---|---|---|---|---|
| 241 | 242 | 243 | 244 | 245 | 246 | 247 | 248 | 249 | 250 |
| W | N | A | G | T | S | V | T | C | T |
| W:4 | N:4 | A:4 | G:4 | T:4 | S:4 | V:4 | T:4 | C:4 | T:4 |

| | | | | C_H2 | | | | | |
|---|---|---|---|---|---|---|---|---|---|
| 251 | 252 | 253 | 254 | 255 | 256 | 257 | 258 | 259 | 260 |
| L | N | H | P | S | L | P | P | Q | R |
| L:4 | N:4 | H:4 | P:4 | S:4 | L:4 | P:4 | P:4 | Q:4 | R:4 |

| | | | C_H2 | | | | C_H3 | | |
|---|---|---|---|---|---|---|---|---|---|
| 261 | 262 | 263 | 264 | 265 | 266 | 267 | 268 | 269 | 270 |
| L | M | A | L | R | E | P | A | A | Q |
| L:4 | M:4 | A:4 | L:4 | R:4 | E:4 | P:4 | A:4 | A:4 | Q:4 |

FIG 34E

| | | | | | | | | | |
|---|---|---|---|---|---|---|---|---|---|
| \multicolumn{10}{|c|}{C_H3} |
| 271 | 272 | 273 | 274 | 275 | 276 | 277 | 278 | 279 | 280 |
| A | P | V | K | L | S | L | N | L | L |
| A:4 | P:4 | V:4 | K:4 | L:4 | S:4 | L:4 | N:4 | L:4 | L:4 |

C_H3

| 281 | 282 | 283 | 284 | 285 | 286 | 287 | 288 | 289 | 290 |
|---|---|---|---|---|---|---|---|---|---|
| A | S | S | D | P | P | E | A | A | S |
| A:4 | S:4 | S:4 | D:4 | P:4 | P:4 | E:4 | A:4 | A:4 | S:4 |

C_H3

| 291 | 292 | 293 | 294 | 295 | 296 | 297 | 298 | 299 | 300 |
|---|---|---|---|---|---|---|---|---|---|
| W | L | L | C | E | V | S | G | F | S |
| W:4 | L:4 | L:4 | C:4 | E:4 | V:4 | S:4 | G:4 | F:4 | S:4 |

C_H3

| 301 | 302 | 303 | 304 | 305 | 306 | 307 | 308 | 309 | 310 |
|---|---|---|---|---|---|---|---|---|---|
| P | P | N | I | L | L | M | W | L | E |
| P:4 | P:4 | N:4 | I:4 | L:4 | L:4 | M:4 | W:4 | L:4 | E:4 |

C_H3

| 311 | 312 | 313 | 314 | 315 | 316 | 317 | 318 | 319 | 320 |
|---|---|---|---|---|---|---|---|---|---|
| D | Q | R | E | V | N | T | S | G | F |
| D:4 | Q:4 | R:4 | E:4 | V:4 | N:4 | T:4 | S:4 | G:4 | F:4 |

C_H3

| 321 | 322 | 323 | 324 | 325 | 326 | 327 | 328 | 329 | 330 |
|---|---|---|---|---|---|---|---|---|---|
| A | P | A | R | P | P | P | Q | P | R |
| A:4 | P:4 | A:4 | R:4 | P:4 | P:4 | P:4 | Q:4 | P:4 | R:2 |
| | | | | | | | | | G:2 |

FIG 34F

| | | | | | | | | | |
|---|---|---|---|---|---|---|---|---|---|
| | | | | C$_H$3 | | | | | |
| 331 | 332 | 333 | 334 | 335 | 336 | 337 | 338 | 339 | 340 |
| S | T | T | F | W | A | W | S | V | L |
| S:4 | T:4 | T:4 | F:4 | W:4 | A:4 | W:4 | S:4 | V:4 | L:4 |

| | | | | | | | | | |
|---|---|---|---|---|---|---|---|---|---|
| | | | | C$_H$3 | | | | | |
| 341 | 342 | 343 | 344 | 345 | 346 | 347 | 348 | 349 | 350 |
| R | V | P | A | P | P | S | P | Q | P |
| R:4 | V:4 | P:4 | A:4 | P:4 | P:4 | S:4 | P:4 | Q:4 | P:4 |

| | | | | | | | | | |
|---|---|---|---|---|---|---|---|---|---|
| | | | | C$_H$3 | | | | | |
| 351 | 352 | 353 | 354 | 355 | 356 | 357 | 358 | 359 | 360 |
| A | T | Y | T | C | V | V | S | H | E |
| A:4 | T:4 | Y:4 | T:4 | C:4 | V:4 | V:4 | S:4 | H:4 | E:4 |

| | | | | | | | | | |
|---|---|---|---|---|---|---|---|---|---|
| | | | | C$_H$3 | | | | | |
| 361 | 362 | 363 | 364 | 365 | 366 | 367 | 368 | 369 | 370 |
| D | S | R | T | L | L | N | A | S | R |
| D:4 | S:4 | R:4 | T:4 | L:4 | L:4 | N:4 | A:4 | S:4 | R:4 |

| | | | | | | | | | |
|---|---|---|---|---|---|---|---|---|---|
| | | | | C$_H$3 | | | | | |
| 371 | 372 | 373 | 374 | 375 | 376 | 377 | 378 | 379 | 380 |
| S | L | E | V | S | Y | V | T | D | H |
| S:4 | L:4 | E:4 | V:4 | S:4 | Y:4 | V:4 | T:4 | D:4 | H:4 |

| | | | |
|---|---|---|---|
| | C$_H$3 | | |
| 381 | 382 | 383 | 384 |
| G | P | M | K |
| G:4 | P:4 | M:4 | K:2 |
| | | | -:2 |

FIG 34G

| | | | | | C_H1 | | | | |
|---|---|---|---|---|---|---|---|---|---|
| 1 | 2 | 3 | 4 | 5 | 6 | 7 | 8 | 9 | 10 |
| A | S | T | Q | S | P | S | V | F | P |
| -:5 | S:5 | T:5 | Q:5 | S:5 | P:5 | S:5 | V:5 | F:5 | P:6 |
| A:3 | -:3 | -:3 | -:3 | -:3 | -:3 | -:3 | -:3 | -:3 | -:2 |

| | | | | | C_H1 | | | | |
|---|---|---|---|---|---|---|---|---|---|
| 11 | 12 | 13 | 14 | 15 | 16 | 17 | 18 | 19 | 20 |
| L | T | R | C | C | K | N | I | P | S |
| L:6 | T:6 | R:6 | C:6 | C:6 | K:6 | N:5 | I:6 | P:6 | S:6 |
| -:2 | -:2 | -:2 | -:2 | -:2 | -:2 | -:2 | -:2 | -:2 | -:2 |
| | | | | | | B:1 | | | |

| | | | | | C_H1 | | | | |
|---|---|---|---|---|---|---|---|---|---|
| 21 | 22 | 23 | 24 | 25 | 26 | 27 | 28 | 29 | 30 |
| N | A | T | S | V | T | L | G | C | L |
| N:6 | A:6 | T:6 | S:6 | V:6 | T:6 | L:6 | G:6 | C:6 | L:6 |
| -:2 | -:2 | -:2 | -:2 | -:2 | -:2 | -:2 | -:2 | -:2 | -:2 |

| | | | | | C_H1 | | | | |
|---|---|---|---|---|---|---|---|---|---|
| 31 | 32 | 33 | 34 | 35 | 36 | 37 | 38 | 39 | 40 |
| A | T | G | Y | F | P | E | P | V | M |
| A:6 | T:6 | G:6 | Y:6 | F:5 | P:6 | E:6 | P:6 | V:6 | M:6 |
| -:2 | -:2 | -:2 | -:2 | -:2 | -:2 | -:2 | -:2 | -:2 | -:2 |
| | | | | P:1 | | | | | |

| | | | | | C_H1 | | | | |
|---|---|---|---|---|---|---|---|---|---|
| 41 | 42 | 43 | 44 | 45 | 46 | 47 | 48 | 49 | 50 |
| V | T | W | D | T | G | S | L | N | G |
| V:6 | T:6 | W:5 | D:5 | T:6 | G:6 | S:6 | L:6 | N:6 | G:6 |
| -:2 | -:2 | -:2 | -:2 | -:2 | -:2 | -:2 | -:2 | -:2 | -:2 |
| | | C:1 | B:1 | | | | | | |

FIG 35A

| | | | | | C_H1 | | | | |
|---|---|---|---|---|---|---|---|---|---|
| 51 | 52 | 53 | 54 | 55 | 56 | 57 | 58 | 59 | 60 |
| T | T | M | T | L | P | A | T | T | L |
| T:6 | T:5 | M:5 | T:6 | L:6 | P:6 | A:6 | T:6 | T:6 | L:6 |
| -:2 | -:3 | -:3 | -:2 | -:2 | -:2 | -:2 | -:2 | -:2 | -:2 |

| | | | | | C_H1 | | | | |
|---|---|---|---|---|---|---|---|---|---|
| 61 | 62 | 63 | 64 | 65 | 66 | 67 | 68 | 69 | 70 |
| T | L | S | G | H | Y | A | T | I | S |
| T:6 | L:6 | S:6 | G:6 | H:6 | Y:6 | A:6 | T:6 | I:6 | S:6 |
| -:2 | -:2 | -:2 | -:2 | -:2 | -:2 | -:2 | -:2 | -:2 | -:2 |

| | | | | | C_H1 | | | | |
|---|---|---|---|---|---|---|---|---|---|
| 71 | 72 | 73 | 74 | 75 | 76 | 77 | 78 | 79 | 80 |
| L | L | T | V | S | G | A | W | A | K |
| L:6 | L:6 | T:6 | V:6 | S:6 | G:6 | A:6 | W:6 | A:6 | K:6 |
| -:2 | -:2 | -:2 | -:2 | -:2 | -:2 | -:2 | -:2 | -:2 | -:2 |

| | | | | | C_H1 | | | | |
|---|---|---|---|---|---|---|---|---|---|
| 81 | 82 | 83 | 84 | 85 | 86 | 87 | 88 | 89 | 90 |
| Q | M | F | T | C | R | V | A | H | T |
| Q:6 | M:6 | F:6 | T:6 | C:6 | R:6 | V:6 | A:6 | H:6 | T:6 |
| -:2 | -:2 | -:2 | -:2 | -:2 | -:2 | -:2 | -:2 | -:2 | -:2 |

| | | | | | C_H1 | | | | |
|---|---|---|---|---|---|---|---|---|---|
| 91 | 92 | 93 | 94 | 95 | 96 | 97 | 98 | 99 | 100 |
| P | S | S | T | D | W | V | D | N | K |
| P:6 | S:6 | S:6 | T:6 | D:5 | W:5 | V:5 | D:5 | N:5 | K:6 |
| -:2 | -:2 | -:2 | -:2 | -:2 | -:3 | -:3 | -:2 | -:2 | -:2 |
| | | | | B:1 | | | | N:1 | V:1 |

FIG 35B

|  C_H1  | C_H2 | | | | | | | | |
|---|---|---|---|---|---|---|---|---|---|
| 101<br>T | 102<br>F | 103<br>S | 104<br>V | 105<br>C | 106<br>S | 107<br>R | 108<br>D | 109<br>F | 110<br>T |
| T:6<br>-:2 | F:6<br>-:2 | S:6<br>-:2 | V:5<br>-:3 | C:5<br>-:3 | S:5<br>-:3 | R:5<br>-:3 | D:4<br>-:3<br>B:1 | F:6<br>-:2 | T:6<br>-:2 |

| C_H2 | | | | | | | | | |
|---|---|---|---|---|---|---|---|---|---|
| 111<br>P | 112<br>P | 113<br>T | 114<br>V | 115<br>K | 116<br>I | 117<br>L | 118<br>Q | 119<br>S | 120<br>S |
| P:6<br>-:2 | P:6<br>-:2 | T:6<br>-:2 | V:6<br>-:2 | K:6<br>-:2 | I:6<br>-:2 | L:6<br>-:2 | Q:5<br>-:2<br>Z:1 | S:6<br>-:2 | S:6<br>-:2 |

| C_H2 | | | | | | | | | |
|---|---|---|---|---|---|---|---|---|---|
| 121<br>C | 122<br>D | 123<br>G | 124<br>G | 125<br>G | 126<br>H | 127<br>F | 128<br>P | 129<br>P | 130<br>T |
| C:6<br>-:2 | D:5<br>-:2<br>B:1 | G:6<br>-:2 | G:5<br>-:2<br>L:1 | G:6<br>-:2 | H:6<br>-:2 | F:6<br>-:2 | P:6<br>-:2 | P:6<br>-:2 | T:6<br>-:2 |

| C_H2 | | | | | | | | | |
|---|---|---|---|---|---|---|---|---|---|
| 131<br>I | 132<br>Q | 133<br>L | 134<br>L | 135<br>C | 136<br>L | 137<br>V | 138<br>S | 139<br>G | 140<br>Y |
| I:6<br>-:2 | Q:5<br>-:2<br>Z:1 | L:5<br>-:3 | L:6<br>-:2 | C:6<br>-:2 | L:6<br>-:2 | V:6<br>-:2 | S:6<br>-:2 | G:6<br>-:2 | Y:6<br>-:2 |

| C_H2 | | | | | | | | | |
|---|---|---|---|---|---|---|---|---|---|
| 141<br>T | 142<br>P | 143<br>G | 144<br>T | 145<br>I | 146<br>N | 147<br>I | 148<br>T | 149<br>W | 150<br>L |
| T:6<br>-:2 | P:6<br>-:2 | G:6<br>-:2 | T:6<br>-:2 | I:6<br>-:2 | N:6<br>-:2 | I:6<br>-:2 | T:6<br>-:2 | W:6<br>-:2 | L:6<br>-:2 |

FIG 35C

| C$_H$2 | | | | | | | | | |
|---|---|---|---|---|---|---|---|---|---|
| 151 | 152 | 153 | 154 | 155 | 156 | 157 | 158 | 159 | 160 |
| E | D | G | Q | V | M | D | V | D | L |
| E:5 | D:5 | G:6 | Q:5 | V:6 | M:6 | D:6 | V:6 | D:6 | L:6 |
| -:2 | -:2 | -:2 | -:2 | -:2 | -:2 | -:2 | -:2 | -:2 | -:2 |
| Z:1 | B:1 | | Z:1 | | | | | | |

| C$_H$2 | | | | | | | | | |
|---|---|---|---|---|---|---|---|---|---|
| 161 | 162 | 163 | 164 | 165 | 166 | 167 | 168 | 169 | 170 |
| S | T | A | S | T | T | Q | E | G | E |
| S:6 | T:6 | A:6 | S:6 | T:6 | T:5 | Q:5 | E:6 | G:6 | E:6 |
| -:2 | -:2 | -:2 | -:2 | -:2 | -:2 | -:2 | -:2 | -:2 | -:2 |
| | | | | | E:1 | S:1 | | | |

| C$_H$2 | | | | | | | | | |
|---|---|---|---|---|---|---|---|---|---|
| 171 | 172 | 173 | 174 | 175 | 176 | 177 | 178 | 179 | 180 |
| L | A | S | T | Q | S | E | L | T | L |
| L:6 | A:6 | S:6 | T:6 | Q:5 | S:6 | E:6 | L:6 | T:6 | L:6 |
| -:2 | -:2 | -:2 | -:2 | -:2 | -:2 | -:2 | -:2 | -:2 | -:2 |
| | | | | E:1 | | | | | |

| C$_H$2 | | | | | | | | | |
|---|---|---|---|---|---|---|---|---|---|
| 181 | 182 | 183 | 184 | 185 | 186 | 187 | 188 | 189 | 190 |
| S | Q | K | H | W | L | S | D | R | T |
| S:6 | Q:6 | K:6 | H:6 | W:6 | L:6 | S:6 | D:6 | R:6 | T:6 |
| -:2 | -:2 | -:2 | -:2 | -:2 | -:2 | -:2 | -:2 | -:2 | -:2 |

| C$_H$2 | | | | | | | | | |
|---|---|---|---|---|---|---|---|---|---|
| 191 | 192 | 193 | 194 | 195 | 196 | 197 | 198 | 199 | 200 |
| Y | T | C | Q | V | T | Y | Q | G | H |
| Y:6 | T:6 | C:6 | Q:5 | V:6 | T:6 | Y:6 | Q:5 | G:6 | H:6 |
| -:2 | -:2 | -:2 | -:2 | -:2 | -:2 | -:2 | -:2 | -:2 | -:2 |
| | | | E:1 | | | | Z:1 | | |

FIG 35D

| CH2 | | | | | | | | | |
|---|---|---|---|---|---|---|---|---|---|
| 201 | 202 | 203 | 204 | 205 | 206 | 207 | 208 | 209 | 210 |
| T | F | E | D | S | T | K | K | C | A |
| T:6 | F:6 | E:5 | D:5 | S:6 | T:6 | K:6 | K:6 | C:6 | A:6 |
| -:2 | -:2 | -:2 | -:2 | -:2 | -:2 | -:2 | -:2 | -:2 | -:2 |
| | | Z:1 | B:1 | | | | | | |

| CH3 | | | | | | | | | |
|---|---|---|---|---|---|---|---|---|---|
| 211 | 212 | 213 | 214 | 215 | 216 | 217 | 218 | 219 | 220 |
| D | S | N | P | R | G | V | S | A | Y |
| D:6 | S:6 | N:5 | P:6 | R:6 | G:6 | V:6 | S:6 | A:6 | Y:6 |
| -:2 | -:2 | -:2 | -:2 | -:2 | -:2 | -:2 | -:2 | -:2 | -:2 |
| | | D:1 | | | | | | | |

| CH3 | | | | | | | | | |
|---|---|---|---|---|---|---|---|---|---|
| 221 | 222 | 223 | 224 | 225 | 226 | 227 | 228 | 229 | 230 |
| L | S | R | P | S | P | F | D | L | F |
| L:6 | S:6 | R:6 | P:6 | S:6 | P:6 | F:6 | D:6 | L:6 | F:6 |
| -:2 | -:2 | -:2 | -:2 | -:2 | -:2 | -:2 | -:2 | -:2 | -:2 |

| CH3 | | | | | | | | | |
|---|---|---|---|---|---|---|---|---|---|
| 231 | 232 | 233 | 234 | 235 | 236 | 237 | 238 | 239 | 240 |
| I | R | K | S | P | T | I | T | C | L |
| I:6 | R:6 | K:6 | S:6 | P:6 | T:6 | I:6 | T:6 | C:6 | L:6 |
| -:2 | -:2 | -:2 | -:2 | -:2 | -:2 | -:2 | -:2 | -:2 | -:2 |

| CH3 | | | | | | | | | |
|---|---|---|---|---|---|---|---|---|---|
| 241 | 242 | 243 | 244 | 245 | 246 | 247 | 248 | 249 | 250 |
| V | V | D | L | A | P | S | K | G | T |
| V:6 | V:6 | D:5 | L:6 | A:6 | P:6 | S:6 | K:6 | G:6 | T:6 |
| -:2 | -:2 | -:2 | -:2 | -:2 | -:2 | -:2 | -:2 | -:2 | -:2 |
| | | B:1 | | | | | | | |

FIG 35E

| | | | | | | | | | |
|---|---|---|---|---|---|---|---|---|---|
| | | | | C_H3 | | | | | |
| 251 | 252 | 253 | 254 | 255 | 256 | 257 | 258 | 259 | 260 |
| V | N | L | T | W | S | R | A | S | G |
| V:6 | N:5 | L:6 | T:6 | W:6 | S:6 | R:6 | A:6 | S:6 | G:6 |
| -:2 | -:2 | -:2 | -:2 | -:2 | -:2 | -:2 | -:2 | -:2 | -:2 |
| | B:1 | | | | | | | | |

| | | | | | | | | | |
|---|---|---|---|---|---|---|---|---|---|
| | | | | C_H3 | | | | | |
| 261 | 262 | 263 | 264 | 265 | 266 | 267 | 268 | 269 | 270 |
| K | P | V | N | H | S | T | R | K | E |
| K:6 | P:6 | V:6 | N:5 | H:6 | S:6 | T:6 | R:6 | K:6 | E:6 |
| -:2 | -:2 | -:2 | -:2 | -:2 | -:2 | -:2 | -:2 | -:2 | -:2 |
| | | | B:1 | | | | | | |

| | | | | | | | | | |
|---|---|---|---|---|---|---|---|---|---|
| | | | | C_H3 | | | | | |
| 271 | 272 | 273 | 274 | 275 | 276 | 277 | 278 | 279 | 280 |
| E | K | Q | R | N | G | T | L | T | V |
| E:6 | K:6 | Q:6 | R:6 | N:5 | G:6 | T:6 | L:6 | T:6 | V:6 |
| -:2 | -:2 | -:2 | -:2 | -:2 | -:2 | -:2 | -:2 | -:2 | -:2 |
| | | | | B:1 | | | | | |

| | | | | | | | | | |
|---|---|---|---|---|---|---|---|---|---|
| | | | | C_H3 | | | | | |
| 281 | 282 | 283 | 284 | 285 | 286 | 287 | 288 | 289 | 290 |
| T | S | T | L | P | V | G | T | R | D |
| T:6 | S:6 | T:6 | L:6 | P:6 | V:6 | G:6 | T:6 | R:6 | D:5 |
| -:2 | -:2 | -:2 | -:2 | -:2 | -:2 | -:2 | -:2 | -:2 | -:2 |
| | | | | | | | | | B:1 |

| | | | | | | | | | |
|---|---|---|---|---|---|---|---|---|---|
| | | | | C_H3 | | | | | |
| 291 | 292 | 293 | 294 | 295 | 296 | 297 | 298 | 299 | 300 |
| W | I | E | G | E | T | Y | Q | C | R |
| W:6 | I:6 | E:6 | G:6 | E:6 | T:6 | Y:6 | Q:5 | C:6 | R:6 |
| -:2 | -:2 | -:2 | -:2 | -:2 | -:2 | -:2 | -:2 | -:2 | -:2 |
| | | | | | | | Z:1 | | |

FIG 35F

| C_H3 | | | | | | | | | |
|---|---|---|---|---|---|---|---|---|---|
| 301 | 302 | 303 | 304 | 305 | 306 | 307 | 308 | 309 | 310 |
| V | T | H | P | H | L | P | R | A | L |
| V:6 | T:6 | H:6 | P:6 | H:6 | L:6 | P:6 | R:6 | A:6 | L:6 |
| -:2 | -:2 | -:2 | -:2 | -:2 | -:2 | -:2 | -:2 | -:2 | -:2 |

| C_H3 | | | | | | | | C_H4 | |
|---|---|---|---|---|---|---|---|---|---|
| 311 | 312 | 313 | 314 | 315 | 316 | 317 | 318 | 319 | 320 |
| M | R | S | T | T | K | T | S | G | P |
| M:6 | R:6 | S:6 | T:7 | T:7 | K:6 | T:7 | S:7 | -:6 | -:6 |
| -:2 | -:2 | -:2 | -:1 | -:1 | -:1 | -:1 | -:1 | G:2 | P:2 |
| | | | | | N:1 | | | | |

| C_H4 | | | | | | | | | |
|---|---|---|---|---|---|---|---|---|---|
| 321 | 322 | 323 | 324 | 325 | 326 | 327 | 328 | 329 | 330 |
| V | G | P | R | A | A | P | E | V | Y |
| -:6 | G:7 | P:7 | R:7 | A:7 | A:7 | P:7 | E:7 | V:7 | Y:7 |
| V:2 | -:1 | -:1 | -:1 | -:1 | -:1 | -:1 | -:1 | -:1 | -:1 |

| C_H4 | | | | | | | | | |
|---|---|---|---|---|---|---|---|---|---|
| 331 | 332 | 333 | 334 | 335 | 336 | 337 | 338 | 339 | 340 |
| A | F | A | T | P | E | W | P | G | S |
| A:7 | F:7 | A:7 | T:7 | P:7 | E:7 | W:7 | P:7 | G:7 | S:7 |
| -:1 | -:1 | -:1 | -:1 | -:1 | -:1 | -:1 | -:1 | -:1 | -:1 |

| C_H4 | | | | | | | | | |
|---|---|---|---|---|---|---|---|---|---|
| 341 | 342 | 343 | 344 | 345 | 346 | 347 | 348 | 349 | 350 |
| R | D | K | R | T | L | A | C | L | I |
| R:7 | D:7 | K:7 | R:7 | T:7 | L:7 | A:7 | C:7 | L:7 | I:7 |
| -:1 | -:1 | -:1 | -:1 | -:1 | -:1 | -:1 | -:1 | -:1 | -:1 |

FIG 35G

| | | | | C$_H$4 | | | | | |
|---|---|---|---|---|---|---|---|---|---|
| 351 | 352 | 353 | 354 | 355 | 356 | 357 | 358 | 359 | 360 |
| Q | N | F | M | P | E | D | I | S | V |
| Q:7 | N:7 | F:7 | M:7 | P:7 | E:7 | D:7 | I:7 | S:6 | V:7 |
| -:1 | -:1 | -:1 | -:1 | -:1 | -:1 | -:1 | -:1 | -:1 | -:1 |
| | | | | | | | | E:1 | |

| | | | | C$_H$4 | | | | | |
|---|---|---|---|---|---|---|---|---|---|
| 361 | 362 | 363 | 364 | 365 | 366 | 367 | 368 | 369 | 370 |
| Q | W | L | H | N | E | V | Q | L | P |
| Q:7 | W:6 | L:7 | H:7 | N:7 | E:7 | V:7 | Q:7 | L:7 | P:7 |
| -:1 | L:1 | -:1 | -:1 | -:1 | -:1 | -:1 | -:1 | -:1 | -:1 |
| | -:1 | | | | | | | | |

| | | | | C$_H$4 | | | | | |
|---|---|---|---|---|---|---|---|---|---|
| 371 | 372 | 373 | 374 | 375 | 376 | 377 | 378 | 379 | 380 |
| D | A | R | H | S | T | T | Q | P | R |
| D:7 | A:7 | R:7 | H:7 | S:7 | T:7 | T:7 | Q:7 | P:7 | R:7 |
| -:1 | -:1 | -:1 | -:1 | -:1 | -:1 | -:1 | -:1 | -:1 | -:1 |

| | | | | C$_H$4 | | | | | |
|---|---|---|---|---|---|---|---|---|---|
| 381 | 382 | 383 | 384 | 385 | 386 | 387 | 388 | 389 | 390 |
| K | T | K | G | S | G | F | F | V | F |
| K:7 | T:7 | K:7 | G:7 | S:8 | G:8 | F:8 | F:8 | V:8 | F:8 |
| -:1 | -:1 | -:1 | -:1 | | | | | | |

| | | | | C$_H$4 | | | | | |
|---|---|---|---|---|---|---|---|---|---|
| 391 | 392 | 393 | 394 | 395 | 396 | 397 | 398 | 399 | 400 |
| S | R | L | E | V | T | R | A | E | W |
| S:8 | R:8 | L:8 | E:8 | V:8 | T:8 | R:8 | A:8 | E:8 | W:8 |

FIG 35H

| \u0007 | | | | C$_H$4 | | | | | |
|---|---|---|---|---|---|---|---|---|---|
| 401 | 402 | 403 | 404 | 405 | 406 | 407 | 408 | 409 | 410 |
| E | Q | K | D | E | F | I | C | R | A |
| E:7 | Q:7 | K:8 | D:8 | E:8 | F:8 | I:8 | C:8 | R:8 | A:8 |
| Q:1 | E:1 | | | | | | | | |

| | | | | C$_H$4 | | | | | |
|---|---|---|---|---|---|---|---|---|---|
| 411 | 412 | 413 | 414 | 415 | 416 | 417 | 418 | 419 | 420 |
| V | H | E | A | A | S | P | S | Q | T |
| V:8 | H:8 | E:8 | A:8 | A:8 | S:8 | P:8 | S:8 | Q:8 | T:8 |

| | | | | C$_H$4 | | | | | |
|---|---|---|---|---|---|---|---|---|---|
| 421 | 422 | 423 | 424 | 425 | 426 | 427 | 428 | 429 | 430 |
| V | Q | R | A | V | S | V | N | P | G |
| V:8 | Q:8 | R:8 | A:8 | V:8 | S:8 | V:8 | N:8 | P:8 | G:6 |
| | | | | | | | | | E:2 |

| | | | | C$_H$4 | | | | | |
|---|---|---|---|---|---|---|---|---|---|
| 431 | 432 | 433 | 434 | 435 | 436 | 437 | 438 | 439 | 440 |
| K | D | V | C | V | E | E | A | E | G |
| K:6 | -:6 | -:6 | -:6 | -:6 | -:6 | -:6 | -:6 | -:6 | -:6 |
| L:2 | D:2 | V:2 | C:2 | V:2 | E:2 | E:2 | A:2 | E:2 | G:2 |

| | | | | C$_H$4 | | | | | |
|---|---|---|---|---|---|---|---|---|---|
| 441 | 442 | 443 | 444 | 445 | 446 | 447 | 448 | 449 | 450 |
| E | A | P | W | T | W | T | G | L | C |
| -:6 | -:6 | -:6 | -:6 | -:6 | -:6 | -:6 | -:6 | -:6 | -:6 |
| E:2 | A:2 | P:2 | W:2 | T:2 | W:2 | T:2 | G:2 | L:2 | C:2 |

FIG 35I

| | | | | C$_H$4 | | | | | |
|---|---|---|---|---|---|---|---|---|---|
| 451 | 452 | 453 | 454 | 455 | 456 | 457 | 458 | 459 | 460 |
| I | F | A | A | L | F | L | L | S | V |
| 2/8 | 2/8 | 2/8 | 2/8 | 2/8 | 2/8 | 2/8 | 2/8 | 2/8 | 2/8 |
| -:6 | -:6 | -:6 | -:6 | -:6 | -:6 | -:6 | -:6 | -:6 | -:6 |
| I:2 | F:2 | A:2 | A:2 | L:2 | F:2 | L:2 | L:2 | S:2 | V:2 |

| | | | | C$_H$4 | | | | | |
|---|---|---|---|---|---|---|---|---|---|
| 461 | 462 | 463 | 464 | 465 | 466 | 467 | 468 | 469 | 470 |
| S | Y | S | A | A | L | T | L | L | M |
| -:7 | -:7 | -:7 | -:7 | -:7 | -:7 | -:7 | -:7 | -:7 | -:7 |
| S:1 | Y:1 | S:1 | A:1 | A:1 | L:1 | T:1 | L:1 | L:1 | M:1 |

| | | | | C$_H$4 | | | | | |
|---|---|---|---|---|---|---|---|---|---|
| 471 | 472 | 473 | 474 | 475 | 476 | 477 | 478 | 479 | 480 |
| V | Q | R | F | L | S | A | T | R | Q |
| -:7 | -:7 | -:7 | -:7 | -:7 | -:7 | -:7 | -:7 | -:7 | -:7 |
| V:1 | Q:1 | R:1 | F:1 | L:1 | S:1 | A:1 | T:1 | R:1 | Q:1 |

| | | | | C$_H$4 | | | | | |
|---|---|---|---|---|---|---|---|---|---|
| 481 | 482 | 483 | 484 | 485 | 486 | 487 | 488 | 489 | 490 |
| G | R | P | Q | T | S | L | D | Y | T |
| -:7 | -:7 | -:7 | -:7 | -:7 | -:7 | -:7 | -:7 | -:7 | -:7 |
| G:1 | R:1 | P:1 | Q:1 | T:1 | S:1 | L:1 | D:1 | Y:1 | T:1 |

| | | | C$_H$4 | | | |
|---|---|---|---|---|---|---|
| 491 | 492 | 493 | 494 | 495 | 496 | 497 |
| N | V | L | Q | P | H | A |
| -:7 | -:7 | -:7 | -:7 | -:7 | -:7 | -:7 |
| N:1 | V:1 | L:1 | Q:1 | P:1 | H:1 | A:1 |

FIG 35J

| | | | | C_H1 | | | | | |
|---|---|---|---|---|---|---|---|---|---|
| 1 | 2 | 3 | 4 | 5 | 6 | 7 | 8 | 9 | 10 |
| A | S | T | K | G | P | S | V | F | P |
| A:4 | S:5 | T:5 | K:5 | G:5 | P:5 | S:5 | V:5 | F:6 | P:5 |
| -:2 | -:1 | -:1 | -:1 | -:1 | -:1 | M:1 | E:1 | | G:1 |

| | | | | C_H1 | | | | | |
|---|---|---|---|---|---|---|---|---|---|
| 11 | 12 | 13 | 14 | 15 | 16 | 17 | 18 | 19 | 20 |
| L | A | P | S | S | K | S | T | S | G |
| L:6 | A:5 | P:5 | S:5 | S:5 | K:5 | S:5 | T:5 | S:5 | G:5 |
| | S:1 | -:1 | -:1 | -:1 | -:1 | -:1 | -:1 | -:1 | -:1 |

| | | | | C_H1 | | | | | |
|---|---|---|---|---|---|---|---|---|---|
| 21 | 22 | 23 | 24 | 25 | 26 | 27 | 28 | 29 | 30 |
| G | T | A | A | L | G | C | L | V | K |
| G:5 | T:5 | A:5 | A:5 | L:6 | G:5 | C:5 | L:5 | V:5 | K:6 |
| -:1 | W:1 | V:1 | F:1 | | V:1 | A:1 | I:1 | L:1 | |

| | | | | C_H1 | | | | | |
|---|---|---|---|---|---|---|---|---|---|
| 31 | 32 | 33 | 34 | 35 | 36 | 37 | 38 | 39 | 40 |
| D | Y | F | P | E | P | V | T | V | S |
| D:5 | Y:5 | F:5 | P:5 | E:5 | P:5 | V:5 | T:5 | V:6 | S:5 |
| G:1 | V:1 | H:1 | C:1 | Q:1 | V:1 | Q:1 | L:1 | | E:1 |

| | | | | C_H1 | | | | | |
|---|---|---|---|---|---|---|---|---|---|
| 41 | 42 | 43 | 44 | 45 | 46 | 47 | 48 | 49 | 50 |
| W | N | S | G | A | L | T | S | G | V |
| W:5 | N:5 | S:5 | G:6 | A:5 | L:5 | T:5 | S:5 | G:6 | V:5 |
| S:1 | G:1 | G:1 | | L:1 | V:1 | Q:1 | P:1 | | G:1 |

FIG 36A

| | | | | C_H1 | | | | | |
|---|---|---|---|---|---|---|---|---|---|
| 51 | 52 | 53 | 54 | 55 | 56 | 57 | 58 | 59 | 60 |
| H | T | F | P | A | V | L | Q | S | S |
| H:5 | T:5 | F:5 | P:5 | A:5 | V:5 | L:5 | Q:5 | S:6 | S:5 |
| S:1 | L:1 | K:1 | L:1 | S:1 | C:1 | A:1 | A:1 | | G:1 |

| | | | | C_H1 | | | | | |
|---|---|---|---|---|---|---|---|---|---|
| 61 | 62 | 63 | 64 | 65 | 66 | 67 | 68 | 69 | 70 |
| G | L | Y | S | L | S | S | V | V | T |
| G:5 | L:5 | Y:5 | S:6 | L:5 | S:6 | S:5 | V:6 | V:5 | T:5 |
| F:1 | T:1 | L:1 | | G:1 | | N:1 | | H:1 | W:1 |

| | | | | C_H1 | | | | | |
|---|---|---|---|---|---|---|---|---|---|
| 71 | 72 | 73 | 74 | 75 | 76 | 77 | 78 | 79 | 80 |
| V | P | S | S | S | L | G | T | Q | T |
| V:6 | P:5 | S:5 | S:5 | S:6 | L:5 | G:5 | T:5 | Q:5 | T:5 |
| | R:1 | Q:1 | A:1 | | G:1 | K:1 | G:1 | L:1 | E:1 |

| | | | | C_H1 | | | | | |
|---|---|---|---|---|---|---|---|---|---|
| 81 | 82 | 83 | 84 | 85 | 86 | 87 | 88 | 89 | 90 |
| Y | I | C | N | V | N | H | K | P | S |
| Y:5 | I:5 | C:5 | N:5 | V:5 | N:5 | H:5 | K:5 | P:5 | S:5 |
| W:1 | V:1 | G:1 | -:1 | -:1 | -:1 | -:1 | -:1 | -:1 | -:1 |

| | | | | C_H1 | | | | HINGE | |
|---|---|---|---|---|---|---|---|---|---|
| 91 | 92 | 93 | 94 | 95 | 96 | 97 | 98 | 99 | 100 |
| N | T | K | V | D | K | K | V | E | P |
| N:5 | T:5 | K:5 | V:5 | D:5 | K:5 | K:4 | V:4 | E:6 | P:5 |
| -:1 | -:1 | R:1 | I:1 | K:1 | R:1 | R:1 | A:2 | | S:1 |
| | | | | | | N:1 | | | |

FIG 36B

| | | | | HINGE | | | | | |
|---|---|---|---|---|---|---|---|---|---|
| 101 | 102 | 103 | 104 | 105 | 106 | 107 | 108 | 109 | 110 |
| K | S | C | D | K | T | H | T | C | P |
| K:5 | S:5 | C:5 | D:5 | K:5 | T:5 | H:5 | T:5 | C:5 | P:5 |
| -:1 | -:1 | -:1 | -:1 | -:1 | -:1 | -:1 | -:1 | -:1 | -:1 |

| | HINGE | | | | C$_H$2 | | | | |
|---|---|---|---|---|---|---|---|---|---|
| 111 | 112 | 113 | 114 | 115 | 116 | 117 | 118 | 119 | 120 |
| P | C | P | A | P | E | L | L | G | G |
| P:5 | C:5 | P:5 | A:5 | P:5 | E:4 | L:5 | L:5 | G:5 | G:5 |
| -:1 | -:1 | -:1 | -:1 | -:1 | Q:1 | -:1 | -:1 | -:1 | -:1 |
|  |  |  |  |  | -:1 |  |  |  |  |

| | | | | C$_H$2 | | | | | |
|---|---|---|---|---|---|---|---|---|---|
| 121 | 122 | 123 | 124 | 125 | 126 | 127 | 128 | 129 | 130 |
| P | S | V | F | L | F | P | P | K | P |
| P:5 | S:5 | V:5 | F:5 | L:5 | F:5 | P:5 | P:5 | K:5 | P:5 |
| -:1 | D:1 | A:1 | T:1 | A:1 | Y:1 | A:1 | A:1 | S:1 | M:1 |

| | | | | C$_H$2 | | | | | |
|---|---|---|---|---|---|---|---|---|---|
| 131 | 132 | 133 | 134 | 135 | 136 | 137 | 138 | 139 | 140 |
| K | D | T | L | M | I | S | R | T | P |
| K:5 | D:5 | T:5 | L:6 | M:5 | I:6 | S:6 | R:6 | T:5 | P:5 |
| R:1 | G:1 | R:1 |  | T:1 |  |  |  | D:1 | -:1 |

| | | | | C$_H$2 | | | | | |
|---|---|---|---|---|---|---|---|---|---|
| 141 | 142 | 143 | 144 | 145 | 146 | 147 | 148 | 149 | 150 |
| E | V | T | C | V | V | V | D | V | S |
| E:5 | V:5 | T:5 | C:5 | V:5 | V:5 | V:5 | D:5 | V:5 | S:5 |
| -:1 | -:1 | -:1 | -:1 | -:1 | -:1 | -:1 | -:1 | -:1 | -:1 |

FIG 36C

| | | | | | C_H2 | | | | |
|---|---|---|---|---|---|---|---|---|---|
| 151 | 152 | 153 | 154 | 155 | 156 | 157 | 158 | 159 | 160 |
| H | E | D | P | E | V | K | F | N | W |
| H:5 | E:5 | D:5 | P:5 | E:5 | V:5 | K:5 | F:6 | N:5 | W:5 |
| -:1 | D:1 | S:1 | K:1 | N:1 | T:1 | A:1 | | -:1 | -:1 |

| | | | | | C_H2 | | | | |
|---|---|---|---|---|---|---|---|---|---|
| 161 | 162 | 163 | 164 | 165 | 166 | 167 | 168 | 169 | 170 |
| Y | V | D | G | V | E | V | H | N | A |
| Y:5 | V:5 | D:5 | G:5 | V:5 | E:5 | V:5 | H:5 | N:5 | A:5 |
| -:1 | -:1 | -:1 | -:1 | L:1 | Q:1 | M:1 | N:1 | S:1 | L:1 |

| | | | | | C_H2 | | | | |
|---|---|---|---|---|---|---|---|---|---|
| 171 | 172 | 173 | 174 | 175 | 176 | 177 | 178 | 179 | 180 |
| K | T | K | P | R | E | E | Q | Y | N |
| K:6 | T:5 | K:5 | P:5 | R:5 | E:5 | E:5 | Q:5 | Y:5 | N:4 |
| | S:1 | D:1 | D:1 | -:1 | -:1 | -:1 | -:1 | -:1 | B:1 |
| | | | | | | | | | T:1 |

| | | | | | C_H2 | | | | |
|---|---|---|---|---|---|---|---|---|---|
| 181 | 182 | 183 | 184 | 185 | 186 | 187 | 188 | 189 | 190 |
| S | T | Y | R | V | V | S | V | L | T |
| S:5 | T:5 | Y:6 | R:5 | V:5 | V:6 | S:5 | V:5 | L:5 | T:5 |
| A:1 | M:1 | | Y:1 | C:1 | | I:1 | R:1 | G:1 | D:1 |

| | | | | | C_H2 | | | | |
|---|---|---|---|---|---|---|---|---|---|
| 191 | 192 | 193 | 194 | 195 | 196 | 197 | 198 | 199 | 200 |
| V | L | H | Q | D | W | L | N | G | K |
| V:6 | L:5 | H:5 | Q:5 | D:5 | W:6 | L:5 | N:3 | G:6 | K:5 |
| | Y:1 | N:1 | R:1 | Q:1 | | G:1 | D:2 | | -:1 |
| | | | | | | | Q:1 | | |

FIG 36D

| CH2 | | | | | | | | | |
|---|---|---|---|---|---|---|---|---|---|
| 201 | 202 | 203 | 204 | 205 | 206 | 207 | 208 | 209 | 210 |
| E | Y | K | C | K | V | S | N | K | A |
| E:5 | Y:5 | K:5 | C:5 | K:5 | V:5 | S:5 | N:5 | K:5 | A:5 |
| -:1 | -:1 | -:1 | -:1 | -:1 | -:1 | -:1 | -:1 | -:1 | -:1 |

| CH2 | | | | | | | | | |
|---|---|---|---|---|---|---|---|---|---|
| 211 | 212 | 213 | 214 | 215 | 216 | 217 | 218 | 219 | 220 |
| L | P | A | P | I | E | K | T | I | S |
| L:5 | P:5 | A:5 | P:5 | I:5 | E:5 | K:5 | T:5 | I:5 | S:5 |
| -:1 | -:1 | -:1 | -:1 | -:1 | -:1 | T:1 | L:1 | V:1 | T:1 |

| CH2 | | | CH3 | | | | | | |
|---|---|---|---|---|---|---|---|---|---|
| 221 | 222 | 223 | 224 | 225 | 226 | 227 | 228 | 229 | 230 |
| K | A | K | G | Q | P | R | E | P | Q |
| K:5 | A:5 | K:5 | G:5 | Q:5 | P:5 | R:5 | E:5 | P:6 | Q:5 |
| V:1 | S:1 | S:1 | A:1 | S:1 | T:1 | K:1 | G:1 | | S:1 |

| CH3 | | | | | | | | | |
|---|---|---|---|---|---|---|---|---|---|
| 231 | 232 | 233 | 234 | 235 | 236 | 237 | 238 | 239 | 240 |
| V | Y | T | L | P | P | S | R | D | E |
| V:6 | Y:5 | T:5 | L:6 | P:5 | P:6 | S:6 | R:5 | D:4 | E:5 |
| | F:1 | P:1 | | A:1 | | | S:1 | K:1 | S:1 |
| | | | | | | | | E:1 | |

| CH3 | | | | | | | | | |
|---|---|---|---|---|---|---|---|---|---|
| 241 | 242 | 243 | 244 | 245 | 246 | 247 | 248 | 249 | 250 |
| L | T | K | N | Q | V | S | L | T | C |
| L:4 | T:5 | K:5 | N:5 | Q:5 | V:5 | S:5 | L:6 | T:5 | C:6 |
| T:1 | S:1 | G:1 | G:1 | T:1 | A:1 | A:1 | | G:1 | |
| M:1 | | | | | | | | | |

FIG 36E

| C_H3 | | | | | | | | | |
|---|---|---|---|---|---|---|---|---|---|
| 251 | 252 | 253 | 254 | 255 | 256 | 257 | 258 | 259 | 260 |
| L | V | K | G | F | Y | P | S | D | I |
| L:6 | V:6 | K:6 | G:5<br>D:1 | F:5<br>Y:1 | Y:5<br>F:1 | P:6 | S:5<br>E:1 | D:5<br>P:1 | I:5<br>V:1 |

| C_H3 | | | | | | | | | |
|---|---|---|---|---|---|---|---|---|---|
| 261 | 262 | 263 | 264 | 265 | 266 | 267 | 268 | 269 | 270 |
| A | V | E | W | E | S | B | N | G | Q |
| A:5<br>T:1 | V:6 | E:5<br>S:1 | W:6 | E:5<br>N:1 | S:6 | -:5<br>B:1 | N:3<br>D:2<br>-:1 | G:6 | Q:4<br>A:1<br>E:1 |

| C_H3 | | | | | | | | | |
|---|---|---|---|---|---|---|---|---|---|
| 271 | 272 | 273 | 274 | 275 | 276 | 277 | 278 | 279 | 280 |
| P | E | N | N | Y | K | T | T | P | P |
| P:5<br>L:1 | E:4<br>Z:1<br>T:1 | N:3<br>D:2<br>S:1 | N:5<br>G:1 | Y:5<br>V:1 | K:5<br>H:1 | T:6 | T:5<br>F:1 | P:6 | P:5<br>A:1 |

| C_H3 | | | | | | | | | |
|---|---|---|---|---|---|---|---|---|---|
| 281 | 282 | 283 | 284 | 285 | 286 | 287 | 288 | 289 | 290 |
| V | L | D | S | D | G | S | F | F | L |
| V:6 | L:6 | D:5<br>Q:1 | S:6 | D:5<br>S:1 | G:6 | S:5<br>L:1 | F:5<br>Y:1 | F:5<br>S:1 | L:6 |

| C_H3 | | | | | | | | | |
|---|---|---|---|---|---|---|---|---|---|
| 291 | 292 | 293 | 294 | 295 | 296 | 297 | 298 | 299 | 300 |
| Y | S | K | L | T | V | D | K | S | R |
| Y:5<br>S:1 | S:6 | K:5<br>V:1 | L:5<br>V:1 | T:6 | V:6 | D:5<br>P:1 | K:5<br>S:1 | S:6 | R:5<br>S:1 |

FIG 36F

| C<sub>H</sub>3 | | | | | | | | | |
|---|---|---|---|---|---|---|---|---|---|
| 301<br>W | 302<br>Q | 303<br>Q | 304<br>G | 305<br>N | 306<br>V | 307<br>F | 308<br>S | 309<br>C | 310<br>S |
| W:5<br>L:1 | Q:5<br>G:1 | Q:5<br>-:1 | G:5<br>T:1 | N:5<br>Q:1 | V:5<br>T:1 | F:5<br>Y:1 | S:5<br>I:1 | C:6 | S:5<br>N:1 |

| C<sub>H</sub>3 | | | | | | | | | |
|---|---|---|---|---|---|---|---|---|---|
| 311<br>V | 312<br>M | 313<br>H | 314<br>E | 315<br>A | 316<br>L | 317<br>H | 318<br>N | 319<br>H | 320<br>Y |
| V:6 | M:5<br>N:1 | H:6 | E:5<br>K:1 | A:5<br>P:1 | L:5<br>S:1 | H:5<br>N:1 | N:5<br>T:1 | H:5<br>K:1 | Y:5<br>V:1 |

| C<sub>H</sub>3 | | | | | | | | | |
|---|---|---|---|---|---|---|---|---|---|
| 321<br>T | 322<br>Q | 323<br>K | 324<br>S | 325<br>L | 326<br>S | 327<br>L | 328<br>S | 329<br>P | 330<br>G |
| T:5<br>D:1 | Q:5<br>K:1 | K:5<br>R:1 | S:5<br>V:1 | L:5<br>E:1 | S:5<br>P:1 | L:5<br>K:1 | S:6 | P:5<br>C:1 | G:5<br>D:1 |

| C<sub>H</sub>3 | | | | | | | | |
|---|---|---|---|---|---|---|---|---|
| 331<br>K | 332<br>T | 333<br>H | 334<br>T | 335<br>C | 336<br>P | 337<br>P | 338<br>C | 339<br>P |
| K:4<br>-:2 | -:5<br>T:1 | -:5<br>H:1 | -:5<br>T:1 | -:5<br>C:1 | -:5<br>P:1 | -:5<br>P:1 | -:5<br>C:1 | -:5<br>P:1 |

| 1 | 2 | 3 | 4 | 5 | 6 | 7 | 8 | 9 | 10 |
|---|---|---|---|---|---|---|---|---|----|
| A | S | T | K | G | P | S | V | F | P |
| A:4<br>-:1 | S:5 | T:5 | K:5 | G:5 | P:5 | S:5 | V:5 | F:5 | P:5 |

C_H1

| 11 | 12 | 13 | 14 | 15 | 16 | 17 | 18 | 19 | 20 |
|----|----|----|----|----|----|----|----|----|-----|
| L | A | P | C | S | R | S | T | S | E |
| L:5 | A:5 | P:5 | C:5 | S:5 | R:4<br>-:1 | S:5 | T:5 | S:5 | E:4<br>Q:1 |

C_H1

| 21 | 22 | 23 | 24 | 25 | 26 | 27 | 28 | 29 | 30 |
|----|----|----|----|----|----|----|----|----|-----|
| S | T | A | A | L | G | C | L | V | K |
| S:5 | T:5 | A:5 | A:5 | L:5 | G:5 | C:5 | L:5 | V:5 | K:5 |

C_H1

| 31 | 32 | 33 | 34 | 35 | 36 | 37 | 38 | 39 | 40 |
|----|----|----|----|----|----|----|----|----|-----|
| D | Y | F | P | E | P | V | T | V | S |
| D:5 | Y:5 | F:5 | P:5 | E:5 | P:5 | V:5 | T:5 | V:5 | S:5 |

C_H1

| 41 | 42 | 43 | 44 | 45 | 46 | 47 | 48 | 49 | 50 |
|----|----|----|----|----|----|----|----|----|-----|
| W | N | S | G | A | L | T | S | G | V |
| W:5 | N:5 | S:5 | G:5 | A:5 | L:5 | T:5 | S:5 | G:5 | V:5 |

FIG 37A

| | | | | | | | | | |
|---|---|---|---|---|---|---|---|---|---|
| | | | | C<sub>H</sub>1 | | | | | |
| 51 | 52 | 53 | 54 | 55 | 56 | 57 | 58 | 59 | 60 |
| H | T | F | P | A | V | L | Q | S | S |
| H:4<br>-:1 | T:5 | F:5 | P:5 | A:5 | V:5 | L:5 | Q:4<br>Z:1 | S:4<br>-:1 | S:3<br>A:1<br>V:1 |

| | | | | | | | | | |
|---|---|---|---|---|---|---|---|---|---|
| | | | | C<sub>H</sub>1 | | | | | |
| 61 | 62 | 63 | 64 | 65 | 66 | 67 | 68 | 69 | 70 |
| G | L | Y | S | L | S | S | V | V | T |
| G:5 | L:5 | Y:5 | S:5 | L:5 | S:5 | S:5 | V:5 | V:5 | T:5 |

| | | | | | | | | | |
|---|---|---|---|---|---|---|---|---|---|
| | | | | C<sub>H</sub>1 | | | | | |
| 71 | 72 | 73 | 74 | 75 | 76 | 77 | 78 | 79 | 80 |
| V | P | S | S | N | F | G | T | Q | T |
| V:5 | P:4<br>T:1 | S:4<br>-:1 | S:5 | N:5 | F:5 | G:5 | T:4<br>A:1 | Q:5 | T:5 |

| | | | | | | | | | |
|---|---|---|---|---|---|---|---|---|---|
| | | | | C<sub>H</sub>1 | | | | | |
| 81 | 82 | 83 | 84 | 85 | 86 | 87 | 88 | 89 | 90 |
| Y | T | C | N | V | D | H | K | P | S |
| Y:5 | T:5 | C:5 | N:5 | V:5 | D:4<br>-:1 | H:4<br>-:1 | K:4<br>-:1 | P:4<br>-:1 | S:4<br>-:1 |

| | | | | | | | | | |
|---|---|---|---|---|---|---|---|---|---|
| | | | C<sub>H</sub>1 | | | | | Hinge | |
| 91 | 92 | 93 | 94 | 95 | 96 | 97 | 98 | 99 | 100 |
| N | T | K | V | D | K | T | V | E | R |
| N:4<br>-:1 | T:4<br>-:1 | K:4<br>-:1 | V:4<br>-:1 | D:4<br>-:1 | K:4<br>-:1 | T:4<br>-:1 | V:4<br>-:1 | E:4<br>-:1 | R:4<br>-:1 |

FIG 37B

| | | | | Hinge | | | | | |
|---|---|---|---|---|---|---|---|---|---|
| 101 | 102 | 103 | 104 | 105 | 106 | 107 | 108 | 109 | 110 |
| K | C | C | V | E | C | P | P | C | P |
| K:4 | C:4 | C:4 | V:4 | E:4 | C:4 | P:4 | P:4 | C:4 | P:4 |
| -:1 | -:1 | -:1 | -:1 | -:1 | -:1 | -:1 | -:1 | -:1 | -:1 |

| | | | | C<sub>H</sub>2 | | | | | |
|---|---|---|---|---|---|---|---|---|---|
| 111 | 112 | 113 | 114 | 115 | 116 | 117 | 118 | 119 | 120 |
| A | P | P | V | A | G | P | S | V | F |
| A:4 | P:4 | P:4 | V:4 | A:4 | G:4 | P:4 | S:4 | V:4 | F:4 |
| -:1 | -:1 | -:1 | -:1 | -:1 | -:1 | -:1 | -:1 | -:1 | -:1 |

| | | | | C<sub>H</sub>2 | | | | | |
|---|---|---|---|---|---|---|---|---|---|
| 121 | 122 | 123 | 124 | 125 | 126 | 127 | 128 | 129 | 130 |
| L | F | P | P | K | P | K | D | T | L |
| L:4 | F:4 | P:4 | P:4 | K:4 | P:4 | K:4 | D:4 | T:4 | L:4 |
| -:1 | -:1 | -:1 | -:1 | -:1 | -:1 | -:1 | -:1 | -:1 | -:1 |

| | | | | C<sub>H</sub>2 | | | | | |
|---|---|---|---|---|---|---|---|---|---|
| 131 | 132 | 133 | 134 | 135 | 136 | 137 | 138 | 139 | 140 |
| M | I | S | R | T | P | E | V | T | C |
| M:4 | I:5 | S:5 | R:5 | T:5 | P:5 | E:5 | V:5 | T:5 | C:5 |
| -:1 | | | | | | | | | |

| | | | | C<sub>H</sub>2 | | | | | |
|---|---|---|---|---|---|---|---|---|---|
| 141 | 142 | 143 | 144 | 145 | 146 | 147 | 148 | 149 | 150 |
| V | V | V | D | V | S | H | E | D | P |
| V:5 | V:5 | V:5 | D:5 | V:5 | S:5 | H:5 | E:5 | D:5 | P:5 |

FIG 37C

| | | | | | | | | | |
|---|---|---|---|---|---|---|---|---|---|
| \|<- | | | | C_H2 | | | | | ->\| |
| 151 | 152 | 153 | 154 | 155 | 156 | 157 | 158 | 159 | 160 |
| E | V | Q | F | N | W | Y | V | D | G |
| E:5 | V:5 | Q:5 | F:5 | N:5 | W:5 | Y:5 | V:5 | D:5 | G:5 |

| | | | | | | | | | |
|---|---|---|---|---|---|---|---|---|---|
| \|<- | | | | C_H2 | | | | | ->\| |
| 161 | 162 | 163 | 164 | 165 | 166 | 167 | 168 | 169 | 170 |
| V | E | V | H | N | A | K | T | K | P |
| V:4 M:1 | E:5 | V:5 | H:5 | N:5 | A:5 | K:5 | T:5 | K:5 | P:5 |

| | | | | | | | | | |
|---|---|---|---|---|---|---|---|---|---|
| \|<- | | | | C_H2 | | | | | ->\| |
| 171 | 172 | 173 | 174 | 175 | 176 | 177 | 178 | 179 | 180 |
| R | E | E | Q | F | N | S | T | F | R |
| R:5 | E:4 -:1 | E:4 -:1 | Q:4 -:1 | F:4 -:1 | N:4 -:1 | S:4 -:1 | T:4 -:1 | F:5 | R:5 |

| | | | | | | | | | |
|---|---|---|---|---|---|---|---|---|---|
| \|<- | | | | C_H2 | | | | | ->\| |
| 181 | 182 | 183 | 184 | 185 | 186 | 187 | 188 | 189 | 190 |
| V | V | S | V | L | T | V | V | H | Q |
| V:5 | V:5 | S:5 | V:5 | L:5 | T:5 | V:5 | V:5 | H:5 | Q:5 |

| | | | | | | | | | |
|---|---|---|---|---|---|---|---|---|---|
| \|<- | | | | C_H2 | | | | | ->\| |
| 191 | 192 | 193 | 194 | 195 | 196 | 197 | 198 | 199 | 200 |
| D | W | L | N | G | K | E | Y | K | C |
| D:5 | W:5 | L:5 | N:3 D:2 | G:5 | K:5 | E:4 Q:1 | Y:5 | K:5 | C:5 |

FIG 37D

| | | | | | C$_H$2 | | | | |
|---|---|---|---|---|---|---|---|---|---|
| 201 | 202 | 203 | 204 | 205 | 206 | 207 | 208 | 209 | 210 |
| K | V | S | N | K | G | L | P | A | P |
| K:5 | V:5 | S:5 | N:5 | K:5 | G:5 | L:5 | P:5 | A:5 | P:5 |

| | | | | C$_H$2 | | | | | C$_H$ |
|---|---|---|---|---|---|---|---|---|---|
| 211 | 212 | 213 | 214 | 215 | 216 | 217 | 218 | 219 | 220 |
| I | E | K | T | I | S | K | T | K | G |
| I:5 | E:5 | K:5 | T:5 | I:5 | S:5 | K:5 | T:5 | K:5 | G:5 |

| | | | | C$_H$3 | | | | | |
|---|---|---|---|---|---|---|---|---|---|
| 221 | 222 | 223 | 224 | 225 | 226 | 227 | 228 | 229 | 230 |
| Q | P | R | E | P | Q | V | Y | T | L |
| Q:5 | P:5 | R:5 | E:5 | P:5 | Q:5 | V:5 | Y:5 | T:5 | L:5 |

| | | | | C$_H$3 | | | | | |
|---|---|---|---|---|---|---|---|---|---|
| 231 | 232 | 233 | 234 | 235 | 236 | 237 | 238 | 239 | 240 |
| P | P | S | R | E | E | M | T | K | N |
| P:5 | P:5 | S:5 | R:5 | E:4 Z:1 | E:5 | M:5 | T:5 | K:5 | N:5 |

| | | | | C$_H$3 | | | | | |
|---|---|---|---|---|---|---|---|---|---|
| 241 | 242 | 243 | 244 | 245 | 246 | 247 | 248 | 249 | 250 |
| Q | V | S | L | T | C | L | V | K | G |
| Q:5 | V:5 | S:5 | L:5 | T:5 | C:5 | L:5 | V:5 | K:5 | G:5 |

FIG 37E

| C$_H$3 | | | | | | | | | |
|---|---|---|---|---|---|---|---|---|---|
| 251 | 252 | 253 | 254 | 255 | 256 | 257 | 258 | 259 | 260 |
| F | Y | P | S | D | I | A | V | E | W |
| F:5 | Y:5 | P:5 | S:5 | D:5 | I:5 | A:5 | V:5 | E:5 | W:5 |

| C$_H$3 | | | | | | | | | |
|---|---|---|---|---|---|---|---|---|---|
| 261 | 262 | 263 | 264 | 265 | 266 | 267 | 268 | 269 | 270 |
| E | S | N | G | Q | P | E | N | N | Y |
| E:5 | S:5 | N:5 | G:5 | Q:5 | P:5 | E:5 | N:5 | N:5 | Y:5 |

| C$_H$3 | | | | | | | | | |
|---|---|---|---|---|---|---|---|---|---|
| 271 | 272 | 273 | 274 | 275 | 276 | 277 | 278 | 279 | 280 |
| K | T | T | P | P | M | L | D | S | D |
| K:5 | T:5 | T:5 | P:5 | P:5 | M:5 | L:5 | D:5 | S:5 | D:5 |

| C$_H$3 | | | | | | | | | |
|---|---|---|---|---|---|---|---|---|---|
| 281 | 282 | 283 | 284 | 285 | 286 | 287 | 288 | 289 | 290 |
| G | S | F | F | L | Y | S | K | L | T |
| G:5 | S:5 | F:5 | F:5 | L:5 | Y:5 | S:5 | K:5 | L:5 | T:5 |

FIG 37F

| C<sub>H</sub>3 | | | | | | | | | |
|---|---|---|---|---|---|---|---|---|---|
| 291 | 292 | 293 | 294 | 295 | 296 | 297 | 298 | 299 | 300 |
| V | D | K | S | R | W | Q | Q | G | N |
| V:5 | D:5 | K:5 | S:5 | R:5 | W:5 | Q:5 | Q:5 | G:5 | N:5 |

| C<sub>H</sub>3 | | | | | | | | | |
|---|---|---|---|---|---|---|---|---|---|
| 301 | 302 | 303 | 304 | 305 | 306 | 307 | 308 | 309 | 310 |
| V | F | S | C | S | V | M | H | E | A |
| V:5 | F:5 | S:5 | C:5 | S:5 | V:5 | M:5 | H:5 | E:5 | A:5 |

| C<sub>H</sub>3 | | | | | | | | | |
|---|---|---|---|---|---|---|---|---|---|
| 311 | 312 | 313 | 314 | 315 | 316 | 317 | 318 | 319 | 320 |
| L | H | N | H | Y | T | Q | K | S | L |
| L:5 | H:5 | N:5 | H:5 | Y:5 | T:5 | Q:5 | K:5 | S:5 | L:5 |

| C<sub>H</sub>3 | | | | | |
|---|---|---|---|---|---|
| 321 | 322 | 323 | 324 | 325 | 326 |
| S | L | S | P | G | K |
| S:5 | L:5 | S:5 | P:5 | G:5 | K:3<br>-:2 |

FIG 37G

| | | | | | C_H1 | | | | |
|---|---|---|---|---|---|---|---|---|---|
| 1 | 2 | 3 | 4 | 5 | 6 | 7 | 8 | 9 | 10 |
| A | S | T | K | G | P | S | V | F | P |
| -:3 | -:3 | -:3 | -:3 | -:3 | -:3 | -:3 | -:3 | -:3 | -:3 |
| A:2 | S:2 | T:2 | K:2 | G:2 | P:2 | S:2 | V:2 | F:2 | P:2 |

| | | | | | C_H1 | | | | |
|---|---|---|---|---|---|---|---|---|---|
| 11 | 12 | 13 | 14 | 15 | 16 | 17 | 18 | 19 | 20 |
| L | A | P | C | S | R | S | T | S | G |
| -:3 | -:3 | -:3 | -:3 | -:3 | -:3 | -:3 | -:3 | -:3 | -:3 |
| L:2 | A:2 | P:2 | C:2 | S:2 | R:2 | S:2 | T:2 | S:2 | G:2 |

| | | | | | C_H1 | | | | |
|---|---|---|---|---|---|---|---|---|---|
| 21 | 22 | 23 | 24 | 25 | 26 | 27 | 28 | 29 | 30 |
| G | T | A | A | L | G | C | L | V | K |
| -:3 | -:3 | -:3 | -:3 | -:3 | -:3 | -:3 | -:3 | -:3 | -:3 |
| G:2 | T:2 | A:2 | A:2 | L:2 | G:2 | C:2 | L:2 | V:2 | K:2 |

| | | | | | C_H1 | | | | |
|---|---|---|---|---|---|---|---|---|---|
| 31 | 32 | 33 | 34 | 35 | 36 | 37 | 38 | 39 | 40 |
| D | Y | F | P | E | P | V | T | V | S |
| -:3 | -:3 | -:3 | -:3 | -:3 | -:3 | -:3 | -:3 | -:3 | -:3 |
| D:2 | Y:2 | F:2 | P:2 | E:2 | P:2 | V:2 | T:2 | V:2 | S:2 |

| | | | | | C_H1 | | | | |
|---|---|---|---|---|---|---|---|---|---|
| 41 | 42 | 43 | 44 | 45 | 46 | 47 | 48 | 49 | 50 |
| W | N | S | G | A | L | T | S | G | V |
| -:3 | -:3 | -:3 | -:3 | -:3 | -:3 | -:3 | -:3 | -:3 | -:3 |
| W:2 | N:2 | S:2 | G:2 | A:2 | L:2 | T:2 | S:2 | G:2 | V:2 |

| | | | | | C_H1 | | | | |
|---|---|---|---|---|---|---|---|---|---|
| 51 | 52 | 53 | 54 | 55 | 56 | 57 | 58 | 59 | 60 |
| H | T | F | P | A | V | L | Q | S | S |
| -:3 | -:3 | -:3 | -:3 | -:3 | -:3 | -:3 | -:3 | -:3 | -:3 |
| H:2 | T:2 | F:2 | P:2 | A:2 | V:2 | L:2 | Q:2 | S:2 | S:2 |

FIG 38A

| | | | | C_H1 | | | | | |
|---|---|---|---|---|---|---|---|---|---|
| 61 | 62 | 63 | 64 | 65 | 66 | 67 | 68 | 69 | 70 |
| G | L | Y | S | L | S | S | V | V | T |
| -:3 | -:3 | -:3 | -:3 | -:3 | -:3 | -:3 | -:3 | -:3 | -:3 |
| G:2 | L:2 | Y:2 | S:2 | L:2 | S:2 | S:2 | V:2 | V:2 | T:2 |

| | | | | C_H1 | | | | | |
|---|---|---|---|---|---|---|---|---|---|
| 71 | 72 | 73 | 74 | 75 | 76 | 77 | 78 | 79 | 80 |
| V | P | S | S | S | L | G | T | Q | T |
| -:3 | -:3 | -:3 | -:3 | -:3 | -:3 | -:3 | -:3 | -:3 | -:3 |
| V:2 | P:2 | S:2 | S:2 | S:2 | L:2 | G:2 | T:2 | Q:2 | T:2 |

| | | | | C_H1 | | | | | |
|---|---|---|---|---|---|---|---|---|---|
| 81 | 82 | 83 | 84 | 85 | 86 | 87 | 88 | 89 | 90 |
| Y | T | C | N | V | N | H | K | P | S |
| -:3 | -:3 | -:3 | -:3 | -:3 | -:3 | -:3 | -:3 | -:3 | -:3 |
| Y:2 | T:2 | C:2 | N:2 | V:2 | N:2 | H:2 | K:2 | P:2 | S:2 |

| | | | | C_H1 | | | | Hinge 1 | |
|---|---|---|---|---|---|---|---|---|---|
| 91 | 92 | 93 | 94 | 95 | 96 | 97 | 98 | 99 | 100 |
| N | T | K | V | D | K | R | V | E | L |
| -:3 | -:3 | -:3 | -:3 | -:3 | -:3 | -:3 | V:3 | E:5 | L:5 |
| N:2 | T:2 | K:2 | V:2 | D:2 | K:2 | R:2 | -:2 | | |

| | | | | Hinge 1 | | | | | |
|---|---|---|---|---|---|---|---|---|---|
| 101 | 102 | 103 | 104 | 105 | 106 | 107 | 108 | 109 | 110 |
| K | T | P | L | G | D | T | T | H | T |
| K:5 | T:5 | P:5 | L:5 | G:4 E:1 | D:5 | T:5 | T:5 | H:5 | T:5 |

| | | Hinge 1 | | | | | Hinge 2 | | |
|---|---|---|---|---|---|---|---|---|---|
| 111 | 112 | 113 | 114 | 115 | 116 | 117 | 118 | 119 | 120 |
| C | P | R | C | P | E | P | K | S | C |
| C:5 | P:5 | R:5 | C:5 | P:5 | E:5 | P:5 | K:5 | S:5 | C:5 |

| | | | | Hinge 2 | | | | | |
|---|---|---|---|---|---|---|---|---|---|
| 121 | 122 | 123 | 124 | 125 | 126 | 127 | 128 | 129 | 130 |
| D | T | P | P | P | C | P | R | C | P |
| D:5 | T:5 | P:5 | P:5 | P:5 | C:5 | P:5 | R:5 | C:5 | P:5 |

FIG 38B

| Hinge 3 | | | | | | | | | |
|---|---|---|---|---|---|---|---|---|---|
| 131 | 132 | 133 | 134 | 135 | 136 | 137 | 138 | 139 | 140 |
| E | P | K | S | C | D | T | P | P | P |
| E:5 | P:5 | K:5 | S:5 | C:5 | D:5 | T:5 | P:5 | P:5 | P:5 |

| Hinge 3 | | | | | Hinge 4 | | | | |
|---|---|---|---|---|---|---|---|---|---|
| 141 | 142 | 143 | 144 | 145 | 146 | 147 | 148 | 149 | 150 |
| C | P | R | C | P | E | P | K | S | C |
| C:5 | P:5 | R:5 | C:5 | P:5 | E:5 | P:5 | K:5 | S:5 | C:5 |

| Hinge 4 | | | | | | | | | |
|---|---|---|---|---|---|---|---|---|---|
| 151 | 152 | 153 | 154 | 155 | 156 | 157 | 158 | 159 | 160 |
| D | T | P | P | P | C | P | R | C | P |
| D:5 | T:5 | P:5 | P:5 | P:5 | C:5 | P:5 | R:4 -:1 | C:5 | P:5 |

| C$_H$2 | | | | | | | | | |
|---|---|---|---|---|---|---|---|---|---|
| 161 | 162 | 163 | 164 | 165 | 166 | 167 | 168 | 169 | 170 |
| A | P | E | L | L | G | G | P | S | V |
| A:5 | P:5 | E:5 | L:5 | L:5 | G:5 | G:5 | P:5 | S:5 | V:5 |

| C$_H$2 | | | | | | | | | |
|---|---|---|---|---|---|---|---|---|---|
| 171 | 172 | 173 | 174 | 175 | 176 | 177 | 178 | 179 | 180 |
| F | L | F | P | P | K | P | K | D | T |
| F:5 | L:5 | F:5 | P:5 | P:5 | K:5 | P:5 | K:5 | D:5 | T:5 |

| C$_H$2 | | | | | | | | | |
|---|---|---|---|---|---|---|---|---|---|
| 181 | 182 | 183 | 184 | 185 | 186 | 187 | 188 | 189 | 190 |
| L | M | I | S | R | T | P | E | V | T |
| L:5 | M:5 | I:5 | S:5 | R:4 -:1 | T:4 -:1 | P:4 -:1 | E:4 -:1 | V:4 -:1 | T:4 -:1 |

| C$_H$2 | | | | | | | | | |
|---|---|---|---|---|---|---|---|---|---|
| 191 | 192 | 193 | 194 | 195 | 196 | 197 | 198 | 199 | 200 |
| C | V | V | V | D | V | S | H | E | D |
| C:4 -:1 | V:4 -:1 | V:4 -:1 | V:4 -:1 | D:4 -:1 | V:4 -:1 | S:4 -:1 | H:4 -:1 | E:4 -:1 | D:4 -:1 |

FIG 38C

| | | | | | C_H2 | | | | |
|---|---|---|---|---|---|---|---|---|---|
| 201<br>P | 202<br>E | 203<br>V | 204<br>Q | 205<br>F | 206<br>K | 207<br>W | 208<br>Y | 209<br>V | 210<br>D |
| P:4<br>-:1 | E:3<br>-:2 | V:4<br>-:1 | Q:4<br>-:1 | F:4<br>-:1 | K:4<br>-:1 | W:4<br>-:1 | Y:4<br>-:1 | V:4<br>-:1 | D:4<br>-:1 |

| | | | | | C_H2 | | | | |
|---|---|---|---|---|---|---|---|---|---|
| 211<br>G | 212<br>V | 213<br>E | 214<br>V | 215<br>H | 216<br>N | 217<br>A | 218<br>K | 219<br>T | 220<br>K |
| G:4<br>-:1 | V:4<br>-:1 | E:3<br>Q:1<br>-:1 | V:4<br>-:1 | H:4<br>-:1 | N:4<br>-:1 | A:4<br>-:1 | K:4<br>-:1 | T:4<br>-:1 | K:4<br>-:1 |

| | | | | | C_H2 | | | | |
|---|---|---|---|---|---|---|---|---|---|
| 221<br>P | 222<br>R | 223<br>E | 224<br>E | 225<br>Q | 226<br>Y | 227<br>N | 228<br>S | 229<br>T | 230<br>F |
| P:3<br>L:1<br>-:1 | R:4<br>-:1 | E:4<br>-:1 | E:3<br>Q:1<br>-:1 | Q:4<br>-:1 | Y:3<br>-:1<br>F:1 | N:4<br>-:1 | S:4<br>-:1 | T:4<br>-:1 | F:4<br>-:1 |

| | | | | | C_H2 | | | | |
|---|---|---|---|---|---|---|---|---|---|
| 231<br>R | 232<br>V | 233<br>V | 234<br>S | 235<br>V | 236<br>L | 237<br>T | 238<br>V | 239<br>L | 240<br>H |
| R:4<br>-:1 | V:4<br>-:1 | V:4<br>-:1 | S:4<br>-:1 | V:4<br>-:1 | L:4<br>-:1 | T:4<br>-:1 | V:4<br>-:1 | L:4<br>-:1 | H:4<br>-:1 |

| | | | | | C_H2 | | | | |
|---|---|---|---|---|---|---|---|---|---|
| 241<br>Q | 242<br>D | 243<br>W | 244<br>L | 245<br>N | 246<br>G | 247<br>K | 248<br>E | 249<br>Y | 250<br>K |
| Q:4<br>-:1 | D:3<br>-:1<br>N:1 | W:4<br>-:1 | L:4<br>-:1 | N:3<br>D:1<br>-:1 | G:4<br>-:1 | K:4<br>-:1 | E:4<br>-:1 | Y:4<br>-:1 | K:4<br>-:1 |

| | | | | | C_H2 | | | | |
|---|---|---|---|---|---|---|---|---|---|
| 251<br>C | 252<br>K | 253<br>V | 254<br>S | 255<br>N | 256<br>K | 257<br>A | 258<br>L | 259<br>P | 260<br>A |
| C:4<br>-:1 | K:4<br>-:1 | V:4<br>-:1 | S:4<br>-:1 | N:4<br>-:1 | K:4<br>-:1 | A:4<br>-:1 | L:4<br>-:1 | P:4<br>-:1 | A:4<br>-:1 |

FIG 38D

| CH2 | | | | | | | | | |
|---|---|---|---|---|---|---|---|---|---|
| 261 | 262 | 263 | 264 | 265 | 266 | 267 | 268 | 269 | 270 |
| P | I | E | K | T | I | S | K | T | K |
| P:4 | I:4 | E:4 | K:4 | T:4 | I:4 | S:4 | K:4 | T:3 | K:4 |
| -:1 | -:1 | -:1 | -:1 | -:1 | -:1 | -:1 | -:1 | A:1 | -:1 |

| CH3 | | | | | | | | | |
|---|---|---|---|---|---|---|---|---|---|
| 271 | 272 | 273 | 274 | 275 | 276 | 277 | 278 | 279 | 280 |
| G | Q | P | R | E | P | Q | V | Y | T |
| G:4 | Q:4 | P:4 | R:3 | E:3 | P:3 | Q:3 | V:3 | Y:3 | T:3 |
| -:1 | -:1 | -:1 | -:2 | -:2 | -:2 | -:2 | -:2 | -:2 | -:2 |

| CH3 | | | | | | | | | |
|---|---|---|---|---|---|---|---|---|---|
| 281 | 282 | 283 | 284 | 285 | 286 | 287 | 288 | 289 | 290 |
| L | P | P | S | R | E | E | M | T | K |
| L:3 | P:3 | P:3 | S:3 | R:3 | E:4 | E:4 | M:4 | T:4 | K:4 |
| -:2 | -:2 | -:2 | -:2 | -:2 | -:1 | -:1 | -:1 | -:1 | -:1 |

| CH3 | | | | | | | | | |
|---|---|---|---|---|---|---|---|---|---|
| 291 | 292 | 293 | 294 | 295 | 296 | 297 | 298 | 299 | 300 |
| N | Q | V | S | L | T | C | L | V | K |
| N:4 | Q:4 | V:4 | S:4 | L:4 | T:4 | C:4 | L:4 | V:4 | K:4 |
| -:1 | -:1 | -:1 | -:1 | -:1 | -:1 | -:1 | -:1 | -:1 | -:1 |

| CH3 | | | | | | | | | |
|---|---|---|---|---|---|---|---|---|---|
| 301 | 302 | 303 | 304 | 305 | 306 | 307 | 308 | 309 | 310 |
| G | F | Y | P | S | D | I | A | V | E |
| G:4 | F:4 | Y:4 | P:4 | S:4 | D:4 | I:4 | A:4 | V:4 | E:4 |
| -:1 | -:1 | -:1 | -:1 | -:1 | -:1 | -:1 | -:1 | -:1 | -:1 |

| CH3 | | | | | | | | | |
|---|---|---|---|---|---|---|---|---|---|
| 311 | 312 | 313 | 314 | 315 | 316 | 317 | 318 | 319 | 320 |
| W | E | S | S | G | Q | P | E | N | N |
| W:4 | E:4 | S:4 | S:3 | G:4 | Q:4 | P:4 | E:4 | N:4 | N:4 |
| -:1 | -:1 | -:1 | -:1 | -:1 | -:1 | -:1 | -:1 | -:1 | -:1 |
| | | | N:1 | | | | | | |

FIG 38E

| | | | | C_H3 | | | | | |
|---|---|---|---|---|---|---|---|---|---|
| 321 | 322 | 323 | 324 | 325 | 326 | 327 | 328 | 329 | 330 |
| Y | N | T | T | P | P | M | L | D | S |
| Y:4 | N:3 | T:4 | T:4 | P:4 | P:4 | M:4 | L:4 | D:4 | S:4 |
| -:1 | K:1 | -:1 | -:1 | -:1 | -:1 | -:1 | -:1 | -:1 | -:1 |
|  | -:1 |  |  |  |  |  |  |  |  |

| | | | | C_H3 | | | | | |
|---|---|---|---|---|---|---|---|---|---|
| 331 | 332 | 333 | 334 | 335 | 336 | 337 | 338 | 339 | 340 |
| D | G | S | F | F | L | Y | S | K | L |
| D:4 | G:4 | S:4 | F:4 | F:4 | L:4 | Y:4 | S:4 | K:4 | L:4 |
| -:1 | -:1 | -:1 | -:1 | -:1 | -:1 | -:1 | -:1 | -:1 | -:1 |

| | | | | C_H3 | | | | | |
|---|---|---|---|---|---|---|---|---|---|
| 341 | 342 | 343 | 344 | 345 | 346 | 347 | 348 | 349 | 350 |
| T | V | D | K | S | R | W | Q | Q | G |
| T:4 | V:4 | D:4 | K:4 | S:4 | R:4 | W:4 | Q:4 | Q:4 | G:4 |
| -:1 | -:1 | -:1 | -:1 | -:1 | -:1 | -:1 | -:1 | -:1 | -:1 |

| | | | | C_H3 | | | | | |
|---|---|---|---|---|---|---|---|---|---|
| 351 | 352 | 353 | 354 | 355 | 356 | 357 | 358 | 359 | 360 |
| N | I | F | S | C | S | V | M | H | E |
| N:4 | I:4 | F:4 | S:4 | C:4 | S:4 | V:4 | M:4 | H:4 | E:4 |
| -:1 | -:1 | -:1 | -:1 | -:1 | -:1 | -:1 | -:1 | -:1 | -:1 |

| | | | | C_H3 | | | | | |
|---|---|---|---|---|---|---|---|---|---|
| 361 | 362 | 363 | 364 | 365 | 366 | 367 | 368 | 369 | 370 |
| A | L | H | N | R | F | T | Q | K | S |
| A:4 | L:4 | H:4 | N:4 | R:4 | F:3 | T:4 | Q:4 | K:4 | S:4 |
| -:1 | -:1 | -:1 | -:1 | -:1 | Y:1 | -:1 | -:1 | -:1 | -:1 |
|  |  |  |  |  | -:1 |  |  |  |  |

| | | | | C_H3 | | |
|---|---|---|---|---|---|---|
| 371 | 372 | 373 | 374 | 375 | 376 | 377 |
| L | S | L | S | P | G | K |
| L:4 | S:4 | L:4 | S:4 | P:4 | G:4 | K:3 |
| -:1 | -:1 | -:1 | -:1 | -:1 | -:1 | -:2 |

| 1 | 2 | 3 | 4 | 5 | 6 | 7 | 8 | 9 | 10 |
|---|---|---|---|---|---|---|---|---|---|
| A | S | T | K | G | P | S | V | F | P |
| A:2<br>-:1 | S:3 | T:3 | K:3 | G:3 | P:3 | S:3 | V:3 | F:3 | P:3 |

C_H1

| 11 | 12 | 13 | 14 | 15 | 16 | 17 | 18 | 19 | 20 |
|---|---|---|---|---|---|---|---|---|---|
| L | A | P | C | S | R | S | T | S | E |
| L:3 | A:3 | P:3 | C:3 | S:3 | R:3 | S:3 | T:3 | S:3 | E:3 |

C_H1

| 21 | 22 | 23 | 24 | 25 | 26 | 27 | 28 | 29 | 30 |
|---|---|---|---|---|---|---|---|---|---|
| S | T | A | A | L | G | C | L | V | K |
| S:3 | T:3 | A:3 | A:3 | L:3 | G:3 | C:3 | L:3 | V:3 | K:3 |

C_H1

| 31 | 32 | 33 | 34 | 35 | 36 | 37 | 38 | 39 | 40 |
|---|---|---|---|---|---|---|---|---|---|
| D | Y | F | P | E | P | V | T | V | S |
| D:2<br>-:1 | Y:2<br>-:1 | F:2<br>-:1 | P:2<br>-:1 | E:2<br>-:1 | P:2<br>-:1 | V:2<br>-:1 | T:2<br>-:1 | V:2<br>-:1 | S:2<br>-:1 |

C_H1

| 41 | 42 | 43 | 44 | 45 | 46 | 47 | 48 | 49 | 50 |
|---|---|---|---|---|---|---|---|---|---|
| W | N | S | G | A | L | T | S | G | V |
| W:2<br>-:1 | N:2<br>-:1 | S:2<br>-:1 | G:2<br>-:1 | A:2<br>-:1 | L:2<br>-:1 | T:2<br>-:1 | S:2<br>-:1 | G:2<br>-:1 | V:2<br>-:1 |

FIG 39A

| | | | | C_H1 | | | | | |
|---|---|---|---|---|---|---|---|---|---|
| 51 | 52 | 53 | 54 | 55 | 56 | 57 | 58 | 59 | 60 |
| H | T | F | P | A | V | L | Q | S | S |
| H:2 | T:2 | F:2 | P:2 | A:2 | V:2 | L:2 | Q:2 | S:2 | S:2 |
| -:1 | -:1 | -:1 | -:1 | -:1 | -:1 | -:1 | -:1 | -:1 | -:1 |

| | | | | C_H1 | | | | | |
|---|---|---|---|---|---|---|---|---|---|
| 61 | 62 | 63 | 64 | 65 | 66 | 67 | 68 | 69 | 70 |
| G | L | Y | S | L | S | S | V | V | T |
| G:2 | L:2 | Y:2 | S:2 | L:2 | S:2 | S:2 | V:2 | V:2 | T:2 |
| -:1 | -:1 | -:1 | -:1 | -:1 | -:1 | -:1 | -:1 | -:1 | -:1 |

| | | | | C_H1 | | | | | |
|---|---|---|---|---|---|---|---|---|---|
| 71 | 72 | 73 | 74 | 75 | 76 | 77 | 78 | 79 | 80 |
| V | P | S | S | S | L | G | T | K | T |
| V:2 | P:2 | S:2 | S:2 | S:2 | L:2 | G:2 | T:2 | K:2 | T:2 |
| -:1 | -:1 | -:1 | -:1 | -:1 | -:1 | -:1 | -:1 | -:1 | -:1 |

| | | | | C_H1 | | | | | |
|---|---|---|---|---|---|---|---|---|---|
| 81 | 82 | 83 | 84 | 85 | 86 | 87 | 88 | 89 | 90 |
| Y | T | C | N | V | D | H | K | P | S |
| Y:3 | T:3 | C:3 | N:3 | V:3 | D:3 | H:3 | K:3 | P:3 | S:3 |

| | | | | C_H1 | | | | Hinge | |
|---|---|---|---|---|---|---|---|---|---|
| 91 | 92 | 93 | 94 | 95 | 96 | 97 | 98 | 99 | 100 |
| N | T | K | V | D | K | R | V | E | S |
| N:3 | T:3 | K:3 | V:3 | D:3 | K:3 | R:3 | V:3 | E:3 | S:3 |

FIG 39B

| Hinge | | | | | | | | | |
|---|---|---|---|---|---|---|---|---|---|
| 101 | 102 | 103 | 104 | 105 | 106 | 107 | 108 | 109 | 110 |
| K | Y | G | P | P | C | P | S | C | P |
| K:3 | Y:3 | G:3 | P:3 | P:3 | C:3 | P:3 | S:2<br>P:1 | C:3 | P:3 |

| $C_H2$ | | | | | | | | | |
|---|---|---|---|---|---|---|---|---|---|
| 111 | 112 | 113 | 114 | 115 | 116 | 117 | 118 | 119 | 120 |
| A | P | E | F | L | G | G | P | S | V |
| A:3 | P:2<br>-:1 | E:2<br>-:1 | F:3 | L:3 | G:3 | G:3 | P:3 | S:3 | V:3 |

| $C_H2$ | | | | | | | | | |
|---|---|---|---|---|---|---|---|---|---|
| 121 | 122 | 123 | 124 | 125 | 126 | 127 | 128 | 129 | 130 |
| F | L | F | P | P | K | P | K | D | T |
| F:3 | L:3 | F:3 | P:3 | P:3 | K:3 | P:3 | K:3 | D:3 | T:3 |

| $C_H2$ | | | | | | | | | |
|---|---|---|---|---|---|---|---|---|---|
| 131 | 132 | 133 | 134 | 135 | 136 | 137 | 138 | 139 | 140 |
| L | M | I | S | R | T | P | E | V | T |
| L:3 | M:3 | I:3 | S:3 | R:3 | T:3 | P:3 | E:3 | V:3 | T:3 |

| $C_H2$ | | | | | | | | | |
|---|---|---|---|---|---|---|---|---|---|
| 141 | 142 | 143 | 144 | 145 | 146 | 147 | 148 | 149 | 150 |
| C | V | V | V | D | V | S | Q | E | D |
| C:3 | V:3 | V:3 | V:3 | D:3 | V:3 | S:3 | Q:3 | E:3 | D:3 |

| $C_H2$ | | | | | | | | | |
|---|---|---|---|---|---|---|---|---|---|
| 151 | 152 | 153 | 154 | 155 | 156 | 157 | 158 | 159 | 160 |
| P | E | V | Q | F | N | W | Y | V | D |
| P:3 | E:2<br>-:1 | V:2<br>-:1 | Q:2<br>-:1 | F:2<br>Z:1 | N:3 | W:3 | Y:3 | V:3 | D:3 |

FIG 39C

| | | | | | | | | | |
|---|---|---|---|---|---|---|---|---|---|
| | | | | C$_H$2 | | | | | |
| 161 | 162 | 163 | 164 | 165 | 166 | 167 | 168 | 169 | 170 |
| G | V | E | V | H | N | A | K | T | K |
| G:3 | V:3 | E:3 | V:3 | H:3 | N:3 | A:3 | K:3 | T:3 | K:3 |

| | | | | | | | | | |
|---|---|---|---|---|---|---|---|---|---|
| | | | | C$_H$2 | | | | | |
| 171 | 172 | 173 | 174 | 175 | 176 | 177 | 178 | 179 | 180 |
| P | R | E | E | Q | F | N | S | T | Y |
| P:3 | R:3 | E:3 | E:3 | Q:3 | F:3 | N:2 B:1 | S:3 | T:3 | Y:3 |

| | | | | | | | | | |
|---|---|---|---|---|---|---|---|---|---|
| | | | | C$_H$2 | | | | | |
| 181 | 182 | 183 | 184 | 185 | 186 | 187 | 188 | 189 | 190 |
| R | V | V | S | V | L | T | V | L | H |
| R:3 | V:3 | V:3 | S:2 -:1 | V:2 -:1 | L:2 -:1 | T:2 -:1 | V:2 -:1 | L:2 -:1 | H:2 -:1 |

| | | | | | | | | | |
|---|---|---|---|---|---|---|---|---|---|
| | | | | C$_H$2 | | | | | |
| 191 | 192 | 193 | 194 | 195 | 196 | 197 | 198 | 199 | 200 |
| Q | D | W | L | N | G | K | E | Y | K |
| Q:2 -:1 | D:2 -:1 | W:2 -:1 | L:2 -:1 | N:2 -:1 | G:2 -:1 | K:3 | E:3 | Y:3 | K:3 |

| | | | | | | | | | |
|---|---|---|---|---|---|---|---|---|---|
| | | | | C$_H$2 | | | | | |
| 201 | 202 | 203 | 204 | 205 | 206 | 207 | 208 | 209 | 210 |
| C | K | V | S | N | K | G | L | P | S |
| C:3 | K:3 | V:3 | S:3 | N:3 | K:3 | G:3 | L:3 | P:3 | S:3 |

| | | | | | | | | | |
|---|---|---|---|---|---|---|---|---|---|
| | | | | C$_H$2 | | | | | |
| 211 | 212 | 213 | 214 | 215 | 216 | 217 | 218 | 219 | 220 |
| S | I | E | K | T | I | S | K | A | K |
| S:3 | I:3 | E:3 | K:3 | T:3 | I:3 | S:3 | K:3 | A:3 | K:3 |

FIG 39D

| | | | | C$_H$3 | | | | | |
|---|---|---|---|---|---|---|---|---|---|
| 221 | 222 | 223 | 224 | 225 | 226 | 227 | 228 | 229 | 230 |
| G | Q | P | R | E | P | Q | V | Y | T |
| G:3 | Q:3 | P:3 | R:3 | E:3 | P:3 | Q:3 | V:3 | Y:3 | T:3 |

| | | | | C$_H$3 | | | | | |
|---|---|---|---|---|---|---|---|---|---|
| 231 | 232 | 233 | 234 | 235 | 236 | 237 | 238 | 239 | 240 |
| L | P | P | S | Q | E | E | M | T | K |
| L:3 | P:3 | P:3 | S:3 | Q:3 | E:3 | E:3 | M:3 | T:3 | K:3 |

| | | | | C$_H$3 | | | | | |
|---|---|---|---|---|---|---|---|---|---|
| 241 | 242 | 243 | 244 | 245 | 246 | 247 | 248 | 249 | 250 |
| N | Q | V | S | L | T | C | L | V | K |
| N:3 | Q:3 | V:3 | S:3 | L:3 | T:3 | C:3 | L:3 | V:3 | K:3 |

| | | | | C$_H$3 | | | | | |
|---|---|---|---|---|---|---|---|---|---|
| 251 | 252 | 253 | 254 | 255 | 256 | 257 | 258 | 259 | 260 |
| G | F | Y | P | S | D | I | A | V | E |
| G:3 | F:3 | Y:3 | P:3 | S:3 | D:3 | I:3 | A:3 | V:3 | E:3 |

| | | | | C$_H$3 | | | | | |
|---|---|---|---|---|---|---|---|---|---|
| 261 | 262 | 263 | 264 | 265 | 266 | 267 | 268 | 269 | 270 |
| W | E | S | N | G | Q | P | E | N | N |
| W:3 | E:2 | S:3 | N:2 | G:2 | Q:2 | P:2 | E:2 | N:2 | N:2 |
| | Z:1 | | -:1 | -:1 | -:1 | -:1 | -:1 | -:1 | -:1 |

FIG 39E

| | | | | C$_H$3 | | | | | |
|---|---|---|---|---|---|---|---|---|---|
| 271 | 272 | 273 | 274 | 275 | 276 | 277 | 278 | 279 | 280 |
| Y | K | T | T | P | P | V | L | D | S |
| Y:2 -:1 | K:3 | T:3 | T:3 | P:3 | P:3 | V:2 -:1 | L:2 -:1 | D:3 | S:3 |

| | | | | C$_H$3 | | | | | |
|---|---|---|---|---|---|---|---|---|---|
| 281 | 282 | 283 | 284 | 285 | 286 | 287 | 288 | 289 | 290 |
| D | G | S | F | F | L | Y | S | R | L |
| D:3 | G:3 | S:3 | F:3 | F:3 | L:3 | Y:3 | S:3 | R:3 | L:3 |

| | | | | C$_H$3 | | | | | |
|---|---|---|---|---|---|---|---|---|---|
| 291 | 292 | 293 | 294 | 295 | 296 | 297 | 298 | 299 | 300 |
| T | V | D | K | S | R | W | Q | E | G |
| T:3 | V:3 | D:3 | K:3 | S:3 | R:3 | W:2 -:1 | Q:2 -:1 | E:2 -:1 | G:2 -:1 |

| | | | | C$_H$3 | | | | | |
|---|---|---|---|---|---|---|---|---|---|
| 301 | 302 | 303 | 304 | 305 | 306 | 307 | 308 | 309 | 310 |
| N | V | F | S | C | S | V | M | H | E |
| N:2 -:1 | V:2 -:1 | F:2 -:1 | S:2 -:1 | C:2 -:1 | S:2 -:1 | V:2 -:1 | M:2 -:1 | H:2 -:1 | E:2 -:1 |

| | | | | C$_H$3 | | | | | |
|---|---|---|---|---|---|---|---|---|---|
| 311 | 312 | 313 | 314 | 315 | 316 | 317 | 318 | 319 | 320 |
| A | L | H | N | H | Y | T | Q | K | S |
| A:2 -:1 | L:2 -:1 | H:2 -:1 | N:2 -:1 | H:2 -:1 | Y:2 M:1 | T:3 | Q:3 | K:3 | S:3 |

| | | | | C$_H$3 | | |
|---|---|---|---|---|---|---|
| 321 | 322 | 323 | 324 | 325 | 326 | 327 |
| L | S | L | S | L | G | K |
| L:3 | S:3 | L:3 | S:3 | L:3 | G:3 | K:2 -:1 |

| 1 | 2 | 3 | 4 | 5 | 6 | 7 | 8 | 9 | 10 |
|---|---|---|---|---|---|---|---|---|---|
| G | S | A | S | A | P | T | L | F | P |
| G:7 | S:8 | A:8 | S:8 | A:8 | P:8 | T:8 | L:8 | F:8 | P:8 |
| -:2 | -:1 | -:1 | -:1 | -:1 | -:1 | -:1 | -:1 | -:1 | -:1 |

$C_H1$

| 11 | 12 | 13 | 14 | 15 | 16 | 17 | 18 | 19 | 20 |
|---|---|---|---|---|---|---|---|---|---|
| L | V | S | C | E | N | S | P | S | D |
| L:8 | V:8 | S:8 | C:7 | E:7 | N:6 | S:6 | P:5 | S:5 | D:5 |
| -:1 | -:1 | -:1 | -:2 | -:2 | -:2 | -:3 | -:3 | -:3 | -:4 |
|  |  |  |  |  | B:1 |  | B:1 | P:1 |  |

$C_H1$

| 21 | 22 | 23 | 24 | 25 | 26 | 27 | 28 | 29 | 30 |
|---|---|---|---|---|---|---|---|---|---|
| T | S | S | V | A | V | G | C | L | A |
| T:5 | S:6 | S:6 | V:7 | A:7 | V:7 | G:7 | C:7 | L:7 | A:7 |
| -:3 | -:3 | -:2 | -:2 | -:2 | -:2 | -:2 | -:2 | -:2 | -:2 |
| S:1 |  | T:1 |  |  |  |  |  |  |  |

$C_H1$

| 31 | 32 | 33 | 34 | 35 | 36 | 37 | 38 | 39 | 40 |
|---|---|---|---|---|---|---|---|---|---|
| Q | D | F | L | P | D | S | I | T | F |
| Q:6 | D:7 | F:7 | L:7 | P:7 | D:7 | S:7 | I:7 | T:7 | F:7 |
| -:2 | -:2 | -:2 | -:2 | -:2 | -:2 | -:2 | -:2 | -:2 | -:2 |
| Z:1 |  |  |  |  |  |  |  |  |  |

$C_H1$

| 41 | 42 | 43 | 44 | 45 | 46 | 47 | 48 | 49 | 50 |
|---|---|---|---|---|---|---|---|---|---|
| S | W | K | Y | K | N | N | S | D | I |
| S:7 | W:7 | K:7 | Y:7 | K:6 | N:5 | N:6 | S:6 | D:6 | I:7 |
| -:2 | -:2 | -:2 | -:2 | -:3 | -:3 | -:3 | -:3 | -:3 | -:2 |
|  |  |  |  |  | B:1 |  |  |  |  |

FIG 40A

| | | | | C$_H$1 | | | | | |
|---|---|---|---|---|---|---|---|---|---|
| 51 | 52 | 53 | 54 | 55 | 56 | 57 | 58 | 59 | 60 |
| S | S | T | R | G | F | P | S | V | L |
| S:7 | S:7 | T:7 | R:7 | G:7 | F:7 | P:7 | S:7 | V:7 | L:7 |
| -:2 | -:2 | -:2 | -:2 | -:2 | -:2 | -:2 | -:2 | -:2 | -:2 |

| | | | | C$_H$1 | | | | | |
|---|---|---|---|---|---|---|---|---|---|
| 61 | 62 | 63 | 64 | 65 | 66 | 67 | 68 | 69 | 70 |
| R | G | G | K | Y | A | A | T | S | Q |
| R:7 | G:7 | G:7 | K:7 | Y:7 | A:7 | A:7 | T:7 | S:6 | Q:6 |
| -:2 | -:2 | -:2 | -:2 | -:2 | -:2 | -:2 | -:2 | -:3 | -:3 |

| | | | | C$_H$1 | | | | | |
|---|---|---|---|---|---|---|---|---|---|
| 71 | 72 | 73 | 74 | 75 | 76 | 77 | 78 | 79 | 80 |
| V | L | L | P | S | K | D | V | M | Q |
| V:7 | L:7 | L:7 | P:7 | S:7 | K:7 | D:7 | V:7 | M:7 | Q:7 |
| -:2 | -:2 | -:2 | -:2 | -:2 | -:2 | -:2 | -:2 | -:2 | -:2 |

| | | | | C$_H$1 | | | | | |
|---|---|---|---|---|---|---|---|---|---|
| 81 | 82 | 83 | 84 | 85 | 86 | 87 | 88 | 89 | 90 |
| G | T | D | E | H | V | V | C | K | V |
| G:7 | T:7 | D:6 | E:7 | H:7 | V:7 | V:6 | C:6 | K:6 | V:7 |
| -:2 | -:2 | -:2 | -:2 | -:2 | -:2 | -:2 | -:2 | -:2 | -:2 |
| | | N:1 | | | | C:1 | K:1 | W:1 | |

| | | | | C$_H$1 | | | | | |
|---|---|---|---|---|---|---|---|---|---|
| 91 | 92 | 93 | 94 | 95 | 96 | 97 | 98 | 99 | 100 |
| Q | H | P | N | G | N | K | E | K | N |
| Q:6 | H:7 | P:7 | N:6 | G:7 | N:5 | K:7 | E:6 | K:7 | N:5 |
| -:2 | -:2 | -:2 | -:2 | -:2 | B:2 | -:2 | -:2 | -:2 | -:2 |
| Z:1 | | | | | B:1 | | Q:1 | | B:1 |
| | | | | | | | | | D:1 |

FIG 40B

| C$_H$1 | | | | C$_H$2 | | | | | |
|---|---|---|---|---|---|---|---|---|---|
| 101 | 102 | 103 | 104 | 105 | 106 | 107 | 108 | 109 | 110 |
| V | P | L | P | V | I | A | E | L | P |
| V:7 | P:7 | L:7 | P:7 | V:9 | I:9 | A:9 | E:8 | L:9 | P:9 |
| -:2 | -:2 | -:2 | -:2 | | | | Z:1 | | |

| C$_H$2 | | | | | | | | | |
|---|---|---|---|---|---|---|---|---|---|
| 111 | 112 | 113 | 114 | 115 | 116 | 117 | 118 | 119 | 120 |
| P | K | V | S | V | F | V | P | P | R |
| P:9 | K:9 | V:9 | S:9 | V:9 | F:9 | V:9 | P:9 | P:9 | R:9 |

| C$_H$2 | | | | | | | | | |
|---|---|---|---|---|---|---|---|---|---|
| 121 | 122 | 123 | 124 | 125 | 126 | 127 | 128 | 129 | 130 |
| D | G | F | F | G | N | P | R | S | K |
| D:8 | G:9 | F:9 | F:9 | G:9 | N:7 | P:9 | R:9 | -:7 | K:9 |
| B:1 | | | | | B:2 | | | S:2 | |

| C$_H$2 | | | | | | | | | |
|---|---|---|---|---|---|---|---|---|---|
| 131 | 132 | 133 | 134 | 135 | 136 | 137 | 138 | 139 | 140 |
| S | K | L | I | C | Q | A | T | G | F |
| S:9 | K:9 | L:9 | I:9 | C:9 | Q:9 | A:9 | T:9 | G:9 | F:9 |

| C$_H$2 | | | | | | | | | |
|---|---|---|---|---|---|---|---|---|---|
| 141 | 142 | 143 | 144 | 145 | 146 | 147 | 148 | 149 | 150 |
| S | P | R | Q | I | Q | V | S | W | L |
| S:9 | P:9 | R:9 | Q:8 | I:8 | Q:8 | V:9 | S:8 | W:8 | L:9 |
| | | | -:1 | -:1 | E:1 | | W:1 | S:1 | |

| C$_H$2 | | | | | | | | | |
|---|---|---|---|---|---|---|---|---|---|
| 151 | 152 | 153 | 154 | 155 | 156 | 157 | 158 | 159 | 160 |
| R | E | G | K | Q | V | G | S | G | V |
| R:9 | E:9 | G:9 | K:9 | Q:9 | V:9 | G:9 | S:9 | G:9 | V:9 |

FIG 40C

| C$_H$2 | | | | | | | | | |
|---|---|---|---|---|---|---|---|---|---|
| 161 | 162 | 163 | 164 | 165 | 166 | 167 | 168 | 169 | 170 |
| T | T | D | Q | V | Q | A | E | A | K |
| T:9 | T:9 | D:7 | Q:6 | V:9 | Q:6 | A:9 | E:7 | A:9 | K:9 |
|  |  | B:1 | E:2 |  | Z:2 |  | Z:2 |  |  |
|  |  | N:1 | Z:1 |  | E:1 |  |  |  |  |

| C$_H$2 | | | | | | | | | |
|---|---|---|---|---|---|---|---|---|---|
| 171 | 172 | 173 | 174 | 175 | 176 | 177 | 178 | 179 | 180 |
| E | S | G | P | T | T | Y | K | V | T |
| E:8 | S:9 | G:9 | P:9 | T:9 | T:9 | Y:9 | K:9 | V:9 | T:9 |
| Z:1 |  |  |  |  |  |  |  |  |  |

| C$_H$2 | | | | | | | | | |
|---|---|---|---|---|---|---|---|---|---|
| 181 | 182 | 183 | 184 | 185 | 186 | 187 | 188 | 189 | 190 |
| S | T | L | T | I | K | E | S | D | W |
| S:9 | T:9 | L:9 | T:9 | I:9 | K:9 | E:8 | S:8 | D:7 | W:8 |
|  |  |  |  |  |  | Z:1 | D:1 | B:1 | -:1 |
|  |  |  |  |  |  |  |  | -:1 |  |

| C$_H$2 | | | | | | | | | |
|---|---|---|---|---|---|---|---|---|---|
| 191 | 192 | 193 | 194 | 195 | 196 | 197 | 198 | 199 | 200 |
| L | S | Q | S | M | F | T | C | R | V |
| L:8 | S:4 | Q:7 | S:8 | M:8 | F:8 | T:8 | C:8 | R:8 | V:8 |
| -:1 | G:4 | E:1 | -:1 | -:1 | -:1 | -:1 | -:1 | -:1 | -:1 |
|  | -:1 | -:1 |  |  |  |  |  |  |  |

| C$_H$2 | | | | | | | | | |
|---|---|---|---|---|---|---|---|---|---|
| 201 | 202 | 203 | 204 | 205 | 206 | 207 | 208 | 209 | 210 |
| D | H | R | G | L | T | F | Q | Q | N |
| D:8 | H:9 | R:9 | G:9 | L:9 | T:9 | F:9 | Q:9 | Q:9 | N:8 |
| -:1 |  |  |  |  |  |  |  |  | B:1 |

FIG 40D

| C$_H$2 | | | | | | | C$_H$3 | | |
|---|---|---|---|---|---|---|---|---|---|
| 211 | 212 | 213 | 214 | 215 | 216 | 217 | 218 | 219 | 220 |
| A | S | S | M | C | V | P | D | Q | D |
| A:9 | S:9 | S:9 | M:9 | C:9 | V:8 G:1 | P:9 | D:9 | Q:8 Z:1 | D:8 B:1 |

| C$_H$3 | | | | | | | | | |
|---|---|---|---|---|---|---|---|---|---|
| 221 | 222 | 223 | 224 | 225 | 226 | 227 | 228 | 229 | 230 |
| T | A | I | R | V | F | A | I | P | P |
| T:9 | A:9 | I:9 | R:9 | V:9 | F:9 | A:9 | I:9 | P:9 | P:9 |

| C$_H$3 | | | | | | | | | |
|---|---|---|---|---|---|---|---|---|---|
| 231 | 232 | 233 | 234 | 235 | 236 | 237 | 238 | 239 | 240 |
| S | F | A | S | I | F | L | T | K | S |
| S:9 | F:9 | A:9 | S:9 | I:9 | F:9 | L:9 | T:9 | K:9 | S:9 |

| C$_H$3 | | | | | | | | | |
|---|---|---|---|---|---|---|---|---|---|
| 241 | 242 | 243 | 244 | 245 | 246 | 247 | 248 | 249 | 250 |
| T | K | L | T | C | L | V | T | D | L |
| T:9 | K:9 | L:9 | T:9 | C:9 | L:9 | V:9 | T:9 | D:9 | L:9 |

| C$_H$3 | | | | | | | | | |
|---|---|---|---|---|---|---|---|---|---|
| 251 | 252 | 253 | 254 | 255 | 256 | 257 | 258 | 259 | 260 |
| T | T | Y | D | S | V | T | I | S | W |
| T:9 | T:8 -:1 | Y:9 | D:8 B:1 | S:9 | V:9 | T:9 | I:9 | S:9 | W:8 -:1 |

| 261 | 262 | 263 | 264 | 265 | 266 | 267 | 268 | 269 | 270 |
|---|---|---|---|---|---|---|---|---|---|
| T | R | Q | N | G | E | A | V | K | T |
| T:8 | R:8 | Q:7 | N:5 | G:7 | E:7 | A:8 | V:8 | K:8 | T:8 |
| -:1 | -:1 | E:1 | D:2 | -:1 | -:1 | -:1 | -:1 | -:1 | -:1 |
|  |  | -:1 | E:1 | N:1 | G:1 |  |  |  |  |
|  |  |  | -:1 |  |  |  |  |  |  |

C$_H$3

| 271 | 272 | 273 | 274 | 275 | 276 | 277 | 278 | 279 | 280 |
|---|---|---|---|---|---|---|---|---|---|
| H | T | N | I | S | E | S | H | P | N |
| H:8 | T:8 | N:7 | I:8 | S:8 | E:7 | S:8 | H:8 | P:8 | N:7 |
| -:1 | -:1 | B:1 | -:1 | -:1 | Z:1 | -:1 | -:1 | -:1 | B:1 |
|  |  | -:1 |  |  | -:1 |  |  |  | -:1 |

C$_H$3

| 281 | 282 | 283 | 284 | 285 | 286 | 287 | 288 | 289 | 290 |
|---|---|---|---|---|---|---|---|---|---|
| A | T | F | S | A | V | G | E | A | S |
| A:8 | T:8 | F:8 | S:8 | A:8 | V:8 | G:8 | E:8 | A:8 | S:8 |
| -:1 | -:1 | -:1 | -:1 | -:1 | -:1 | -:1 | -:1 | -:1 | -:1 |

C$_H$3

| 291 | 292 | 293 | 294 | 295 | 296 | 297 | 298 | 299 | 300 |
|---|---|---|---|---|---|---|---|---|---|
| I | C | E | D | D | W | N | S | G | E |
| I:8 | C:8 | E:8 | D:7 | D:6 | W:8 | N:7 | S:9 | G:9 | E:9 |
| -:1 | -:1 | -:1 | B:1 | B:2 | D:1 | D:1 |  |  |  |
|  |  |  | -:1 | -:1 |  | W:1 |  |  |  |

C$_H$3

| 301 | 302 | 303 | 304 | 305 | 306 | 307 | 308 | 309 | 310 |
|---|---|---|---|---|---|---|---|---|---|
| R | F | T | C | T | V | T | H | T | D |
| R:9 | F:9 | T:9 | C:9 | T:9 | V:9 | T:9 | H:9 | T:9 | D:9 |

FIG 40F

| | | | | | C_H3 | | | | |
|---|---|---|---|---|---|---|---|---|---|
| 311 | 312 | 313 | 314 | 315 | 316 | 317 | 318 | 319 | 320 |
| L | P | S | P | L | K | Q | T | I | S |
| L:9 | P:9 | S:9 | P:9 | L:9 | K:9 | Q:9 | T:9 | I:9 | S:9 |

| | C_H3 | | | | | C_H4 | | | |
|---|---|---|---|---|---|---|---|---|---|
| 321 | 322 | 323 | 324 | 325 | 326 | 327 | 328 | 329 | 330 |
| R | P | K | G | V | A | L | H | R | P |
| 9/9 | 9/9 | 9/9 | 9/9 | 9/9 | 9/9 | 9/9 | 9/9 | 9/9 | 9/9 |
| R:9 | P:9 | K:9 | G:9 | V:9 | A:9 | L:9 | H:9 | R:9 | P:9 |

| | | | | C_H4 | | | | | |
|---|---|---|---|---|---|---|---|---|---|
| 331 | 332 | 333 | 334 | 335 | 336 | 337 | 338 | 339 | 340 |
| D | V | Y | L | L | P | P | A | R | E |
| D:8 | V:9 | Y:9 | L:9 | L:9 | P:9 | P:9 | A:9 | R:9 | E:8 |
| B:1 | | | | | | | | | Z:1 |

| | | | | C_H4 | | | | | |
|---|---|---|---|---|---|---|---|---|---|
| 341 | 342 | 343 | 344 | 345 | 346 | 347 | 348 | 349 | 350 |
| Q | L | N | L | R | E | S | A | T | I |
| Q:8 | L:9 | N:9 | L:9 | R:9 | E:9 | S:9 | A:9 | T:9 | I:9 |
| Z:1 | | | | | | | | | |

| | | | | C_H4 | | | | | |
|---|---|---|---|---|---|---|---|---|---|
| 351 | 352 | 353 | 354 | 355 | 356 | 357 | 358 | 359 | 360 |
| T | C | L | V | T | G | F | S | P | A |
| T:9 | C:9 | L:9 | V:9 | T:9 | G:9 | F:9 | S:9 | P:9 | A:9 |

FIG 40G

| | | | | | C<sub>H</sub>4 | | | | |
|---|---|---|---|---|---|---|---|---|---|
| 361 | 362 | 363 | 364 | 365 | 366 | 367 | 368 | 369 | 370 |
| D | V | F | V | Q | W | Q | M | Q | R |
| D:9 | V:9 | F:9 | V:9 | Q:8 | W:9 | -:8 | M:9 | Q:9 | R:9 |
| | | | | E:1 | | Q:1 | | | |

| | | | | | C<sub>H</sub>4 | | | | |
|---|---|---|---|---|---|---|---|---|---|
| 371 | 372 | 373 | 374 | 375 | 376 | 377 | 378 | 379 | 380 |
| G | Q | P | L | S | P | E | K | Y | V |
| G:9 | Q:8 | P:9 | L:9 | S:9 | P:9 | E:8 | K:9 | Y:9 | V:9 |
| | E:1 | | | | | Q:1 | | | |

| | | | | | C<sub>H</sub>4 | | | | |
|---|---|---|---|---|---|---|---|---|---|
| 381 | 382 | 383 | 384 | 385 | 386 | 387 | 388 | 389 | 390 |
| T | S | A | P | M | P | E | P | Q | A |
| T:9 | S:9 | A:9 | P:9 | M:9 | P:9 | E:9 | P:9 | Q:9 | A:9 |

| | | | | | C<sub>H</sub>4 | | | | |
|---|---|---|---|---|---|---|---|---|---|
| 391 | 392 | 393 | 394 | 395 | 396 | 397 | 398 | 399 | 400 |
| P | G | R | Y | F | A | H | S | I | L |
| P:9 | G:9 | R:9 | Y:9 | F:9 | A:9 | H:9 | S:9 | I:9 | L:9 |

| | | | | | C<sub>H</sub>4 | | | | |
|---|---|---|---|---|---|---|---|---|---|
| 401 | 402 | 403 | 404 | 405 | 406 | 407 | 408 | 409 | 410 |
| T | V | S | E | E | E | W | N | T | G |
| T:9 | V:9 | S:9 | E:9 | E:9 | E:9 | W:9 | N:9 | T:9 | G:9 |

| | | | | | C<sub>H</sub>4 | | | | |
|---|---|---|---|---|---|---|---|---|---|
| 411 | 412 | 413 | 414 | 415 | 416 | 417 | 418 | 419 | 420 |
| E | T | Y | T | C | V | V | A | H | E |
| E:8 | T:9 | Y:9 | T:9 | C:9 | V:6 | V:9 | A:9 | H:9 | E:8 |
| Q:1 | | | | | -:3 | | | | D:1 |

FIG 40H

| | | | | C_H4 | | | | | |
|---|---|---|---|---|---|---|---|---|---|
| 421<br>A | 422<br>L | 423<br>P | 424<br>N | 425<br>R | 426<br>V | 427<br>T | 428<br>E | 429<br>R | 430<br>T |
| A:9 | L:9 | P:9 | N:9 | R:9 | V:9 | T:9 | E:9 | R:9 | T:9 |

| | | | | C_H4 | | | | | |
|---|---|---|---|---|---|---|---|---|---|
| 431<br>V | 432<br>D | 433<br>K | 434<br>S | 435<br>T | 436<br>G | 437<br>K | 438<br>P | 439<br>T | 440<br>S |
| V:9 | D:9 | K:9 | S:9 | T:9 | G:8<br>E:1 | K:8<br>G:1 | P:8<br>E:1 | T:8<br>V:1 | -:8<br>S:1 |

| | | | | C_H4 | | | | | |
|---|---|---|---|---|---|---|---|---|---|
| 441<br>A | 442<br>D | 443<br>E | 444<br>E | 445<br>G | 446<br>F | 447<br>E | 448<br>N | 449<br>L | 450<br>W |
| -:8<br>A:1 | -:8<br>D:1 | -:8<br>E:1 | -:8<br>E:1 | -:8<br>G:1 | -:8<br>F:1 | -:8<br>E:1 | -:8<br>N:1 | -:8<br>L:1 | -:8<br>W:1 |

| | | | | C_H4 | | | | | |
|---|---|---|---|---|---|---|---|---|---|
| 451<br>A | 452<br>T | 453<br>A | 454<br>S | 455<br>T | 456<br>F | 457<br>I | 458<br>V | 459<br>L | 460<br>Y |
| -:8<br>A:1 | -:8<br>T:1 | -:8<br>A:1 | -:8<br>S:1 | -:8<br>T:1 | -:8<br>F:1 | -:8<br>I:1 | -:8<br>V:1 | L:9 | Y:8<br>F:1 |

| | | | | C_H4 | | | | | |
|---|---|---|---|---|---|---|---|---|---|
| 461<br>N | 462<br>V | 463<br>S | 464<br>L | 465<br>V | 466<br>M | 467<br>S | 468<br>D | 469<br>T | 470<br>A |
| N:7<br>B:1<br>L:1 | V:8<br>L:1 | S:9 | L:9 | V:8<br>F:1 | M:8<br>Y:1 | S:9 | D:7<br>B:1<br>T:1 | T:9 | A:8<br>V:1 |

FIG 40I

| C$_H$4 | | | | | |
|---|---|---|---|---|---|
| 471 | 472 | 473 | 474 | 475 | 476 |
| G | T | C | Y | V | K |
| | | | | | |
| G:8 | T:8 | C:8 | Y:8 | -:8 | -:8 |
| T:1 | L:1 | F:1 | K:1 | V:1 | K:1 |

FIG 40J

Light chain kappa constant region (IgKc)

| 1 | 2 | 3 | 4 | 5 | 6 | 7 | 8 | 9 | 10 |
|---|---|---|---|---|---|---|---|---|---|
| R | T | V | A | A | P | S | V | F | I |
| R:9<br>D:1<br>-:1<br>G:1 | T:12 | V:12 | A:12 | A:12 | P:12 | S:12 | V:12 | F:12 | I:12 |

Light chain kappa constant region (IgKc)

| 11 | 12 | 13 | 14 | 15 | 16 | 17 | 18 | 19 | 20 |
|---|---|---|---|---|---|---|---|---|---|
| F | P | P | S | D | E | Q | L | K | S |
| F:12 | P:12 | P:12 | S:12 | D:10<br>N:2 | E:12 | Q:12 | L:12 | K:12 | S:12 |

Light chain kappa constant region (IgKc)

| 21 | 22 | 23 | 24 | 25 | 26 | 27 | 28 | 29 | 30 |
|---|---|---|---|---|---|---|---|---|---|
| G | T | A | S | V | V | C | L | L | N |
| G:12 | T:12 | A:12 | S:12 | V:12 | V:12 | C:12 | L:12 | L:12 | N:11<br>D:1 |

Light chain kappa constant region (IgKc)

| 31 | 32 | 33 | 34 | 35 | 36 | 37 | 38 | 39 | 40 |
|---|---|---|---|---|---|---|---|---|---|
| N | F | Y | P | R | E | A | K | V | Q |
| N:11<br>D:1 | F:12 | Y:12 | P:12 | R:12 | E:11<br>-:1 | A:12 | K:12 | V:12 | Q:12 |

Light chain kappa constant region (IgKc)

| 41 | 42 | 43 | 44 | 45 | 46 | 47 | 48 | 49 | 50 |
|---|---|---|---|---|---|---|---|---|---|
| W | K | V | D | N | A | L | Q | S | G |
| W:12 | K:12 | V:12 | D:11<br>N:1 | N:11<br>D:1 | A:12 | L:12 | Q:12 | S:12 | G:12 |

FIG 41A

| | | | | Light chain kappa constant region (IgKc) | | | | | |
|---|---|---|---|---|---|---|---|---|---|
| 51 | 52 | 53 | 54 | 55 | 56 | 57 | 58 | 59 | 60 |
| N | S | Q | E | S | V | T | E | Q | D |
| N:12 | S:12 | Q:12 | E:12 | S:11<br>-:1 | V:11<br>-:1 | T:11<br>-:1 | E:8<br>Q:2<br>Z:1<br>-:1 | Q:10<br>Z:1<br>-:1 | D:11<br>-:1 |

| | | | | Light chain kappa constant region (IgKc) | | | | | |
|---|---|---|---|---|---|---|---|---|---|
| 61 | 62 | 63 | 64 | 65 | 66 | 67 | 68 | 69 | 70 |
| S | K | D | S | T | Y | S | L | S | S |
| S:12 | K:12 | D:12 | S:12 | T:12 | Y:12 | S:12 | L:12 | S:12 | S:12 |

| | | | | Light chain kappa constant region (IgKc) | | | | | |
|---|---|---|---|---|---|---|---|---|---|
| 71 | 72 | 73 | 74 | 75 | 76 | 77 | 78 | 79 | 80 |
| T | L | T | L | S | K | A | D | Y | E |
| T:11<br>Y:1 | L:12 | T:12 | L:12 | S:12 | K:12 | A:12 | D:12 | Y:12 | E:12 |

| | | | | Light chain kappa constant region (IgKc) | | | | | |
|---|---|---|---|---|---|---|---|---|---|
| 81 | 82 | 83 | 84 | 85 | 86 | 87 | 88 | 89 | 90 |
| K | H | K | V | Y | A | C | E | V | T |
| K:12 | H:12 | K:12 | V:11<br>L:1 | Y:12 | A:12 | C:12 | E:12 | V:12 | T:12 |

| | | | | Light chain kappa constant region (IgKc) | | | | | |
|---|---|---|---|---|---|---|---|---|---|
| 91 | 92 | 93 | 94 | 95 | 96 | 97 | 98 | 99 | 100 |
| H | Q | G | L | S | S | P | V | T | K |
| H:12 | Q:12 | G:12 | L:12 | S:12 | S:12 | P:12 | V:12 | T:12 | K:12 |

| | | Light chain kappa constant region (IgKc) | | | | |
|---|---|---|---|---|---|---|
| 101 | 102 | 103 | 104 | 105 | 106 | 107 |
| S | F | N | R | G | E | C |
| S:12 | F:12 | N:11<br>D:1 | R:12 | G:12 | E:12 | C:12 |

FIG 41B

| | | | | Light chain lambda constant region (IgLambda) | | | | | |
|---|---|---|---|---|---|---|---|---|---|
| 1 | 2 | 3 | 4 | 5 | 6 | 7 | 8 | 9 | 10 |
| G | Q | P | K | A | A | P | S | V | T |
| -:16 | Q:25 | P:27 | K:28 | A:28 | A:20 | P:28 | S:24 | V:28 | T:28 |
| G:11 | -:3 | -:1 | | | T:4 | | T:4 | | |
| S:1 | | | | | N:4 | | | | |

| | | | | Light chain lambda constant region (IgLambda) | | | | | |
|---|---|---|---|---|---|---|---|---|---|
| 11 | 12 | 13 | 14 | 15 | 16 | 17 | 18 | 19 | 20 |
| L | F | P | P | S | S | E | E | L | Q |
| L:28 | F:28 | P:26 | P:28 | S:28 | S:28 | E:26 | E:26 | L:28 | Q:27 |
| | | S:1 | | | | Z:2 | Z:2 | | Z:1 |
| | | L:1 | | | | | | | |

| | | | | Light chain lambda constant region (IgLambda) | | | | | |
|---|---|---|---|---|---|---|---|---|---|
| 21 | 22 | 23 | 24 | 25 | 26 | 27 | 28 | 29 | 30 |
| A | N | K | A | T | L | V | C | L | I |
| A:28 | N:27 | K:27 | A:28 | T:28 | L:28 | V:28 | C:28 | L:28 | I:22 |
| | B:1 | R:1 | | | | | | | M:4 |
| | | | | | | | | | V:2 |

| | | | | Light chain lambda constant region (IgLambda) | | | | | |
|---|---|---|---|---|---|---|---|---|---|
| 31 | 32 | 33 | 34 | 35 | 36 | 37 | 38 | 39 | 40 |
| S | D | F | Y | P | G | A | V | T | V |
| S:24 | D:28 | F:28 | Y:28 | P:26 | G:28 | A:24 | V:24 | T:26 | V:28 |
| N:4 | | | | L:2 | | I:4 | L:4 | K:2 | |

| | | | | Light chain lambda constant region (IgLambda) | | | | | |
|---|---|---|---|---|---|---|---|---|---|
| 41 | 42 | 43 | 44 | 45 | 46 | 47 | 48 | 49 | 50 |
| A | W | K | A | D | S | S | P | V | K |
| A:23 | W:27 | K:28 | A:27 | D:28 | S:15 | S:24 | P:28 | V:23 | K:22 |
| T:4 | -:1 | | G:1 | | G:13 | T:4 | | I:5 | T:4 |
| -:1 | | | | | | | | | N:2 |

FIG 42A

Light chain lambda constant region (IgLambda)

| 51 | 52 | 53 | 54 | 55 | 56 | 57 | 58 | 59 | 60 |
|----|----|----|----|----|----|----|----|----|----|
| A  | G  | V  | E  | T  | T  | T  | P  | S  | K  |
| A:18 | G:27 | V:28 | E:28 | T:23 | T:28 | T:21 | P:28 | S:28 | K:26 |
| Q:4  | A:1  |      |      | M:4  |      | K:6  |      |      | N:2  |
| V:3  |      |      |      | A:1  |      | A:1  |      |      |      |
| T:2  |      |      |      |      |      |      |      |      |      |
| G:1  |      |      |      |      |      |      |      |      |      |

Light chain lambda constant region (IgLambda)

| 61 | 62 | 63 | 64 | 65 | 66 | 67 | 68 | 69 | 70 |
|----|----|----|----|----|----|----|----|----|----|
| Q  | S  | N  | N  | K  | Y  | A  | A  | S  | S  |
| Q:27 | S:28 | N:26 | N:25 | K:26 | Y:26 | A:26 | A:27 | S:28 | S:27 |
| H:1  |      | I:1  | S:2  | R:1  | F:2  | M:2  | G:1  |      | R:1  |
|      |      | B:1  | B:1  | M:1  |      |      |      |      |      |

Light chain lambda constant region (IgLambda)

| 71 | 72 | 73 | 74 | 75 | 76 | 77 | 78 | 79 | 80 |
|----|----|----|----|----|----|----|----|----|----|
| Y  | L  | S  | L  | T  | P  | E  | Q  | W  | K  |
| Y:28 | L:27 | S:27 | L:27 | T:27 | P:27 | E:26 | Q:26 | W:27 | K:24 |
|      | -:1  | -:1  | -:1  | -:1  | -:1  | Z:1  | Z:1  | -:1  | R:4  |
|      |      |      |      |      |      | -:1  | -:1  |      |      |

Light chain lambda constant region (IgLambda)

| 81 | 82 | 83 | 84 | 85 | 86 | 87 | 88 | 89 | 90 |
|----|----|----|----|----|----|----|----|----|----|
| S  | H  | R  | K  | S  | Y  | S  | C  | Q  | V  |
| S:28 | H:24 | R:23 | -:27 | S:28 | Y:28 | S:28 | C:28 | Q:23 | V:28 |
|      | R:4  | K:5  | K:1  |      |      |      |      | R:2  |      |
|      |      |      |      |      |      |      |      | Z:2  |      |
|      |      |      |      |      |      |      |      | L:1  |      |

Light chain lambda constant region (IgLambda)

| 91 | 92 | 93 | 94 | 95 | 96 | 97 | 98 | 99 | 100 |
|----|----|----|----|----|----|----|----|----|-----|
| T  | H  | E  | G  | S  | T  | V  | E  | K  | T   |
| T:23 | H:27 | E:26 | G:27 | S:27 | T:27 | V:24 | E:25 | K:25 | T:25 |
| M:4  | -:1  | Z:1  | -:1  | -:1  | -:1  | A:2  | -:2  | -:3  | -:3  |
| -:1  |      | -:1  |      |      |      | -:2  | Z:1  |      |      |

FIG 42B

| Light chain lambda constant region (IgLambda) | | | | | | |
|---|---|---|---|---|---|---|
| 101 | 102 | 103 | 104 | 105 | 106 | 107 |
| V | A | P | T | E | C | S |
| V:25 | A:25 | P:26 | T:19 | E:26 | C:25 | S:25 |
| -:3 | -:3 | -:2 | A:7 | -:2 | -:2 | -:2 |
|  |  |  | -:2 |  | R:1 | A:1 |

FIG 42C

HUMAN EPO MIMETIC HINGE CORE MIMETIBODIES, COMPOSITIONS, METHODS AND USES

BACKGROUND OF THE INVENTION

1. Field of the Invention

The present invention relates to mammalian EPO mimetic hinge core mimetibodies, specified portions and variants specific for biologically active proteins, fragment or ligands, EPO mimetic hinge core mimetibody encoding and complementary nucleic acids, host cells, and methods of making and using thereof, including therapeutic formulations, administration and devices.

2. Related Art

Recombinant proteins are an emerging class of therapeutic agents. Such recombinant therapeutics have engendered advances in protein formulation and chemical modification. Such modifications can potentially enhance the therapeutic utility of therapeutic proteins, such as by increasing half lives (e.g., by blocking their exposure to proteolytic enzymes), enhancing biological activity, or reducing unwanted side effects. One such modification is the use of immunoglobulin fragments fused to receptor proteins, such as enteracept. Therapeutic proteins have also been constructed using the Fc domain to attempt to provide a longer half-life or to incorporate functions such as Fc receptor binding, protein A binding, and complement fixation. One specific and vital role of the mammalian hematopoietic system is the production of erythrocytes, or red blood cells, which transport oxygen to the various tissues of the animal's body. The process of producing erythrocytes ("erythropoiesis") occurs continuously throughout an animal's life span to offset erythrocyte destruction. The typical red blood cell has a relatively short life-span, usually 100 to 120 days. Erythropoiesis is a precisely controlled physiological mechanism whereby sufficient numbers of erythrocytes are produced to enable proper tissue oxygenation, but not so many as to impede circulation.

Erythropoiesis is now known to be primarily controlled by the polypeptide erythropoietin (EPO), an acidic glycoprotein. Erythropoietin is produced as the result of the expression of a single copy gene located in a chromosome of a mammal. The amino acid sequence for recombinant human EPO ("rHuEPO") is substantially identical to the amino acid sequence for EPO obtained from human urinary sources. However, the glycosylation of rHuEPO differs from that of urinary EPO and human serum EPO.

In a healthy mammal, EPO is present in the blood plasma in very low concentrations, as the tissues are being sufficiently oxygenated by the existing number of circulating erythrocytes. The EPO present stimulates the production of new erythrocytes to replace those lost to the aging process. Additionally, EPO production is stimulated under conditions of hypoxia, wherein the oxygen supply to the body's tissues is reduced below normal physiological levels despite adequate perfusion of the tissue by blood. Hypoxia may be caused by hemorrhaging, radiation-induced erythrocyte destruction, various anemias, high altitude, or long periods of unconsciousness. In contrast, should the number of red blood cells in circulation exceed what is needed for normal tissue oxygenation, EPO production is reduced.

However, certain disease states involve abnormal erythropoiesis. Recombinant human EPO (rHuEPO) is being used therapeutically in a number of countries. In the United States, the U.S. Food and Drug Administration (FDA) has approved rHuEPO's use in treating anemia associated with end-stage renal disease. Patients undergoing hemodialysis to treat this disorder typically suffer severe anemia, caused by the rupture and premature death of erythrocytes as a result of the dialysis treatment. EPO is also useful in the treatment of other types of anemia. For instance, chemotherapy-induced anemia, anemia associated with myelodysplasia, those associated with various congenital disorders, AIDS-related anemia, and prematurity-associated anemia, may be treated with EPO. Additionally, EPO may play a role in other areas, such as helping to more quickly restore a normal hematocrit in bone marrow transplantation patients, in patients preparing for autologous blood transfusions, and in patients suffering from iron overload disorders.

Erythropoietin (EPO) is a glycoprotein hormone composed of 165 amino acids and four carbohydrate chains that functions as the primary regulator of erythropoiesis by binding to a specific receptor on the surface of erythrocyte precursor cells. This binding signals their proliferation and differentiation into mature red blood cells. The erythropoietin receptor is a 484-amino acid glycoprotein with high affinity for erythropoietin. For the erythropoietin receptor, ligand-induced homodimerization may be one of the key event that governs activation.

Erythropoietin has a relatively short half-life. Intravenously administered erythropoietin is eliminated at a rate consistent with first order kinetics with a circulating half-life ranging from approximately 3 to 4 hours in patients with CRF. Within the therapeutic dose range, detectable levels of plasma erythropoietin are maintained for at least 24 hours. After subcutaneous administration of erythropoietin, peak serum levels are achieved within 5-24 hours and decline slowly thereafter.

Small peptidomimetics of erythropoietin were identified by several groups through screening of random phage display peptide libraries for affinity to the erythropoietin receptor. These sequences have no homology with erythropoietin. In functional assays several of these peptides showed activity, but only $1/100,000^{th}$ that of recombinant erythropoietin. Although several attempts have been made to increase the potency of these peptides by preparing covalent dimers or multimers of peptidomimetics, these compounds are still 1,000-10,000 fold less active than erythropoietin on a molar basis and have very short half lives that has made them not suitable for use as therapeutics.

Accordingly, there is a need to provide improved and/or modified versions of EPO therapeutic proteins, which overcome one more of these and other problems known in the art.

SUMMARY OF THE INVENTION

The present invention provides human EPO mimetic hinge core mimetibodies, including modified immunoglobulins, cleavage products and other specified portions and variants thereof, as well as EPO mimetic hinge core mimetibody compositions, encoding or complementary nucleic acids, vectors, host cells, compositions, formulations, devices, transgenic animals, transgenic plants, and methods of making and using thereof, as described and/or enabled herein, in combination with what is known in the art.

The present invention also provides at least one isolated EPO mimetic hinge core mimetibody or specified portion or variant as described herein and/or as known in the art. The EPO mimetic hinge core mimetibody can optionally comprise at least one CH3 region directly linked with at least one CH2 region directly linked with at least one portion of at least one hinge region or fragment thereof (H), directly linked with an optional linker sequence (L), directly linked to at least one EPO mimetic therapeutic peptide (P), optionally further directly linked with at least a portion of at least one variable antibody sequence (V). In a preferred embodiment a pair of a CH3-CH2-hinge-linker-therapeutic peptide with an optional N-terminal antibody sequence, the pair optionally linked by association or covalent linkage, such as, but not limited to, at least one Cys-Cys disulfide bond or at least one CH4 or other immunoglobulin sequence. In one embodiment, an EPO mimetic hinge core mimetibody comprises formula (I):

$$((V(m)-P(n)-L(o)-H(p)-CH2(q)-CH3(r))(s),$$

where V is at least one portion of an N-terminus of an immunoglobulin variable region, P is at least one bioactive EPO mimetic polypeptide, L is at least one linker sequence, H is least one portion of a n immunoglobulin variable region, CH2 is at least a portion of an immunoglobulin CH2 constant region, CH3 is at least a portion of an immunoglobulin CH3 constant region, m, n, o p, q, r, and s can be independently an integer between 0, 1 or 2 and 10, mimicking different types of immunoglobulin molecules, e.g., but not limited to IgG1, IgG2, IgG3, IgG4, IgA1, IgA2, IgM, IgD, IgE, or any subclass thereof, and the like, or any combination thereof.

Thus, an EPO mimetic hinge core mimetibody of the present invention mimics at least a portion of an antibody or immunoglobulin structure or function with its inherent properties and functions, while providing a therapeutic peptide and its inherent or acquired in vitro, in vivo or in situ properties or activities. The various portions of the antibody and therapeutic peptide portions of at least one EPO mimetic hinge core mimetibody of the present invention can vary as described herein in combination with what is known in the art.

The present invention provides, in one aspect, isolated nucleic acid molecules comprising, complementary, having significant identity or hybridizing to, a polynucleotide encoding specific mimetibodies or specified portions or variants thereof, comprising at least one specified sequence, domain, portion or variant thereof. The present invention further provides recombinant vectors comprising at least one of said isolated EPO mimetic hinge core mimetibody nucleic acid molecules, host cells containing such nucleic acids and/or recombinant vectors, as well as methods of making and/or using such EPO mimetic hinge core mimetibody nucleic acids, vectors and/or host cells.

At least one EPO mimetic hinge core mimetibody or specified portion or variant of the invention mimics the binding of the P portion of the mimetibody to at least one ligand, or has at least one biological activity of, at least one protein, subunit, fragment, portion or any combination thereof.

The present invention also provides at least one isolated EPO mimetic hinge core mimetibody or specified portion or variant as described herein and/or as known in the art, wherein the EPO mimetic hinge core mimetibody or specified portion or variant has at least one activity, such as, but not limited to known biological activities of at least one bioactive peptide or polypeptide corresponding to the P portion of Formula I. An EPO mimetic hinge core mimetibody can thus be screened for a corresponding activity according to known methods, such as at least one neutralizing activity towards a protein or fragment thereof.

The present invention also provides at least one composition comprising (a) at least one isolated EPO mimetic hinge core mimetibody or specified portion or variant encoding nucleic acid and/or EPO mimetic hinge core mimetibody as described herein; and (b) a suitable carrier or diluent. The carrier or diluent can optionally be pharmaceutically acceptable, according to known methods. The composition can optionally further comprise at least one further compound, protein or composition.

The present invention also provides at least one method for expressing at least one EPO mimetic hinge core mimetibody or specified portion or variant in a host cell, comprising culturing a host cell as described herein and/or as known in the art under conditions wherein at least one EPO mimetic hinge core mimetibody or specified portion or variant is expressed in detectable and/or recoverable amounts.

The present invention further provides at least one EPO mimetic hinge core mimetibody, specified portion or variant in a method or composition, when administered in a therapeutically effective amount, for modulation, for treating or reducing the symptoms of at least one of a bone and joint disorder, cardiovascular disorder, a dental or oral disorder, a dermatologic disorder, an ear, nose or throat disorder, an endocrine or metabolic disorder, a gastrointestinal disorder, a gynecologic disorder, a hepatic or biliary disorder, a an obstetric disorder, a hematologic disorder, an immunologic or allergic disorder, an infectious disease, a musculoskeletal disorder, a oncologic disorder, a neurologic disorder, a nutritional disorder, an ophthalmologic disorder, a pediatric disorder, a poisoning disorder, a psychiatric disorder, a renal disorder, a pulmonary disorder, or any other known disorder. (See., e.g., The Merck Manual, 17th ed., Merck Research Laboratories, Merck and Co., Whitehouse Station, N.J. (1999), entirely incorporated herein by reference), as needed in many different conditions, such as but not limited to, prior to, subsequent to, or during a related disease or treatment condition, as known in the art.

The present invention further provides at least one EPO mimetic hinge core mimetibody, specified portion or variant in a method or composition, when administered in a therapeutically effective amount, for modulation, for treating or reducing the symptoms of, at least one immune, cardiovascular, infectious, malignant, and/or neurologic disease in a cell, tissue, organ, animal or patient and/or, as needed in many different conditions, such as but not limited to, prior to, subsequent to, or during a related disease or treatment condition, as known in the art and/or as described herein.

The present invention also provides at least one composition, device and/or method of delivery of a therapeutically or prophylactically effective amount of at least one EPO mimetic hinge core mimetibody or specified portion or variant, according to the present invention.

The present invention further provides at least one anti-idiotype antibody to at least one EPO mimetic hinge core mimetibody of the present invention. The anti-idiotype antibody includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, that competitively binds an EPO receptor binding region of at least one EPO mimetic hinge core mimetibody of the present invention. Such idiotype antibodies of the invention can include or be derived from any mammal, such as but not limited to a human, a mouse, a rabbit, a rat, a rodent, a primate, and the like.

The present invention also provides at least one isolated nucleic acid molecule comprising, complementary, or hybridizing to, a polynucleotide encoding at least one EPO mimetic hinge core mimetibody anti-idiotype antibody, comprising at least one specified sequence, domain, portion or variant thereof. The present invention further provides recombinant vectors comprising said EPO mimetic hinge core mimetibody anti-idiotype antibody encoding nucleic acid molecules, host cells containing such nucleic acids and/or recombinant vectors, as well as methods of making and/or using such anti-idiotype antibody nucleic acids, vectors and/or host cells.

The present invention also provides at least one method for expressing at least one EPO mimetic hinge core mimetibody, or EPO mimetic hinge core mimetibody anti-idiotype antibody, in a host cell, comprising culturing a host cell as described herein under conditions wherein at least one EPO mimetic hinge core mimetibody or anti-idiotype antibody is expressed in detectable and/or recoverable amounts.

The present invention also provides at least one composition comprising (a) an isolated EPO mimetic hinge core mimetibody encoding nucleic acid and/or EPO mimetic hinge core mimetibody as described herein; and (b) a suitable carrier or diluent. The carrier or diluent can optionally be pharmaceutically acceptable, according to known carriers or diluents. The composition can optionally further comprise at least one further compound, protein or composition.

The present invention further provides at least one EPO mimetic hinge core mimetibody method or composition, for administering a therapeutically effective amount to modulate or treat at least one protein related condition in a cell, tissue, organ, animal or patient and/or, prior to, subsequent to, or during a related condition, as known in the art and/or as described herein.

The present invention also provides at least one composition, device and/or method of delivery of a therapeutically or prophylactically effective amount of at least one EPO mimetic hinge core mimetibody, according to the present invention.

The present invention further provides at least one EPO mimetic hinge core mimetibody method or composition, for diagnosing at least one EPO related condition in a cell, tissue, organ, animal or patient and/or, prior to, subsequent to, or during a related condition, as known in the art and/or as described herein.

The present invention also provides at least one composition, device and/or method of delivery for diagnosing of at least one EPO mimetic hinge core mimetibody, according to the present invention.

In one aspect, the present invention provides at least one isolated human EPO mimetic hinge core mimetibody, comprising at least one P(n) region comprising at least a portion of at least one of SEQ ID NOS:1-30, e.g., as presented in Table 1 below, or optionally with one or more substitutions, deletions or insertions as described herein or as known in the art. In other aspect the present invention provides at least one isolated human EPO mimetic hinge core mimetibody, wherein the EPO mimetic hinge core mimetibody specifically binds at least one epitope comprising at least 1-3 of at least one ligand or binding region which ligand binds to at least a portion of at least one of SEQ ID NOS:1-30 as presented in Table 1 below, or optionally with one or more substitutions, deletions or insertions as described herein or as known in the art.

The at least one EPO mimetic hinge core mimetibody can optionally further at least one of: bind protein with an affinity of at least one selected from at least $10^{-9}$ M, at least $10^{-10}$ M, at least $10^{-11}$ M, or at least $10^{-12}$ M; substantially neutralize at least one activity of at least one protein or portion thereof. Also provided is an isolated nucleic acid encoding at least one isolated human EPO mimetic hinge core mimetibody; an isolated nucleic acid vector comprising the isolated nucleic acid, and/or a prokaryotic or eukaryotic host cell comprising the isolated nucleic acid. The host cell can optionally be at least one selected from COS-1, COS-7, HEK293, BHK21, CHO, BSC-1, Hep G2, 653, SP2/0, 293, HeLa, myeloma, or lymphoma cells, or any derivative, immortalized or transformed cell thereof. Also provided is a method for producing at least one EPO mimetic hinge core mimetibody, comprising translating the EPO mimetic hinge core mimetibody encoding nucleic acid under conditions in vitro, in vivo or in situ, such that the EPO mimetic hinge core mimetibody is expressed in detectable or recoverable amounts.

Also provided is a composition comprising at least one isolated human EPO mimetic hinge core mimetibody and at least one pharmaceutically acceptable carrier or diluent. The composition can optionally further comprise an effective amount of at least one compound or protein selected from at least one of a detectable label or reporter, an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplactic, an immunomodulation drug, an ophthalmic, otic or nasal drug, a topical drug, a nutritional drug, a TNF antagonist, an antirheumatic, a muscle relaxant, a narcotic, a non-steroid anti-inflammatory drug (NTHE), an analgesic, an anesthetic, a sedative, a local anethetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

The present invention further provides an anti-idiotype antibody or fragment that specifically binds at least one EPO mimetic hinge core mimetibody of the present invention.

Also provided is a method for diagnosing or treating a disease condition in a cell, tissue, organ or animal, comprising (a) contacting or administering a composition comprising an effective amount of at least one isolated human EPO mimetic hinge core mimetibody of the invention with, or to, the cell, tissue, organ or animal. The method can optionally further comprise using an effective amount of 0.001-50 mg/kilogram of the cells, tissue, organ or animal. The method can optionally further comprise using the contacting or the administrating by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal. The method can optionally further comprise administering, prior, concurrently or after the (a) contacting or administering, at least one composition comprising an effective amount of at least one compound or protein selected from at least one of a detectable label or reporter, an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplactic, an immunomodulation drug, an ophthalmic, otic or nasal drug, a topical drug, a nutritional drug, a TNF antagonist, an antirheumatic, a muscle relaxant, a narcotic, a non-steroid anti-inflammatory drug (NSAID), an analgesic, an anesthetic, a sedative, a local anethetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

Also provided is a medical device, comprising at least one isolated human EPO mimetic hinge core mimetibody of the invention, wherein the device is suitable to contacting or administering the at least one EPO mimetic hinge core mimetibody by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

Also provided is an article of manufacture for human pharmaceutical or diagnostic use, comprising packaging material and a container comprising a solution or a lyophilized form of at least one isolated human EPO mimetic hinge core mimetibody of the present invention. The article of manufacture can optionally comprise having the container as a component of a parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

Also provided is a method for producing at least one isolated human EPO mimetic hinge core mimetibody of the present invention, comprising providing a host cell or transgenic animal or transgenic plant or plant cell capable of expressing in recoverable amounts the EPO mimetic hinge core mimetibody. Further provided in the present invention is at least one EPO mimetic hinge core mimetibody produced by the above method.

The present invention also provides at least one method for expressing at least one EPO mimetic hinge core mimetibody, or anti-idiotype antibody, in a host cell, comprising culturing a host cell as described herein under conditions wherein at least one EPO mimetic hinge core mimetibody is expressed in detectable and/or recoverable amounts.

The present invention further provides any invention described herein.

DESCRIPTION OF THE FIGURES

FIGS. 1-42 (SEQ ID NOS:31-72) show examples of heavy/light chain variable/constant region sequences, frameworks/subdomains and substitutions, portions of which can be used in Ig derived proteins of the present invention, as taught herein. Framework, CDR and hinge regions are labeled in boxes. Sequence residues are numbered for each amino acid position. A list of amino acid substitutions or gaps (denoted by a "-") observed at each position in the aligned sequences are shown below each sequence residue.

FIG. 1 depicts Vh1 heavy chain variable region sequences, frameworks and substitutions (SEQ ID NO:31).

FIG. 2 depicts Vh2 heavy chain variable region sequences, frameworks and substitutions (SEQ ID NO:32).

FIG. 3 depicts Vh3a heavy chain variable region sequences, frameworks and substitutions (SEQ ID NO:33).

FIG. 4 depicts Vh3b heavy chain variable region sequences, frameworks and substitutions (SEQ ID NO:34).

FIG. 5 depicts Vh3c heavy chain variable region sequences, frameworks and substitutions (SEQ ID NO:35).

FIG. 6 depicts Vh4 heavy chain variable region sequences, frameworks and substitutions (SEQ ID NO:36).

FIG. 7 depicts Vh5 heavy chain variable region sequences, frameworks and substitutions (SEQ ID NO:37).

FIG. 8 depicts Vh6 heavy chain variable region sequences, frameworks and substitutions (SEQ ID NO:38).

FIG. 9 depicts Vh7 heavy chain variable region sequences, frameworks and substitutions (SEQ ID NO:39).

FIG. 10 depicts $\kappa 1\_4$ light chain variable region sequences, frameworks and substitutions (SEQ ID NO:40).

FIG. 11 depicts $\kappa_2$ light chain variable region sequences, frameworks and substitutions (SEQ ID NO:41).

FIG. 12 depicts $\kappa 3$ light chain variable region sequences, frameworks and substitutions (SEQ ID NO:42).

FIG. 13 depicts $\kappa_5$ light chain variable region sequences, frameworks and substitutions (SEQ ID NO:43).

FIG. 14 depicts κNew1 light chain variable region sequences, frameworks and substitutions (SEQ ID NO:44).

FIG. 15 depicts κNew2 light chain variable region sequences, frameworks and substitutions (SEQ ID NO:45).

FIG. 16 depicts κNew3 light chain variable region sequences, frameworks and substitutions (SEQ ID NO:46).

FIG. 17 depicts λ1a light chain variable region sequences, frameworks and substitutions (SEQ ID NO:47).

FIG. 18 depicts λ1b light chain variable region sequences, frameworks and substitutions (SEQ ID NO:48).

FIG. 19 depicts λ2 light chain variable region sequences, frameworks and substitutions (SEQ ID NO:49).

FIG. 20 depicts λ3a light chain variable region sequences, frameworks and substitutions (SEQ ID NO:50).

FIG. 21 depicts λ3b light chain variable region sequences, frameworks and substitutions (SEQ ID NO:51).

FIG. 22 depicts λ3c light chain variable region sequences, frameworks and substitutions (SEQ ID NO:52).

FIG. 23 depicts λ3e light chain variable region sequences, frameworks and substitutions (SEQ ID NO:53).

FIG. 24 depicts λ4a light chain variable region sequences, frameworks and substitutions (SEQ ID NO:54).

FIG. 25 depicts λ4b light chain variable region sequences, frameworks and substitutions (SEQ ID NO:55).

FIG. 26 depicts λ5 light chain variable region sequences, frameworks and substitutions (SEQ ID NO:56).

FIG. 27 depicts λ6 light chain variable region sequences, frameworks and substitutions (SEQ ID NO:57).

FIG. 28 depicts λ7 light chain variable region sequences, frameworks and substitutions (SEQ ID NO:58).

FIG. 29 depicts λ8 light chain variable region sequences, frameworks and substitutions (SEQ ID NO:59).

FIG. 30 depicts λ9 light chain variable region sequences, frameworks and substitutions (SEQ ID NO:60).

FIG. 31 depicts λ10 light chain variable region sequences, frameworks and substitutions (SEQ ID NO:61).

FIG. 32 depicts IgA1 heavy chain constant region sequences, subdomains and substitutions (SEQ ID NO:62).

FIG. 33 depicts IgA2 heavy chain constant region sequences, subdomains and substitutions (SEQ ID NO:63).

FIG. 34 depicts IgD heavy chain constant region sequences, subdomains and substitutions (SEQ ID NO:64).

FIG. 35 depicts IgE heavy chain constant region sequences, subdomains and substitutions (SEQ ID NO:65).

FIG. 36 depicts IgG1 heavy chain constant region sequences, subdomains and substitutions (SEQ ID NO:66).

FIG. 37 depicts IgG2 heavy chain constant region sequences, subdomains and substitutions (SEQ ID NO:67).

FIG. 38 depicts IgG3 heavy chain constant region sequences, subdomains and substitutions (SEQ ID NO:68).

FIG. 39 depicts IgG4 heavy chain constant region sequences, subdomains and substitutions (SEQ ID NO:69).

FIG. 40 depicts IgM heavy chain constant region sequences, subdomains and substitutions (SEQ ID NO:70).

FIG. 41 depicts Igκc light chain constant region sequences and substitutions (SEQ ID NO:71).

FIG. 42 depicts Igλc light chain constant region sequences and substitutions (SEQ ID NO:72).

DESCRIPTION OF THE INVENTION

Figure 6C:

The present invention provides isolated, recombinant and/or synthetic mimetibodies or specified portions or variants, as well as compositions and encoding nucleic acid molecules comprising at least one polynucleotide encoding at least one EPO mimetic hinge core mimetibody. Such mimetibodies or specified portions or variants of the present invention comprise specific EPO mimetic hinge core mimetibody sequences, domains, fragments and specified variants thereof, and methods of making and using said nucleic acids and mimetibodies or specified portions or variants, including therapeutic compositions, methods and devices.

The present invention also provides at least one isolated EPO mimetic hinge core mimetibody or specified portion or variant as described herein and/or as known in the art. The EPO mimetic hinge core mimetibody can optionally comprise at least one CH3 region directly linked with at least one CH2 region directly linked with at least one hinge region or fragment thereof (H), directly linked with an optional linker sequence (L), directly linked to at least one therapeutic peptide (P), optionally further directly linked with at least a portion of at least one variable (V) antibody sequence.

In a preferred embodiment an EPO mimetic hinge core mimetibody comprises formula (I):

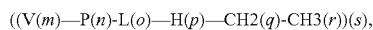

((V(m)—P(n)-L(o)—H(p)—CH2(q)-CH3(r))(s), where V is at least one portion of an N-terminus of an immunoglobulin variable region, P is at least one bioactive peptide, L is polypeptide that provides structural flexibility by allowing the mimietibody to have alternative orientations and binding properties, H is at least a portion of an immunoglobulin variable hinge region, CH2 is at least a portion of an immunoglobulin CH2 constant region, CH3 is at least a portion of an immunoglobulin CH3 constant region, m, n, o, p, q, r, and s can be independently an integer between 0, 1 or 2 and 10, mimicking different types of immunoglobulin molecules, e.g., but not limited to IgG1, IgG2, IgG3, IgG4, IgA, IgM, IgD, IgE, and the like, or combination thereof. The monomer where m=1 can be linked to other monomers by association or covalent linkage, such as, but not limited to, a Cys-Cys disulfide bond or other immunoglobulin sequence. EPO mimetic hinge core mimetibody of the present invention mimics an antibody structure with its inherent properties and functions, while providing a therapeutic peptide and its inherent or acquired in vitro, in vivo or in situ properties or activities. The various portions of the antibody and therapeutic peptide portions of at least one EPO mimetic hinge core mimetibody of the present invention can vary as described herein in combination with what is known in the art.

As used herein, a "EPO mimetic hinge core mimetibody," "EPO mimetic hinge core mimetibody portion," or "EPO mimetic hinge core mimetibody fragment" and/or "EPO mimetic hinge core mimetibody variant" and the like mimics, has or simulates at least one ligand binding or at least one biological activity of at least one protein, such as ligand binding or activity in vitro, in situ and/or preferably in vivo, such as but not limited to at least one of SEQ ID NOS:1-30. For example, a suitable EPO mimetic hinge core mimetibody, specified portion or variant of the present invention can bind at least one protein ligand and includes at least one protein ligand, receptor, soluble receptor, and the like. A suitable EPO mimetic hinge core mimetibody, specified portion, or variant can also modulate, increase, modify, activate, at least one protein receptor signaling or other measurable or detectable activity.

Mimetibodies useful in the methods and compositions of the present invention are characterized by suitable affinity binding to protein ligands or receptors and optionally and preferably having low toxicity. In particular, an EPO mimetic hinge core mimetibody, where the individual components, such as the portion of variable region, constant region (without a CH1 portion) and framework, or any portion thereof (e.g., a portion of the J, D or V regions of the variable heavy or light chain; at least a portion of at least one hinge region, the constant heavy chain or light chain, and the like) individually and/or collectively optionally and preferably possess low immunogenicity, is useful in the present invention. The mimetibodies that can be used in the invention are optionally characterized by their ability to treat patients for extended periods with good to excellent alleviation of symptoms and low toxicity. Low immunogenicity and/or high affinity, as well as other undefined properties, may contribute to the therapeutic results achieved. "Low immunogenicity" is defined herein as raising significant HAMA, HACA or HAHA responses in less than about 75%, or preferably less than about 50, 45, 40, 35, 30, 35, 20, 15, 10, 9, 8, 7, 6, 5, 4, 3, 2, and/or 1% of the patients treated and/or raising low titres in the patient treated (less than about 300, preferably less than about 100 measured with a double antigen enzyme immunoassay) (see, e.g., Elliott et al., *Lancet* 344:1125-1127 (1994)).

Utility

The isolated nucleic acids of the present invention can be used for production of at least one EPO mimetic hinge core mimetibody, fragment or specified variant thereof, which can be used to effect in an cell, tissue, organ or animal (including mammals and humans), to modulate, treat, alleviate, help prevent the incidence of, or reduce the symptoms of, at least one protein related condition, selected from, but not limited to, at least one of an immune disorder or disease, a cardiovascular disorder or disease, an infectious, malignant, and/or neurologic disorder or disease, a(n) anemia; a(n) immune/autoimmune; and/or a(n) cancer/infectious, as well as other known or specified protein related conditions.

Such a method can comprise administering an effective amount of a composition or a pharmaceutical composition comprising at least one EPO mimetic hinge core mimetibody or specified portion or variant to a cell, tissue, organ, animal or patient in need of such modulation, treatment, alleviation, prevention, or reduction in symptoms, effects or mechanisms.

The effective amount can comprise an amount of about 0.0001 to 500 mg/kg per single or multiple administration, or to achieve a serum concentration of 0.0001-5000 µg/ml serum concentration per single or multiple administration, or any effective range or value therein, as done and determined using known methods, as described herein or known in the relevant arts.

Citations

All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2003); Sambrook, et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2003); Colligan et al., Current Protocols in Protein Science, John Wiley & Sons, NY, N.Y., (1997-2003).

Mimetibodies of the Present Invention

The EPO mimetic hinge core mimetibody can optionally comprise at least one CH3 region directly linked with at least one CH2 region directly linked with at least one portion of at least one hinge region fragment (H) such as comprising at least one core hinge region, directly linked with an optional linker sequence (L), directly linked to at least one therapeutic peptide (P), optionally further directly linked with at least a portion of at least one variable antibody sequence (V). In a preferred embodiment a pair of a CH3—CH2—H-L-V, the pair linked by association or covalent linkage Thus, an EPO mimetic hinge core mimetibody of the present invention mimics an antibody structure with its inherent properties and functions, while providing a therapeutic peptide and its inherent or acquired in vitro, in vivo or in situ properties or activities. The various portions of the antibody and therapeutic peptide portions of at least one EPO mimetic hinge core mimetibody of the present invention can vary as described herein in combination with what is known in the art.

Mimetibodies of the present invention thus provide at least one suitable property as compared to known proteins, such as, but not limited to, at least one of increased half-life, increased activity, more specific activity, increased avidity, increased or decrease off rate, a selected or more suitable subset of activities, less immunogenicity, increased quality or duration of at least one desired therapeutic effect, less side effects, and the like.

Fragments of mimetibodies according to Formula (I) can be produced by enzymatic cleavage, synthetic or recombinant techniques, as known in the art and/or as described herein. Mimetibodies can also be produced in a variety of truncated forms using antibody genes in which one or more stop codons have been introduced upstream of the natural stop site. The various portions of mimetibodies can be joined together chemically by conventional techniques, or can be prepared as a contiguous protein using genetic engineering techniques. For example, a nucleic acid encoding at least one of the constant regions of a human antibody chain can be expressed to produce a contiguous protein for use in mimetibodies of the present invention. See, e.g., Ladner et al., U.S. Pat. No. 4,946,778 and Bird, R. E. et al, *Science,* 242: 423-426 (1988), regarding single chain antibodies.

As used herein, the term "human mimetibody" refers to an antibody in which substantially every part of the protein (e.g., EPO mimetic peptide, framework, $C_L$, $C_H$ domains (e.g., $C_H2$, $C_H3$), hinge, ($V_L$, $V_H$)) is expected to be substantially non-immunogenic in humans with only minor sequence changes or variations. Such changes or variations optionally and preferably retain or reduce the immunogenicity in humans relative to non-modified human antibodies, or mimetibodies of the present invention. Thus, a human antibody and corresponding EPO mimetic hinge core mimetibody of the present invention is distinct from a chimeric or humanized antibody. It is pointed out that a human antibody and EPO mimetic hinge core mimetibody can be produced by a non-human animal or cell that is capable of expressing human immunoglobulins (e.g., heavy chain and/or light chain) genes.

Human mimetibodies that are specific for at least one protein ligand or receptor thereof can be designed against an appropriate ligand, such as isolated and/or EPO protein receptor or ligand, or a portion thereof (including synthetic molecules, such as synthetic peptides). Preparation of such mimetibodies are performed using known techniques to identify and characterize ligand binding regions or sequences of at least one protein or portion thereof.

In a preferred embodiment, at least one EPO mimetic hinge core mimetibody or specified portion or variant of the present invention is produced by at least one cell line, mixed cell line, immortalized cell or clonal population of immortalized and/or cultured cells. Immortalized protein producing cells can be produced using suitable methods. Preferably, the at least one EPO mimetic hinge core mimetibody or specified portion or variant is generated by providing nucleic acid or vectors comprising DNA derived or having a substantially similar sequence to, at least one human immunoglobulin locus that is functionally rearranged, or which can undergo functional rearrangement, and which further comprises a mimetibody structure as described herein, e.g., but not limited to Formula (I), wherein portions of C- and N-terminal variable regions can be used for V, hinge regions for H, CH2 for CH2 and CH3 for CH3, as known in the art.

The term "functionally rearranged," as used herein refers to a segment of nucleic acid from an immunoglobulin locus that has undergone V(D)J recombination, thereby producing an immunoglobulin gene that encodes an immunoglobulin chain (e.g., heavy chain), or any portion thereof. A functionally rearranged immunoglobulin gene can be directly or indirectly identified using suitable methods, such as, for example, nucleotide sequencing, hybridization (e.g., Southern blotting, Northern blotting) using probes that can anneal to coding joints between gene segments or enzymatic amplification of immunoglobulin genes (e.g., polymerase chain reaction) with primers that can anneal to coding joints between gene segments. Whether a cell produces an EPO mimetic hinge core mimetibody or portion or variant comprising a particular variable region or a variable region comprising a particular sequence (e.g., at least one P sequence) can also be determined using suitable methods.

Mimetibodies, specified portions and variants of the present invention can also be prepared using at least one EPO mimetic hinge core mimetibody or specified portion or variant encoding nucleic acid to provide transgenic animals or mammals, such as goats, cows, horses, sheep, and the like, that produce such mimetibodies or specified portions or variants in their milk. Such animals can be provided using known methods as applied for antibody encoding sequences. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

Mimetibodies, specified portions and variants of the present invention can additionally be prepared using at least one EPO mimetic hinge core mimetibody or specified portion or variant encoding nucleic acid to provide transgenic plants and cultured plant cells (e.g., but not limited to tobacco and maize) that produce such mimetibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize or corn have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain mimetibodies (scFv's), including tobacco seeds and potato tubers. See, e.g., Conrad et al., Plant Mol. Biol. 38:101-109 (1998) and references cited therein. Thus, mimetibodies, specified portions and variants of the present invention can also be produced using transgenic plants, according to know methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein.

The above references are entirely incorporated herein by reference. The mimetibodies of the invention can bind human protein ligands with a wide range of affinities ($K_D$). In a preferred embodiment, at least one human EPO mimetic hinge core mimetibody of the present invention can optionally bind at least one protein ligand with high affinity. For example, at least one EPO mimetic hinge core mimetibody of the present invention can bind at least one protein ligand with a $K_D$ equal to or less than about $10^{-7}$ M or, more preferably, with a $K_D$ equal to or less than about 0.1-9.9 (or any range or value therein) X $10^{-7}$, $10^{-8}$, $10^{-9}$, $10^{-10}$, $10^{-11}$, $10^{-12}$, or $10^{-13}$ M, or any range or value therein.

The affinity or avidity of an EPO mimetic hinge core mimetibody for at least one protein ligand can be determined experimentally using any suitable method, e.g., as used for determining antibody-antigen binding affinity or avidity. (See, for example, Berzofsky, et al, "Antibody-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular EPO mimetic hinge core mimetibody-ligand interaction can vary if measured under different conditions (e.g., salt concentration, pH). Thus, measurements of affinity and other ligand-binding parameters (e.g., $K_D$, $K_a$, $K_d$) are preferably made with standardized solutions of EPO mimetic hinge core mimetibody and ligand, and a standardized buffer, such as the buffer described herein.

Nucleic Acid Molecules

Using the information provided herein, such as the nucleotide sequences encoding at least 90-100% of the contiguous amino acids of at least one of SEQ ID NOS:1-30 as well as at least one portion of an antibody, wherein the above sequences are inserted as the P sequence of Formula (I) to provide an EPO mimetic hinge core mimetibody of the present invention, further comprising specified fragments, variants or consensus sequences thereof, or a deposited vector comprising at least one of these sequences, a nucleic acid molecule of the present invention encoding at least one EPO mimetic hinge core mimetibody or specified portion or variant can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combination thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, nucleic acid molecules comprising the coding sequence for an EPO mimetic hinge core mimetibody or specified portion or variant; and nucleic acid molecules which comprise a nucleotide sequence substantially different from those described above but which, due to the degeneracy of the genetic code, still encode at least one EPO mimetic hinge core mimetibody as described herein and/or as known in the art. Of course, the genetic code is well known in the art. Thus, it would be routine for one skilled in the art to generate such degenerate nucleic acid variants that code for specific EPO mimetic hinge core mimetibody or specified portion or variants of the present invention. See, e.g., Ausubel, et al., supra, and such nucleic acid variants are included in the present invention.

As indicated herein, nucleic acid molecules of the present invention which comprise a nucleic acid encoding an EPO mimetic hinge core mimetibody or specified portion or variant can include, but are not limited to, those encoding the amino acid sequence of an EPO mimetic hinge core mimetibody fragment, by itself; the coding sequence for the entire EPO mimetic hinge core mimetibody or a portion thereof; the coding sequence for an EPO mimetic hinge core mimetibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an EPO mimetic hinge core mimetibody or specified portion or variant can be fused to a marker sequence, such as a sequence encoding a peptide that facilitates purification of the fused EPO mimetic hinge core mimetibody or specified portion or variant comprising an EPO mimetic hinge core mimetibody fragment or portion.

Polynucleotides which Selectively Hybridize to a Polynucleotide as Described Herein The present invention provides isolated nucleic acids that hybridize under selective hybridization conditions to a polynucleotide disclosed herein, or others disclosed herein, including specified variants or portions thereof. Thus, the polynucleotides of this embodiment can be used for isolating, detecting, and/or quantifying nucleic acids comprising such polynucleotides.

Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 40-99% sequence identity and can be employed to identify orthologous or paralogous sequences.

Optionally, polynucleotides of this invention will encode at least a portion of an EPO mimetic hinge core mimetibody or specified portion or variant encoded by the polynucleotides described herein. The polynucleotides of this invention embrace nucleic acid sequences that can be employed for selective hybridization to a polynucleotide encoding an EPO mimetic hinge core mimetibody or specified portion or variant of the present invention. See, e.g., Ausubel, supra; Colligan, supra, each entirely incorporated herein by reference.

Construction of Nucleic Acids

The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. See, e.g., Ausubel, supra; or Sambrook, supra.

Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under suitable stringency conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra).

Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention further provides recombinant expression cassettes comprising a nucleic acid of the present invention. A nucleic acid sequence of the present invention, for example a cDNA or a genomic sequence encoding an EPO mimetic hinge core mimetibody or specified portion or variant of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution, as known in the art. A polynucleotide of the present invention can be expressed in either sense or anti-sense orientation as desired. It will be appreciated that control of gene expression in either sense or anti-sense orientation can have a direct impact on the observable characteristics. Another method of suppression is sense suppression. Introduction of nucleic acid configured in the sense orientation has been shown to be an effective means by which to block the transcription of target genes.

Vectors and Host Cells

The present invention also relates to vectors that include isolated nucleic acid molecules of the present invention, host cells that are genetically engineered with the recombinant vectors, and the production of at least one EPO mimetic hinge core mimetibody or specified portion or variant by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced into a cell using suitable known methods, such as electroporation and the like, other known methods include the use of the vector as a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites optionally for at least one of transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, US Pat. Nos. 5,122,464; 5,770,359; 5,827,739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one EPO mimetic hinge core mimetibody or specified portion or variant of the present invention can be expressed in a modified form, such as a fusion protein, and can include not only secretion signals, but also additional heterologous functional regions. For instance, a region of additional amino acids, particularly charged amino acids, can be added to the N-terminus of an EPO mimetic hinge core mimetibody or specified portion or variant to improve stability and persistence in the host cell, during purification, or during subsequent handling and storage. Also, peptide moieties can be added to an EPO mimetic hinge core mimetibody or specified portion or variant of the present invention to facilitate purification. Such regions can be removed prior to final preparation of an EPO mimetic hinge core mimetibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention.

Illustrative of cell cultures useful for the production of the mimetibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610, DG-44) and BSC-1 (e.g., ATCC CRL-26) cell lines, hepG2 cells, P3X63Ag8.653, SP2/0-Ag14, 293 cells, HeLa cells and the like, which are readily available from, for example, American Type Culture Collection, Manassas, Va. Preferred host cells include cells of lymphoid origin such as myeloma and lymphoma cells. Particularly preferred host cells are P3X63Ag8.653 cells (ATCC Accession Number CRL-1580) and SP2/0-Ag14 cells (ATCC Accession Number CRL-1851).

Expression vectors for these cells can include one or more of the following expression control sequences, such as, but not limited to an origin of replication; a promoter (e.g., late or early SV40 promoters, the CMV promoter (e.g., U.S. Pat. Nos. 5,168,062; 5,385,839), an HSV tk promoter, a pgk (phosphoglycerate kinase) promoter, an EF-1 alpha promoter (e.g, U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an EPO Mimetic Hinge Core Mimetibody or Specified Portion or Variant thereof An EPO mimetic hinge core mimetibody or specified portion or variant can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2003), e.g., Chapters 1, 4, 6, 8, 9, 10, each entirely incorporated herein by reference.

Mimetibodies or specified portions or variants of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the EPO mimetic hinge core mimetibody or specified portion or variant of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Mimetibodies, Specified Fragments and/or Variants

The isolated mimetibodies of the present invention comprise an EPO mimetic hinge core mimetibody or specified portion or variant encoded by any one of the polynucleotides of the present invention as discussed more fully herein, or any isolated or prepared EPO mimetic hinge core mimetibody or specified portion or variant thereof.

Preferably, the EPO mimetic hinge core mimetibody or ligand-binding portion or variant binds at least one EPO protein ligand or receptor, and, thereby provides at least one EPO biological activity of the corresponding protein or a fragment thereof. Different therapeutically or diagnostically significant proteins are well known in the art and suitable assays or biological activities of such proteins are also well known in the art.

Non-limiting examples of suitable EPO mimetic peptides for this invention appear in Table 1 below. These peptides can be prepared by methods disclosed and/or known in the art. Single letter amino acid abbreviations are used in most cases. The X in these sequences (and throughout this specification, unless specified otherwise in a particular instance) means that any of the 20 naturally occurring or known amino acid residues or know derivatives thereof may be present, or any know modified amino acid thereof. Any of these peptides may be linked in tandem (i.e., sequentially), with or without linkers, and a few tandem linked examples are provided in the table. Linkers are listed as "Δ" and may be any of the linkers described herein. Tandem repeats and linkers are shown separated by dashes for clarity. Any peptide containing a cysteinyl residue may optionally be cross-linked with another Cys-containing peptide, either or both of which may be linked to a vehicle. A few crosslinked examples are provided in the table. Any peptide having more than one Cys residue may form an intrapeptide disulfide bond, as well; see, for example, EPO-mimetic peptides in Table 1. A few examples of intrapeptide disulfide-bonded peptides are specified in the table. Any of these peptides may be derivatized as described herein, and a few derivatized examples are provided in the table. For derivatives in which the carboxyl terminus may be capped with an amino group, the capping amino group is shown as —NH$_2$. For derivatives in which amino acid residues are substituted by moieties other than amino acid residues, the substitutions are denoted by a δ, which signifies any of the moieties known in the art, e.g., as described in Bhatnagar et al. (1996), J. Med. Chem. 39: 3814-9 and Cuthbertson et al. (1997), J. Med. Chem. 40:2876-82, which are entirely incorporated by reference. The J substituent and the Z substituents ($Z_5, Z_6, \ldots Z_{40}$) are as defined in U.S. Pat. Nos. 5,608,035, 5,786,331, and 5,880,096, which are entirely incorporated herein by reference. For the EPO-mimetic sequences (Table 1), the substituents $X_2$ through $X_{11}$ and the integer "n" are as defined in WO 96/40772, which is entirely incorporated by reference. Residues appearing in boldface are D-amino acids, but can be optionally L-amino acids. All peptides are linked through peptide bonds unless otherwise noted. Abbreviations are listed at the end of this specification. In the "SEQ ID NO." column, "NR" means that no sequence listing is required for the given sequence.

TABLE 1

EPO-mimetic peptide sequences

| Sequence/structure | SEQ ID NO: |
|---|---|
| YXCXXGPXTWXCXP | 1 |
| YXCXXGPXTWXCXP-YXCXXGPXTWXCXP | 1 |
| YXCXXGPXTWXCXP-Λ-YXCXXGPXTWXCXP | 1 |
| YXCXXGPXTWXCXP-Λ-(ε-amine)↘K/βA/ | 1 |
| YXCXXGPXTWXCXP-Λ-(α-amine) | 1 |
| GGTYSCHFGPLTWVCKPQGG | 2 |
| GGDYHCRMGPLTWVCKPLGG | 3 |
| GGVYACRMGPITWVCSPLGG | 4 |
| VGNYMCHFGPITWVCRPGGG | 5 |
| GGLYLCRFGPVTWDCGYKGG | 6 |
| GGTYSCHFGPLTWVCKPQGG | 7 |
| GGTYSCHFGPLTWVCKPQGG-GGTYSCHFGPLTWVCKPQGG | 7 |
| GGTYSCHFGPLTWVCKPQGG-Λ-GGTYSCHFGPLTWVCKPQGG | 7 |
| GGTYSCHFGPLTWVCKPQGGSSK | 8 |
| GGTYSCHFGPLTWVCKPQGGSSK-GGTYSCHFGPLTWVCKPQGGSSK | 8 |
| GGTYSCHFGPLTWVCKPQGGSSK-Λ-GGTYSCHFGPLTWVCKPQGGSSK | 8 |
| GGTYSCHFGPLTWVCKPQGGSS(ε-amine)↘K/βA/ | |
| GGTYSCHFGPLTWVCKPQGGSS(α-amine) | 8 |
| GGTYSCHFGPLTWVCKPQGGSSK(-Λ-biotin) | 8 |
| $CX_4X_5GPX_6TWX_7C$ | 9 |
| GGTYSCHGPLTWVCKPQGG | 10 |
| VGNYMAHMGPITWVCRPGG | 11 |
| GGPHHVYACRMGPLTWIC | 12 |
| GGTYSCHFGPLTWVCKPQ | 13 |
| GGLYACHMGPMTWVCQPLRG | 14 |
| TIAQYICYMGPETWECRPSPKA | 15 |
| YSCHFGPLTWVCK | 16 |
| YCHFGPLTWVC | 17 |
| $X_3X_4X_5GPX_6TWX_7X_8$ | 18 |
| $YX_2X_3X_4X_5GPX_6TWX_7X_8$ | 19 |
| $X_1YX_2X_3X_4X_5GPX_6X_7X_8X_9X_{10}X_{11}$ | 20 |
| $X_1YX_2CX_4X_5GPX_6TWX_7CX_9X_{10}X_{11}$ | 21 |
| GGLYLCRFGPVTWDCGYKGG | 22 |
| GGTYSCHFGPLTWVCKPQGG | 23 |
| VGNYMCHFGPITWVCRPGGG | 24 |
| GGVYACRMGPITWVCSPLGG | 25 |
| TIAQYICYMGPETWECRPSPKA | 26 |
| YSCHFGPLTWVCK | 27 |
| YCHFGPLTWVC | 28 |
| SCHFGPLTWVCK | 29 |
| $(AX_2)_nX_3X_4X_5GPX_6TWX_7X_8$ | 30 |

EPO biological activities are well known in the art. See, e.g., Anagnostou A et al Erythropoietin has a mitogenic and positive chemotactic effect on endothelial cells. Proceedings of the National Academy of Science (USA) 87: 5978-82 (1990); Fandrey J and Jelkman W E Interleukin 1 and tumor necrosis factor-alpha inhibit erythropoietin production in vitro. Annals of the New York Academy of Science 628: 250-5 (1991); Geissler K et al Recombinant human erythropoietin: A multipotential hemopoietic growth factor in vivo and in vitro. Contrib. Nephrol. 87: 1-10 (1990); Gregory C J Erythropoietin sensitivity as a differentiation marker in the hemopoietic system. Studies of three erythropoietic colony responses in culture. Journal of Cellular Physiology 89: 289-301 (1976); Jelkman W et al Monokines inhibiting erythropoietin production in human hepatoma cultures and in isolated perfused rat kidneys. Life Sci. 50: 301-8 (1992); Kimata H et al Human recombinant erythropoietin directly stimulates B cell immunoglobulin production and proliferation in serum-free medium. Clinical and Experimental Immunology 85: 151-6 (1991); Kimata H et al Erythropoietin enhances immunoglobulin production and proliferation by human plasma cells in a serum-free medium. Clin. Immunology Immunopathol. 59: 495-501 (1991); Kimata H et al Effect of recombinant human erythropoietin on human IgE production in vitro Clinical and Experimental Immunology 83: 483-7 (1991); Koury M J and Bondurant M C Erythropoietin retards DNA breakdown and prevents programmed cell death in erythroid progenitor cells. Science 248: 378-81 (1990); Lim V S et al Effect of recombinant human erythropoietin on renal function in humans. Kidney International 37: 131-6 (1990); Mitjavila M T et al Autocrine stimulation by erythropoietin and autonomous growth of human erythroid leukemic cells in vitro. Journal of Clinical Investigation 88: 789-97 (1991); Andre M et al Performance of an immunoradiometric assay of erythropoietin and results for specimens from anemic and polycythemic patients. Clinical Chemistry 38: 758-63 (1992); Hankins W D et al Erythropoietin-dependent and erythropoietin-producing cell lines. Implications for research and for leukemia therapy. Annals of the New York Academy of Science 554: 21-8 (1989); Kendall R G T et al Storage and preparation of samples for erythropoietin radioimmunoassay. Clin. Lab. Haematology 13: 189-96 (1991); Krumvieh D et al Comparison of relevant biological assays for the determination of biological active erythropoietin. Dev. Biol. Stand. 69: 15-22 (1988); Ma D D et al Assessment of an EIA for measuring human serum erythropoietin as compared with RIA and an in-vitro bioassay. British Journal of Haematology 80: 431-6 (1992); Noe G et al A sensitive sandwich ELISA for measuring erythropoietin in human serum British Journal of Haematology 80: 285-92 (1992); Pauly J U et al Highly specific and highly sensitive enzyme immunoassays for antibodies to human interleukin 3 (IL3) and human erythropoietin (EPO) in serum. Behring Institut Mitteilungen 90: 112-25 (1991); Sakata S and Enoki Y Improved microbioassay for plasma erythropoietin based on CFU-E colony formation. Ann. Hematology 64: 224-30 (1992); Sanengen T et al Immunoreactive erythropoietin and erythropoiesis stimulating factor(s) in plasma from hypertransfused neonatal and adult mice. Studies with a radioimmunoassay and a cell culture assay for erythropoietin. Acta Physiol. Scand. 135: 11-6 (1989); Widness J A et al A sensitive and specific erythropoietin immunoprecipitation assay: application to pharmacokinetic studies. Journal of Lab. Clin. Med. 119: 285-94 (1992); for further information see also individual cell lines used in individual bioassays. Each of the above references are entirely incorporated herein by reference. EPO can be assayed by employing cell lines such as HCD57, NFS-60, TF-1 and UT-7, which respond to the factor. EPO activity can be assessed also in a Colony formation assay by determining the number of CFU-E from bone marrow cells. An alternative and entirely different detection method is RT-PCR quantitation of cytokines.

An EPO mimetic hinge core mimetibody, or specified portion or variant thereof, that partially or preferably substantially provides at least one biological activity of at least one protein or fragment, can bind the protein or fragment ligand and thereby provide at least one activity that is otherwise mediated through the binding of protein to at least one protein ligand or receptor or through other protein-dependent or mediated mechanisms. As used herein, the term "EPO mimetic hinge core mimetibody activity" refers to an EPO mimetic hinge core mimetibody that can modulate or cause at least one protein-dependent activity by about 20-10,000%, preferably by at least about 60, 70, 80, 90, 91, 92, 93, 94, 95, 96, 97, 98, 99, 100, 110, 120, 130, 140, 150, 160, 170, 180, 190, 200, 250, 300, 350, 400, 450, 500, 550, 600, 700, 800, 900, 1000, 2000, 3000, 4000, 5000, 6000, 7000, 8000, 9000% or more depending on the assay.

The capacity of an EPO mimetic hinge core mimetibody or specified portion or variant to provide at least one protein-dependent activity is preferably assessed by at least one suitable protein biological assay, as described herein and/or as known in the art. A human EPO mimetic hinge core mimetibody or specified portion or variant of the invention can be similar to any class (IgG, IgA, IgM, etc.) or isotype and can comprise at least a portion of a kappa or lambda light chain. In one embodiment, the human EPO mimetic hinge core mimetibody or specified portion or variant comprises an IgG heavy chain variable fragment, hinge region, CH2 and CH3, for example, at least one of isotypes, IgG1, IgG2, IgG3 or IgG4.

At least one EPO mimetic hinge core mimetibody or specified portion or variant of the invention binds at least one specified ligand specific to at least one protein, subunit, fragment, portion or any combination thereof. The at least one EPO mimetic peptide of at least one EPO mimetic hinge core mimetibody, specified portion or variant of the present invention can optionally bind at least one specified ligand epitope of the ligand. The binding epitope can comprise any combination of at least one amino acid sequence of at least 1-3 amino acids to the entire specified portion of contiguous amino acids of the sequences selected from the group consisting of a protein ligand, such as an EPO receptors or portion thereof.

Such mimetibodies can be prepared by joining together the various portions of Formula (I) of the EPO mimetic hinge core mimetibody using known techniques, by preparing and expressing at least one (i.e., one or more) nucleic acid molecules that encode the EPO mimetic hinge core mimetibody, using known techniques of recombinant DNA technology or by using any other suitable method, such as chemical synthesis.

Mimetibodies that bind to human EPO ligands or receptors and that comprise at least a one portion defined heavy or light chain variable region can be prepared using suitable methods, such as phage display (Katsube, Y., et al, *Int J Mol Med*, 1 (5):863-868 (1998)) or methods that employ transgenic animals, as known in the art and/or as described herein. The EPO mimetic hinge core mimetibody, specified portion or variant can be expressed using the encoding nucleic acid or portion thereof in a suitable host cell.

Preferably, such mimetibodies or ligand-binding fragments thereof can bind human EPO ligands or receptors with high affinity (e.g., $K_D$ less than or equal to about $10^{-7}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g. charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes

The amino acids that make up mimetibodies or specified portions or variants of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994), as presented in Table

TABLE 2

| SINGLE LETTER CODE | THREE LETTER CODE | NAME | THREE NUCLEOTIDE CODON(S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

An EPO mimetic hinge core mimetibody or specified portion or variant of the present invention can include one or more amino acid substitutions, deletions or additions, either from natural mutations or human manipulation, as specified herein. Such or other sequences that can be used in the present invention, include, but are not limited to the following sequences presented in Table 3, as further described in FIGS. 1-42, with corresponding SEQ ID NOS31-72.

TABLE 3

| SEQ ID NO | | AA | NO | REGIONS | | | | | | |
|---|---|---|---|---|---|---|---|---|---|---|
| | | | | FR1 | CDR1 | FR2 | CDR2 | FR3 | CDR3 | FR4 |
| 31 | Heavy chain | Vh1 | 125 | 1-31 | 32 | 33-46 | 47 | 48-79 | 80 | 81-125 |
| 32 | variable | Vh2 | 124 | 1-30 | 31 | 32-45 | 46 | 47-78 | 79 | 80-124 |
| 33 | region | Vh3a | 100 | 1-31 | 32 | 33-46 | 47 | 48-79 | 80 | 81-100 |
| 34 | | Vh3b | 102 | 1-30 | 31 | 32-45 | 46 | 47-78 | 79 | 80-102 |
| 35 | | Vh3c | 101 | 1-30 | 31 | 32-45 | 46 | 47-79 | 80 | 81-101 |
| 36 | | Vh4 | 108 | 1-33 | 34 | 35-48 | 49 | 50-81 | 82 | 83-108 |
| 37 | | Vh5 | 132 | 1-31 | 32 | 33-46 | 47 | 48-79 | 80 | 81-132 |
| 38 | | Vh6 | 125 | 1-30 | 31 | 32-45 | 46 | 47-78 | 79 | 80-125 |
| 39 | | Vh7 | 91 | 1-30 | 31 | 32-45 | 46 | 47-78 | 79 | 80-91 |
| 40 | Light chain | κ1-4 | 93 | 1-24 | 25 | 26-40 | 41 | 42-73 | 74 | 75-93 |
| 41 | variable | κ2 | 92 | 1-23 | 24 | 25-39 | 40 | 41-72 | 73 | 74-92 |
| 42 | region | κ3 | 91 | 1-23 | 24 | 25-39 | 40 | 41-72 | 73 | 74-91 |
| 43 | | κ5 | 85 | 1-23 | 24 | 25-39 | 40 | 41-72 | 73 | 74-85 |
| 44 | | κ new1 | 79 | 1-17 | 18 | 19-33 | 34 | 35-66 | 67 | 68-79 |
| 45 | | κ new2 | 77 | 1-15 | 16 | 17-31 | 32 | 33-64 | 65 | 66-77 |
| 46 | | κ new3 | 95 | 1-24 | 25 | 26-40 | 41 | 42-73 | 74 | 75-95 |
| 47 | | λ1a | 98 | 1-22 | 23 | 24-38 | 39 | 40-71 | 72 | 73-98 |
| 48 | | λ1b | 99 | 1-23 | 24 | 25-39 | 40 | 41-72 | 73 | 74-99 |
| 49 | | λ2 | 99 | 1-22 | 23 | 24-38 | 39 | 40-71 | 72 | 73-99 |
| 50 | | λ3a | 107 | 1-22 | 23 | 24-38 | 39 | 40-71 | 72 | 73-107 |
| 51 | | λ3b | 93 | 1-22 | 23 | 24-39 | 40 | 41-72 | 73 | 74-93 |
| 52 | | λ3c | 98 | 1-22 | 23 | 24-38 | 39 | 40-71 | 72 | 73-98 |
| 53 | | λ3e | 98 | 1-22 | 23 | 24-38 | 39 | 40-71 | 72 | 73-98 |
| 54 | | λ4a | 94 | 1-22 | 23 | 24-38 | 39 | 40-71 | 72 | 73-94 |
| 55 | | λ4b | 95 | 1-22 | 23 | 24-38 | 39 | 40-71 | 72 | 73-95 |
| 56 | | λ5 | 88 | 1-22 | 23 | 24-39 | 40 | 41-74 | 75 | 76-88 |
| 57 | | λ6 | 101 | 1-22 | 23 | 24-38 | 39 | 40-73 | 74 | 75-101 |
| 58 | | λ7 | 89 | 1-22 | 23 | 24-38 | 39 | 40-71 | 72 | 73-89 |
| 59 | | λ8 | 89 | 1-22 | 23 | 24-38 | 39 | 40-71 | 72 | 73-89 |
| 60 | | λ9 | 91 | 1-22 | 23 | 24-38 | 39 | 40-79 | 80 | 81-91 |
| 61 | | λ10 | 87 | 1-22 | 23 | 24-38 | 39 | 40-71 | 72 | 73-87 |

TABLE 3-continued

| SEQ ID NO | | | AA NO | REGIONS | | | | | | |
|---|---|---|---|---|---|---|---|---|---|---|
| | | | | CH1 | hinge1 | hinge2 | hinge3 | hinge4 | CH2 | CH3 |
| 62 | Heavy chain | IgA1 | 354 | 1-102 | 103-121 | | | | 122-222 | 223-354 |
| 63 | constant | IgA2 | 340 | 1-102 | 103-108 | | | | 109-209 | 210-340 |
| 64 | region | IgD | 384 | 1-101 | 102-135 | 136-159 | | | 160-267 | 268-384 |
| 65 | | IgE | 497 | 1-103 | | | | | 104-210 | 211-318 |
| 66 | | IgG1 | 339 | 1-98 | 99-113 | | | | 114-223 | 224-339 |
| 67 | | IgG2 | 326 | 1-98 | 99-110 | | | | 111-219 | 220-326 |
| 68 | | IgG3 | 377 | 1-98 | 99-115 | 116-130 | 131-145 | 146-160 | 161-270 | 271-377 |
| 69 | | IgG4 | 327 | 1-98 | 99-110 | | | | 111-220 | 221-327 |
| 70 | | IgM | 476 | 1-104 | | | | | 105-217 | 218-323 |
| 71 | Light chain | Igκc | 107 | | | | | | | |
| 72 | constant region | Igλc | 107 | | | | | | | |

Of course, the number of amino acid substitutions a skilled artisan would make depends on many factors, including those described above. Generally speaking, the number of amino acid substitutions, insertions or deletions for at least one of an EPO mimetic hinge core mimetibody will not be more than 40, 30, 20, 19, 18, 17, 16, 15, 14, 13, 12, 11, 10, 9, 8, 7, 6, 5, 4, 3, 2, 1 amino acids, such as 1-30 or any range or value therein, as specified herein.

The following description of the components of an EPO hinge core mimetibody of the present invention is based on the use of the formula I of the present invention,

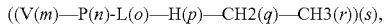

$((V(m)—P(n)-L(o)—H(p)—CH2(q)—CH3(r))(s)$, where V is at least one portion of an N-terminus of an immunoglobulin variable region, P is at least one bioactive peptide, L is at least one linker polypeptide H is at least one portion of at least one immunoglobulin hinge region, CH2 is at least a portion of an immunoglobulin CH2 constant region, CH3 is at least a portion of an immunoglobulin CH3 constant region, m, n, o, p, q, r and s are independently an integer between 0, 1 or 2 and 10, mimicking different types of immunoglobulin molecules, e.g., but not limited to IgG1, IgG2, IgG3, IgG4, IgA, IgM, IgD, IgE, and the like, or any subclass thereof, or any combination thereof.

Figure 6C:
Figure 6C:
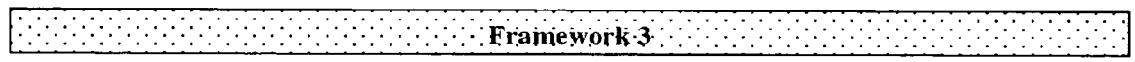

In hinge core mimetibodies of the present invention, the optional N-terminal V portion can comprise 1-20 amino acids of at least one heavy chain variable framework 1 (FR1) region, e.g., as presented in FIGS. 1-9 (SEQ ID NOS:31-39) or at least one LC variable region, e.g., as presented in FIGS. 10-31 (SEQ ID NOS:40-61), including substitutions, deletions or insertions as presented in these Figures, with those of FIGS. 5, 6, and 8 preferred. Also preferred are variable sequences that comprise the sequence Q-X-Q.

The P portion can comprise at least one any therapeutic peptide as known in the art or as described herein, such as, but not limited to those presented in Table 1, SEQ ID NOS:1-30, or as known in the art, or any combination or consensus sequence thereof, or any fusion protein thereof.

The optional linker sequence can be any suitable peptide linker as known in the art.

Preferred sequence include any combination of G and S. e.g., X1-X2-X3-X4-Xn, where X can be G or S, and n can be 5-30. Non-limiting examples include, GS, GGGS, GSGGGS, GSGGGSGG, and the like.

In the present invention, the CH1 portion is not used and a variable number of amino acids from the N-terminus of the hinge region are deleted, e.g., as referenced to FIGS. 1-42 and Table 3. The variable number of amino acids used for the hinge core portion of a mimetibody of the present invention include, but are not limited to, deletion of any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, or 1-3, 2-5, 2-7, 2-8, 3-9, 4-10, 5-9, 5-10, 5-15, 10-20, 2-30, 20-40, 10-50, or any range or value therein, of the N-terminal amino acids of at least one hinge region, e.g., as presented in FIGS. 32-40, or Table 3 above, e.g., but not limited to, deletion of any 0 to all of the amino acids 99-101 to 105-157 of amino acids 99-105, 99-108, 99-111, 99-112, 99-113, 99-114, 99-115, 99-119, 99-125, 99-128, 99-134, 99-140, 99-143, 99-149, 99-155 and 99-158 of FIGS. 32-40, corresponding to SEQ ID NOS:62-70, including the substitutions, insertions or deletions described in FIGS. 32-40. In preferred embodiments, a hinge core regions of the present invention includes a deletion of the N-terminus of the hinge region to provide a hinge core region that includes a deletion up to but not including a Cys residue or up to but not including a sequence Cys-Pro-Xaa-Cys. In further preferred embodiment, such hinge core sequences used in a hinge core mimetibody of the present invention include amino acids 109-113 or 112-113 of FIG. 36 (SEQ ID NO:66) (IgG1); 105-110 or 109-110 of FIG. 37 (SEQ ID NO:67) (IgG2); 111-160, 114-160, 120-160, 126-160, 129-160, 135-160, 141-160, 144-160, 150-160, 156-160 and 159-160 of FIG. 38 (SEQ ID NO:68) (IgG3); or 106-110 or 109-110 of FIG. 39 (SEQ ID NO:69) (IgG4).

The CH2, CH3 and optional CH4 sequence can be any suitable human or human compatable sequence, e.g., as presented in FIGS. 1-42 and Table 3, or as known in the art, or any combination or consensus sequence thereof, or any fusion protein thereof.

Amino acids in an EPO mimetic hinge core mimetibody or specified portion or variant of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least one protein related activity, as specified herein or as known in the art. Sites that are critical for EPO mimetic hinge core mimetibody or specified portion or variant binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

Mimetibodies or specified portions or variants of the present invention can comprise as the P portion of Formula (I), but are not limited to, at least one portion, sequence or combination selected from 3 to all the of at least one of SEQ ID NOS:1-30. Non-limiting variants that can enhance or maintain at least one of the listed activities above include, but are not limited to, any of the above polypeptides, further comprising at least one mutation corresponding to at least one substitution, insertion or deletion that does not significantly affect the suitable biological activities or functions of said EPO mimetic hinge core mimetibody.

An EPO mimetic hinge core mimetibody or specified portion or variant can further optionally comprise at least one functional portion of at least one polypeptide as P portion of Formula (I), at least one of 90-100% of SEQ ID NOS:1-30. An EPO mimetic hinge core mimetibody can further optionally comprise an amino acid sequence for the P portion of Formula (I), selected from one or more of SEQ ID NOS:1-30.

In one embodiment, the P amino acid sequence, or portion thereof has about 90-100% identity (i.e., 90, 91, 92, 93, 94, 95, 96, 97, 98, 99, 100 or any range or value therein) to the corresponding amino acid sequence of the corresponding portion of at least one of SEQ ID NOS:1-30. Preferably, 90-100% amino acid identity (i.e., 90, 91, 92, 93, 94, 95, 96, 97, 98, 99, 100 or any range or value therein) is determined using a suitable computer algorithm, as known in the art.

Mimetibodies or specified portions or variants of the present invention can comprise any number of contiguous amino acid residues from an EPO mimetic hinge core mimetibody or specified portion or variant of the present invention, wherein that number is selected from the group of integers consisting of from 10-100% of the number of contiguous residues in an EPO mimetic hinge core mimetibody. Optionally, this subsequence of contiguous amino acids is at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, 5, 6, 7, 8, 9, 10, 11, 12, 13, 14, 15, 16, 17, 18, 19, 20, or more.

As those of skill will appreciate, the present invention includes at least one biologically active EPO mimetic hinge core mimetibody or specified portion or variant of the present invention. Biologically active mimetibodies or specified portions or variants have a specific activity at least 20%, 30%, or 40%, and preferably at least 50%, 60%, or 70%, and most preferably at least 80%, 90%, or 95%-1000% of that of the native (non-synthetic), endogenous or related and known inserted or fused protein or specified portion or variant. Methods of assaying and quantifying measures of enzymatic activity and substrate specificity, are well known to those of skill in the art.

In another aspect, the invention relates to human mimetibodies and ligand-binding fragments, as described herein, which are modified by the covalent attachment of an organic moiety. Such modification can produce an EPO mimetic hinge core mimetibody or ligand-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified mimetibodies and ligand-binding fragments of the invention can comprise one or more organic moieties that are covalently bonded, directly or indirectly, to the EPO mimetic hinge core mimetibody or specified portion or variant. Each organic moiety that is bonded to an EPO mimetic hinge core mimetibody or ligand-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an EPO mimetic hinge core mimetibody modified by the covalent attachment of polylysine is encompassed by the invention. Hydrophilic polymers suitable for modifying mimetibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the EPO mimetic hinge core mimetibody of the invention has a molecular weight of about 800 to about 150,000 Daltons as a separate molecular entity. For example, $PEG_{2500}$, $PEG_{5000}$, $PEG_{7500}$, $PEG_{9000}$, $PEG_{10000}$, $PEG_{12500}$, $PEG_{15000}$, and $PEG_{20,000}$, wherein the subscript is the average molecular weight of the polymer in Daltons, can be used.

The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying mimetibodies of the invention can be saturated or can contain one or more units of unsaturation. Fatty acids that are suitable for modifying mimetibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-Δ9-octadecanoate ($C_{18}$, oleate), all cis-Δ5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified human mimetibodies and ligand-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—$C_H$—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl)carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al, WO 92/16221 the entire teachings of which are incorporated herein by reference).

The modified mimetibodies of the invention can be produced by reacting an human EPO mimetic hinge core mimetibody or ligand-binding fragment with a modifying agent. For example, the organic moieties can be bonded to the EPO mimetic hinge core mimetibody in a non-site specific manner by employing an amine-reactive modifying agent, for example, an NHS ester of PEG. Modified human mimetibodies or ligand-binding fragments can also be prepared by reducing disulfide bonds (e.g., intra-chain disulfide bonds) of an EPO mimetic hinge core mimetibody or ligand-binding fragment. The reduced EPO mimetic hinge core mimetibody or ligand-binding fragment can then be reacted with a thiol-reactive modifying agent to produce the modified EPO mimetic hinge core mimetibody of the invention. Modified human mimetibodies and ligand-binding fragments comprising an organic moiety that is bonded to specific sites of an EPO mimetic hinge core mimetibody or specified portion or variant of the present invention can be prepared using suitable methods, such as reverse proteolysis (Fisch et al., *Bioconjugate Chem.*, 3:147-153 (1992); Werlen et al, *Bioconjugate Chem.*, 5:411-417 (1994); Kumaran et al, *Protein Sci.* 6 (10): 2233-2241 (1997); Itoh et al, *Bioorg. Chem.*, 24 (1): 59-68 (1996); Capellas et al, *Biotechnol Bioeng.*, 56 (4):456-463 (1997)), and the methods described in Hermanson, G. T., *Bioconjugate Techniques*, Academic Press: San Diego, Calif. (1996).

EPO Mimetic Hinge Core Mimetibody Compositions

The present invention also provides at least one EPO mimetic hinge core mimetibody or specified portion or variant composition comprising at least one, at least two, at least three, at least four, at least five, at least six or more mimetibodies or specified portions or variants thereof, as described herein and/or as known in the art that are provided in a non-naturally occurring composition, mixture or form. Such composition percentages are by weight, volume, concentration, molarity, or molality as liquid or dry solutions, mixtures, suspension, emulsions or colloids, as known in the art or as described herein.

Such compositions can comprise 0.00001-99.9999 percent by weight, volume, concentration, molarity, or molality as liquid, gas, or dry solutions, mixtures, suspension, emulsions or colloids, as known in the art or as described herein, on any range or value therein, such as but not limited to 0.00001, 0.00003, 0.00005, 0.00009, 0.0001, 0.0003, 0.0005, 0.0009, 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, 5, 6, 7, 8, 9, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9%. Such compositions of the present invention thus include but are not limited to 0.00001-100 mg/ml and/or 0.00001-100 mg/g.

The composition can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see., e.g., Nursing 2001 Handbook of Drugs, $21^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

The anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, miscellaneous anti-infectives. The CV drug can be at least one selected from inotropics, antiarrhythmics, antianginals, antihypertensives, antilipemics, miscellaneous cardiovascular drugs. The CNS drug can be at least one selected from nonnarcotic analgesics or at least one selected from antipyretics, nonsteroidal anti-inflammatory drugs, narcotic or at least one opiod analgesics, sedative-hypnotics, anticonvulsants, antidepressants, antianxiety drugs, antipsychotics, central nervous system stimulants, antiparkinsonians, miscellaneous central nervous system drugs. The ANS drug can be at least one selected from cholinergics (parasympathomimetics), anticholinergics, adrenergics (sympathomimetics), adrenergic blockers (sympatholytics), skeletal muscle relaxants, neuromuscular blockers. The respiratory tract drug can be at least one selected from antihistamines, bronchodilators, expectorants or at least one antitussives, miscellaneous respiratory drugs. The GI tract drug can be at least one selected from antacids or at least one adsorbents or at least one antiflatulents, digestive enzymes or at least one gallstone solubilizers, antidiarrheals, laxatives, antiemetics, antiulcer drugs. The hormonal drug can be at least one selected from corticosteroids, androgens or at least one anabolic steroids, estrogens or at least one progestins, gonadotropins, antidiabetic drugs or at least one glucagon, thyroid hormones, thyroid hormone antagonists, pituitary hormones, parathyroid-like drugs. The drug for fluid and electrolyte balance can be at least one selected from diuretics, electrolytes or at least one replacement solutions, acidifiers or at least one alkalinizers. The hematologic drug can be at least one selected from hematinics, anticoagulants, blood derivatives, thrombolytic enzymes. The antineoplastics can be at least one selected from alkylating drugs, antimetabolites, antibiotic antineoplastics, antineoplastics that alter hormone balance, miscellaneous antineoplastics. The immunomodulation drug can be at least one selected from immunosuppressants, vaccines or at least one toxoids, antitoxins or at least one antivenins, immune serums, biological response modifiers. The ophthalmic, otic, and nasal drugs can be at least one selected from ophthalmic anti-infectives, ophthalmic anti-inflammatories, miotics, mydriatics, ophthalmic vasoconstrictors, miscellaneous ophthalmics, otics, nasal drugs. The topical drug can be at least one selected from local anti-infectives, scabicides or at least one pediculicides, topical corticosteroids. The nutritional drug can be at least one selected from vitamins, minerals, or calorics. See, e.g., contents of *Nursing* 2001 *Drug Handbook*, supra.

The at least one amebicide or antiprotozoal can be at least one selected from atovaquone, chloroquine hydrochloride, chloroquine phosphate, metronidazole, metronidazole hydrochloride, pentamidine isethionate. The at least one anthelmintic can be at least one selected from mebendazole, pyrantel pamoate, thiabendazole. The at least one antifungal can be at least one selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, terbinafine hydrochloride. The at least one antimalarial can be at least one selected from chloroquine hydrochloride, chloroquine phosphate, doxycycline, hydroxychloroquine sulfate, mefloquine hydrochloride, primaquine phosphate, pyrimethamine, pyrimethamine with sulfadoxine. The at least one antituberculotic or antileprotic can be at least one selected from clofazimine, cycloserine, dapsone, ethambutol hydrochloride, isoniazid, pyrazinamide, rifabutin, rifampin, rifapentine, streptomycin sulfate. The at least one aminoglycoside can be at least one selected from amikacin sulfate, gentamicin sulfate, neomycin sulfate, streptomycin sulfate, tobramycin sulfate. The at least one penicillin can be at least one selected from amoxcillin/clavulanate potassium, amoxicillin trihydrate, ampicillin, ampicillin sodium, ampicillin trihydrate, ampicillin sodium/sulbactam sodium, cloxacillin sodium, dicloxacillin sodium, mezlocillin sodium, nafcillin sodium, oxacillin sodium, penicillin G benzathine, penicillin G potassium, penicillin G procaine, penicillin G sodium, penicillin V potassium, piperacillin sodium, piperacillin sodium/tazobactam sodium, ticarcillin disodium, ticarcillin disodium/clavulanate potassium. The at least one cephalosporin can be at least one selected from at least one of cefaclor, cefadroxil, cefazolin sodium, cefdinir, cefepime hydrochloride, cefixime, cefmetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, loracarbef. The at least one tetracycline can be at least one selected from demeclocycline hydrochloride, doxycycline calcium, doxycycline hyclate, doxycycline hydrochloride, doxycycline monohydrate, minocycline hydrochloride, tetracycline hydrochloride. The at least one sulfonamide can be at least one selected from co-trimoxazole, sulfadiazine, sulfamethoxazole, sulfisoxazole, sulfisoxazole acetyl. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, trovafloxacin mesylate. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, trovafloxacin mesylate. The at least one antiviral can be at least one selected from abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, zidovudine. The at least one macroline anti-infective can be at least one selected from azithromycin, clarithromycin, dirithromycin, erythromycin base, erythromycin estolate, erythromycin ethylsuccinate, erythromycin lactobionate, erythromycin stearate. The at least one miscellaneous anti-infective can be at least one selected from aztreonam, bacitracin, chloramphenicol sodium sucinate, clindamycin hydrochloride, clindamycin palmitate hydrochloride, clindamycin phosphate, imipenem and cilastatin sodium, meropenem, nitrofurantoin macrocrystals, nitrofurantoin microcrystals, quinupristin/dalfopristin, spectinomycin hydrochloride, trimethoprim, vancomycin hydrochloride. (See, e.g., pp. 24-214 of *Nursing* 2001 *Drug Handbook*).

The at least one inotropic can be at least one selected from amrinone lactate, digoxin, milrinone lactate. The at least one antiarrhythmic can be at least one selected from adenosine, amiodarone hydrochloride, atropine sulfate, bretylium tosylate, diltiazem hydrochloride, disopyramide, disopyramide phosphate, esmolol hydrochloride, flecamide acetate, ibutilide fumarate, lidocaine hydrochloride, mexiletine hydrochloride, moricizine hydrochloride, phenyloin, phenyloin sodium, procainamide hydrochloride, propafenone hydrochloride, propranolol hydrochloride, quinidine bisulfate, quinidine gluconate, quinidine polygalacturonate, quinidine sulfate, sotalol, tocamide hydrochloride, verapamil hydrochloride. The at least one antianginal can be at least one selected from amlodipidine besylate, amyl nitrite, bepridil hydrochloride, diltiazem hydrochloride, isosorbide dinitrate, isosorbide mononitrate, nadolol, nicardipine hydrochloride, nifedipine, nitroglycerin, propranolol hydrochloride, verapamil, verapamil hydrochloride. The at least one antihypertensive can be at least one selected from acebutolol hydrochloride, amlodipine besylate, atenolol, benazepril hydrochloride, betaxolol hydrochloride, bisoprolol fumarate, candesartan cilexetil, captopril, carteolol hydrochloride, carvedilol, clonidine, clonidine hydrochloride, diazoxide, diltiazem hydrochloride, doxazosin mesylate, enalaprilat, enalapril maleate, eprosartan mesylate, felodipine, fenoldopam mesylate, fosinopril sodium, guanabenz acetate, guanadrel sulfate, guanfacine hydrochloride, hydralazine hydrochloride, irbesartan, isradipine, labetalol hydrochloride, lisinopril, losartan potassium, methyldopa, methyldopate hydrochloride, metoprolol succinate, metoprolol tartrate, minoxidil, moexipril hydrochloride, nadolol, nicardipine hydrochloride, nifedipine, nisoldipine, nitroprusside sodium, penbutolol sulfate, perindopril erbumine, phentolamine mesylate, pindolol, prazosin hydrochloride, propranolol hydrochloride, quinapril hydrochloride, ramipril, telmisartan, terazosin hydrochloride, timolol maleate, trandolapril, valsartan, verapamil hydrochloride The at least one antilipemic can be at least one selected from atorvastatin calcium, cerivastatin sodium, cholestyramine, colestipol hydrochloride, fenofibrate (micronized), fluvastatin sodium, gemfibrozil, lovastatin, niacin, pravastatin sodium, simvastatin. The at least one miscellaneous CV drug can be at least one selected from abciximab, alprostadil, arbutamine hydrochloride, cilostazol, clopidogrel bisulfate, dipyridamole, eptifibatide, midodrine hydrochloride, pentoxifylline, ticlopidine hydrochloride, tirofiban hydrochloride. (See, e.g., pp. 215-336 of Nursing 2001 Drug Handbook).

The at least one nonnarcotic analgesic or antipyretic can be at least one selected from acetaminophen, aspirin, choline magnesium trisalicylate, diflunisal, magnesium salicylate. The at least one nonsteroidal anti-inflammatory drug can be at least one selected from celecoxib, diclofenac potassium, diclofenac sodium, etodolac, fenoprofen calcium, flurbiprofen, ibuprofen, indomethacin, indomethacin sodium trihydrate, ketoprofen, ketorolac tromethamine, nabumetone, naproxen, naproxen sodium, oxaprozin, piroxicam, rofecoxib, sulindac. The at least one narcotic or opiod analgesic can be at least one selected from alfentanil hydrochloride, buprenorphine hydrochloride, butorphanol tartrate, codeine phosphate, codeine sulfate, fentanyl citrate, fentanyl transdermal system, fentanyl transmucosal, hydromorphone hydrochloride, meperidine hydrochloride, methadone hydrochloride, morphine hydrochloride, morphine sulfate, morphine tartrate, nalbuphine hydrochloride, oxycodone hydrochloride, oxycodone pectinate, oxymorphone hydrochloride, pentazocine hydrochloride, pentazocine hydrochloride and naloxone hydrochloride, pentazocine lactate, propoxyphene hydrochloride, propoxyphene napsylate, remifentanil hydrochloride, sufentanil citrate, tramadol hydrochloride. The at least one sedative-hypnotic can be at least one selected from chloral hydrate, estazolam, flurazepam hydrochloride, pentobarbital, pentobarbital sodium, phenobarbital sodium, secobarbital sodium, temazepam, triazolam, zaleplon, zolpidem tartrate. The at least one anticonvulsant can be at least one selected from acetazolamide sodium, carbamazepine, clonazepam, clorazepate dipotassium, diazepam, divalproex sodium, ethosuximde, fosphenytoin sodium, gabapentin, lamotrigine, magnesium sulfate, phenobarbital, phenobarbital sodium, phenyloin, phenyloin sodium, phenyloin sodium (extended), primidone, tiagabine hydrochloride, topiramate, valproate sodium, valproic acid. The at least one antidepressant can be at least one selected from amitriptyline hydrochloride, amitriptyline pamoate, amoxapine, bupropion hydrochloride, citalopram hydrobromide, clomipramine hydrochloride, desipramine hydrochloride, doxepin hydrochloride, fluoxetine hydrochloride, imipramine hydrochloride, imipramine pamoate, mirtazapine, nefazodone hydrochloride, nortriptyline hydrochloride, paroxetine hydrochloride, phenelzine sulfate, sertraline hydrochloride, tranylcypromine sulfate, trimipramine maleate, venlafaxine hydrochloride. The at least one antianxiety drug can be at least one selected from alprazolam, buspirone hydrochloride, chlordiazepoxide, chlordiazepoxide hydrochloride, clorazepate dipotassium, diazepam, doxepin hydrochloride, hydroxyzine embonate, hydroxyzine hydrochloride, hydroxyzine pamoate, lorazepam, mephrobamate, midazolam hydrochloride, oxazepam. The at least one antipsychotic drug can be at least one selected from chlorpromazine hydrochloride, clozapine, fluphenazine decanoate, fluephenazine enanthate, fluphenazine hydrochloride, haloperidol, haloperidol decanoate, haloperidol lactate, loxapine hydrochloride, loxapine succinate, mesoridazine besylate, molindone hydrochloride, olanzapine, perphenazine, pimozide, prochlorperazine, quetiapine fumarate, risperidone, thioridazine hydrochloride, thiothixene, thiothixene hydrochloride, trifluoperazine hydrochloride. The at least one central nervous system stimulant can be at least one selected from amphetamine sulfate, caffeine, dextroamphetamine sulfate, doxapram hydrochloride, methamphetamine hydrochloride, methylphenidate hydrochloride, modafinil, pemoline, phentermine hydrochloride. The at least one antiparkinsonian can be at least one selected from amantadine hydrochloride, benztropine mesylate, biperiden hydrochloride, biperiden lactate, bromocriptine mesylate, carbidopa-levodopa, entacapone, levodopa, pergolide mesylate, pramipexole dihydrochloride, ropinirole hydrochloride, selegiline hydrochloride, tolcapone, trihexyphenidyl hydrochloride. The at least one miscellaneous central nervous system drug can be at least one selected from bupropion hydrochloride, donepezil hydrochloride, droperidol, fluvoxamine maleate, lithium carbonate, lithium citrate, naratriptan hydrochloride, nicotine polacrilex, nicotine transdermal system, propofol, rizatriptan benzoate, sibutramine hydrochloride monohydrate, sumatriptan succinate, tacrine hydrochloride, zolmitriptan. (See, e.g., pp. 337-530 of Nursing 2001 Drug Handbook).

The at least one cholinergic (e.g., parasymathomimetic) can be at least one selected from bethanechol chloride, edrophonium chloride, neostigmine bromide, neostigmine methylsulfate, physostigmine salicylate, pyridostigmine bromide. The at least one anticholinergics can be at least one selected from atropine sulfate, dicyclomine hydrochloride, glycopyrrolate, hyoscyamine, hyoscyamine sulfate, propantheline bromide, scopolamine, scopolamine butylbromide, scopolamine hydrobromide. The at least one adrenergics (sympathomimetics) can be at least one selected from dobutamine hydrochloride, dopamine hydrochloride, metaraminol bitartrate, norepinephrine bitartrate, phenylephrine hydrochloride, pseudoephedrine hydrochloride, pseudoephedrine sulfate. The at least one adrenergic blocker (sympatholytic) can be at least one selected from dihydroergotamine mesylate, ergotamine tartrate, methysergide maleate, propranolol hydrochloride. The at least one skeletal muscle relaxant can be at least one selected from baclofen, carisoprodol, chlorzoxazone, cyclobenzaprine hydrochloride, dantrolene sodium, methocarbamol, tizanidine hydrochloride. The at least one neuromuscular blockers can be at least one selected from atracurium besylate, cisatracurium besylate, doxacurium chloride, mivacurium chloride, pancuronium bromide, pipecuronium bromide, rapacuronium bromide, rocuronium bromide, succinylcholine chloride, tubocurarine chloride, vecuronium bromide. (See, e.g., pp. 531-84 of Nursing 2001 Drug Handbook).

The at least one antihistamine can be at least one selected from brompheniramine maleate, cetirizine hydrochloride, chlorpheniramine maleate, clemastine fumarate, cyproheptadine hydrochloride, diphenhydramine hydrochloride, fexofenadine hydrochloride, loratadine, promethazine hydrochloride, promethazine theoclate, triprolidine hydrochloride. The at least one bronchodilators can be at least one selected from albuterol, albuterol sulfate, aminophylline, atropine sulfate, ephedrine sulfate, epinephrine, epinephrine bitartrate, epinephrine hydrochloride, ipratropium bromide, isoproterenol, isoproterenol hydrochloride, isoproterenol sulfate, levalbuterol hydrochloride, metaproterenol sulfate, oxtriphylline, pirbuterol acetate, salmeterol xinafoate, terbutaline sulfate, theophylline. The at least one expectorants or antitussives can be at least one selected from benzonatate, codeine phosphate, codeine sulfate, dextramethorphan hydrobromide, diphenhydramine hydrochloride, guaifenesin, hydromorphone hydrochloride. The at least one miscellaneous respiratory drug can be at least one selected from acetylcysteine, beclomethasone dipropionate, beractant, budesonide, calfactant, cromolyn sodium, dornase alfa, epoprostenol sodium, flunisolide, fluticasone propionate, montelukast sodium, nedocromil sodium, palivizumab, triamcinolone acetonide, zafirlukast, zileuton. (See, e.g., pp. 585-642 of *Nursing* 2001 *Drug Handbook*).

The at least one antacid, adsorbents, or antiflatulents can be at least one selected from aluminum carbonate, aluminum hydroxide, calcium carbonate, magaldrate, magnesium hydroxide, magnesium oxide, simethicone, sodium bicarbonate. The at least one digestive enzymes or gallstone solubilizers can be at least one selected from pancreatin, pancrelipase, ursodiol. The at least one antidiarrheal can be at least one selected from attapulgite, bismuth subsalicylate, calcium polycarbophil, diphenoxylate hydrochloride or atropine sulfate, loperamide, octreotide acetate, opium tincture, opium tincure (camphorated). The at least one laxative can be at least one selected from bisocodyl, calcium polycarbophil, cascara sagrada, cascara sagrada aromatic fluidextract, cascara sagrada fluidextract, castor oil, docusate calcium, docusate sodium, glycerin, lactulose, magnesium citrate, magnesium hydroxide, magnesium sulfate, methylcellulose, mineral oil, polyethylene glycol or electrolyte solution, psyllium, senna, sodium phosphates. The at least one antiemetic can be at least one selected from chlorpromazine hydrochloride, dimenhydrinate, dolasetron mesylate, dronabinol, granisetron hydrochloride, meclizine hydrochloride, metocloproamide hydrochloride, ondansetron hydrochloride, perphenazine, prochlorperazine, prochlorperazine edisylate, prochlorperazine maleate, promethazine hydrochloride, scopolamine, thiethylperazine maleate, trimethobenzamide hydrochloride. The at least one antiulcer drug can be at least one selected from cimetidine, cimetidine hydrochloride, famotidine, lansoprazole, misoprostol, nizatidine, omeprazole, rabeprozole sodium, rantidine bismuth citrate, ranitidine hydrochloride, sucralfate. (See, e.g., pp. 643-95 of *Nursing* 2001 *Drug Handbook*). The at least one corticosteroids can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, triamcinolone diacetate. The at least one androgen or anabolic steroids can be at least one selected from danazol, fluoxymesterone, methyltestosterone, nandrolone decanoate, nandrolone phenpropionate, testosterone, testosterone cypionate, testosterone enanthate, testosterone propionate, testosterone transdermal system. The at least one estrogen or progestin can be at least one selected from esterified estrogens, estradiol, estradiol cypionate, estradiol/norethindrone acetate transdermal system, estradiol valerate, estrogens (conjugated), estropipate, ethinyl estradiol, ethinyl estradiol and desogestrel, ethinyl estradiol and ethynodiol diacetate, ethinyl estradiol and desogestrel, ethinyl estradiol and ethynodiol diacetate, ethinyl estradiol and levonorgestrel, ethinyl estradiol and norethindrone, ethinyl estradiol and norethindrone acetate, ethinyl estradiol and norgestimate, ethinyl estradiol and norgestrel, ethinyl estradiol and norethindrone and acetate and ferrous fumarate, levonorgestrel, medroxyprogesterone acetate, mestranol and norethindron, norethindrone, norethindrone acetate, norgestrel, progesterone. The at least one gonadroptropin can be at least one selected from ganirelix acetate, gonadoreline acetate, histrelin acetate, menotropins. The at least one antidiabetic or glucaon can be at least one selected from acarbose, chlorpropamide, glimepiride, glipizide, glucagon, glyburide, insulins, metformin hydrochloride, miglitol, pioglitazone hydrochloride, repaglinide, rosiglitazone maleate, troglitazone. The at least one thyroid hormone can be at least one selected from levothyroxine sodium, liothyronine sodium, liotrix, thyroid. The at least one thyroid hormone antagonist can be at least one selected from methimazole, potassium iodide, potassium iodide (saturated solution), propylthiouracil, radioactive iodine (sodium iodide $^{131}$I), strong iodine solution. The at least one pituitary hormone can be at least one selected from corticotropin, cosyntropin, desmophressin acetate, leuprolide acetate, repository corticotropin, somatrem, somatropin, vasopressin. The at least one parathyroid-like drug can be at least one selected from calcifediol, calcitonin (human), calcitonin (salmon), calcitriol, dihydrotachysterol, etidronate disodium. (See, e.g., pp. 696-796 of *Nursing* 2001 *Drug Handbook*).

The at least one diuretic can be at least one selected from acetazolamide, acetazolamide sodium, amiloride hydrochloride, bumetanide, chlorthalidone, ethacrynate sodium, ethacrynic acid, furosemide, hydrochlorothiazide, indapamide, mannitol, metolazone, spironolactone, torsemide, triamterene, urea. The at least one electrolyte or replacement solution can be at least one selected from calcium acetate, calcium carbonate, calcium chloride, calcium citrate, calcium glubionate, calcium gluceptate, calcium gluconate, calcium lactate, calcium phosphate (dibasic), calcium phosphate (tribasic), dextran (high-molecular-weight), dextran (low-molecular-weight), hetastarch, magnesium chloride, magnesium sulfate, potassium acetate, potassium bicarbonate, potassium chloride, potassium gluconate, Ringer's injection, Ringer's injection (lactated), sodium chloride. The at least one acidifier or alkalinizer can be at least one selected from sodium bicarbonate, sodium lactate, tromethamine. (See, e.g., pp. 797-833 of *Nursing* 2001 *Drug Handbook*).

The at least one hematinic can be at least one selected from ferrous fumarate, ferrous gluconate, ferrous sulfate, ferrous sulfate (dried), iron dextran, iron sorbitol, polysaccharide-iron complex, sodium ferric gluconate complex. The at least one anticoagulant can be at least one selected from ardeparin sodium, dalteparin sodium, danaparoid sodium, enoxaparin sodium, heparin calcium, heparin sodium, warfarin sodium. The at least one blood derivative can be at least one selected from albumin 5%, albumin 25%, antihemophilic factor, anti-inhibitor coagulant complex, antithrombin III (human), factor IX (human), factor IX complex, plasma protein fractions. The at least one thrombolytic enzyme can be at least one selected from alteplase, anistreplase, reteplase (recombinant), streptokinase, urokinase. (See, e.g., pp. 834-66 of *Nursing* 2001 *Drug Handbook*).

The at least one alkylating drug can be at least one selected from busulfan, carboplatin, carmustine, chlorambucil, cisplatin, cyclophosphamide, ifosfamide, lomustine, mechlorethamine hydrochloride, melphalan, melphalan hydrochloride, streptozocin, temozolomide, thiotepa. The at least one antimetabolite can be at least one selected from capecitabine, cladribine, cytarabine, floxuridine, fludarabine phosphate, fluorouracil, hydroxyurea, mercaptopurine, methotrexate, methotrexate sodium, thioguanine. The at least one antibiotic antineoplastic can be at least one selected from bleomycin sulfate, dactinomycin, daunorubicin citrate liposomal, daunorubicin hydrochloride, doxorubicin hydrochloride, doxorubicin hydrochloride liposomal, epirubicin hydrochloride, idarubicin hydrochloride, mitomycin, pentostatin, plicamycin, valrubicin. The at least one antineoplastics that alter hormone balance can be at least one selected from anastrozole, bicalutamide, estramustine phosphate sodium, exemestane, flutamide, goserelin acetate, letrozole, leuprolide acetate, megestrol acetate, nilutamide, tamoxifen citrate, testolactone, toremifene citrate. The at least one miscellaneous antineoplastic can be at least one selected from asparaginase, bacillus Calmette-Guerin (BCG) (live intravesical), dacarbazine, docetaxel, etoposide, etoposide phosphate, gemcitabine hydrochloride, irinotecan hydrochloride, mitotane, mitoxantrone hydrochloride, paclitaxel, pegaspargase, porfimer sodium, procarbazine hydrochloride, rituximab, teniposide, topotecan hydrochloride, trastuzumab, tretinoin, vinblastine sulfate, vincristine sulfate, vinorelbine tartrate. (See, e.g., pp. 867-963 of Nursing 2001 Drug Handbook).

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, tacrolimus. The at least one vaccine or toxoid can be at least one selected from BCG vaccine, cholera vaccine, diphtheria and tetanus toxoids (adsorbed), diphtheria and tetanus toxoids and acellular pertussis vaccine adsorbed, diphtheria and tetanus toxoids and whole-cell pertussis vaccine, Haemophilus b conjugate vaccines, hepatitis A vaccine (inactivated), hepatisis B vaccine (recombinant), influenza virus vaccine 1999-2000 trivalent types A & B (purified surface antigen), influenza virus vaccine 1999-2000 trivalent types A & B (subvirion or purified subvirion), influenza virus vaccine 1999-2000 trivalent types A & B (whole virion), Japanese encephalitis virus vaccine (inactivated), Lyme disease vaccine (recombinant OspA), measles and mumps and rubella virus vaccine (live), measles and mumps and rubella virus vaccine (live attenuated), measles virus vaccine (live attenuated), meningococcal polysaccharide vaccine, mumps virus vaccine (live), plague vaccine, pneumococcal vaccine (polyvalent), poliovirus vaccine (inactivated), poliovirus vaccine (live, oral, trivalent), rabies vaccine (adsorbed), rabies vaccine (human diploid cell), rubella and mumps virus vaccine (live), rubella virus vaccine (live, attenuated), tetanus toxoid (adsorbed), tetanus toxoid (fluid), typhoid vaccine (oral), typhoid vaccine (parenteral), typhoid Vi polysaccharide vaccine, varicella virus vaccine, yellow fever vaccine. The at least one antitoxin or antivenin can be at least one selected from black widow spider antivenin, Crotalidae antivenom (polyvalent), diphtheria antitoxin (equine), Micrurus fulvius antivenin). The at least one immune serum can be at least one selected from cytomegalovirus immune globulin (intraveneous), hepatitis B immune globulin (human), immune globulin intramuscular, immune globulin intravenous, rabies immune globulin (human), respiratory syncytial virus immune globulin intravenous (human), $Rh_0(D)$ immune globulin (human), $Rh_0(D)$ immune globulin intravenous (human), tetanus immune globulin (human), varicella-zoster immune globulin. The at least one biological response modifiers can be at least one selected from aldesleukin, epoetin alfa, filgrastim, glatiramer acetate for injection, interferon alfacon-1, interferon alfa-2a (recombinant), interferon alfa-2b (recombinant), interferon beta-1a, interferon beta-1b (recombinant), interferon gamma-1b, levamisole hydrochloride, oprelvekin, sargramostim. (See, e.g., pp. 964-1040 of Nursing 2001 Drug Handbook).

The at least one ophthalmic anti-infectives can be selected form bacitracin, chloramphenicol, ciprofloxacin hydrochloride, erythromycin, gentamicin sulfate, ofloxacin 0.3%, polymyxin B sulfate, sulfacetamide sodium 10%, sulfacetamide sodium 15%, sulfacetamide sodium 30%, tobramycin, vidarabine. The at least one ophthalmic anti-inflammatories can be at least one selected from dexamethasone, dexamethasone sodium phosphate, diclofenac sodium 0.1%, fluorometholone, flurbiprofen sodium, ketorolac tromethamine, prednisolone acetate (suspension) prednisolone sodium phosphate (solution). The at least one miotic can be at least one selected from acetylocholine chloride, carbachol (intraocular), carbachol (topical), echothiophate iodide, pilocarpine, pilocarpine hydrochloride, pilocarpine nitrate. The at least one mydriatic can be at least one selected from atropine sulfate, cyclopentolate hydrochloride, epinephrine hydrochloride, epinephryl borate, homatropine hydrobromide, phenylephrine hydrochloride, scopolamine hydrobromide, tropicamide. The at least one ophthalmic vasoconstrictors can be at least one selected from naphazoline hydrochloride, oxymetazoline hydrochloride, tetrahydrozoline hydrochloride. The at least one miscellaneous ophthalmics can be at least one selected from apraclonidine hydrochloride, betaxolol hydrochloride, brimonidine tartrate, carteolol hydrochloride, dipivefrin hydrochloride, dorzolamide hydrochloride, emedastine difumarate, fluorescein sodium, ketotifen fumarate, latanoprost, levobunolol hydrochloride, metipranolol hydrochloride, sodium chloride (hypertonic), timolol maleate. The at least one otic can be at least one selected from boric acid, carbamide peroxide, chloramphenicol, triethanolamine polypeptide oleate-condensate. The at least one nasal drug can be at least one selected from beclomethasone dipropionate, budesonide, ephedrine sulfate, epinephrine hydrochloride, flunisolide, fluticasone propionate, naphazoline hydrochloride, oxymetazoline hydrochloride, phenylephrine hydrochloride, tetrahydrozoline hydrochloride, triamcinolone acetonide, xylometazoline hydrochloride. (See, e.g., pp. 1041-97 of Nursing 2001 Drug Handbook).

The at least one local anti-infectives can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, tolnaftate. The at least one scabicide or pediculicide can be at least one selected from crotamiton, lindane, permethrin, pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, triamcinolone acetonide. (See, e.g., pp. 1098-1136 of Nursing 2001 Drug Handbook).

The at least one vitamin or mineral can be at least one selected from vitamin A, vitamin B complex, cyanocobalamin, folic acid, hydroxocobalamin, leucovorin calcium, niacin, niacinamide, pyridoxine hydrochloride, riboflavin, thiamine hydrochloride, vitamin C, vitamin D, cholecalciferol, ergocalciferol, vitamin D analogue, doxercalciferol, paricalcitol, vitamin E, vitamin K analogue, phytonadione, sodium fluoride, sodium fluoride (topical), trace elements, chromium, copper, iodine, manganese, selenium, zinc. The at least one calorics can be at least one selected from amino acid infusions (crystalline), amino acid infusions in dextrose, amino acid infusions with electrolytes, amino acid infusions with electrolytes in dextrose, amino acid infusions for hepatic failure, amino acid infusions for high metabolic stress, amino acid infusions for renal failure, dextrose, fat emulsions, medium-chain triglycerides. (See, e.g., pp. 1137-63 of *Nursing* 2001 *Drug Handbook*).

EPO mimetic hinge core mimetibody antibody or polypeptide compositions of the present invention can further comprise at least one of any suitable and/or effective amount of a composition or pharmaceutical composition comprising at least one EPO mimetic hinge core mimetibody protein or antibody to a cell, tissue, organ, animal or patient in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, enteracept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a fluoroquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Non-limiting examples of such cytokines include, but are not limited to, any of IL-1 to IL-23. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such compositions can also include toxin molecules that are associated, bound, co-formulated or co-administered with at least one antibody or polypeptide of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii*, and *Shigella sonnei*), *Salmonella* species (e.g., *Salmonella typhi, Salmonella cholera-suis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa*, and Streptococci. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, New York (1990); Berkow et al, eds., *The Merck Manual,* 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

EPO mimetic hinge core mimetibody or specified portion or variant compositions of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences,* $18^{th}$ Edition, Mack Publishing Co. (Easton, Pa.) 1990. Pharmaceutically acceptable carriers can be routinely selected that are suitable for the mode of administration, solubility and/or stability of the EPO mimetic hinge core mimetibody composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/EPO mimetic hinge core mimetibody or specified portion or variant components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

EPO mimetic hinge core mimetibody compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, the EPO mimetic hinge core mimetibody or specified portion or variant compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the EPO mimetic hinge core mimetibody compositions according to the invention are known in the art, e.g., as listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

Formulations

As noted above, the invention provides for stable formulations, which can preferably include a suitable buffer with saline or a chosen salt, as well as optional preserved solutions and formulations containing a preservative as well as multi-use preserved formulations suitable for pharmaceutical or veterinary use, comprising at least one EPO mimetic hinge core mimetibody or specified portion or variant in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one EPO mimetic hinge core mimetibody or specified portion or variant with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one EPO mimetic hinge core mimetibody or specified portion or variant, and a second vial comprising an aqueous diluent of prescribed buffer or preservative, wherein said packaging material comprises a label that instructs a patient to reconstitute the at least one EPO mimetic hinge core mimetibody or specified portion or variant in the aqueous diluent to form a solution that can be held over a period of twenty-four hours or greater.

The at least one EPO mimetic hinge core mimetibody or specified portion or variant used in accordance with the present invention can be produced by recombinant means, including from mammalian cell or transgenic preparations, or can be purified from other biological sources, as described herein or as known in the art.

The range of amounts of at least one EPO mimetic hinge core mimetibody or specified portion or variant in the product of the present invention includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one EPO mimetic hinge core mimetibody or specified portion or variant and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one EPO mimetic hinge core mimetibody or specified portion or variant and preservative in an aqueous diluent is carried out using conventional dissolution and mixing procedures. To prepare a suitable formulation, for example, a measured amount of at least one EPO mimetic hinge core mimetibody or specified portion or variant in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that may be optimized for the concentration and means of administration used.

The claimed formulations can be provided to patients as clear solutions or as dual vials comprising a vial of lyophilized at least one EPO mimetic hinge core mimetibody or specified portion or variant that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to at least one of 1-12 months, one-half, one and a half, and/or two years.

The solutions of at least one EPO mimetic hinge core mimetibody or specified portion or variant in the invention can be prepared by a process that comprises mixing at least one EPO mimetic hinge core mimetibody or specified portion or variant in an aqueous diluent. Mixing is carried out using conventional dissolution and mixing procedures. To prepare a suitable diluent, for example, a measured amount of at least one EPO mimetic hinge core mimetibody or specified portion or variant in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that may be optimized for the concentration and means of administration.

The claimed products can be provided to patients as clear solutions or as dual vials comprising a vial of lyophilized at least one EPO mimetic hinge core mimetibody or specified portion or variant that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one EPO mimetic hinge core mimetibody or specified portion or variant that is reconstituted with a second vial containing the aqueous diluent. The clear solution in this case can be up to one liter or even larger in size, providing a large reservoir from which smaller portions of the at least one EPO mimetic hinge core mimetibody or specified portion or variant solution can be retrieved one or multiple times for transfer into smaller vials and provided by the pharmacy or clinic to their customers and/or patients.

Recognized devices comprising these single vial systems include those pen-injector devices for delivery of a solution such as Humaject® NovoPen®, B-D® Pen, AutoPen®, and OptiPen®. Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product can be used. The packaging material of the present invention provides instructions to the patient to reconstitute the at least one EPO mimetic hinge core mimetibody or specified portion or variant in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one EPO mimetic hinge core mimetibody or specified portion or variant and a selected buffer, preferably a phosphate buffer containing saline or a chosen salt. Mixing the at least one EPO mimetic hinge core mimetibody or specified portion or variant and buffer in an aqueous diluent is carried out using conventional dissolution and mixing procedures. To prepare a suitable formulation, for example, a measured amount of at least one EPO mimetic hinge core mimetibody or specified portion or variant in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one EPO mimetic hinge core mimetibody or specified portion or variant that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one EPO mimetic hinge core mimetibody or specified portion or variant in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention for mimetibodies also provides a method for modulating or treating anemia, in a cell, tissue, organ, animal, or patient including, but not limited to, at least one of any anemia, cancer treatment related anemia, radiotherapy or chemotherapy related anemia, viral or bacterial infection treatment related anemia, renal anemia, anemia of prematurity, pediatric and/or adult cancer-associated anemia, anemia associated with lymphoma, myeloma, multiple myeloma, AIDS-associated anemia, concomitant treatment for patients with or without autologous blood donation awaiting elective surgery, preoperative and post operative for surgery, autologous blood donation or transfusion, perioperative management, cyclic neutropenia or Kostmann syndrome (congenital agranulocytosis), end-stage renal disease, anemia associated with dialysis, chronic renal insufficiency, primary hemopoietic diseases, such as congenital hypoplastic anemia, thalassemia major, or sickle cell disease, vaso-occlusive complications of sickle cell disease. Furman et al., Pediatrics 1992; 90: 716-728, Goldberg Science. 1988; 242:1412-1415; Paul et al., Exp Hematol. 1984; 12:825-830; Erslev et al., Arch Intern Med. 1968; 122:230-235; Ersley et al., Ann Clin Lab Sci. 1980; 10:250-257; Jacobs et al., Nature. 1985; 313: 806-810; Lin et al., Proc Natl Acad Sci USA. 1985; 82:7580-7584; Law et al., Proc Natl Acad Sci USA. 1986; 83:6920-6924; Goldwasser et al., J Biol. Chem. 1974; 249:4202-4206; Eaves et al., Blood. 1978; 52:1196-1210; Sawyer et al., Blood. 1989; 74:103-109; Winearls et al., Lancet. 1986; 2:1175-1178; Eschbach et al., N Engl J Med. 1987; 316:73-78; Eschbach et al., Ann Intern Med. 1989; 111:992-1000, each reference entirely incorporated herein by reference.

Mimetibodies of the present invention can also be used for non-renal forms of anemia induced, for example, by chronic infections, inflammatory processes, radiation therapy, and cytostatic drug treatment, and encouraging results in patients with non-renal anemia have been reported. See, e.g., Abels R I and Rudnick S A Erythropoietin: evolving clinical applications. Experimental Hematology 19: 842-50 (1991); Graber S E and Krantz S B Erythropoietin: biology and clinical use. Hematology/Oncol. Clin. North Amer. 3: 369-400 (1989); Jelkman W and Gross A J (eds) Erythropoietin. Springer, Berlin 1989; Koury M J and Bondurant M C The molecular mechanism of erythropoietin action. European Journal of Biochemistry 210: 649-63 (1992); Krantz S B Erythropoietin. Blood 77: 419-34 (1991); Tabbara I A Erythropoietin. Biology and clinical applications. Archives of Internal Medicine 153: 298-304 (1993), each entirely incorporated herein by reference.

The present invention also provides a method for modulating or treating an anemia or blood cell related condition, in a cell, tissue, organ, animal, or patient, wherein said anemia or blood cell related condition is associated with at least one including, but not limited to, at least one of immune related disease, cardiovascular disease, infectious, malignant and/or neurologic disease. Such a method can optionally comprise administering an effective amount of at least one composition or pharmaceutical composition comprising at least one EPO mimetic hinge core mimetibody or specified portion or variant to a cell, tissue, organ, animal or patient in need of such modulation, treatment or therapy.

The present invention also provides a method for modulating or treating cancer/infectious disease in a cell, tissue, organ, animal or patient, including, but not limited to, at least one of acute or chronic bacterial infection, acute and chronic parasitic or infectious processes, including bacterial, viral and fungal infections, HIV infection/HIV neuropathy, meningitis, hepatitis, septic arthritis, peritonitis, pneumonia, epiglottis, e. coli 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, mycobacterium tuberculosis, mycobacterium avium intracellulare, pneumocystis carinii pneumonia, pelvic inflammatory disease, orchitis/epidydimitis, legionella, lyme disease, influenza a, epstein-barr virus, vital-associated hemaphagocytic syndrome, vital encephalitis/aseptic meningitis, and the like; (ii) leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, and the like; or (iii) neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi.system disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16th Edition, Merck & Company, Rahway, N.J. (1992)

Such a method can optionally comprise administering an effective amount of at least one composition or pharmaceutical composition comprising at least one EPO mimetic hinge core mimetibody or specified portion or variant to a cell, tissue, organ, animal or patient in need of such modulation, treatment or therapy.

The present invention also provides a method for modulating or treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, arteriosclerosis, atherosclerosis, diabetic arteriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occlusion of the abdominal aorta and its branches, peripheral vascular disorders, occlusive arterial disorders, peripheral atherosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such a method can optionally comprise administering an effective amount of a composition or pharmaceutical composition comprising at least one EPO mimetic hinge core mimetibody or specified portion or variant to a cell, tissue, organ, animal or patient in need of such modulation, treatment or therapy.

Any method of the present invention can comprise administering an effective amount of a composition or pharmaceutical composition comprising at least one EPO mimetic hinge core mimetibody or specified portion or variant to a cell, tissue, organ, animal or patient in need of such modulation, treatment or therapy. Such a method can optionally further comprise co-administration or combination therapy for treating such immune diseases, wherein the administering of said at least one EPO mimetic hinge core mimetibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an antirheumatic, a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a fluoroquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Mimetibodies can also be used ex vivo, such as in autologous marrow culture. Briefly, bone marrow is removed from a patient prior to chemotherapy and treated with TPO and/or EPO, optionally in combination with mimetibodies, optionally in combination with one or more additional cytokines. The treated marrow is then returned to the patient after chemotherapy to speed the recovery of the marrow. In addition, TPO, alone and in combination with EPO mimetibodies and/or EPO, can also be used for the ex vivo expansion of marrow or peripheral blood progenitor (PBPC) cells. Prior to chemotherapy treatment, marrow can be stimulated with stem cell factor (SCF) or G-CSF to release early progenitor cells into peripheral circulation. These progenitors are optionally collected and concentrated from peripheral blood and then treated in culture with TPO and mimetibodies, optionally in combination with one or more other cytokines, including but not limited to SCF, G-CSF, IL-3, GM-CSF, IL-6 or IL-1, to differentiate and proliferate into high-density megakaryocyte cultures, which are optionally then be returned to the patient following high-dose chemotherapy. Doses of TPO for ex vivo treatment of bone marrow will be in the range of 100 pg/ml to 10 ng/ml, preferably 500 pg/ml to 3 ng/ml. Doses of mimetibodies will be equivalent in activity to EPO which can be used from 0.1 units/ml to 20 units/ml, preferably from 0.5 units/ml to 2 units/ml, or any range or value therein.

TNF antagonists suitable for compositions, combination therapy, co-administration, devices and/or methods of the present invention (further comprising at least one anti body, specified portion and variant thereof, of the present invention), include, but are not limited to, anti-TNF antibodies, ligand-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g, pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

As used herein, a "tumor necrosis factor antibody," "TNF antibody," "TNFα antibody," or fragment and the like decreases, blocks, inhibits, abrogates or interferes with TNFα activity in vitro, in situ and/or preferably in vivo. For example, a suitable TNF human antibody of the present invention can bind TNFα and includes anti-TNF antibodies, antigen-binding fragments thereof, and specified mutants or domains thereof that bind specifically to TNFα. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

Chimeric antibody cA2 consists of the antigen binding variable region of the high-affinity neutralizing mouse anti-human TNFα IgG1 antibody, designated A2, and the constant regions of a human IgG1, kappa immunoglobulin. The human IgG1 Fc region improves allogeneic antibody effector function, increases the circulating serum half-life and decreases the immunogenicity of the antibody. The avidity and epitope specificity of the chimeric antibody cA2 is derived from the variable region of the murine antibody A2. In a particular embodiment, a preferred source for nucleic acids encoding the variable region of the murine antibody A2 is the A2 hybridoma cell line.

Chimeric A2 (cA2) neutralizes the cytotoxic effect of both natural and recombinant human TNFα in a dose dependent manner. From binding assays of chimeric antibody cA2 and recombinant human TNFα, the affinity constant of chimeric antibody cA2 was calculated to be $1.04 \times 10^{10} M^{-1}$. Preferred methods for determining monoclonal antibody specificity and affinity by competitive inhibition can be found in Harlow, et al., *Antibodies: A Laboratory Manual*, Cold Spring Harbor Laboratory Press, Cold Spring Harbor, N.Y., 1988; Colligan et al., eds., *Current Protocols in Immunology*, Greene Publishing Assoc. and Wiley Interscience, New York, (1992-2003); Kozbor et al., *Immunol. Today*, 4:72-79 (1983); Ausubel et al, eds. *Current Protocols in Molecular Biology*, Wiley Interscience, New York (1987-2003); and Muller, *Meth. Enzymol*, 92:589-601 (1983), which references are entirely incorporated herein by reference.

In a particular embodiment, murine monoclonal antibody A2 is produced by a cell line designated c134A. Chimeric antibody cA2 is produced by a cell line designated c168A.

Additional examples of monoclonal anti-TNF antibodies that can be used in the present invention are described in the art (see, e.g., U.S. Pat. No. 5,231,024; Möller, A. et al., *Cytokine* 2 (3):162-169 (1990); U.S. application Ser. No. 07/943,852 (filed Sep. 11, 1992); Rathjen et al., International Publication No. WO 91/02078 (published Feb. 21, 1991); Rubin et al, EPO Patent Publication No. 0 218 868 (published Apr. 22, 1987); Yone et al., EPO Patent Publication No. 0 288 088 (Oct. 26, 1988); Liang, et al., *Biochem. Biophys. Res. Comm.* 137:847-854 (1986); Meager, et al., *Hybridoma* 6:305-311 (1987); Fendly et al., *Hybridoma* 6:359-369 (1987); Bringman, et al., *Hybridoma* 6:489-507 (1987); and Hirai, et al., *J. Immunol. Meth.* 96:57-62 (1987), which references are entirely incorporated herein by reference).

TNF Receptor Molecules

Preferred TNF receptor molecules useful in the present invention are those that bind TNFα with high affinity (see, e.g., Feldmann et al., International Publication No. WO 92/07076 (published Apr. 30, 1992); Schall et al., *Cell* 61:361-370 (1990); and Loetscher et al., *Cell* 61:351-359 (1990), which references are entirely incorporated herein by reference) and optionally possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran et al., *Eur. J. Biochem.* 223:831-840 (1994)), are also useful in the present invention. Truncated forms of the TNF receptors, comprising the ECD, have been detected in urine and serum as 30 kDa and 40 kDa TNFα inhibitory binding proteins (Engelmann, H. et al., *J. Biol. Chem.* 265:1531-1536 (1990)). TNF receptor multimeric molecules and TNF immunoreceptor fusion molecules, and derivatives and fragments or portions thereof, are additional examples of TNF receptor molecules which are useful in the methods and compositions of the present invention. The TNF receptor molecules which can be used in the invention are characterized by their ability to treat patients for extended periods with good to excellent alleviation of symptoms and low toxicity. Low immunogenicity and/or high affinity, as well as other undefined properties, may contribute to the therapeutic results achieved.

TNF receptor multimeric molecules useful in the present invention comprise all or a functional portion of the ECD of two or more TNF receptors linked via one or more polypeptide linkers or other nonpeptide linkers, such as polyethylene glycol (PEG). The multimeric molecules can further comprise a signal peptide of a secreted protein to direct expression of the multimeric molecule. These multimeric molecules and methods for their production have been described in U.S. application Ser. No. 08/437,533 (filed May 9, 1995), the content of which is entirely incorporated herein by reference.

TNF immunoreceptor fusion molecules useful in the methods and compositions of the present invention comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent. An example of such a TNF immunoreceptor fusion molecule is TNF receptor/IgG fusion protein. TNF immunoreceptor fusion molecules and methods for their production have been described in the art (Lesslauer et al., *Eur. J. Immunol.* 21:2883-2886 (1991); Ashkenazi et al., *Proc. Natl. Acad. Sci. USA* 88:10535-10539 (1991); Peppel et al., *J. Exp. Med.* 174:1483-1489 (1991); Kolls et al., *Proc. Natl. Acad. Sci. USA* 91:215-219 (1994); Butler et al., *Cytokine* 6 (6):616-623 (1994); Baker et al., *Eur. J. Immunol.* 24:2040-2048 (1994); Beutler et al., U.S. Pat. No. 5,447,851; and U.S. application Ser. No. 08/442,133 (filed May 16, 1995), each of which references are entirely incorporated herein by reference). Methods for producing immunoreceptor fusion molecules can also be found in Capon et al., U.S. Pat. No. 5,116,964; Capon et al., U.S. Pat. No. 5,225,538; and Capon et al., *Nature* 337:525-531 (1989), which references are entirely incorporated herein by reference.

A functional equivalent, derivative, fragment or region of TNF receptor molecule refers to the portion of the TNF receptor molecule, or the portion of the TNF receptor molecule sequence which encodes TNF receptor molecule, that is of sufficient size and sequences to functionally resemble TNF receptor molecules that can be used in the present invention (e.g., bind TNFα with high affinity and possess low immunogenicity). A functional equivalent of TNF receptor molecule also includes modified TNF receptor molecules that functionally resemble TNF receptor molecules that can be used in the present invention (e.g., bind TNFα with high affinity and possess low immunogenicity). For example, a functional equivalent of TNF receptor molecule can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., *Current Protocols in Molecular Biology*, Greene Publishing Assoc. and Wiley-Interscience, New York (1987-2003).

Cytokines include, but are not limited to all known cytokines. See, e.g., CopewithCytokines.com. Cytokine antagonists include, but are not limited to, any antibody, fragment or mimetic, any soluble receptor, fragment or mimetic, any small molecule antagonist, or any combination thereof.

Any method of the present invention can comprise a method for treating a protein mediated disorder, comprising administering an effective amount of a composition or pharmaceutical composition comprising at least one EPO mimetic hinge core mimetibody or specified portion or variant to a cell, tissue, organ, animal or patient in need of such modulation, treatment or therapy. Such a method can optionally further comprise co-administration or combination therapy for treating such immune diseases, wherein the administering of said at least one EPO mimetic hinge core mimetibody, specified portion or variant thereof, further comprises administering, before concurrently, and/or after, at least one selected from at least one other cytokines such as IL-3, -6 and -11; stem cell factor; G-CSF and GM-CSF.

Typically, treatment of pathologic conditions is effected by administering an effective amount or dosage of at least one EPO mimetic hinge core mimetibody composition that total, on average, a range from at least about 0.01 to 500 milligrams of at least one EPO mimetic hinge core mimetibody or specified portion or variant/kilogram of patient per dose, and preferably from at least about 0.1 to 100 milligrams EPO mimetic hinge core mimetibody or specified portion or variant/kilogram of patient per single or multiple administration, depending upon the specific activity of contained in the composition. Alternatively, the effective serum concentration can comprise 0.1-5000 µg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.01, 0.02, 0.03, 0.04, 0.05. 0.06, 0.07, 0.08, 009, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, and/or 30 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one EPO mimetic hinge core mimetibody or specified portion or variant of the present invention 0.01 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20, or any combination thereof, using single, infusion or repeated doses.

Dosage forms (composition) suitable for internal administration generally contain from about 0.001 milligram to about 500 milligrams of active ingredient per unit or container. In these pharmaceutical compositions the active ingredient will ordinarily be present in an amount of about 0.5-95% by weight based on the total weight of the composition.

For parenteral administration, the EPO mimetic hinge core mimetibody or specified portion or variant can be formulated as a solution, suspension, emulsion or lyophilized powder in association, or separately provided, with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Therapeutic Administration

Many known and developed modes of can be used according to the present invention for administering pharmaceutically effective amounts of at least one EPO mimetic hinge core mimetibody or specified portion or variant according to the present invention. While pulmonary administration is used in the following description, other modes of administration can be used according to the present invention with suitable results.

An EPO mimetic hinge core mimetibody of the present invention can be delivered in a carrier, as a solution, emulsion, colloid, or suspension, or as a powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthtetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

Alternative Delivery

The invention further relates to the administration of at least one EPO mimetic hinge core mimetibody or specified portion or variant by parenteral, subcutaneous, intramuscular, intravenous, bolus, vaginal, rectal, buccal, sublingual, intranasal, or transdermal means. Protein, EPO mimetic hinge core mimetibody or specified portion or variant compositions can be prepared for use for parenteral (subcutaneous, intramuscular or intravenous) administration particularly in the form of liquid solutions or suspensions; for use in vaginal or rectal administration particularly in semisolid forms such as creams and suppositories; for buccal, or sublingual administration particularly in the form of tablets or capsules; or intranasally particularly in the form of powders, nasal drops or aerosols or certain agents; or transdermally particularly in the form of a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

Pulmonary/Nasal Administration

For pulmonary administration, preferably at least one EPO mimetic hinge core mimetibody or specified portion or variant composition is delivered in a particle size effective for reaching the lower airways of the lung or sinuses. According to the invention, at least one EPO mimetic hinge core mimetibody or specified portion or variant can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of EPO mimetic hinge core mimetibody or specified portion or variants are also known in the art. All such devices can use of formulations suitable for the administration for the dispensing of EPO mimetic hinge core mimetibody or specified portion or variant in an aerosol. Such aerosols can be comprised of either solutions (both aqueous and non aqueous) or solid particles. Metered dose inhalers like the Ventolin® metered dose inhaler, typically use a propellent gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one EPO mimetic hinge core mimetibody or specified portion or variant is delivered by a dry powder inhaler or a sprayer. There are a several desirable features of an inhalation device for administering at least one EPO mimetic hinge core mimetibody or specified portion or variant of the present invention. For example, delivery by the inhalation device is advantageously reliable, reproducible, and accurate. The inhalation device can optionally deliver small dry particles, e.g. less than about 10 µm, preferably about 1-5 µm, for good respirability.

Administration of EPO Mimetic Hinge Core Mimetibody or Specified Portion or Variant Compositions as a Spray A spray including EPO mimetic hinge core mimetibody or specified portion or variant composition protein can be produced by forcing a suspension or solution of at least one EPO mimetic hinge core mimetibody or specified portion or variant through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one EPO mimetic hinge core mimetibody or specified portion or variant composition protein delivered by a sprayer have a particle size less than about 10 µm, preferably in the range of about 1 µm to about 5 µm, and most preferably about 2 µm to about 3 µm.

Formulations of at least one EPO mimetic hinge core mimetibody or specified portion or variant composition protein suitable for use with a sprayer typically include EPO mimetic hinge core mimetibody or specified portion or variant composition protein in an aqueous solution at a concentration of about 1 mg to about 20 mg of at least one EPO mimetic hinge core mimetibody or specified portion or variant composition protein per ml of solution. The formulation can include agents such as an excipient, a buffer, an isotonicity agent, a preservative, a surfactant, and, preferably, zinc. The formulation can also include an excipient or agent for stabilization of the EPO mimetic hinge core mimetibody or specified portion or variant composition protein, such as a buffer, a reducing agent, a bulk protein, or a carbohydrate. Bulk proteins useful in formulating EPO mimetic hinge core mimetibody or specified portion or variant composition proteins include albumin, protamine, or the like. Typical carbohydrates useful in formulating EPO mimetic hinge core mimetibody or specified portion or variant composition proteins include sucrose, mannitol, lactose, trehalose, glucose, or the like. The EPO mimetic hinge core mimetibody or specified portion or variant composition protein formulation can also include a surfactant, which can reduce or prevent surface-induced aggregation of the EPO mimetic hinge core mimetibody or specified portion or variant composition protein caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as mimetibodies, or specified portions or variants, can also be included in the formulation.

Administration of EPO Mimetic Hinge Core Mimetibody or Specified Portion or Variant Compositions by a Nebulizer EPO mimetic hinge core mimetibody or specified portion or variant composition protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of EPO mimetic hinge core mimetibody or specified portion or variant composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of EPO mimetic hinge core mimetibody or specified portion or variant composition protein either directly or through a coupling fluid, creating an aerosol including the EPO mimetic hinge core mimetibody or specified portion or variant composition protein. Advantageously, particles of EPO mimetic hinge core mimetibody or specified portion or variant composition protein delivered by a nebulizer have a particle size less than about 10 µm, preferably in the range of about 1 µm to about 5 µm, and most preferably about 2 µm to about 3 µm.

Formulations of at least one EPO mimetic hinge core mimetibody or specified portion or variant suitable for use with a nebulizer, either jet or ultrasonic, typically include EPO mimetic hinge core mimetibody or specified portion or variant composition protein in an aqueous solution at a concentration of about 1 mg to about 20 mg of at least one EPO mimetic hinge core mimetibody or specified portion or variant protein per ml of solution. The formulation can include agents such as an excipient, a buffer, an isotonicity agent, a preservative, a surfactant, and, preferably, zinc. The formulation can also include an excipient or agent for stabilization of the at least one EPO mimetic hinge core mimetibody or specified portion or variant composition protein, such as a buffer, a reducing agent, a bulk protein, or a carbohydrate. Bulk proteins useful in formulating at least one EPO mimetic hinge core mimetibody or specified portion or variant composition proteins include albumin, protamine, or the like. Typical carbohydrates useful in formulating at least one EPO mimetic hinge core mimetibody or specified portion or variant include sucrose, mannitol, lactose, trehalose, glucose, or the like. The at least one EPO mimetic hinge core mimetibody or specified portion or variant formulation can also include a surfactant, which can reduce or prevent surface-induced aggregation of the at least one EPO mimetic hinge core mimetibody or specified portion or variant caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as at least one EPO mimetic hinge core mimetibody or specified portion or variant protein can also be included in the formulation.

Administration of EPO Mimetic Hinge Core Mimetibody or Specified Portion or Variant Compositions by a Metered Dose Inhaler In a metered dose inhaler (MDI), a propellant, at least one EPO mimetic hinge core mimetibody or specified portion or variant, and any excipients or other additives are contained in a canister as a mixture including a liquefied compressed gas. Actuation of the metering valve releases the mixture as an aerosol, preferably containing particles in the size range of less than about 10 µm, preferably about 1 µm to about 5 µm, and most preferably about 2 µm to about 3 µm. The desired aerosol particle size can be obtained by employing a formulation of EPO mimetic hinge core mimetibody or specified portion or variant composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one EPO mimetic hinge core mimetibody or specified portion or variant for use with a metered-dose inhaler device will generally include a finely divided powder containing at least one EPO mimetic hinge core mimetibody or specified portion or variant as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluoroalkane-227), or the like. Preferably the propellant is a hydrofluorocarbon. The surfactant can be chosen to stabilize the at least one EPO mimetic hinge core mimetibody or specified portion or variant as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein such as protein can also be included in the formulation.

One of ordinary skill in the art will recognize that the methods of the current invention can be achieved by pulmonary administration of at least one EPO mimetic hinge core mimetibody or specified portion or variant compositions via devices not described herein.

Mucosal Formulations and Administration

For absorption through mucosal surfaces, compositions and methods of administering at least one EPO mimetic hinge core mimetibody or specified portion or variant include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. Nos. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. Nos. 5,849,695).

Oral Formulations and Administration

Formulations for oral rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, .alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations may contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. No. 5,879,681 and U.S. Pat. No. 5,5,871,753 are used to deliver biologically active agents orally are known in the art.

Transdermal Formulations and Administration

For transdermal administration, the at least one EPO mimetic hinge core mimetibody or specified portion or variant is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

Prolonged Administration and Formulations

It can be sometimes desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, depot or implant formulations, e.g. gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

Having generally described the invention, the same will be more readily understood by reference to the following examples, which are provided by way of illustration and are not intended as limiting.

EXAMPLE 1

Cloning and Expression of an EPO Mimetic Hinge Core Mimetibody in Mammalian Cells A typical mammalian expression vector contains at least one promoter element, which mediates the initiation of transcription of mRNA, the EPO mimetic hinge core mimetibody or specified portion or variant coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded EPO mimetic hinge core mimetibody or specified portion or variant. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227: 277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of EPO mimetic hinge core mimetibody or specified portion or variants.

The expression vectors pC1 and pC4 contain the strong promoter (LTR) of the Rous Sarcoma Virus (Cullen, et al., Molec. Cell. Biol. 5:438-447 (1985)) plus a fragment of the CMV-enhancer (Boshart, et al., Cell 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells

The vector pC4 is used for the expression of EPO mimetic hinge core mimetibody or specified portion or variant. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (e.g., alpha minus MEM, Life Technologies, Gaithersburg, Md.) supplemented with the chemotherapeutic agent methotrexate. The amplification of the DHFR genes in cells resistant to methotrexate (MTX) has been well documented (see, e.g., F. W. Alt, et al., J. Biol. Chem. 253:1357-1370 (1978); J. L. Hamlin and C. Ma, Biochem. et Biophys. Acta 1097:107-143 (1990); and M. J. Page and M. A. Sydenham, Biotechnology 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., Molec. Cell. Biol. 5:438-447 (1985)) plus a fragment isolated from the enhancer of the immediate early gene of human cytomegalovirus (CMV) (Boshart, et al., Cell 41:521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human b-actin promoter, the SV40 early or late promoters or the long terminal repeats from other retroviruses, e.g., HIV and HTLVI. Clontech's Tet-Off and Tet-On gene expression systems and similar systems can be used to express the EPO in a regulated way in mammalian cells (M. Gossen, and H. Bujard, Proc. Natl. Acad. Sci. USA 89: 5547-5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with restriction enzymes and then dephosphorylated using calf intestinal phosphatase by procedures known in the art. The vector is then isolated from a 1% agarose gel.

The DNA sequence encoding the complete EPO mimetic hinge core mimetibody or specified portion or variant is used, corresponding to HC and LC variable regions of an EPO mimetic hinge core mimetibody of the present invention, according to known method steps. Isolated nucleic acid encoding a suitable human constant region (i.e., HC and LC regions) is also used in this construct.

The isolated variable and constant region encoding DNA and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 µg of the expression plasmid pC4 is cotransfected with 0.5 µg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 µg/ml G418. After 2 days, the cells are trypsinized and seeded in hybridoma cloning plates (Greiner, Germany) in alpha minus MEM supplemented with 10, 25, or 50 ng/ml of methotrexate plus 1 µg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100-200 mM. Expression of the desired gene product is analyzed, for instance, by SDS-PAGE and Western blot or by reverse phase HPLC analysis.

EXAMPLE 2

Non-Limiting Example of an EPO Mimetic Hinge Core Mimetibody of the Invention

Background: EMP-1 (EPO mimetic peptide-1) is a 20 amino acid peptide with no sequence homology to human erythropoietin (HuEPO), but with the ability (as a dimer) to activate the EPO receptor (Wrighton et al, 1996, Science, vol. 273, 458-463). However, its relatively low activity (10,000 to 100,000 fold less than HuEPO) and short half-life (ex-vivo half-life of 8 hours in 50% serum, in vivo half-life unknown), compromise its utility as a therapeutic. Therefore, a way was needed to confer upon the peptide a longer half-life, without disturbing, and possibly improving its potency. To this end, several attempts have been made to increase the activity of EMP-1 by stabilizing the dimerization of the peptide or by incorporating the peptide into larger structures to increase half-life. Wrighten et al. (1997, Nature Biotechnology, vol. 15, 1261-65) combined biotin labeled EMP-1 with streptavidin to stabilize dimerization. They saw a 100 fold increase in activity in an in vitro cell proliferation assay. They also used anti-biotin antibodies to stabilize the peptide dimer, however only a 10-fold increase in activity was seen. The same authors prepared a chemically defined dimeric form of EMP-1. In this case an 100-fold increase in activity was seen in vivo. Another group sought to improve the activity of EMP-1 through covalent linkage to polyethylene glycol (PEG) (Johnson et al., 1997, Chem. & Bio., vol. 4 (12), 939-50). They reported an increase in potency of up to 1000 fold, however the construct was found to be immunogenic in mice (the antibodies were directed to the peptide) (Dana Johnson, Personal communications). Kuai et al. (2000, J. Peptide Res., vol. 56, 59-62) inserted the EMP-1 peptide into the sequence of plasminogen activator inhibitor-1, (PAI-1). It was thought that the insertion of EMP-1 into this scaffold would both stabilize dimerization and increase half-life. In an in vivo assay the potency of this construct was seen to be significantly higher, such as more than 2500 fold higher than EMP-1 alone. It should be noted that different in vitro assays and in vivo models were used in these studies and the reported potencies may not be comparable to each other or to results presented herein.

EPO Mimetic Hinge Core Mimetibody of the Present Invention

A specific, non-limiting, example of this invention is the EMP-hinge core mimetibody construct where V is the first several N-terminal amino acids of a naturally occurring HC or LC antibody, P is a single copy of the bioactive EMP-1 peptide and L is a tandem repeat of either Gly-Ser or Gly-Gly-Gly-Ser flexible linker, H is a hinge core region and CH2 & CH3 are of the IgG1 or IgG4 isotype subclass. It is thought that this structure will constrain the EMP-1 peptide, but allow sufficient flexibility such that the dimerization of the peptides as part of the assembled homodimer is stabilized. In support of this, the activity of EMP-hinge core mimetibody in an in vitro cell proliferation assay is more than 500 fold greater than the EMP-1 peptide and only substantially similar to recombinant HuEPO (rHuEPO). In addition, it is expected that the half-life of this construct will be many times that of rHuEPO or the EMP-1 peptide alone and similar to that of an IgG. Consistently, normal mice treated with EMP-hinge core mimetibody attain a significantly higher maximal hematocrit compared to mice treated with rHuEPO, when equal activity units are given, and elevated levels are maintained for a longer period. This construct is efficiently secreted from cells and appears to be properly folded; overcoming problems associated with $1^{st}$ generation mimetibodies.

In addition to the basic structure described above, variants with potentially favorable biological characteristics are described. These include constructs that may have a decreased tendency to self-associate, reduced immune effector functions or decreased immunogenicity. Other modifications that confer desired characteristics such as improved conformation of the biologically active peptide, and transfer across the blood-brain barrier are envisioned. The proposed variants and modifications may be combined in any fashion to yield constructs with desired activities.

Using recombinant DNA methods, the EMP-1 peptide was inserted into an intermediate vector between an immunoglobulin signal peptide and a human J sequence. This was done using complementary synthetic oligonucletides with ends compatible with the restriction sites present in the vector These oligonucleotides comprised coding sequences for the signal peptidase consensus site (QIQ), the EMP-1 peptide (SEQ ID NO:2), and a flexible linker composed of either GS or GGGS. A restriction fragment containing the above-mentioned functional elements was then transferred into an expression vector. This vector contained the anti-CD4 immunoglobulin promoter and enhancer, and the coding sequence for a human IgG1 hinge core sequence, and a portion of an IgG1 hinge core region, CPPCP (109-113 of SEQ ID NO:66, as shown in FIG. 36C), an HC constant region 2 (CH2) and constant region 3 (CH3) as well as the necessary elements for plasmid replication and selection in bacteria and selection for stable expressers in mammalian cells.

This plasmid was linearized and introduced into the NSO mouse myeloma cell line via electroporation. Resistant cells were selected and high expressers of EMP-hinge core mimetibody were identified by ELISA assay of culture supernatants. Purification of the construct from cell culture supernatants was accomplished by standard proteinA affinity chromatography. Passage of the purified product through SDS-containing polyacrylamide gels under both denaturing and reducing conditions confirmed the expected size of the purified product. The identity of the purified protein was further confirmed by mass spectrometry and N-terminal sequencing.

The amino acid sequences of EMP-hinge core mimetibodes are shown below. Functional domains are annotated above the peptide coding sequence. The three amino acid signal peptide consensus sequence corresponds to the first three amino acids of a naturally occurring immunoglobulin. These amino acids are thought to contribute to the efficient removal of the signal peptide by signal peptidase in the endoplasmic reticulum. This sequence is immediately followed by the EMP-1 coding sequence. The two C-terminal amino acids of the EMP-1 sequence combined with the next six amino acids form a flexible linker characterized by the Gly-Gly-Gly-Ser repeat. A human joining (J) region sequence follows. It is thought that the J sequence will provide even more flexibility to allow the EMP-1 dimmer to assume the proper conformation, and allow the dimmer to protrude from the globular structure of the immunoglobulin and penetrate into the cleft between two EPO receptors. The HC hinge region is also included in the construct immediately following the J region. There are three cysteines in the IgG1 hinge region (highlighted). The first would normally pair to the immunoglobulin light chain (LC) and the second two participate in interchain bonds between two HCs. The remainder of the sequence is composed of the CH2 & CH3 regions, which constitute the bulk of the protein. One of the reasons that immunoglobulins are believed to have a long serum half-life is their ability to bind the FcRn that extends the serum half-life by returning pinocytosed immunoglobulin back to the extracellular space. The binding site of the FcRn overlaps the junction of the CH2 and CH3 regions (Sheilds et al, 2001, J. Biol. Chem., vol. 276 (9), 6591-6604).

The peptide sequence of EMP-hinge core mimetibody showing important functional domains.

```
                                                        (SEQ ID NO: 82)
    V    EMP-1 Peptide       Linker Hinge IgG1 CH2
  1 QIQGGTYSCHFGPLTWVCKPQGG GS    CPPCP APELLGGP IgG1 CH2 ------------------------------------------------------
 61 SVFLFPPKPKDTLMISRTPEVTCVVVDVSHEDPEVKFNWYVDGVEVHNAKTKPREEQYNS ~~~~~~~~~~~~~~~~~~~~~~~~~~~~~~~~~~~~~~~~~~~~  IgG1 CH3
122 TYRVVSVLTVLHQDWLNGKEYKCKVSNKALPAPTEKTISKAKGQPREPQVYTLPPSRDEL IgG1 CH3
183 TKNQVSLTCLVKGFYPSDIAVEWESNGQPENNYKTTPPVLDSDGSFFLYSKLTVDKSRWQ IgG1 CH3
241 QGNVFSCSVMHEALHNHYTQKSLSLSPGK (SEQ ID NO: 83)
    V    EMP-1 Peptide       Linker Hinge IgG1 CH2
  1 QIQGGTYSCHFGPLTWVCKPQGG GGGS   CPPCP APELLGGP IgG1 CH2 ------------------------------------------------------
 61 SVFLFPPKPKDTLMISRTPEVTCVVVDVSHEDPEVKFNWYVDGVEVHNAKTKPREEQYNS ~~~~~~~~~~~~~~~~~~~~~~~~~~~~~~~~~~~~~~~~~~~~  IgG1 CH3
122 TYRVVSVLTVLHQDWLNGKEYKCKVSNKALPAPIEKTISKAKGQPREPQVYTLPPSRDEL IgG1 CH3
183 TKNQVSLTCLVKGFYPSDIAVEWESNGQPENNYKTTPPVLDSDGSFFLYSKLTVDKSRWQ IgG1 CH3
241 QGNVFSCSVMHEALHNHYTQKSLSLSPGK (SEQ ID NO: 84)
    V    EMP-1 Peptide       Linker Hinge IgG1 CH2
  1 QIQGGTYSCHFGPLTWVCKPQGG GSGGGS CPPCP APELLGGP IgG1 CH2 ------------------------------------------------------
 61 SVFLFPPKPKDTLMISRTPEVTCVVVDVSHEDPEVKFNWYVDGVEVHNAKTKPREEQYNS ~~~~~~~~~~~~~~~~~~~~~~~~~~~~~~~~~~~~~~~~~~~~  IgG1 CH3
122 TYRVVSVLTVLHQDWLNGKEYKCKVSNKALPAPIEKTISKAKGQPREPQVYTLPPSRDEL IgG1 CH3
183 TKNQVSLTCLVKGFYPSDIAVEWESNGQPENNYKTTPPVLDSDGSFFLYSKLTVDKSRWQ IgG1 CH3
241 QGNVFSCSVMHEALHNHYTQKSLSLSPGK (SEQ ID NO: 85)
    V    EMP-1 Peptide       Linker Hinge IgG1 CH2
  1 QIQGGTYSCHFGPLTWVCKPQGG GS    CPPCP APEAAGGP IgG1 CH2 ------------------------------------------------------
 61 SVFLFPPKPKDTLMISRTPEVTCVVVDVSHEDPEVKFNWYVDGVEVHNAKTKPREEQYNS ~~~~~~~~~~~~~~~~~~~~~~~~~~~~~~~~~~~~~~~~~~~~  IgG1 CH3
122 TYRVVSVLTVLHQDWLNGKEYKCKVSNKALPAPIEKTISKAKGQPREPQVYTLPPSRDEL IgG1 CH3
183 TKNQVSLTCLVKGFYPSDIAVEWESNGQPENNYKTTPPVLDSDGSFFLYSKLTVDKSRWQ IgG1 CH3
241 QGNVFSCSVMHEALRNHYTQKSLSLSPGK (SEQ ID NO: 86)
    V    EMP-1 Peptide       Linker Hinge IgG1 CH2
  1 QIQGGTYSCHFGPLTWVCKPQGG GGGS    CPPCP APEAAGGP IgG1 CH2 ------------------------------------------------------
 61 SVFLFPPKPKDTLMISRTPEVTCVVVDVSHEDPEVKFNWYVDGVEVRNAKTKPREEQYNS ~~~~~~~~~~~~~~~~~~~~~~~~~~~~~~~~~~~~~~~~~~~~  IgG1 CH3
122 TYRVVSVLTVLHQDWLNGKEYKCKVSNKALPAPIEKTISKAKGQPREPQVYTLPPSRDEL IgG1 CH3
183 TKNQVSLTCLVKGFYPSDIAVEWESNGQPENNYKTTPPVLDSDGSFFLYSKLTVDKSRWQ IgG1 CH3
241 QGNVFSCSVMHEALHNHYTQKSLSLSPGK
```

-continued

```
                                                                    (SEQ ID NO: 87)
       V    EMP-1 Peptide        Linker  Hinge IgG4 CH2
     1 QIQGGTYSCHFGPLTWVCKPQGG GS      CPPCP APEFLGGP IgG 4 CH2 ---------------------------------------
    61 SVFLFPPKPKDTLMISRTPEVTCVVVDVSQEDPEVQFNWYVDGVEVHNAKTKPREEQFNS ~~~~~~~~~~~~~~~~~~~~~~~~~~~~~~~~~~~~~~~~~~  IgG4 CH3
   121 TYRVVSVLTVLHQDWLNGKEYKCKVSNKGLPSSIEKTISKAKGQPREPQVYTLPPSQEEM IgG4 CH3
   183 TKNQVSLTCLVKGFYPSDIAVEWESNGQPENNYKTTPPVLDSDGSFFLYSRLTVDKSRWQ IgG4 CH3
   241 EGNVFSCSVMHEALHNHYTQKSLSLSLGK (SEQ ID NO: 88)
       V    EMP-1 Peptide        Linker  Hinge IgG4 CH2
     1 QIQGGTYSCHFGPLTWVCKPQGG GS      CPPCP APEAAGGP IgG 4 CH2 ---------------------------------------
    61 SVFLFPPKPKDTLMISRTPEVTCVVVDVSQEDPEVQFNWYVDGVEVHNAKTKPREEQFNS ~~~~~~~~~~~~~~~~~~~~~~~~~~~~~~~~~~~~~~~~~~  IgG4 CH3
   121 TYRVVSVLTVLHQDWLNGKEYKCKVSNKGLPSSIEKTISKAKGQPREPQVYTLPPSQEEM IgG4 CH3
   183 TKNQVSLTCLVKGFYPSDIAVEWESNGQPENNYKTTPPVLDSDGSFFLYSRLTVDKSRWQ IgG4 CH3
   241 EGNVFSCSVMHEALHNHYTQKSLSLSLGK (SEQ ID NO: 89)
       V    EMP-1 Peptide        Linker  Hinge IgG4 CH2
     1 QIQGGTYSCHFGPLTWVCKPQGG GGGS    CPPCP APEAAGGP IgG 4 CH2 ---------------------------------------
    61 SVFLFPPKPKDTLMISRTPEVTCVVVDVSQEDPEVQFNWYVDGVEVHNAKTKPREEQFNS ~~~~~~~~~~~~~~~~~~~~~~~~~~~~~~~~~~~~~~~~~~  IgG4 CH3
   121 TYRVVSVLTVLHQDWLNGKEYKCKVSNKGLPSSIEKTISKAKGQPREPQVYTLPPSQEEM IgG4 CH3
   183 TKNQVSLTCLVKGFYPSDIAVEWESNGQPENNYKTTPPVLDSDGSFFLYSRLTVDKSRWQ IgG4 CH3
   241 EGNVFSCSVMHEALHNHYTQKSLSLSLGK
```

It is well known that two IgG heavy chains are assembled during cellular processing via disulfide bonds between cysteines located in the hinge region to form a homodimer. It is expected that this will also occur between the modified peptides to form the assembled EMP-hinge core mimetibody construct. In addition, it is expected that the intrachain disulfide bond between the two cysteines in the EMP-1 peptide will also form. The expected structure of EMP-Hinge core mimetibody contains two EMP-1 peptides. The spatial arrangement of the peptides at the N-terminus along with the flexibility of adjoining sequences should allow the peptides to form the bioacive dimer.

The activity of EMP-Hinge core mimetibody was first tested in an in vitro bioactivity assay. For this assay, the EPO dependent UT-7/EPO cell line, derived from a patient with acute megakaryoblastic leukemia, was used (Komatsu et al., 1993, Blood, vol. 82 (2), 456-464). These cells undergo programmed cell death 48 to 72 hours after withdraw from media supplemented with rHuEPO. Cells that have been incubated in the absence of rHuEPO for 24 hours can be saved if treated with rHuEPO or an EPO agonist. EMP-Hinge core mimetibody was added to cells starved without rHuEPO and cell viability was determined 48 hours after treatment using the tetrazolium compound MTS (CellTiter 96 Aq$_{ueous}$ One Solution, Promega) that is metabolized by living cells to yield a product with an absorbance that can be measured. Results of a typical assay showed the potency of EMP-Hinge core mimetibody on a molar basis to be 500 fold greater than the EMP-1 peptide and 5 fold less than rHuEPO. In addition, these same cells were stimulated with EMP-Hinge core mimetibody and tyrosine phosphorylation patterns visualized by running cell lysate through a polyacrylamide gel. The pattern exhibited by EMP-Hinge core mimetibody was similar to that of rHuEPO, indicating that the mechanism by which EMP-Hinge core mimetibody acts on these cells is like that of rHuEPO.

In vivo studies were done in normal mice to compare the half-life of EMP-Hinge core mimetibody to that of rHuEPO and to compare their effects on erythropoiesis. When mice were dosed equally, EMP-Hinge core mimetibody gave a higher maximal response and the response was prolonged compared to rHuEPO.

The serum concentrations of both rHuEPO and EMP-Hinge core mimetibody were measured by ELISA. The approximate half-life of EMP hinge core mimetibodies was at least several times that of rHuEPO.

It has been shown that mutation of two lysine (L) residues, L234 & L235, in the IgG1 lower hinge region to alanine (A) will abrogate the ability of the immunoglobulin to mediate complement dependent cytotoxicity (CDC) and antibody dependant cellular cytotoxicity (ADCC) (Hezereh et al., 2001, J. Virol., vol. 75 (24), 12161-68). Preliminary studies have shown that EMP-Hinge core mimetibody does not mediate complement lysis of cells that express the EPO receptor. This may be due to the low number of receptors that are found on erythroid progenitor cells. In addition the in vivo expansion of erythroid progenitors as evidenced by significant increases in hematocrit supports the possible functional irrelevance of immune effector functions. However, while no effector function associated affects have been observed, there remains an interest in introducing these mutations as a precautionary step.

Another modification that would result in a decrease in mediation of immune effector functions is the removal of the glycosylation attachment site. This can be accomplished by mutation of the asparagine at position 297 (N297) to glutamine (Q). Additional changes can optionally include replacing the threonine (T) with an alternative amino acid to reduce or modify O-glycosylation, e.g., T34 or T47 with Aglycosylated versions of the IgG1 subclass are known to be poor mediators of immune effector function (Jefferis et al. 1998, 1 mmol. Rev., vol. 163, 50-76).

Advantages: The novel construct, EMP-Hinge core mimetibody described above offers an alternative way of displaying the bioactive peptide EMP-1. The activity of this construct is in the range of rHuEPO and the in vivo half-life is similar to that of an IgG. In addition, proposed modifications are expected to, in combination and in addition to the novel features of EMP-Hinge core mimetibody, enhance the utility of the EMP-Hinge core mimetibody construct.

It will be clear that the invention can be practiced otherwise than as particularly described in the foregoing description and examples.

Numerous modifications and variations of the present invention are possible in light of the above teachings and, therefore, are within the scope of the present invention

What is claimed is:

1. A method for treating a human having an erythropoietin deficiency related condition, comprising
   (a) administering to said human having an erythropoietin deficiency related condition, a composition comprising an effective amount of a polypeptide comprising the amino acid sequence of SEQ ID NO: 88.

2. A method according to claim 1, wherein said effective amount is 0.001-50 mg per kilogram of said human.

3. A method according to claim 1, wherein said administering is a mode selected from the group consisting of parenteral administration, subcutaneous administration, intramuscular administration, and intravenous administration.

4. A method according to claim 1, wherein said erythropoietin deficiency related condition is selected from the group consisting of anemia, myelodysplastic syndrome, cancer treatment related anemia, radiotherapy or chemotherapy related anemia, viral or bacterial infection treatment related anemia, renal anemia, anemia of prematurity, pediatric or adult cancer-associated anemia, anemia associated with lymphoma, myeloma, multiple myeloma, AIDS-associated anemia, concomitant treatment for patients with or without autologous blood donation awaiting elective surgery, preoperative and post operative for surgery, autologous blood donation or transfusion, preoperative management, cyclic neutropenia, congenital agranulocytosis, end-stage renal disease, anemia associated with dialysis, chronic renal insufficiency, and a primary hemopoietic disease.

5. A method according to claim 1, wherein said primary hemopoietic disease is selected from the group consisting of congenital hypoplastic anemia, thalassemia major, beta thalassemia, sickle cell disease, and vaso-occlusive complications of sickle cell disease.

* * * * *

SEQUENCE LISTING

```
<160> NUMBER OF SEQ ID NOS: 89

<210> SEQ ID NO 1
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 1

Tyr Xaa Cys Xaa Xaa Gly Pro Xaa Thr Trp Xaa Cys Xaa Pro
1               5                   10

<210> SEQ ID NO 2
<211> LENGTH: 20
<212> TYPE: PRT
<213> ORGANISM: Artificial
<220> FEATURE:
<223> OTHER INFORMATION: synthetic peptide

<400> SEQUENCE: 2

Gly Gly Thr Tyr Ser Cys His Phe Gly Pro Leu Thr Trp Val Cys Lys
1               5                   10                  15

Pro Gln Gly Gly
```

```
<210> SEQ ID NO 3
<211> LENGTH: 20
<212> TYPE: PRT
<213> ORGANISM: Artificial
<220> FEATURE:
<223> OTHER INFORMATION: synthetic peptide

<400> SEQUENCE: 3

Gly Gly Asp Tyr His Cys Arg Met Gly Pro Leu Thr Trp Val Cys Lys
1               5                   10                  15

Pro Leu Gly Gly
            20

<210> SEQ ID NO 4
<211> LENGTH: 20
<212> TYPE: PRT
<213> ORGANISM: Artificial
<220> FEATURE:
<223> OTHER INFORMATION: synthetic peptide

<400> SEQUENCE: 4

Gly Gly Val Tyr Ala Cys Arg Met Gly Pro Ile Thr Trp Val Cys Ser
1               5                   10                  15

Pro Leu Gly Gly
            20

<210> SEQ ID NO 5
<211> LENGTH: 20
<212> TYPE: PRT
<213> ORGANISM: Artificial
<220> FEATURE:
<223> OTHER INFORMATION: synthetic peptide

<400> SEQUENCE: 5

Val Gly Asn Tyr Met Cys His Phe Gly Pro Ile Thr Trp Val Cys Arg
1               5                   10                  15

Pro Gly Gly Gly
            20

<210> SEQ ID NO 6
<211> LENGTH: 20
<212> TYPE: PRT
<213> ORGANISM: Artificial
<220> FEATURE:
<223> OTHER INFORMATION: synthetic peptide

<400> SEQUENCE: 6

Gly Gly Leu Tyr Leu Cys Arg Phe Gly Pro Val Thr Trp Asp Cys Gly
1               5                   10                  15

Tyr Lys Gly Gly
            20

<210> SEQ ID NO 7
<211> LENGTH: 20
<212> TYPE: PRT
<213> ORGANISM: Artificial
<220> FEATURE:
<223> OTHER INFORMATION: synthetic peptide

<400> SEQUENCE: 7

Gly Gly Thr Tyr Ser Cys His Phe Gly Pro Leu Thr Trp Val Cys Lys
1               5                   10                  15
```

```
Pro Gln Gly Gly
        20

<210> SEQ ID NO 8
<211> LENGTH: 23
<212> TYPE: PRT
<213> ORGANISM: Artificial
<220> FEATURE:
<223> OTHER INFORMATION: synthetic peptide

<400> SEQUENCE: 8

Gly Gly Thr Tyr Ser Cys His Phe Gly Pro Leu Thr Trp Val Cys Lys
1               5                   10                  15

Pro Gln Gly Gly Ser Ser Lys
        20

<210> SEQ ID NO 9
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 9

Cys Xaa Xaa Gly Pro Xaa Thr Trp Xaa Cys
1               5                   10

<210> SEQ ID NO 10
<211> LENGTH: 19
<212> TYPE: PRT
<213> ORGANISM: Artificial
<220> FEATURE:
<223> OTHER INFORMATION: synthetic peptide

<400> SEQUENCE: 10

Gly Gly Thr Tyr Ser Cys His Gly Pro Leu Thr Trp Val Cys Lys Pro
1               5                   10                  15

Gln Gly Gly

<210> SEQ ID NO 11
<211> LENGTH: 19
<212> TYPE: PRT
<213> ORGANISM: Artificial
<220> FEATURE:
<223> OTHER INFORMATION: synthetic peptide

<400> SEQUENCE: 11

Val Gly Asn Tyr Met Ala His Met Gly Pro Ile Thr Trp Val Cys Arg
1               5                   10                  15

Pro Gly Gly
```

<210> SEQ ID NO 12
<211> LENGTH: 18
<212> TYPE: PRT
<213> ORGANISM: Artificial
<220> FEATURE:
<223> OTHER INFORMATION: synthetic peptide

<400> SEQUENCE: 12

Gly Gly Pro His His Val Tyr Ala Cys Arg Met Gly Pro Leu Thr Trp
1               5                   10                  15

Ile Cys

<210> SEQ ID NO 13
<211> LENGTH: 18
<212> TYPE: PRT
<213> ORGANISM: Artificial
<220> FEATURE:
<223> OTHER INFORMATION: synthetic peptide

<400> SEQUENCE: 13

Gly Gly Thr Tyr Ser Cys His Phe Gly Pro Leu Thr Trp Val Cys Lys
1               5                   10                  15

Pro Gln

<210> SEQ ID NO 14
<211> LENGTH: 20
<212> TYPE: PRT
<213> ORGANISM: Artificial
<220> FEATURE:
<223> OTHER INFORMATION: synthetic peptide

<400> SEQUENCE: 14

Gly Gly Leu Tyr Ala Cys His Met Gly Met Thr Trp Val Cys Gln
1               5                   10                  15

Pro Leu Arg Gly
            20

<210> SEQ ID NO 15
<211> LENGTH: 22
<212> TYPE: PRT
<213> ORGANISM: Artificial
<220> FEATURE:
<223> OTHER INFORMATION: synthetic peptide

<400> SEQUENCE: 15

Thr Ile Ala Gln Tyr Ile Cys Tyr Met Gly Pro Glu Thr Trp Glu Cys
1               5                   10                  15

Arg Pro Ser Pro Lys Ala
            20

<210> SEQ ID NO 16
<211> LENGTH: 13
<212> TYPE: PRT
<213> ORGANISM: Artificial
<220> FEATURE:
<223> OTHER INFORMATION: synthetic peptide

<400> SEQUENCE: 16

Tyr Ser Cys His Phe Gly Pro Leu Thr Trp Val Cys Lys
1               5                   10

<210> SEQ ID NO 17
<211> LENGTH: 11
<212> TYPE: PRT
<213> ORGANISM: Artificial

```
<220> FEATURE:
<223> OTHER INFORMATION: synthetic peptide

<400> SEQUENCE: 17

Tyr Cys His Phe Gly Pro Leu Thr Trp Val Cys
1               5                   10

<210> SEQ ID NO 18
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 18

Xaa Xaa Xaa Gly Pro Xaa Thr Trp Xaa Xaa
1               5                   10

<210> SEQ ID NO 19
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (12)..(12)
```

-continued

<223> OTHER INFORMATION: Xaa can be any naturally occurring amino acid

<400> SEQUENCE: 19

Tyr Xaa Xaa Xaa Xaa Gly Pro Xaa Thr Trp Xaa Xaa
1               5                   10

<210> SEQ ID NO 20
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 20

Xaa Tyr Xaa Xaa Xaa Xaa Gly Pro Xaa Xaa Xaa Xaa Xaa Xaa
1               5                   10

<210> SEQ ID NO 21
<211> LENGTH: 18
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

```
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 21

Xaa Tyr Xaa Cys Xaa Xaa Gly Pro Xaa Thr Trp Xaa Cys Xaa Xaa Xaa
1               5                   10                  15

Leu Leu

<210> SEQ ID NO 22
<211> LENGTH: 20
<212> TYPE: PRT
<213> ORGANISM: Artificial
<220> FEATURE:
<223> OTHER INFORMATION: synthetic peptide

<400> SEQUENCE: 22

Gly Gly Leu Tyr Leu Cys Arg Phe Gly Pro Val Thr Trp Asp Cys Gly
1               5                   10                  15

Tyr Lys Gly Gly
            20

<210> SEQ ID NO 23
<211> LENGTH: 20
<212> TYPE: PRT
<213> ORGANISM: Artificial
<220> FEATURE:
<223> OTHER INFORMATION: synthetic peptide

<400> SEQUENCE: 23

Gly Gly Thr Tyr Ser Cys His Phe Gly Pro Leu Thr Trp Val Cys Lys
1               5                   10                  15

Pro Gln Gly Gly
            20

<210> SEQ ID NO 24
<211> LENGTH: 20
<212> TYPE: PRT
<213> ORGANISM: Artificial
<220> FEATURE:
<223> OTHER INFORMATION: synthetic peptide

<400> SEQUENCE: 24

Val Gly Asn Tyr Met Cys His Phe Gly Pro Ile Thr Trp Val Cys Arg
1               5                   10                  15

Pro Gly Gly Gly
            20
```

<210> SEQ ID NO 25
<211> LENGTH: 20
<212> TYPE: PRT
<213> ORGANISM: Artificial
<220> FEATURE:
<223> OTHER INFORMATION: synthetic peptide

<400> SEQUENCE: 25

Gly Gly Val Tyr Ala Cys Arg Met Gly Pro Ile Thr Trp Val Cys Ser
1               5                   10                  15
Pro Leu Gly Gly
            20

<210> SEQ ID NO 26
<211> LENGTH: 22
<212> TYPE: PRT
<213> ORGANISM: Artificial
<220> FEATURE:
<223> OTHER INFORMATION: synthetic peptide

<400> SEQUENCE: 26

Thr Ile Ala Gln Tyr Ile Cys Tyr Met Gly Pro Glu Thr Trp Glu Cys
1               5                   10                  15
Arg Pro Ser Pro Lys Ala
            20

<210> SEQ ID NO 27
<211> LENGTH: 13
<212> TYPE: PRT
<213> ORGANISM: Artificial
<220> FEATURE:
<223> OTHER INFORMATION: synthetic peptide

<400> SEQUENCE: 27

Tyr Ser Cys His Phe Gly Pro Leu Thr Trp Val Cys Lys
1               5                   10

<210> SEQ ID NO 28
<211> LENGTH: 11
<212> TYPE: PRT
<213> ORGANISM: Artificial
<220> FEATURE:
<223> OTHER INFORMATION: synthetic peptide

<400> SEQUENCE: 28

Tyr Cys His Phe Gly Pro Leu Thr Trp Val Cys
1               5                   10

<210> SEQ ID NO 29
<211> LENGTH: 12
<212> TYPE: PRT
<213> ORGANISM: Artificial
<220> FEATURE:
<223> OTHER INFORMATION: synthetic peptide

<400> SEQUENCE: 29

Ser Cys His Phe Gly Pro Leu Thr Trp Val Cys Lys
1               5                   10

<210> SEQ ID NO 30
<211> LENGTH: 12
<212> TYPE: PRT
<213> ORGANISM: Artificial
<220> FEATURE:
<223> OTHER INFORMATION: synthetic peptide -continued

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 30

Ala Xaa Xaa Xaa Xaa Gly Pro Xaa Thr Trp Xaa Xaa
1               5                   10

<210> SEQ ID NO 31
<211> LENGTH: 125
<212> TYPE: PRT
<213> ORGANISM: Homo sapiens
<220> FEATURE:
<221> NAME/KEY: MISC_FEATURE
<222> LOCATION: (1)..(125)
<223> OTHER INFORMATION: Vh1 heavy chain variable region
<220> FEATURE:
<221> NAME/KEY: MISC_FEATURE
<222> LOCATION: (1)..(31)
<223> OTHER INFORMATION: framework 1
<220> FEATURE:
<221> NAME/KEY: MISC_FEATURE
<222> LOCATION: (32)..(32)
<223> OTHER INFORMATION: complementarity determinng region 1 (CDR1), X
     is 3-20 (5) of any amino acids.
<220> FEATURE:
<221> NAME/KEY: MISC_FEATURE
<222> LOCATION: (33)..(46)
<223> OTHER INFORMATION: framework 2
<220> FEATURE:
<221> NAME/KEY: MISC_FEATURE
<222> LOCATION: (47)..(47)
<223> OTHER INFORMATION: complementarity determinng region 2 (CDR2), X
     is 10-30 (17) of any amino acids.
<220> FEATURE:
<221> NAME/KEY: MISC_FEATURE
<222> LOCATION: (48)..(79)
<223> OTHER INFORMATION: framework 3
<220> FEATURE:
<221> NAME/KEY: MISC_FEATURE
<222> LOCATION: (80)..(80)
<223> OTHER INFORMATION: complementarity determinng region 3 (CDR3), X
     is 25-55 (42) of any amino acids.
<220> FEATURE:
<221> NAME/KEY: MISC_FEATURE
<222> LOCATION: (81)..(125)
<223> OTHER INFORMATION: framework 4

<400> SEQUENCE: 31

Gln Val Gln Leu Leu Val Gln Ser Gly Ala Glu Val Lys Lys Pro Gly
1               5                   10                  15
```

```
Ala Ser Val Lys Val Ser Cys Lys Ala Ser Gly Tyr Thr Phe Thr Xaa
            20                  25                  30

Trp Val Arg Gln Ala Pro Gly Gln Gly Leu Glu Trp Met Gly Xaa Arg
            35                  40                  45

Val Thr Met Thr Arg Asp Thr Ser Thr Ser Thr Ala Tyr Met Glu Leu
            50                  55                  60

Ser Ser Leu Arg Ser Glu Asp Thr Ala Val Tyr Tyr Cys Ala Arg Xaa
 65                  70                  75                  80

Trp Gly Gln Gly Thr Leu Val Thr Val Ser Ser Gly Ser Thr Lys Gly
                    85                  90                  95

Pro Ser Val Phe Pro Leu Ala Pro Ser Ser Lys Ser Thr Ser Gly Gly
                    100                 105                 110

Thr Ala Ala Leu Gly Cys Leu Val Lys Asp Tyr Phe Pro
                    115                 120                 125

<210> SEQ ID NO 32
<211> LENGTH: 124
<212> TYPE: PRT
<213> ORGANISM: Homo sapiens
<220> FEATURE:
<221> NAME/KEY: MISC_FEATURE
<222> LOCATION: (1)..(124)
<223> OTHER INFORMATION: Vh2 heavy chain variable region
<220> FEATURE:
<221> NAME/KEY: MISC_FEATURE
<222> LOCATION: (1)..(30)
<223> OTHER INFORMATION: framework 1
<220> FEATURE:
<221> NAME/KEY: MISC_FEATURE
<222> LOCATION: (31)..(31)
<223> OTHER INFORMATION: complementarity determinng region 1 (CDR1), X
      is 3-20 (7) of any amino acids.
<220> FEATURE:
<221> NAME/KEY: MISC_FEATURE
<222> LOCATION: (32)..(45)
<223> OTHER INFORMATION: framework 2
<220> FEATURE:
<221> NAME/KEY: MISC_FEATURE
<222> LOCATION: (46)..(46)
<223> OTHER INFORMATION: complementarity determinng region 2 (CDR2), X
      is 10-30 (16) of any amino acids.
<220> FEATURE:
<221> NAME/KEY: MISC_FEATURE
<222> LOCATION: (47)..(78)
<223> OTHER INFORMATION: framework 3
<220> FEATURE:
<221> NAME/KEY: MISC_FEATURE
<222> LOCATION: (79)..(79)
<223> OTHER INFORMATION: complementarity determinng region 3 (CDR3), X
      is 15-40 (16) of any amino acids.
<220> FEATURE:
<221> NAME/KEY: MISC_FEATURE
<222> LOCATION: (80)..(124)
<223> OTHER INFORMATION: framework 4

<400> SEQUENCE: 32

Gln Ile Thr Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Xaa Trp
            20                  25                  30

Ile Arg Gln Pro Pro Gly Lys Ala Leu Glu Trp Leu Ala Xaa Arg Leu
            35                  40                  45

Thr Ile Thr Lys Asp Thr Ser Lys Asn Gln Val Val Leu Thr Met Thr
 50                  55                  60

Asn Met Asp Pro Val Asp Thr Ala Thr Tyr Tyr Cys Ala Arg Xaa Trp
 65                  70                  75                  80
```

```
Gly Gln Gly Thr Leu Val Thr Val Ser Ser Ala Ser Pro Thr Ser Pro
                85                  90                  95

Lys Val Phe Pro Leu Ser Leu Ser Ser Lys Ser Thr Ser Gly Gly Thr
            100                 105                 110

Ala Ala Leu Gly Cys Leu Val Lys Asp Tyr Phe Pro
            115                 120
```

<210> SEQ ID NO 33
<211> LENGTH: 100
<212> TYPE: PRT
<213> ORGANISM: Homo sapiens
<220> FEATURE:
<221> NAME/KEY: MISC_FEATURE
<222> LOCATION: (1)..(100)
<223> OTHER INFORMATION: Vh3a heavy chain variable region
<220> FEATURE:
<221> NAME/KEY: MISC_FEATURE
<222> LOCATION: (1)..(31)
<223> OTHER INFORMATION: framework 1
<220> FEATURE:
<221> NAME/KEY: MISC_FEATURE
<222> LOCATION: (32)..(32)
<223> OTHER INFORMATION: complementarity determinng region 1 (CDR1), X
      is 3-20 (5) of any amino acids.
<220> FEATURE:
<221> NAME/KEY: MISC_FEATURE
<222> LOCATION: (33)..(46)
<223> OTHER INFORMATION: framework 2
<220> FEATURE:
<221> NAME/KEY: MISC_FEATURE
<222> LOCATION: (47)..(47)
<223> OTHER INFORMATION: complementarity determinng region 2 (CDR2), X
      is 10-30 (18) of any amino acids.
<220> FEATURE:
<221> NAME/KEY: MISC_FEATURE
<222> LOCATION: (48)..(79)
<223> OTHER INFORMATION: framework 3
<220> FEATURE:
<221> NAME/KEY: MISC_FEATURE
<222> LOCATION: (80)..(80)
<223> OTHER INFORMATION: complementarity determinng region 3 (CDR3), X
      is 20-40 (31) of any amino acids.
<220> FEATURE:
<221> NAME/KEY: MISC_FEATURE
<222> LOCATION: (81)..(100)
<223> OTHER INFORMATION: framework 4

<400> SEQUENCE: 33

```
Glu Val Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Xaa
            20                  25                  30

Trp Val Arg Gln Ala Pro Gly Lys Gly Leu Glu Trp Val Ser Xaa Arg
        35                  40                  45

Phe Thr Ile Ser Arg Asp Asn Ser Lys Asn Thr Leu Tyr Leu Gln Met
    50                  55                  60

Asn Ser Leu Arg Ala Glu Asp Thr Ala Val Tyr Tyr Cys Ala Arg Xaa
65                  70                  75                  80

Trp Gly Gln Gly Thr Leu Val Thr Val Ser Ser Gly Thr Lys Ala
                85                  90                  95

Pro Ser Val Phe
            100
```

<210> SEQ ID NO 34
<211> LENGTH: 102
<212> TYPE: PRT
<213> ORGANISM: Homo sapiens

```
<220> FEATURE:
<221> NAME/KEY: MISC_FEATURE
<222> LOCATION: (1)..(102)
<223> OTHER INFORMATION: Vh3b heavy chain variable region
<220> FEATURE:
<221> NAME/KEY: MISC_FEATURE
<222> LOCATION: (1)..(30)
<223> OTHER INFORMATION: framework 1
<220> FEATURE:
<221> NAME/KEY: MISC_FEATURE
<222> LOCATION: (31)..(31)
<223> OTHER INFORMATION: complementarity determinng region 1 (CDR1), X
      is 3-20 (5) of any amino acids.
<220> FEATURE:
<221> NAME/KEY: MISC_FEATURE
<222> LOCATION: (32)..(45)
<223> OTHER INFORMATION: framework 2
<220> FEATURE:
<221> NAME/KEY: MISC_FEATURE
<222> LOCATION: (46)..(46)
<223> OTHER INFORMATION: complementarity determinng region 2 (CDR2), X
      is 5-25 (11) of any amino acids.
<220> FEATURE:
<221> NAME/KEY: MISC_FEATURE
<222> LOCATION: (47)..(78)
<223> OTHER INFORMATION: framework 3
<220> FEATURE:
<221> NAME/KEY: MISC_FEATURE
<222> LOCATION: (79)..(79)
<223> OTHER INFORMATION: complementarity determinng region 3 (CDR3), X
      is 15-40 (23) of any amino acids.
<220> FEATURE:
<221> NAME/KEY: MISC_FEATURE
<222> LOCATION: (80)..(102)
<223> OTHER INFORMATION: framework 4

<400> SEQUENCE: 34

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Xaa Trp
            20                  25                  30

Val Arg Gln Ala Pro Gly Lys Gly Leu Glu Trp Val Gly Xaa Arg Phe
        35                  40                  45

Thr Ile Ser Arg Asp Asp Ser Lys Asn Thr Leu Tyr Leu Gln Met Asn
    50                  55                  60

Ser Leu Lys Thr Glu Asp Thr Ala Val Tyr Tyr Cys Thr Thr Xaa Trp
65                  70                  75                  80

Gly Gln Gly Thr Leu Val Thr Val Ser Ser Ala Ser Thr Lys Gly Pro
                85                  90                  95

Ser Val Phe Pro Leu Ala
            100

<210> SEQ ID NO 35
<211> LENGTH: 101
<212> TYPE: PRT
<213> ORGANISM: Homo sapiens
<220> FEATURE:
<221> NAME/KEY: MISC_FEATURE
<222> LOCATION: (1)..(101)
<223> OTHER INFORMATION: Vh3c heavy chain variable region
<220> FEATURE:
<221> NAME/KEY: MISC_FEATURE
<222> LOCATION: (1)..(30)
<223> OTHER INFORMATION: framework 1
<220> FEATURE:
<221> NAME/KEY: MISC_FEATURE
<222> LOCATION: (31)..(31)
<223> OTHER INFORMATION: complementarity determinng region 1 (CDR1), X
      is 3-20 (5) of any amino acids.
<220> FEATURE:
<221> NAME/KEY: MISC_FEATURE
```

<222> LOCATION: (32)..(45)
<223> OTHER INFORMATION: framework 2
<220> FEATURE:
<221> NAME/KEY: MISC_FEATURE
<222> LOCATION: (46)..(46)
<223> OTHER INFORMATION: complementarity determinng region 2 (CDR2), X
       is 10-30 (19) of any amino acids.
<220> FEATURE:
<221> NAME/KEY: MISC_FEATURE
<222> LOCATION: (47)..(79)
<223> OTHER INFORMATION: framework 3
<220> FEATURE:
<221> NAME/KEY: MISC_FEATURE
<222> LOCATION: (80)..(80)
<223> OTHER INFORMATION: complementarity determinng region 3 (CDR3), X
       is 15-40 (25) of any amino acids.
<220> FEATURE:
<221> NAME/KEY: MISC_FEATURE
<222> LOCATION: (81)..(101)
<223> OTHER INFORMATION: framework 4

<400> SEQUENCE: 35

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Xaa Trp
            20                  25                  30

Val Arg Gln Ala Pro Gly Lys Gly Leu Glu Trp Val Gly Xaa Arg Phe
        35                  40                  45

Thr Ile Ser Arg Asp Asp Ser Lys Ser Ile Ala Tyr Leu Gln Met Asn
    50                  55                  60

Ser Leu Lys Thr Glu Asp Thr Ala Val Tyr Tyr Cys Thr Arg Asn Xaa
65                  70                  75                  80

Trp Gly Gln Gly Thr Leu Val Thr Val Ser Ser Gly Ser Thr Lys Gly
                85                  90                  95

Pro Ser Val Leu Pro
            100

<210> SEQ ID NO 36
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: Vh4 heavy chain variable region
<220> FEATURE:
<221> NAME/KEY: MISC_FEATURE
<222> LOCATION: (1)..(33)
<223> OTHER INFORMATION: framework 1
<220> FEATURE:
<221> NAME/KEY: MISC_FEATURE
<222> LOCATION: (34)..(34)
<223> OTHER INFORMATION: complementarity determinng region 1 (CDR1), X
       is 3-20 (7) of any amino acids.
<220> FEATURE:
<221> NAME/KEY: MISC_FEATURE
<222> LOCATION: (35)..(48)
<223> OTHER INFORMATION: framework 2
<220> FEATURE:
<221> NAME/KEY: MISC_FEATURE
<222> LOCATION: (49)..(49)
<223> OTHER INFORMATION: complementarity determinng region 2 (CDR2), X
       is 10-30 (16) of any amino acids.
<220> FEATURE:
<221> NAME/KEY: MISC_FEATURE
<222> LOCATION: (50)..(81)
<223> OTHER INFORMATION: framework 3
<220> FEATURE:
<221> NAME/KEY: MISC_FEATURE
<222> LOCATION: (82)..(82)
<223> OTHER INFORMATION: complementarity determinng region 3 (CDR3), X

```
          is 20-45 (32) of any amino acids.
<220> FEATURE:
<221> NAME/KEY: MISC_FEATURE
<222> LOCATION: (83)..(108)
<223> OTHER INFORMATION: framework 4

<400> SEQUENCE: 36

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser
            20                  25                  30

Ser Xaa Trp Ile Arg Gln Pro Pro Gly Lys Gly Leu Glu Trp Ile Gly
        35                  40                  45

Xaa Arg Val Thr Ile Ser Val Asp Thr Ser Lys Asn Gln Phe Ser Leu
    50                  55                  60

Lys Leu Ser Ser Val Thr Ala Ala Asp Thr Ala Val Tyr Tyr Cys Ala
65                  70                  75                  80

Arg Xaa Trp Gly Gln Gly Thr Leu Val Thr Val Ser Ser Ala Pro Thr
        85                  90                  95

Lys Ala Pro Asp Val Phe Pro Ile Ile Ser Gly Cys
            100                 105

<210> SEQ ID NO 37
<211> LENGTH: 132
<212> TYPE: PRT
<213> ORGANISM: Homo sapiens
<220> FEATURE:
<221> NAME/KEY: MISC_FEATURE
<222> LOCATION: (1)..(132)
<223> OTHER INFORMATION: Vh5 heavy chain variable region
<220> FEATURE:
<221> NAME/KEY: MISC_FEATURE
<222> LOCATION: (1)..(31)
<223> OTHER INFORMATION: MISC_FEATURE
<220> FEATURE:
<221> NAME/KEY: MISC_FEATURE
<222> LOCATION: (32)..(32)
<223> OTHER INFORMATION: complementarity determinng region 1 (CDR1), X
      is 3-20 (5) of any amino acids.
<220> FEATURE:
<221> NAME/KEY: MISC_FEATURE
<222> LOCATION: (33)..(46)
<223> OTHER INFORMATION: framework 2
<220> FEATURE:
<221> NAME/KEY: MISC_FEATURE
<222> LOCATION: (47)..(47)
<223> OTHER INFORMATION: complementarity determinng region 2 (CDR2), X
      is 10-30 (17) of any amino acids.
<220> FEATURE:
<221> NAME/KEY: MISC_FEATURE
<222> LOCATION: (48)..(79)
<223> OTHER INFORMATION: framework 3
<220> FEATURE:
<221> NAME/KEY: MISC_FEATURE
<222> LOCATION: (80)..(80)
<223> OTHER INFORMATION: complementarity determinng region 3 (CDR3), X
      is 15-40 (23) of any amino acids.
<220> FEATURE:
<221> NAME/KEY: MISC_FEATURE
<222> LOCATION: (81)..(132)
<223> OTHER INFORMATION: framework 4

<400> SEQUENCE: 37

Glu Glu Val Gln Leu Val Gln Ser Gly Ala Glu Val Lys Lys Pro Gly
1               5                   10                  15

Glu Ser Leu Lys Ile Ser Cys Lys Gly Ser Gly Tyr Ser Phe Thr Xaa
            20                  25                  30

Trp Val Arg Gln Met Pro Gly Lys Gly Leu Glu Trp Met Gly Xaa Gln
```

```
                35                  40                  45
Val Thr Ile Ser Ala Asp Lys Ser Ile Ser Thr Ala Tyr Leu Gln Trp
            50                  55                  60

Ser Ser Leu Lys Ala Ser Asp Thr Ala Met Tyr Tyr Cys Ala Arg Xaa
 65                 70                  75                  80

Trp Gly Gln Gly Thr Leu Val Thr Val Ser Ser Ala Ser Thr Lys Ala
                85                  90                  95

Pro Ser Val Phe Pro Leu Val Ser Cys Glu Asn Ser Pro Ser Asp Thr
                100                 105                 110

Ser Ser Val Ala Val Gly Cys Leu Ala Gln Asp Phe Leu Pro Asp Ser
                115                 120                 125

Ile Thr Phe Ser
        130

<210> SEQ ID NO 38
<211> LENGTH: 125
<212> TYPE: PRT
<213> ORGANISM: Homo sapiens
<220> FEATURE:
<221> NAME/KEY: MISC_FEATURE
<222> LOCATION: (1)..(125)
<223> OTHER INFORMATION: Vh6 heavy chain variable region
<220> FEATURE:
<221> NAME/KEY: MISC_FEATURE
<222> LOCATION: (1)..(30)
<223> OTHER INFORMATION: framework 1
<220> FEATURE:
<221> NAME/KEY: MISC_FEATURE
<222> LOCATION: (31)..(31)
<223> OTHER INFORMATION: complementarity determinng region 1 (CDR1), X
      is 3-20 (7) of any amino acids.
<220> FEATURE:
<221> NAME/KEY: MISC_FEATURE
<222> LOCATION: (32)..(45)
<223> OTHER INFORMATION: framework 2
<220> FEATURE:
<221> NAME/KEY: MISC_FEATURE
<222> LOCATION: (46)..(46)
<223> OTHER INFORMATION: complementarity determinng region 2 (CDR2), X
      is 10-30 (18) of any amino acids.
<220> FEATURE:
<221> NAME/KEY: MISC_FEATURE
<222> LOCATION: (47)..(78)
<223> OTHER INFORMATION: framework 3
<220> FEATURE:
<221> NAME/KEY: MISC_FEATURE
<222> LOCATION: (79)..(79)
<223> OTHER INFORMATION: complementarity determinng region 3 (CDR3), X
      is 5-30 (13) of any amino acids.
<220> FEATURE:
<221> NAME/KEY: MISC_FEATURE
<222> LOCATION: (80)..(125)
<223> OTHER INFORMATION: framework 4

<400> SEQUENCE: 38

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Xaa Trp
                20                  25                  30

Ile Arg Gln Ser Pro Ser Arg Gly Leu Glu Trp Leu Gly Xaa Arg Ile
            35                  40                  45

Thr Ile Asn Pro Asp Thr Ser Lys Asn Gln Phe Ser Leu Gln Leu Asn
        50                  55                  60

Ser Val Thr Pro Glu Asp Thr Ala Val Tyr Tyr Cys Ala Arg Xaa Trp
 65                 70                  75                  80

Gly Gln Gly Thr Leu Val Thr Val Ser Ser Gly Ser Ala Ser Ala Pro
```

-continued

```
                85                  90                  95
Thr Leu Phe Pro Leu Val Ser Cys Glu Asn Ser Pro Ser Asp Thr Ser
            100                 105                 110

Ser Val Ala Val Gly Cys Leu Ala Gln Asp Phe Leu Pro
            115                 120                 125

<210> SEQ ID NO 39
<211> LENGTH: 91
<212> TYPE: PRT
<213> ORGANISM: Homo sapiens
<220> FEATURE:
<221> NAME/KEY: MISC_FEATURE
<222> LOCATION: (1)..(91)
<223> OTHER INFORMATION: Vh7 heavy chain variable region
<220> FEATURE:
<221> NAME/KEY: MISC_FEATURE
<222> LOCATION: (1)..(30)
<223> OTHER INFORMATION: framework 1
<220> FEATURE:
<221> NAME/KEY: MISC_FEATURE
<222> LOCATION: (31)..(31)
<223> OTHER INFORMATION: complementarity determinng region 1 (CDR1), X
      is 3-20 (5) of any amino acids.
<220> FEATURE:
<221> NAME/KEY: MISC_FEATURE
<222> LOCATION: (32)..(45)
<223> OTHER INFORMATION: framework 2
<220> FEATURE:
<221> NAME/KEY: MISC_FEATURE
<222> LOCATION: (46)..(46)
<223> OTHER INFORMATION: complementarity determinng region 2 (CDR2), X
      is 10-30 (17) of any amino acids.
<220> FEATURE:
<221> NAME/KEY: MISC_FEATURE
<222> LOCATION: (47)..(78)
<223> OTHER INFORMATION: framework 3
<220> FEATURE:
<221> NAME/KEY: MISC_FEATURE
<222> LOCATION: (79)..(79)
<223> OTHER INFORMATION: complementarity determinng region 3 (CDR3), X
      is 5-30 (13) of any amino acids.
<220> FEATURE:
<221> NAME/KEY: MISC_FEATURE
<222> LOCATION: (80)..(91)
<223> OTHER INFORMATION: framework 4

<400> SEQUENCE: 39

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Xaa Trp
            20                  25                  30

Val Arg Gln Ala Pro Gly Gln Gly Leu Glu Trp Met Gly Xaa Arg Phe
            35                  40                  45

Val Phe Ser Leu Asp Thr Ser Val Ser Thr Ala Tyr Leu Gln Ile Ser
    50                  55                  60

Ser Leu Lys Ala Glu Asp Thr Ala Val Tyr Tyr Cys Ala Arg Xaa Trp
65                  70                  75                  80

Gly Gln Gly Thr Leu Val Thr Val Ser Ser Ser
                85                  90

<210> SEQ ID NO 40
<211> LENGTH: 93
<212> TYPE: PRT
<213> ORGANISM: Homo sapiens
<220> FEATURE:
<221> NAME/KEY: MISC_FEATURE
<222> LOCATION: (1)..(93)
<223> OTHER INFORMATION: Kappa 1_4 light chain variable region
<220> FEATURE:
```

```
<221> NAME/KEY: MISC_FEATURE
<222> LOCATION: (1)..(24)
<223> OTHER INFORMATION: framework 1
<220> FEATURE:
<221> NAME/KEY: MISC_FEATURE
<222> LOCATION: (25)..(25)
<223> OTHER INFORMATION: complementarity determinng region 1 (CDR1), X
      is 10-30 (17) of any amino acids.
<220> FEATURE:
<221> NAME/KEY: MISC_FEATURE
<222> LOCATION: (26)..(40)
<223> OTHER INFORMATION: framework 2
<220> FEATURE:
<221> NAME/KEY: MISC_FEATURE
<222> LOCATION: (41)..(41)
<223> OTHER INFORMATION: complementarity determinng region 2 (CDR2), X
      is 3-20 (7) of any amino acids.
<220> FEATURE:
<221> NAME/KEY: MISC_FEATURE
<222> LOCATION: (42)..(73)
<223> OTHER INFORMATION: framework 3
<220> FEATURE:
<221> NAME/KEY: MISC_FEATURE
<222> LOCATION: (74)..(74)
<223> OTHER INFORMATION: complementarity determinng region 3 (CDR3), X
      is 20-40 (30) of any amino acids.
<220> FEATURE:
<221> NAME/KEY: MISC_FEATURE
<222> LOCATION: (75)..(93)
<223> OTHER INFORMATION: framework 4

<400> SEQUENCE: 40

Asp Ile Gln Met Thr Gln Ser Pro Ser Ser Leu Ser Ala Ser Val Gly
1               5                   10                  15

Asp Arg Arg Val Thr Ile Thr Cys Xaa Trp Tyr Gln Gln Lys Pro Gly
            20                  25                  30

Lys Ala Pro Lys Leu Leu Ile Tyr Xaa Gly Val Pro Ser Arg Phe Ser
        35                  40                  45

Gly Ser Gly Ser Gly Thr Asp Phe Thr Leu Thr Ile Ser Ser Leu Gln
    50                  55                  60

Pro Glu Asp Phe Ala Thr Tyr Tyr Cys Xaa Phe Gly Gln Gly Thr Lys
65                  70                  75                  80

Val Glu Ile Lys Arg Thr Val Ala Ala Pro Ser Val Phe
            85                  90

<210> SEQ ID NO 41
<211> LENGTH: 92
<212> TYPE: PRT
<213> ORGANISM: Homo sapiens
<220> FEATURE:
<221> NAME/KEY: MISC_FEATURE
<222> LOCATION: (1)..(92)
<223> OTHER INFORMATION: Kappa2 light chain variable region
<220> FEATURE:
<221> NAME/KEY: MISC_FEATURE
<222> LOCATION: (1)..(23)
<223> OTHER INFORMATION: framework 1
<220> FEATURE:
<221> NAME/KEY: MISC_FEATURE
<222> LOCATION: (24)..(24)
<223> OTHER INFORMATION: complementarity determinng region 1 (CDR1), X
      is 10-30 (17) of any amino acids.
<220> FEATURE:
<221> NAME/KEY: MISC_FEATURE
<222> LOCATION: (25)..(39)
<223> OTHER INFORMATION: framework 2
<220> FEATURE:
<221> NAME/KEY: MISC_FEATURE
<222> LOCATION: (40)..(40)
<223> OTHER INFORMATION: complementarity determinng region 2 (CDR2), X
      is 3-20 (7) of any amino acids.
<220> FEATURE:
```

```
<221> NAME/KEY: MISC_FEATURE
<222> LOCATION: (41)..(72)
<223> OTHER INFORMATION: framework 3
<220> FEATURE:
<221> NAME/KEY: MISC_FEATURE
<222> LOCATION: (73)..(73)
<223> OTHER INFORMATION: complementarity determinng region 3 (CDR3), X
      is 20-40 (29) of any amino acids.
<220> FEATURE:
<221> NAME/KEY: MISC_FEATURE
<222> LOCATION: (74)..(92)
<223> OTHER INFORMATION: framework 4

<400> SEQUENCE: 41

Asp Ile Val Met Thr Gln Ser Pro Leu Ser Leu Pro Val Thr Pro Gly
1               5                   10                  15

Gln Pro Ala Ser Ile Ser Cys Xaa Trp Tyr Leu Gln Lys Pro Gly Gln
            20                  25                  30

Ser Pro Gln Leu Leu Ile Tyr Xaa Gly Val Pro Asp Arg Phe Ser Gly
        35                  40                  45

Ser Gly Ser Gly Thr Asp Phe Thr Leu Lys Ile Ser Arg Val Glu Ala
    50                  55                  60

Glu Asp Val Gly Val Tyr Tyr Cys Xaa Phe Gly Gln Gly Thr Lys Val
65                  70                  75                  80

Glu Ile Lys Arg Thr Val Ala Ala Pro Ser Val Phe
                85                  90

<210> SEQ ID NO 42
<211> LENGTH: 91
<212> TYPE: PRT
<213> ORGANISM: Homo sapiens
<220> FEATURE:
<221> NAME/KEY: MISC_FEATURE
<222> LOCATION: (1)..(91)
<223> OTHER INFORMATION: Kappa3 light chain variable region
<220> FEATURE:
<221> NAME/KEY: MISC_FEATURE
<222> LOCATION: (1)..(23)
<223> OTHER INFORMATION: framework 1
<220> FEATURE:
<221> NAME/KEY: MISC_FEATURE
<222> LOCATION: (24)..(24)
<223> OTHER INFORMATION: complementarity determinng region 1 (CDR1), X
      is 5-30 (13) of any amino acids.
<220> FEATURE:
<221> NAME/KEY: MISC_FEATURE
<222> LOCATION: (25)..(39)
<223> OTHER INFORMATION: framework 2
<220> FEATURE:
<221> NAME/KEY: MISC_FEATURE
<222> LOCATION: (40)..(40)
<223> OTHER INFORMATION: complementarity determinng region 2 (CDR2), X
      is 3-20 (7) of any amino acids.
<220> FEATURE:
<221> NAME/KEY: MISC_FEATURE
<222> LOCATION: (41)..(72)
<223> OTHER INFORMATION: framework 3
<220> FEATURE:
<221> NAME/KEY: MISC_FEATURE
<222> LOCATION: (73)..(73)
<223> OTHER INFORMATION: complementarity determinng region 3 (CDR3), X
      is 20-40 (30) of any amino acids.
<220> FEATURE:
<221> NAME/KEY: MISC_FEATURE
<222> LOCATION: (74)..(91)
<223> OTHER INFORMATION: framework 4

<400> SEQUENCE: 42

Glu Ile Val Leu Thr Gln Ser Pro Gly Thr Leu Ser Leu Ser Pro Gly
1               5                   10                  15
```

```
Glu Arg Ala Thr Leu Ser Cys Xaa Trp Tyr Gln Gln Lys Pro Gly Gln
            20                  25                  30

Ala Pro Arg Leu Leu Ile Tyr Xaa Gly Ile Pro Asp Arg Phe Ser Gly
        35                  40                  45

Ser Gly Ser Gly Thr Asp Phe Thr Leu Thr Ile Ser Arg Leu Glu Pro
 50                  55                  60

Glu Asp Phe Ala Val Tyr Tyr Cys Xaa Phe Gly Gln Gly Thr Lys Val
65                  70                  75                  80

Glu Ile Lys Arg Thr Val Ala Ala Pro Ser Val
                85                  90

<210> SEQ ID NO 43
<211> LENGTH: 85
<212> TYPE: PRT
<213> ORGANISM: Homo sapiens
<220> FEATURE:
<221> NAME/KEY: MISC_FEATURE
<222> LOCATION: (1)..(85)
<223> OTHER INFORMATION: Kappa5 light chain variable region
<220> FEATURE:
<221> NAME/KEY: MISC_FEATURE
<222> LOCATION: (1)..(23)
<223> OTHER INFORMATION: framework 1
<220> FEATURE:
<221> NAME/KEY: MISC_FEATURE
<222> LOCATION: (24)..(24)
<223> OTHER INFORMATION: complementarity determinng region 1 (CDR1), X
      is 5-20 (11) of any amino acids.
<220> FEATURE:
<221> NAME/KEY: MISC_FEATURE
<222> LOCATION: (25)..(39)
<223> OTHER INFORMATION: framework 2
<220> FEATURE:
<221> NAME/KEY: MISC_FEATURE
<222> LOCATION: (40)..(40)
<223> OTHER INFORMATION: complementarity determinng region 2 (CDR2), X
      is 3-20 (7) of any amino acids.
<220> FEATURE:
<221> NAME/KEY: MISC_FEATURE
<222> LOCATION: (41)..(72)
<223> OTHER INFORMATION: framework 3
<220> FEATURE:
<221> NAME/KEY: MISC_FEATURE
<222> LOCATION: (73)..(73)
<223> OTHER INFORMATION: complementarity determinng region 3 (CDR3), X
      is 10-30 (19) of any amino acids.
<220> FEATURE:
<221> NAME/KEY: MISC_FEATURE
<222> LOCATION: (74)..(85)
<223> OTHER INFORMATION: framework 4

<400> SEQUENCE: 43

Glu Thr Thr Leu Thr Gln Ser Pro Ala Phe Met Ser Ala Thr Pro Gly
1               5                  10                  15

Asp Lys Val Asn Ile Ser Cys Xaa Trp Tyr Gln Gln Lys Pro Gly Glu
            20                  25                  30

Ala Ala Ile Phe Ile Ile Gln Xaa Gly Ile Pro Pro Arg Phe Ser Gly
        35                  40                  45

Ser Gly Tyr Gly Thr Asp Phe Thr Leu Thr Ile Asn Asn Ile Glu Ser
 50                  55                  60

Glu Asp Ala Ala Tyr Tyr Phe Cys Xaa Leu Arg His Phe Trp Pro Gly
65                  70                  75                  80

Asp Gln Ala Ala Gly
                85

<210> SEQ ID NO 44
<211> LENGTH: 79
```

```
<212> TYPE: PRT
<213> ORGANISM: Homo sapiens
<220> FEATURE:
<221> NAME/KEY: MISC_FEATURE
<222> LOCATION: (1)..(67)
<223> OTHER INFORMATION: KappaNew1 light chain variable region
<220> FEATURE:
<221> NAME/KEY: MISC_FEATURE
<222> LOCATION: (1)..(17)
<223> OTHER INFORMATION: framework 1
<220> FEATURE:
<221> NAME/KEY: MISC_FEATURE
<222> LOCATION: (18)..(18)
<223> OTHER INFORMATION: complementarity determinng region 1 (CDR1), X
      is 10-30 (17) of any amino acids.
<220> FEATURE:
<221> NAME/KEY: MISC_FEATURE
<222> LOCATION: (19)..(33)
<223> OTHER INFORMATION: framework 2
<220> FEATURE:
<221> NAME/KEY: MISC_FEATURE
<222> LOCATION: (34)..(34)
<223> OTHER INFORMATION: complementarity determinng region 2 (CDR2), X
      is 3-20 (7) of any amino acids.
<220> FEATURE:
<221> NAME/KEY: MISC_FEATURE
<222> LOCATION: (35)..(66)
<223> OTHER INFORMATION: framework 3
<220> FEATURE:
<221> NAME/KEY: MISC_FEATURE
<222> LOCATION: (67)..(67)
<223> OTHER INFORMATION: complementarity determinng region 3 (CDR3), X
      is 10-30 (21) of any amino acids.
<220> FEATURE:
<221> NAME/KEY: MISC_FEATURE
<222> LOCATION: (68)..(79)
<223> OTHER INFORMATION: framework 4

<400> SEQUENCE: 44

Glu Ile Val Met Thr Gln Ser Pro Val Asn Leu Ser Met Ser Ala Gly
1               5                   10                  15

Glu Xaa Trp Tyr Gln Gln Lys Pro Gly Gln Ala Pro Arg Leu Phe Ile
            20                  25                  30

Tyr Xaa Gly Ile Ser Ala Arg Phe Ser Gly Ser Gly Ser Gly Thr Asp
        35                  40                  45

Phe Thr Leu Thr Ile Thr Ser Leu Gln Ser Glu Asp Phe Ala Val Tyr
    50                  55                  60

Tyr Cys Xaa Phe Gly Gln Gly Thr Lys Leu Asp Ile Lys Arg Thr
65                  70                  75

<210> SEQ ID NO 45
<211> LENGTH: 77
<212> TYPE: PRT
<213> ORGANISM: Homo sapiens
<220> FEATURE:
<221> NAME/KEY: MISC_FEATURE
<222> LOCATION: (1)..(65)
<223> OTHER INFORMATION: KappaNew2 light chain variable region
<220> FEATURE:
<221> NAME/KEY: MISC_FEATURE
<222> LOCATION: (1)..(15)
<223> OTHER INFORMATION: framework 1
<220> FEATURE:
<221> NAME/KEY: MISC_FEATURE
<222> LOCATION: (16)..(16)
<223> OTHER INFORMATION: complementarity determinng region 1 (CDR1), X
      is 10-30 (18) of any amino acids.
<220> FEATURE:
<221> NAME/KEY: MISC_FEATURE
<222> LOCATION: (17)..(31)
<223> OTHER INFORMATION: framework 2
<220> FEATURE:
<221> NAME/KEY: MISC_FEATURE
```

```
<222> LOCATION: (32)..(32)
<223> OTHER INFORMATION: complementarity determinng region 2 (CDR2), X
      is 3-20 (7) of any amino acids.
<220> FEATURE:
<221> NAME/KEY: MISC_FEATURE
<222> LOCATION: (33)..(64)
<223> OTHER INFORMATION: framework 3
<220> FEATURE:
<221> NAME/KEY: MISC_FEATURE
<222> LOCATION: (65)..(65)
<223> OTHER INFORMATION: complementarity determinng region 3 (CDR3), X
      is 10-30 (21) of any amino acids.
<220> FEATURE:
<221> NAME/KEY: MISC_FEATURE
<222> LOCATION: (66)..(77)
<223> OTHER INFORMATION: framework 4

<400> SEQUENCE: 45

Glu Leu Thr Gln Ser Pro Gly Thr Leu Ser Leu Ser Pro Gly Glu Xaa
1               5                   10                  15

Trp Tyr Gln His Lys Pro Gly Gln Ala Pro Arg Leu Val Ile His Xaa
            20                  25                  30

Gly Ile Ser Asp Arg Phe Ser Gly Ser Gly Ser Gly Thr Asp Phe Thr
                35                  40                  45

Leu Thr Ile Thr Arg Leu Glu Pro Glu Asp Phe Ala Leu Tyr Tyr Cys
        50                  55                  60

Xaa Phe Gly Gln Gly Thr Lys Leu Asp Phe Lys Arg Thr
65                  70                  75

<210> SEQ ID NO 46
<211> LENGTH: 95
<212> TYPE: PRT
<213> ORGANISM: Homo sapiens
<220> FEATURE:
<221> NAME/KEY: MISC_FEATURE
<222> LOCATION: (1)..(95)
<223> OTHER INFORMATION: KappaNew3 light chain variable region
<220> FEATURE:
<221> NAME/KEY: MISC_FEATURE
<222> LOCATION: (1)..(24)
<223> OTHER INFORMATION: framework 1
<220> FEATURE:
<221> NAME/KEY: MISC_FEATURE
<222> LOCATION: (25)..(25)
<223> OTHER INFORMATION: complementarity determinng region 1 (CDR1), X
      is 10-30 (17) of any amino acids.
<220> FEATURE:
<221> NAME/KEY: MISC_FEATURE
<222> LOCATION: (26)..(40)
<223> OTHER INFORMATION: framework 2
<220> FEATURE:
<221> NAME/KEY: MISC_FEATURE
<222> LOCATION: (41)..(41)
<223> OTHER INFORMATION: complementarity determinng region 2 (CDR2), X
      is 3-20 (7) of any amino acids.
<220> FEATURE:
<221> NAME/KEY: MISC_FEATURE
<222> LOCATION: (42)..(73)
<223> OTHER INFORMATION: framework 3
<220> FEATURE:
<221> NAME/KEY: MISC_FEATURE
<222> LOCATION: (74)..(74)
<223> OTHER INFORMATION: complementarity determinng region 3 (CDR3), X
      is 3-30 (9) of any amino acids.
<220> FEATURE:
<221> NAME/KEY: MISC_FEATURE
<222> LOCATION: (75)..(95)
<223> OTHER INFORMATION: framework 4

<400> SEQUENCE: 46

Asp Ile Val Met Thr Gln Ser Pro Asp Ser Leu Ala Val Ser Leu Gly
1               5                   10                  15
```

```
Gly Arg Arg Ala Thr Ile Asn Cys Xaa Trp Tyr Gln Gln Lys Pro Gly
            20                  25                  30

Gln Pro Pro Lys Leu Leu Ile Tyr Xaa Gly Val Pro Asp Arg Phe Ser
            35                  40                  45

Gly Ser Gly Ser Gly Thr Asp Phe Thr Leu Thr Ile Ser Ser Leu Gln
    50                  55                  60

Ala Glu Asp Val Ala Val Tyr Tyr Cys Xaa Phe Gly Gly Gly Thr Lys
65                  70                  75                  80

Val Glu Ile Lys Arg Thr Val Ala Ala Pro Ser Val Phe Lys Phe
                85                  90                  95

<210> SEQ ID NO 47
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Lambda1a light chain variable region
<220> FEATURE:
<221> NAME/KEY: MISC_FEATURE
<222> LOCATION: (1)..(22)
<223> OTHER INFORMATION: framework 1
<220> FEATURE:
<221> NAME/KEY: MISC_FEATURE
<222> LOCATION: (23)..(23)
<223> OTHER INFORMATION: complementarity determinng region 1 (CDR1). X
      is 5-25 (14) of any amino acids.
<220> FEATURE:
<221> NAME/KEY: MISC_FEATURE
<222> LOCATION: (24)..(38)
<223> OTHER INFORMATION: framework 2
<220> FEATURE:
<221> NAME/KEY: MISC_FEATURE
<222> LOCATION: (39)..(39)
<223> OTHER INFORMATION: complementarity determinng region 2 (CDR2). X
      is 3-20 (7) of any amino acids.
<220> FEATURE:
<221> NAME/KEY: MISC_FEATURE
<222> LOCATION: (40)..(71)
<223> OTHER INFORMATION: framework 3
<220> FEATURE:
<221> NAME/KEY: MISC_FEATURE
<222> LOCATION: (72)..(72)
<223> OTHER INFORMATION: complementarity determinng region 3 (CDR3). X
      is 30-50 (39) of any amino acids.
<220> FEATURE:
<221> NAME/KEY: MISC_FEATURE
<222> LOCATION: (73)..(98)
<223> OTHER INFORMATION: framework 4

<400> SEQUENCE: 47

Gln Ser Val Leu Thr Gln Pro Pro Ser Val Ser Gly Ala Pro Gly Gln
1               5                   10                  15

Arg Val Thr Ile Ser Cys Xaa Trp Tyr Gln Gln Leu Pro Gly Thr Ala
            20                  25                  30

Pro Lys Leu Leu Ile Tyr Xaa Gly Val Pro Asp Arg Phe Ser Gly Ser
            35                  40                  45

Lys Ser Gly Thr Ser Ala Ser Leu Ala Ile Ser Gly Leu Gln Ser Glu
    50                  55                  60

Asp Glu Ala Asp Tyr Tyr Cys Xaa Phe Gly Gly Gly Thr Lys Leu Thr
65                  70                  75                  80

Val Leu Gly Gln Pro Lys Ala Ala Pro Ser Val Thr Leu Phe Pro Pro
                85                  90                  95

Ser Ser
```

```
<210> SEQ ID NO 48
<211> LENGTH: 99
<212> TYPE: PRT
<213> ORGANISM: Homo sapiens
<220> FEATURE:
<221> NAME/KEY: MISC_FEATURE
<222> LOCATION: (1)..(99)
<223> OTHER INFORMATION: Lambda1b light chain variable region
<220> FEATURE:
<221> NAME/KEY: MISC_FEATURE
<222> LOCATION: (1)..(23)
<223> OTHER INFORMATION: framework 1
<220> FEATURE:
<221> NAME/KEY: MISC_FEATURE
<222> LOCATION: (24)..(24)
<223> OTHER INFORMATION: complementarity determinng region 1 (CDR1), X
     is 3-25 (13) of any amino acids.
<220> FEATURE:
<221> NAME/KEY: MISC_FEATURE
<222> LOCATION: (25)..(39)
<223> OTHER INFORMATION: framework 2
<220> FEATURE:
<221> NAME/KEY: MISC_FEATURE
<222> LOCATION: (40)..(40)
<223> OTHER INFORMATION: complementarity determinng region 2 (CDR2), X
     is 3-20 (7) of any amino acids.
<220> FEATURE:
<221> NAME/KEY: MISC_FEATURE
<222> LOCATION: (41)..(72)
<223> OTHER INFORMATION: framework 3
<220> FEATURE:
<221> NAME/KEY: MISC_FEATURE
<222> LOCATION: (73)..(73)
<223> OTHER INFORMATION: complementarity determinng region 3 (CDR3), X
     is 30-50 (41) of any amino acids.
<220> FEATURE:
<221> NAME/KEY: MISC_FEATURE
<222> LOCATION: (74)..(99)
<223> OTHER INFORMATION: framework 4

<400> SEQUENCE: 48

Ala Gln Ser Val Leu Thr Gln Pro Pro Ser Val Ser Ala Ala Pro Gly
1               5                   10                  15

Gln Lys Val Thr Ile Ser Cys Xaa Trp Tyr Gln Gln Leu Pro Gly Thr
            20                  25                  30

Ala Pro Lys Leu Leu Ile Tyr Xaa Gly Ile Pro Asp Arg Phe Ser Gly
        35                  40                  45

Ser Lys Ser Gly Thr Ser Ala Thr Leu Gly Ile Thr Gly Leu Gln Thr
    50                  55                  60

Gly Asp Glu Ala Asp Tyr Tyr Cys Xaa Phe Gly Gly Gly Thr Lys Leu
65                  70                  75                  80

Thr Val Leu Gly Gln Pro Lys Ala Ala Pro Ser Val Thr Leu Phe Pro
                85                  90                  95

Pro Ser Ser

<210> SEQ ID NO 49
<211> LENGTH: 99
<212> TYPE: PRT
<213> ORGANISM: Homo sapiens
<220> FEATURE:
<221> NAME/KEY: MISC_FEATURE
<222> LOCATION: (1)..(72)
<223> OTHER INFORMATION: Lambda2 light chain variable region
<220> FEATURE:
<221> NAME/KEY: MISC_FEATURE
<222> LOCATION: (1)..(22)
<223> OTHER INFORMATION: framework 1
<220> FEATURE:
<221> NAME/KEY: MISC_FEATURE
<222> LOCATION: (23)..(23)
```

<223> OTHER INFORMATION: complementarity determinng region 1 (CDR1), X
      is 8-25 (14) of any amino acids.
<220> FEATURE:
<221> NAME/KEY: MISC_FEATURE
<222> LOCATION: (24)..(38)
<223> OTHER INFORMATION: framework 2
<220> FEATURE:
<221> NAME/KEY: MISC_FEATURE
<222> LOCATION: (39)..(39)
<223> OTHER INFORMATION: complementarity determinng region 2 (CDR2), X
      is 3-20 (7) of any amino acids.
<220> FEATURE:
<221> NAME/KEY: MISC_FEATURE
<222> LOCATION: (40)..(71)
<223> OTHER INFORMATION: framework 3
<220> FEATURE:
<221> NAME/KEY: MISC_FEATURE
<222> LOCATION: (72)..(72)
<223> OTHER INFORMATION: complementarity determinng region 3 (CDR3), X
      is 25-50 (38) of any amino acids.
<220> FEATURE:
<221> NAME/KEY: MISC_FEATURE
<222> LOCATION: (73)..(99)
<223> OTHER INFORMATION: framework 4

<400> SEQUENCE: 49

Gln Ser Ala Leu Thr Gln Pro Ala Ser Val Ser Gly Ser Pro Gly Gln
1               5                   10                  15

Ser Ile Thr Ile Ser Cys Xaa Trp Tyr Gln Gln His Pro Gly Lys Ala
            20                  25                  30

Pro Lys Leu Met Ile Tyr Xaa Gly Val Ser Asn Arg Phe Ser Gly Ser
        35                  40                  45

Lys Ser Gly Asn Thr Ala Ser Leu Thr Ile Ser Gly Leu Gln Ala Glu
    50                  55                  60

Asp Glu Ala Asp Tyr Tyr Cys Xaa Phe Gly Gly Gly Thr Thr Lys Leu
65                  70                  75                  80

Thr Val Leu Gly Gln Pro Lys Ala Ala Pro Ser Val Thr Leu Phe Pro
                85                  90                  95

Pro Ser Ser

<210> SEQ ID NO 50
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Lambda3a light chain variable region
<220> FEATURE:
<221> NAME/KEY: MISC_FEATURE
<222> LOCATION: (1)..(22)
<223> OTHER INFORMATION: framework 1
<220> FEATURE:
<221> NAME/KEY: MISC_FEATURE
<222> LOCATION: (23)..(23)
<223> OTHER INFORMATION: complementarity determinng region 1 (CDR1), X
      is 5-20 (11) of any amino acids.
<220> FEATURE:
<221> NAME/KEY: MISC_FEATURE
<222> LOCATION: (24)..(38)
<223> OTHER INFORMATION: framework 2vv
<220> FEATURE:
<221> NAME/KEY: MISC_FEATURE
<222> LOCATION: (39)..(39)
<223> OTHER INFORMATION: complementarity determinng region 2 (CDR2), X
      is 3-20 (7) of any amino acids.
<220> FEATURE:
<221> NAME/KEY: MISC_FEATURE
<222> LOCATION: (40)..(71)
<223> OTHER INFORMATION: framework 3
<220> FEATURE:

```
<221> NAME/KEY: MISC_FEATURE
<222> LOCATION: (72)..(72)
<223> OTHER INFORMATION: complementarity determinng region 3 (CDR3), X
      is 15-40 (26) of any amino acids.
<220> FEATURE:
<221> NAME/KEY: MISC_FEATURE
<222> LOCATION: (73)..(107)
<223> OTHER INFORMATION: framework 4

<400> SEQUENCE: 50

Ser Tyr Glu Leu Thr Gln Pro Pro Ser Val Ser Val Ser Pro Gly Gln
1               5                   10                  15

Thr Ala Arg Ile Thr Cys Xaa Trp Tyr Gln Gln Lys Pro Gly Gln Ala
            20                  25                  30

Pro Val Leu Val Ile Tyr Xaa Gly Ile Pro Glu Arg Phe Ser Gly Ser
        35                  40                  45

Ser Ser Gly Thr Thr Ala Thr Leu Thr Ile Ser Gly Val Gln Ala Glu
    50                  55                  60

Asp Glu Ala Asp Tyr Tyr Cys Xaa Phe Gly Gly Gly Thr Lys Leu Thr
65                  70                  75                  80

Val Leu Gly Gln Pro Lys Ala Ala Pro Ser Val Thr Leu Phe Pro Pro
                85                  90                  95

Ser Ser Glu Glu Leu Gln Ala Asn Lys Ala Thr
            100                 105

<210> SEQ ID NO 51
<211> LENGTH: 93
<212> TYPE: PRT
<213> ORGANISM: Homo sapiens
<220> FEATURE:
<221> NAME/KEY: MISC_FEATURE
<222> LOCATION: (1)..(93)
<223> OTHER INFORMATION: Lambda3b light chain variable region
<220> FEATURE:
<221> NAME/KEY: MISC_FEATURE
<222> LOCATION: (1)..(22)
<223> OTHER INFORMATION: framework 1
<220> FEATURE:
<221> NAME/KEY: MISC_FEATURE
<222> LOCATION: (23)..(23)
<223> OTHER INFORMATION: complementarity determinng region 1 (CDR1), X
      is 5-20 (11) of any amino acids.
<220> FEATURE:
<221> NAME/KEY: MISC_FEATURE
<222> LOCATION: (24)..(39)
<223> OTHER INFORMATION: framework 2
<220> FEATURE:
<221> NAME/KEY: MISC_FEATURE
<222> LOCATION: (40)..(40)
<223> OTHER INFORMATION: complementarity determinng region 2 (CDR2), X
      is 3-20 (7) of any amino acids.
<220> FEATURE:
<221> NAME/KEY: MISC_FEATURE
<222> LOCATION: (41)..(72)
<223> OTHER INFORMATION: framework 3
<220> FEATURE:
<221> NAME/KEY: MISC_FEATURE
<222> LOCATION: (73)..(73)
<223> OTHER INFORMATION: complementarity determinng region 3 (CDR3), X
      is 15-40 (27) of any amino acids.
<220> FEATURE:
<221> NAME/KEY: MISC_FEATURE
<222> LOCATION: (74)..(93)
<223> OTHER INFORMATION: framework 4

<400> SEQUENCE: 51

Ser Tyr Val Leu Thr Gln Pro Pro Ser Val Ser Val Ala Pro Gly Gln
1               5                   10                  15

Thr Ala Arg Ile Thr Cys Xaa Trp Tyr Gln Gln Lys Pro Gly Gln Ala
```

```
                20                  25                  30
Pro Val Leu Val Val Tyr Asp Xaa Gly Ile Pro Glu Arg Phe Ser Gly
            35                  40                  45

Ser Asn Ser Gly Asn Thr Ala Thr Leu Thr Ile Ser Arg Val Glu Ala
        50                  55                  60

Gly Asp Glu Ala Asp Tyr Tyr Cys Xaa Phe Gly Gly Thr Lys Leu
65                  70                  75                  80

Thr Val Leu Gly Gln Pro Lys Ala Ala Pro Thr Val Thr
                85                  90

<210> SEQ ID NO 52
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Lambda3c light chain variable region
<220> FEATURE:
<221> NAME/KEY: MISC_FEATURE
<222> LOCATION: (1)..(22)
<223> OTHER INFORMATION: framework 1
<220> FEATURE:
<221> NAME/KEY: MISC_FEATURE
<222> LOCATION: (23)..(23)
<223> OTHER INFORMATION: complementarity determinng region 1 (CDR1), X
      is 5-20 (11) of any amino acids.
<220> FEATURE:
<221> NAME/KEY: MISC_FEATURE
<222> LOCATION: (24)..(38)
<223> OTHER INFORMATION: framework 2
<220> FEATURE:
<221> NAME/KEY: MISC_FEATURE
<222> LOCATION: (39)..(39)
<223> OTHER INFORMATION: complementarity determinng region 2 (CDR2), X
      is 3-20 (7) of any amino acids.
<220> FEATURE:
<221> NAME/KEY: MISC_FEATURE
<222> LOCATION: (40)..(71)
<223> OTHER INFORMATION: framework 3
<220> FEATURE:
<221> NAME/KEY: MISC_FEATURE
<222> LOCATION: (72)..(72)
<223> OTHER INFORMATION: complementarity determinng region 3 (CDR3), X
      is 25-50 (37) of any amino acids.
<220> FEATURE:
<221> NAME/KEY: MISC_FEATURE
<222> LOCATION: (73)..(98)
<223> OTHER INFORMATION: framework 4

<400> SEQUENCE: 52

Ser Tyr Glu Leu Thr Gln Pro Pro Ser Val Ser Val Ser Pro Gly Gln
1               5                   10                  15

Thr Ala Ser Ile Thr Cys Xaa Trp Tyr Gln Gln Lys Pro Gly Gln Ser
            20                  25                  30

Pro Val Leu Val Ile Tyr Xaa Gly Ile Pro Glu Arg Phe Ser Gly Ser
        35                  40                  45

Asn Ser Gly Asn Thr Ala Thr Leu Thr Ile Ser Gly Thr Gln Ala Met
    50                  55                  60

Asp Glu Ala Asp Tyr Tyr Cys Xaa Phe Gly Gly Gly Thr Lys Leu Thr
65                  70                  75                  80

Val Leu Gly Gln Pro Lys Ala Ala Pro Ser Arg Ser Leu Cys Pro Pro
                85                  90                  95

Pro Pro

<210> SEQ ID NO 53
```

```
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Lambda3e light chain variable region
<220> FEATURE:
<221> NAME/KEY: MISC_FEATURE
<222> LOCATION: (1)..(22)
<223> OTHER INFORMATION: framework 1
<220> FEATURE:
<221> NAME/KEY: MISC_FEATURE
<222> LOCATION: (23)..(23)
<223> OTHER INFORMATION: complementarity determinng region 1 (CDR1), X
      is 5-20 (11) of any amino acids.
<220> FEATURE:
<221> NAME/KEY: MISC_FEATURE
<222> LOCATION: (24)..(38)
<223> OTHER INFORMATION: framework 2
<220> FEATURE:
<221> NAME/KEY: MISC_FEATURE
<222> LOCATION: (39)..(39)
<223> OTHER INFORMATION: complementarity determinng region 2 (CDR2), X
      is 3-20 (7) of any amino acids.
<220> FEATURE:
<221> NAME/KEY: MISC_FEATURE
<222> LOCATION: (40)..(71)
<223> OTHER INFORMATION: framework 3
<220> FEATURE:
<221> NAME/KEY: MISC_FEATURE
<222> LOCATION: (72)..(72)
<223> OTHER INFORMATION: complementarity determinng region 3 (CDR3), X
      is 15-40 (26) of any amino acids.
<220> FEATURE:
<221> NAME/KEY: MISC_FEATURE
<222> LOCATION: (73)..(98)
<223> OTHER INFORMATION: framework 4

<400> SEQUENCE: 53

Ser Ser Glu Leu Thr Gln Asp Pro Ala Val Ser Val Ala Leu Gly Gln
1               5                   10                  15

Thr Val Arg Ile Thr Cys Xaa Trp Tyr Gln Gln Lys Pro Gly Gln Ala
            20                  25                  30

Pro Val Leu Val Ile Tyr Xaa Gly Ile Pro Asp Arg Phe Ser Gly Ser
        35                  40                  45

Ser Ser Gly Asn Thr Ala Ser Leu Thr Ile Thr Gly Ala Gln Ala Glu
    50                  55                  60

Asp Glu Ala Asp Tyr Tyr Cys Xaa Phe Gly Gly Gly Thr Lys Leu Thr
65                  70                  75                  80

Val Leu Gly Gln Pro Lys Ala Ala Pro Ser Val Thr Leu Phe Pro Pro
                85                  90                  95

Ser Ser

<210> SEQ ID NO 54
<211> LENGTH: 94
<212> TYPE: PRT
<213> ORGANISM: Homo sapiens
<220> FEATURE:
<221> NAME/KEY: MISC_FEATURE
<222> LOCATION: (1)..(94)
<223> OTHER INFORMATION: Lambda4a light chain variable region
<220> FEATURE:
<221> NAME/KEY: MISC_FEATURE
<222> LOCATION: (1)..(22)
<223> OTHER INFORMATION: framework 1
<220> FEATURE:
<221> NAME/KEY: MISC_FEATURE
<222> LOCATION: (23)..(23)
<223> OTHER INFORMATION: complementarity determinng region 1 (CDR1), X
      is 5-25 (12) of any amino acids.
```

```
<220> FEATURE:
<221> NAME/KEY: MISC_FEATURE
<222> LOCATION: (24)..(38)
<223> OTHER INFORMATION: framework 2
<220> FEATURE:
<221> NAME/KEY: MISC_FEATURE
<222> LOCATION: (39)..(39)
<223> OTHER INFORMATION: complementarity determinng region 2 (CDR2), X
      is 5-25 (11) of any amino acids.
<220> FEATURE:
<221> NAME/KEY: MISC_FEATURE
<222> LOCATION: (40)..(71)
<223> OTHER INFORMATION: framework 3
<220> FEATURE:
<221> NAME/KEY: MISC_FEATURE
<222> LOCATION: (72)..(72)
<223> OTHER INFORMATION: complementarity determinng region 3 (CDR3), X
      is 10-40 (23) of any amino acids.
<220> FEATURE:
<221> NAME/KEY: MISC_FEATURE
<222> LOCATION: (73)..(94)
<223> OTHER INFORMATION: framework 4

<400> SEQUENCE: 54

Gln Pro Val Leu Thr Gln Ser Ser Ala Ser Ala Ser Leu Gly Ser
1               5                   10                  15

Ser Val Lys Leu Thr Cys Xaa Trp His Gln Gln Pro Gly Lys Ala
                20                  25                  30

Pro Arg Tyr Leu Met Lys Xaa Gly Val Pro Asp Arg Phe Ser Gly
            35                  40                  45

Ser Ser Gly Ala Asp Arg Tyr Leu Thr Ile Ser Asn Leu Gln Ser Glu
        50                  55                  60

Asp Glu Ala Asp Tyr Tyr Cys Xaa Phe Gly Gly Gly Thr Lys Leu Thr
65                  70                  75                  80

Val Leu Gly Gln Pro Lys Ala Ala Pro Ser Val Thr Leu Phe
                85                  90

<210> SEQ ID NO 55
<211> LENGTH: 95
<212> TYPE: PRT
<213> ORGANISM: Homo sapiens
<220> FEATURE:
<221> NAME/KEY: MISC_FEATURE
<222> LOCATION: (1)..(95)
<223> OTHER INFORMATION: Lambda4b light chain variable region
<220> FEATURE:
<221> NAME/KEY: MISC_FEATURE
<222> LOCATION: (1)..(22)
<223> OTHER INFORMATION: framework 1
<220> FEATURE:
<221> NAME/KEY: MISC_FEATURE
<222> LOCATION: (23)..(23)
<223> OTHER INFORMATION: complementarity determinng region 1 (CDR1), X
      is 5-25 (12) of any amino acids.
<220> FEATURE:
<221> NAME/KEY: MISC_FEATURE
<222> LOCATION: (24)..(38)
<223> OTHER INFORMATION: framework 2
<220> FEATURE:
<221> NAME/KEY: MISC_FEATURE
<222> LOCATION: (39)..(39)
<223> OTHER INFORMATION: complementarity determinng region 2 (CDR2), X
      is 5-25 (11) of any amino acids.
<220> FEATURE:
<221> NAME/KEY: MISC_FEATURE
<222> LOCATION: (40)..(71)
<223> OTHER INFORMATION: framework 3
<220> FEATURE:
<221> NAME/KEY: MISC_FEATURE
<222> LOCATION: (72)..(72)
<223> OTHER INFORMATION: complementarity determinng region 3 (CDR3), X
      is 15-40 (25) of any amino acids.
```

```
<220> FEATURE:
<221> NAME/KEY: MISC_FEATURE
<222> LOCATION: (73)..(95)
<223> OTHER INFORMATION: framework 4

<400> SEQUENCE: 55

Gln Leu Val Leu Thr Gln Ser Pro Ser Ala Ser Ala Ser Leu Gly Ala
1               5                   10                  15

Ser Val Lys Leu Thr Cys Xaa Trp His Gln Gln Pro Glu Lys Gly
            20                  25                  30

Pro Arg Tyr Leu Met Lys Xaa Gly Ile Pro Asp Arg Phe Ser Gly Ser
            35                  40                  45

Ser Ser Gly Ala Glu Arg Tyr Leu Thr Ile Ser Ser Leu Gln Ser Glu
        50                  55                  60

Asp Glu Ala Asp Tyr Tyr Cys Xaa Phe Gly Gly Ile Gly Gly Gly Thr
65                  70                  75                  80

Lys Leu Thr Val Leu Gly Gln Pro Lys Ala Ala Pro Ser Val Ser
                85                  90                  95

<210> SEQ ID NO 56
<211> LENGTH: 88
<212> TYPE: PRT
<213> ORGANISM: Homo sapiens
<220> FEATURE:
<221> NAME/KEY: MISC_FEATURE
<222> LOCATION: (1)..(75)
<223> OTHER INFORMATION: Lambda5 light chain variable region
<220> FEATURE:
<221> NAME/KEY: MISC_FEATURE
<222> LOCATION: (1)..(22)
<223> OTHER INFORMATION: framework 1
<220> FEATURE:
<221> NAME/KEY: MISC_FEATURE
<222> LOCATION: (23)..(23)
<223> OTHER INFORMATION: complementarity determinng region 1 (CDR1), X
      is 5-25 (14) of any amino acids.
<220> FEATURE:
<221> NAME/KEY: MISC_FEATURE
<222> LOCATION: (24)..(39)
<223> OTHER INFORMATION: framework 2
<220> FEATURE:
<221> NAME/KEY: MISC_FEATURE
<222> LOCATION: (40)..(40)
<223> OTHER INFORMATION: complementarity determinng region 2 (CDR2), X
      is 5-20 (10) of any amino acids.
<220> FEATURE:
<221> NAME/KEY: MISC_FEATURE
<222> LOCATION: (41)..(74)
<223> OTHER INFORMATION: framework 3
<220> FEATURE:
<221> NAME/KEY: MISC_FEATURE
<222> LOCATION: (75)..(75)
<223> OTHER INFORMATION: complementarity determinng region 3 (CDR3), X
      is 10-35 (22) of any amino acids.
<220> FEATURE:
<221> NAME/KEY: MISC_FEATURE
<222> LOCATION: (76)..(88)
<223> OTHER INFORMATION: framework 4

<400> SEQUENCE: 56

Gln Ala Val Leu Thr Gln Pro Ser Ser Leu Ser Ala Ser Pro Gly Ala
1               5                   10                  15

Ser Ala Ser Leu Thr Cys Xaa Trp Tyr Gln Gln Lys Pro Gly Ser Pro
            20                  25                  30

Pro Gln Tyr Leu Leu Arg Tyr Xaa Gly Val Pro Ser Arg Phe Ser Gly
            35                  40                  45

Ser Lys Asp Ala Ser Ala Asn Ala Gly Ile Leu Leu Ile Ser Gly Leu
        50                  55                  60
```

```
Gln Ser Glu Asp Glu Ala Asp Tyr Tyr Cys Xaa Phe Gly Gly Gly Thr
65                  70                  75                  80

Lys Leu Thr Val Leu Ser Gln Pro
                85

<210> SEQ ID NO 57
<211> LENGTH: 101
<212> TYPE: PRT
<213> ORGANISM: Homo sapiens
<220> FEATURE:
<221> NAME/KEY: MISC_FEATURE
<222> LOCATION: (1)..(101)
<223> OTHER INFORMATION: Lambda6 light chain variable region
<220> FEATURE:
<221> NAME/KEY: MISC_FEATURE
<222> LOCATION: (1)..(22)
<223> OTHER INFORMATION: framewrok 1
<220> FEATURE:
<221> NAME/KEY: MISC_FEATURE
<222> LOCATION: (23)..(23)
<223> OTHER INFORMATION: complementarity determinng region 1 (CDR1), X
      is 5-25 (13) of any amino acids.
<220> FEATURE:
<221> NAME/KEY: MISC_FEATURE
<222> LOCATION: (24)..(38)
<223> OTHER INFORMATION: framewrok 2
<220> FEATURE:
<221> NAME/KEY: MISC_FEATURE
<222> LOCATION: (39)..(39)
<223> OTHER INFORMATION: complementarity determinng region 2 (CDR2), X
      is 3-20 (7) of any amino acids.
<220> FEATURE:
<221> NAME/KEY: MISC_FEATURE
<222> LOCATION: (40)..(73)
<223> OTHER INFORMATION: framewrok 3
<220> FEATURE:
<221> NAME/KEY: MISC_FEATURE
<222> LOCATION: (74)..(74)
<223> OTHER INFORMATION: complementarity determinng region 3 (CDR3), X
      is 25-50 (38) of any amino acids.
<220> FEATURE:
<221> NAME/KEY: MISC_FEATURE
<222> LOCATION: (75)..(101)
<223> OTHER INFORMATION: framewrok 4

<400> SEQUENCE: 57

Asn Phe Met Leu Thr Gln Pro His Ser Val Ser Glu Ser Pro Gly Lys
1               5                   10                  15

Thr Val Thr Ile Ser Cys Xaa Trp Tyr Gln Gln Arg Pro Gly Ser Ala
                20                  25                  30

Pro Thr Thr Val Ile Tyr Xaa Gly Val Pro Asp Arg Phe Ser Gly Ser
            35                  40                  45

Ile Asp Ser Ser Ser Asn Ser Ala Ser Leu Thr Ile Ser Gly Leu Lys
    50                  55                  60

Thr Glu Asp Glu Ala Asp Tyr Tyr Cys Xaa Phe Gly Gly Gly Thr Lys
65                  70                  75                  80

Leu Thr Val Leu Gly Gln Pro Lys Ala Ala Pro Ser Val Thr Leu Phe
                85                  90                  95

Pro Pro Ser Ser Ser
            100

<210> SEQ ID NO 58
<211> LENGTH: 89
<212> TYPE: PRT
<213> ORGANISM: Homo sapiens
<220> FEATURE:
<221> NAME/KEY: MISC_FEATURE
<222> LOCATION: (1)..(72)
```

```
<223> OTHER INFORMATION: Lambda7 light chain variable region
<220> FEATURE:
<221> NAME/KEY: MISC_FEATURE
<222> LOCATION: (1)..(22)
<223> OTHER INFORMATION: framework 1
<220> FEATURE:
<221> NAME/KEY: MISC_FEATURE
<222> LOCATION: (23)..(23)
<223> OTHER INFORMATION: complementarity determinng region 1 (CDR1), X
      is 5-25 (14) of any amino acids.
<220> FEATURE:
<221> NAME/KEY: MISC_FEATURE
<222> LOCATION: (24)..(38)
<223> OTHER INFORMATION: framework 2
<220> FEATURE:
<221> NAME/KEY: MISC_FEATURE
<222> LOCATION: (39)..(39)
<223> OTHER INFORMATION: complementarity determinng region 2 (CDR2), X
      is 3-20 (7) of any amino acids.
<220> FEATURE:
<221> NAME/KEY: MISC_FEATURE
<222> LOCATION: (40)..(71)
<223> OTHER INFORMATION: framework 3
<220> FEATURE:
<221> NAME/KEY: MISC_FEATURE
<222> LOCATION: (72)..(72)
<223> OTHER INFORMATION: complementarity determinng region 3 (CDR3), X
      is 10-35 (23) of any amino acids.
<220> FEATURE:
<221> NAME/KEY: MISC_FEATURE
<222> LOCATION: (73)..(89)
<223> OTHER INFORMATION: framework 4

<400> SEQUENCE: 58

Gln Ala Val Val Thr Gln Glu Pro Ser Leu Thr Val Ser Pro Gly Gly
1               5                   10                  15

Thr Val Thr Leu Thr Cys Xaa Trp Phe Gln Gln Lys Pro Gly Gln Ala
            20                  25                  30

Pro Arg Ala Leu Ile Tyr Xaa Trp Thr Pro Ala Arg Phe Ser Gly Ser
        35                  40                  45

Leu Leu Gly Gly Lys Ala Ala Leu Thr Leu Ser Gly Val Gln Pro Glu
    50                  55                  60

Asp Glu Ala Glu Tyr Tyr Cys Xaa Phe Gly Gly Gly Thr Lys Leu Thr
65                  70                  75                  80

Val Leu Gly Gln Pro Lys Ala Ala Pro
                85

<210> SEQ ID NO 59
<211> LENGTH: 89
<212> TYPE: PRT
<213> ORGANISM: Homo sapiens
<220> FEATURE:
<221> NAME/KEY: MISC_FEATURE
<222> LOCATION: (1)..(89)
<223> OTHER INFORMATION: Lambda8 light chain variable region
<220> FEATURE:
<221> NAME/KEY: MISC_FEATURE
<222> LOCATION: (1)..(22)
<223> OTHER INFORMATION: framework 1
<220> FEATURE:
<221> NAME/KEY: MISC_FEATURE
<222> LOCATION: (23)..(23)
<223> OTHER INFORMATION: complementarity determinng region 1 (CDR1), X
      is 5-25 (14) of any amino acids.
<220> FEATURE:
<221> NAME/KEY: MISC_FEATURE
<222> LOCATION: (24)..(38)
<223> OTHER INFORMATION: framework 2
<220> FEATURE:
<221> NAME/KEY: MISC_FEATURE
<222> LOCATION: (39)..(39)
<223> OTHER INFORMATION: complementarity determinng region 2 (CDR2), X
```

```
            is 3-20 (7) of any amino acids.
<220> FEATURE:
<221> NAME/KEY: MISC_FEATURE
<222> LOCATION: (40)..(71)
<223> OTHER INFORMATION: framework 3
<220> FEATURE:
<221> NAME/KEY: MISC_FEATURE
<222> LOCATION: (72)..(72)
<223> OTHER INFORMATION: complementarity determinng region 3 (CDR3), X
      is 15-35 (25) of any amino acids.
<220> FEATURE:
<221> NAME/KEY: MISC_FEATURE
<222> LOCATION: (73)..(89)
<223> OTHER INFORMATION: framework 4

<400> SEQUENCE: 59

Gln Thr Val Val Thr Gln Glu Pro Ser Phe Ser Val Ser Pro Gly Gly
1               5                   10                  15

Thr Val Thr Leu Thr Cys Xaa Trp Tyr Gln Gln Thr Pro Gly Gln Ala
            20                  25                  30

Pro Arg Thr Leu Ile Tyr Xaa Gly Val Pro Asp Arg Phe Ser Gly Ser
        35                  40                  45

Ile Leu Gly Asn Lys Ala Ala Leu Thr Ile Thr Gly Ala Gln Ala Asp
    50                  55                  60

Asp Glu Ser Asp Tyr Tyr Cys Xaa Phe Gly Gly Gly Thr Lys Leu Thr
65                  70                  75                  80

Val Leu Gly Gln Pro Lys Ala Ala Pro
                85

<210> SEQ ID NO 60
<211> LENGTH: 91
<212> TYPE: PRT
<213> ORGANISM: Homo sapiens
<220> FEATURE:
<221> NAME/KEY: MISC_FEATURE
<222> LOCATION: (1)..(91)
<223> OTHER INFORMATION: Lambda9 light chain variable region
<220> FEATURE:
<221> NAME/KEY: MISC_FEATURE
<222> LOCATION: (1)..(22)
<223> OTHER INFORMATION: framework 1
<220> FEATURE:
<221> NAME/KEY: MISC_FEATURE
<222> LOCATION: (23)..(23)
<223> OTHER INFORMATION: complementarity determinng region 1 (CDR1), X
      is 5-25 (12) of any amino acids.
<220> FEATURE:
<221> NAME/KEY: MISC_FEATURE
<222> LOCATION: (24)..(38)
<223> OTHER INFORMATION: framework 2
<220> FEATURE:
<221> NAME/KEY: MISC_FEATURE
<222> LOCATION: (39)..(39)
<223> OTHER INFORMATION: complementarity determinng region 2 (CDR2), X
      is 5-25 (12) of any amino acids.
<220> FEATURE:
<221> NAME/KEY: MISC_FEATURE
<222> LOCATION: (40)..(79)
<223> OTHER INFORMATION: framework 3
<220> FEATURE:
<221> NAME/KEY: MISC_FEATURE
<222> LOCATION: (80)..(80)
<223> OTHER INFORMATION: complementarity determinng region 3 (CDR3), X
      is 15-40 (28) of any amino acids.
<220> FEATURE:
<221> NAME/KEY: MISC_FEATURE
<222> LOCATION: (81)..(91)
<223> OTHER INFORMATION: framework 4

<400> SEQUENCE: 60

Gln Pro Val Leu Thr Gln Pro Pro Ser Ala Ser Ala Ser Leu Gly Ala
```

```
                  1               5                  10                 15

Ser Val Thr Leu Thr Cys Xaa Trp Tyr Gln Gln Arg Pro Gly Lys Gly
                20                  25                 30

Pro Arg Phe Val Met Arg Xaa Gly Ile Pro Asp Arg Phe Ser Val Leu
                35                  40                 45

Gly Ser Gly Leu Asn Arg Tyr Leu Thr Ile Lys Asn Ile Gln Glu Glu
                50                  55                 60

Asp Glu Ser Asp Tyr His Cys Xaa Phe Gly Gly Gly Thr Lys Leu Thr
65                  70                  75                     80

Val Leu Gly Gln Pro Lys Ala Ala Pro Ser Val
                85                  90
```

<210> SEQ ID NO 61
<211> LENGTH: 87
<212> TYPE: PRT
<213> ORGANISM: Homo sapiens
<220> FEATURE:
<221> NAME/KEY: MISC_FEATURE
<222> LOCATION: (1)..(87)
<223> OTHER INFORMATION: Lambda10 light chain variable region
<220> FEATURE:
<221> NAME/KEY: MISC_FEATURE
<222> LOCATION: (1)..(22)
<223> OTHER INFORMATION: framework 1
<220> FEATURE:
<221> NAME/KEY: MISC_FEATURE
<222> LOCATION: (23)..(23)
<223> OTHER INFORMATION: complementarity determinng region 1 (CDR1), X
      is 5-25 (13) of any amino acids.
<220> FEATURE:
<221> NAME/KEY: MISC_FEATURE
<222> LOCATION: (24)..(38)
<223> OTHER INFORMATION: framework 2
<220> FEATURE:
<221> NAME/KEY: MISC_FEATURE
<222> LOCATION: (39)..(39)
<223> OTHER INFORMATION: complementarity determinng region 2 (CDR2), X
      is 3-20 (7) of any amino acids.
<220> FEATURE:
<221> NAME/KEY: MISC_FEATURE
<222> LOCATION: (40)..(71)
<223> OTHER INFORMATION: framework 3
<220> FEATURE:
<221> NAME/KEY: MISC_FEATURE
<222> LOCATION: (72)..(72)
<223> OTHER INFORMATION: complementarity determinng region 3 (CDR3), X
      is 15-40 (27) of any amino acids.
<220> FEATURE:
<221> NAME/KEY: MISC_FEATURE
<222> LOCATION: (73)..(87)
<223> OTHER INFORMATION: framework 4

<400> SEQUENCE: 61

```
Gln Ala Gly Leu Thr Gln Pro Pro Ser Val Ser Lys Gly Leu Arg Gln
1               5                  10                 15

Thr Ala Thr Leu Thr Cys Xaa Trp Leu Gln Gln His Gln Gly His Pro
                20                  25                 30

Pro Lys Leu Leu Ser Tyr Xaa Gly Ile Ser Glu Arg Phe Ser Ala Ser
                35                  40                 45

Arg Ser Gly Asn Thr Ala Ser Leu Thr Ile Thr Gly Leu Gln Pro Glu
                50                  55                 60

Asp Glu Ala Asp Tyr Tyr Cys Xaa Phe Gly Gly Gly Thr Lys Leu Thr
65                  70                  75                     80

Val Leu Gly Gln Pro Lys Ala
                85
```

-continued

```
<210> SEQ ID NO 62
<211> LENGTH: 354
<212> TYPE: PRT
<213> ORGANISM: Homo sapiens
<220> FEATURE:
<221> NAME/KEY: MISC_FEATURE
<222> LOCATION: (1)..(354)
<223> OTHER INFORMATION: IgA1 heavy chain constant region
<220> FEATURE:
<221> NAME/KEY: MISC_FEATURE
<222> LOCATION: (1)..(102)
<223> OTHER INFORMATION: CH1
<220> FEATURE:
<221> NAME/KEY: MISC_FEATURE
<222> LOCATION: (103)..(121)
<223> OTHER INFORMATION: hinge
<220> FEATURE:
<221> NAME/KEY: MISC_FEATURE
<222> LOCATION: (122)..(222)
<223> OTHER INFORMATION: CH2
<220> FEATURE:
<221> NAME/KEY: MISC_FEATURE
<222> LOCATION: (223)..(354)
<223> OTHER INFORMATION: CH3

<400> SEQUENCE: 62
```

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Pro Ser Glx Glu Glu
225                 230                 235                 240

Leu Ala Leu Asn Glu Leu Val Thr Leu Thr Cys Leu Ala Arg Gly Phe
                245                 250                 255

Ser Pro Lys Asp Val Leu Val Arg Trp Leu Gln Gly Ser Gln Glu Leu
            260                 265                 270

Pro Arg Glu Lys Tyr Leu Thr Trp Ala Ser Arg Gln Glu Pro Ser Gln

```
                    275                 280                 285
Gly Thr Thr Thr Phe Ala Val Thr Ser Ile Leu Arg Val Ala Ala Glu
    290                 295                 300

Asp Trp Lys Lys Gly Asp Thr Phe Ser Cys Met Val Gly His Glu Ala
305                 310                 315                 320

Leu Pro Leu Ala Phe Thr Gln Lys Thr Ile Asp Arg Leu Ala Gly Lys
                325                 330                 335

Pro Thr His Val Asn Val Ser Val Val Met Ala Glu Val Asp Gly Thr
                340                 345                 350

Cys Tyr

<210> SEQ ID NO 63
<211> LENGTH: 340
<212> TYPE: PRT
<213> ORGANISM: Homo sapiens
<220> FEATURE:
<221> NAME/KEY: MISC_FEATURE
<222> LOCATION: (1)..(340)
<223> OTHER INFORMATION: IgA2 heavy chain constant region
<220> FEATURE:
<221> NAME/KEY: MISC_FEATURE
<222> LOCATION: (1)..(102)
<223> OTHER INFORMATION: CH1
<220> FEATURE:
<221> NAME/KEY: MISC_FEATURE
<222> LOCATION: (103)..(108)
<223> OTHER INFORMATION: hinge
<220> FEATURE:
<221> NAME/KEY: MISC_FEATURE
<222> LOCATION: (109)..(209)
<223> OTHER INFORMATION: CH2
<220> FEATURE:
<221> NAME/KEY: MISC_FEATURE
<222> LOCATION: (210)..(340)
<223> OTHER INFORMATION: CH3

<400> SEQUENCE: 63

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190
```

```
Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
        290                 295                 300

Glu Ala Leu Pro Leu Ala Phe Thr Gln Lys Thr Ile Asp Arg Leu Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 64
<211> LENGTH: 384
<212> TYPE: PRT
<213> ORGANISM: Homo sapiens
<220> FEATURE:
<221> NAME/KEY: MISC_FEATURE
<222> LOCATION: (1)..(384)
<223> OTHER INFORMATION: IgD heavy chain constant region
<220> FEATURE:
<221> NAME/KEY: MISC_FEATURE
<222> LOCATION: (1)..(101)
<223> OTHER INFORMATION: CH1
<220> FEATURE:
<221> NAME/KEY: MISC_FEATURE
<222> LOCATION: (102)..(135)
<223> OTHER INFORMATION: hinge 1
<220> FEATURE:
<221> NAME/KEY: MISC_FEATURE
<222> LOCATION: (136)..(159)
<223> OTHER INFORMATION: hinge 2
<220> FEATURE:
<221> NAME/KEY: MISC_FEATURE
<222> LOCATION: (160)..(267)
<223> OTHER INFORMATION: CH2
<220> FEATURE:
<221> NAME/KEY: MISC_FEATURE
<222> LOCATION: (268)..(384)
<223> OTHER INFORMATION: CH3

<400> SEQUENCE: 64

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
```

```
                    85                  90                  95
Ile Phe Arg Trp Pro Glu Ser Pro Lys Ala Gln Ala Ser Ser Val Pro
                100                 105                 110

Thr Ala Gln Pro Gln Ala Glu Gly Ser Leu Ala Lys Ala Thr Thr Ala
                115                 120                 125

Pro Ala Thr Thr Arg Asn Thr Gly Arg Gly Gly Glu Glu Lys Lys Lys
            130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
                180                 185                 190

Val Gly Ser Asp Leu Lys Asp Ala His Leu Thr Trp Glu Val Ala Gly
            195                 200                 205

Lys Val Pro Thr Gly Gly Val Glu Glu Gly Leu Leu Glu Arg His Ser
210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
                260                 265                 270

Val Lys Leu Ser Leu Asn Leu Leu Ala Ser Ser Asp Pro Pro Glu Ala
            275                 280                 285

Ala Ser Trp Leu Leu Cys Glu Val Ser Gly Phe Ser Pro Pro Asn Ile
290                 295                 300

Leu Leu Met Trp Leu Glu Asp Gln Arg Glu Val Asn Thr Ser Gly Phe
305                 310                 315                 320

Ala Pro Ala Arg Pro Pro Pro Gln Pro Arg Ser Thr Thr Phe Trp Ala
                325                 330                 335

Trp Ser Val Leu Arg Val Pro Ala Pro Pro Ser Pro Gln Pro Ala Thr
                340                 345                 350

Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met Lys
370                 375                 380

<210> SEQ ID NO 65
<211> LENGTH: 497
<212> TYPE: PRT
<213> ORGANISM: Homo sapiens
<220> FEATURE:
<221> NAME/KEY: MISC_FEATURE
<222> LOCATION: (1)..(497)
<223> OTHER INFORMATION: IgE heavy chain constant region
<220> FEATURE:
<221> NAME/KEY: MISC_FEATURE
<222> LOCATION: (1)..(103)
<223> OTHER INFORMATION: CH1
<220> FEATURE:
<221> NAME/KEY: MISC_FEATURE
<222> LOCATION: (104)..(210)
<223> OTHER INFORMATION: CH2
<220> FEATURE:
<221> NAME/KEY: MISC_FEATURE
<222> LOCATION: (211)..(318)
<223> OTHER INFORMATION: CH3
<220> FEATURE:
<221> NAME/KEY: MISC_FEATURE
```

<222> LOCATION: (319)..(497)
<223> OTHER INFORMATION: CH4

<400> SEQUENCE: 65

```
Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
        35                  40                  45

Asn Gly Thr Thr Met Thr Leu Pro Ala Thr Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser Val Cys Ser Arg Asp Phe Thr Pro Pro
            100                 105                 110

Thr Val Lys Ile Leu Gln Ser Ser Cys Asp Gly Gly Gly His Phe Pro
        115                 120                 125

Pro Thr Ile Gln Leu Leu Cys Leu Val Ser Gly Tyr Thr Pro Gly Thr
    130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
                165                 170                 175

Glu Leu Thr Leu Ser Gln Lys His Trp Leu Ser Asp Arg Thr Tyr Thr
            180                 185                 190

Cys Gln Val Thr Tyr Gln Gly His Thr Phe Glu Asp Ser Thr Lys Lys
        195                 200                 205

Cys Ala Asp Ser Asn Pro Arg Gly Val Ser Ala Tyr Leu Ser Arg Pro
    210                 215                 220

Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
                245                 250                 255

Arg Ala Ser Gly Lys Pro Val Asn His Ser Thr Arg Lys Glu Glu Lys
            260                 265                 270

Gln Arg Asn Gly Thr Leu Thr Val Thr Ser Thr Leu Pro Val Gly Thr
        275                 280                 285

Arg Asp Trp Ile Glu Gly Glu Thr Tyr Gln Cys Arg Val Thr His Pro
    290                 295                 300

His Leu Pro Arg Ala Leu Met Arg Ser Thr Thr Lys Thr Ser Gly Pro
305                 310                 315                 320

Val Gly Pro Arg Ala Ala Pro Glu Val Tyr Ala Phe Ala Thr Pro Glu
                325                 330                 335

Trp Pro Gly Ser Arg Asp Lys Arg Thr Leu Ala Cys Leu Ile Gln Asn
            340                 345                 350

Phe Met Pro Glu Asp Ile Ser Val Gln Trp Leu His Asn Glu Val Gln
        355                 360                 365

Leu Pro Asp Ala Arg His Ser Thr Thr Gln Pro Arg Lys Thr Lys Gly
    370                 375                 380

Ser Gly Phe Phe Val Phe Ser Arg Leu Glu Val Thr Arg Ala Glu Trp
385                 390                 395                 400
```

-continued

```
Glu Gln Lys Asp Glu Phe Ile Cys Arg Ala Val His Glu Ala Ala Ser
                405                 410                 415

Pro Ser Gln Thr Val Gln Arg Ala Val Ser Val Asn Pro Gly Lys Asp
            420                 425                 430

Val Cys Val Glu Glu Ala Glu Gly Glu Ala Pro Trp Thr Trp Thr Gly
        435                 440                 445

Leu Cys Ile Phe Ala Ala Leu Phe Leu Leu Ser Val Ser Tyr Ser Ala
    450                 455                 460

Ala Leu Thr Leu Leu Met Val Gln Arg Phe Leu Ser Ala Thr Arg Gln
465                 470                 475                 480

Gly Arg Pro Gln Thr Ser Leu Asp Tyr Thr Asn Val Leu Gln Pro His
                485                 490                 495

Ala

<210> SEQ ID NO 66
<211> LENGTH: 339
<212> TYPE: PRT
<213> ORGANISM: Homo sapiens
<220> FEATURE:
<221> NAME/KEY: MISC_FEATURE
<222> LOCATION: (1)..(339)
<223> OTHER INFORMATION: IgG1 heavy chain constant region
<220> FEATURE:
<221> NAME/KEY: MISC_FEATURE
<222> LOCATION: (1)..(98)
<223> OTHER INFORMATION: CH1
<220> FEATURE:
<221> NAME/KEY: MISC_FEATURE
<222> LOCATION: (99)..(113)
<223> OTHER INFORMATION: hinge
<220> FEATURE:
<221> NAME/KEY: MISC_FEATURE
<222> LOCATION: (114)..(223)
<223> OTHER INFORMATION: CH2
<220> FEATURE:
<221> NAME/KEY: MISC_FEATURE
<222> LOCATION: (224)..(339)
<223> OTHER INFORMATION: CH3

<400> SEQUENCE: 66

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asx Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys Thr His Thr Cys Pro
                325                 330                 335

Pro Cys Pro

<210> SEQ ID NO 67
<211> LENGTH: 326
<212> TYPE: PRT
<213> ORGANISM: Homo sapiens
<220> FEATURE:
<221> NAME/KEY: MISC_FEATURE
<222> LOCATION: (1)..(326)
<223> OTHER INFORMATION: IgG2 heavy chain constant region
<220> FEATURE:
<221> NAME/KEY: MISC_FEATURE
<222> LOCATION: (1)..(98)
<223> OTHER INFORMATION: CH1
<220> FEATURE:
<221> NAME/KEY: MISC_FEATURE
<222> LOCATION: (99)..(110)
<223> OTHER INFORMATION: hinge
<220> FEATURE:
<221> NAME/KEY: MISC_FEATURE
<222> LOCATION: (111)..(219)
<223> OTHER INFORMATION: CH2
<220> FEATURE:
<221> NAME/KEY: MISC_FEATURE
<222> LOCATION: (220)..(326)
<223> OTHER INFORMATION: CH3

<400> SEQUENCE: 67

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
```

-continued

```
                    85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
    130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
            325
```

```
<210> SEQ ID NO 68
<211> LENGTH: 377
<212> TYPE: PRT
<213> ORGANISM: Homo sapiens
<220> FEATURE:
<221> NAME/KEY: MISC_FEATURE
<222> LOCATION: (1)..(377)
<223> OTHER INFORMATION: IgG3 heavy chain constant region
<220> FEATURE:
<221> NAME/KEY: MISC_FEATURE
<222> LOCATION: (1)..(98)
<223> OTHER INFORMATION: CH1
<220> FEATURE:
<221> NAME/KEY: MISC_FEATURE
<222> LOCATION: (99)..(115)
<223> OTHER INFORMATION: hinge 1
<220> FEATURE:
<221> NAME/KEY: MISC_FEATURE
<222> LOCATION: (116)..(130)
<223> OTHER INFORMATION: hinge 2
<220> FEATURE:
<221> NAME/KEY: MISC_FEATURE
<222> LOCATION: (131)..(145)
<223> OTHER INFORMATION: hinge 3
<220> FEATURE:
<221> NAME/KEY: MISC_FEATURE
<222> LOCATION: (146)..(160)
<223> OTHER INFORMATION: hinge 4
<220> FEATURE:
<221> NAME/KEY: MISC_FEATURE
<222> LOCATION: (161)..(270)
```

```
<223> OTHER INFORMATION: CH2
<220> FEATURE:
<221> NAME/KEY: MISC_FEATURE
<222> LOCATION: (271)..(377)
<223> OTHER INFORMATION: CH3

<400> SEQUENCE: 68
```

| | | | | | | | | | | | | | | | |
|---|---|---|---|---|---|---|---|---|---|---|---|---|---|---|---|
| Ala | Ser | Thr | Lys | Gly | Pro | Ser | Val | Phe | Pro | Leu | Ala | Pro | Cys | Ser | Arg |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | | 35 | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Thr | Cys | Asn | Val | Asn | His | Lys | Pro | Ser | Asn | Thr | Lys | Val | Asp | Lys |
| | | | | 85 | | | | | 90 | | | | | 95 | |
| Arg | Val | Glu | Leu | Lys | Thr | Pro | Leu | Gly | Asp | Thr | Thr | His | Thr | Cys | Pro |
| | | | 100 | | | | | 105 | | | | | 110 | | |
| Arg | Cys | Pro | Glu | Pro | Lys | Ser | Cys | Asp | Thr | Pro | Pro | Pro | Cys | Pro | Arg |
| | | 115 | | | | | 120 | | | | | 125 | | | |
| Cys | Pro | Glu | Pro | Lys | Ser | Cys | Asp | Thr | Pro | Pro | Pro | Cys | Pro | Arg | Cys |
| | 130 | | | | | 135 | | | | | 140 | | | | |
| Pro | Glu | Pro | Lys | Ser | Cys | Asp | Thr | Pro | Pro | Pro | Cys | Pro | Arg | Cys | Pro |
| 145 | | | | | 150 | | | | | 155 | | | | | 160 |
| Ala | Pro | Glu | Leu | Leu | Gly | Gly | Pro | Ser | Val | Phe | Leu | Phe | Pro | Pro | Lys |
| | | | | 165 | | | | | 170 | | | | | 175 | |
| Pro | Lys | Asp | Thr | Leu | Met | Ile | Ser | Arg | Thr | Pro | Glu | Val | Thr | Cys | Val |
| | | | 180 | | | | | 185 | | | | | 190 | | |
| Val | Val | Asp | Val | Ser | His | Glu | Asp | Pro | Glu | Val | Gln | Phe | Lys | Trp | Tyr |
| | | 195 | | | | | 200 | | | | | 205 | | | |
| Val | Asp | Gly | Val | Glu | Val | His | Asn | Ala | Lys | Thr | Lys | Pro | Arg | Glu | Glu |
| | 210 | | | | | 215 | | | | | 220 | | | | |
| Gln | Tyr | Asn | Ser | Thr | Phe | Arg | Val | Val | Ser | Val | Leu | Thr | Val | Leu | His |
| 225 | | | | | 230 | | | | | 235 | | | | | 240 |
| Gln | Asp | Trp | Leu | Asn | Gly | Lys | Glu | Tyr | Lys | Cys | Lys | Val | Ser | Asn | Lys |
| | | | | 245 | | | | | 250 | | | | | 255 | |
| Ala | Leu | Pro | Ala | Pro | Ile | Glu | Lys | Thr | Ile | Ser | Lys | Thr | Lys | Gly | Gln |
| | | | 260 | | | | | 265 | | | | | 270 | | |
| Pro | Arg | Glu | Pro | Gln | Val | Tyr | Thr | Leu | Pro | Pro | Ser | Arg | Glu | Glu | Met |
| | | 275 | | | | | 280 | | | | | 285 | | | |
| Thr | Lys | Asn | Gln | Val | Ser | Leu | Thr | Cys | Leu | Val | Lys | Gly | Phe | Tyr | Pro |
| | 290 | | | | | 295 | | | | | 300 | | | | |
| Ser | Asp | Ile | Ala | Val | Glu | Trp | Glu | Ser | Ser | Gly | Gln | Pro | Glu | Asn | Asn |
| 305 | | | | | 310 | | | | | 315 | | | | | 320 |
| Tyr | Asn | Thr | Thr | Pro | Pro | Met | Leu | Asp | Ser | Asp | Gly | Ser | Phe | Phe | Leu |
| | | | | 325 | | | | | 330 | | | | | 335 | |
| Tyr | Ser | Lys | Leu | Thr | Val | Asp | Lys | Ser | Arg | Trp | Gln | Gln | Gly | Asn | Ile |
| | | | 340 | | | | | 345 | | | | | 350 | | |
| Phe | Ser | Cys | Ser | Val | Met | His | Glu | Ala | Leu | His | Asn | Arg | Phe | Thr | Gln |
| | | 355 | | | | | 360 | | | | | 365 | | | |
| Lys | Ser | Leu | Ser | Leu | Ser | Pro | Gly | Lys | | | | | | | |
| | 370 | | | | | 375 | | | | | | | | | |

```
<210> SEQ ID NO 69
<211> LENGTH: 327
<212> TYPE: PRT
<213> ORGANISM: Homo sapiens
<220> FEATURE:
<221> NAME/KEY: MISC_FEATURE
<222> LOCATION: (1)..(327)
<223> OTHER INFORMATION: IgG4 heavy chain constant region
<220> FEATURE:
<221> NAME/KEY: MISC_FEATURE
<222> LOCATION: (1)..(98)
<223> OTHER INFORMATION: CH1
<220> FEATURE:
<221> NAME/KEY: MISC_FEATURE
<222> LOCATION: (99)..(110)
<223> OTHER INFORMATION: hinge
<220> FEATURE:
<221> NAME/KEY: MISC_FEATURE
<222> LOCATION: (111)..(220)
<223> OTHER INFORMATION: CH2
<220> FEATURE:
<221> NAME/KEY: MISC_FEATURE
<222> LOCATION: (221)..(327)
<223> OTHER INFORMATION: CH3

<400> SEQUENCE: 69

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 70
<211> LENGTH: 476
<212> TYPE: PRT
<213> ORGANISM: Homo sapiens
<220> FEATURE:
<221> NAME/KEY: MISC_FEATURE
<222> LOCATION: (1)..(476)
<223> OTHER INFORMATION: IgM heavy chain constant region
<220> FEATURE:
<221> NAME/KEY: MISC_FEATURE
<222> LOCATION: (1)..(104)
<223> OTHER INFORMATION: CH1
<220> FEATURE:
<221> NAME/KEY: MISC_FEATURE
<222> LOCATION: (105)..(217)
<223> OTHER INFORMATION: CH2
<220> FEATURE:
<221> NAME/KEY: MISC_FEATURE
<222> LOCATION: (218)..(323)
<223> OTHER INFORMATION: CH3
<220> FEATURE:
<221> NAME/KEY: MISC_FEATURE
<222> LOCATION: (324)..(476)
<223> OTHER INFORMATION: CH4

<400> SEQUENCE: 70

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
            35                  40                  45

Asp Ile Ser Ser Thr Arg Gly Phe Pro Ser Val Leu Arg Gly Gly Lys
        50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
                100                 105                 110

Val Ser Val Phe Val Pro Pro Arg Asp Gly Phe Phe Gly Asn Pro Arg
            115                 120                 125

Ser Lys Ser Lys Leu Ile Cys Gln Ala Thr Gly Phe Ser Pro Arg Gln
        130                 135                 140

Ile Gln Val Ser Trp Leu Arg Glu Gly Lys Gln Val Gly Ser Gly Val
145                 150                 155                 160

Thr Thr Asp Gln Val Gln Ala Glu Ala Lys Glu Ser Gly Pro Thr Thr
                165                 170                 175

Tyr Lys Val Thr Ser Thr Leu Thr Ile Lys Glu Ser Asp Trp Leu Ser
            180                 185                 190

Gln Ser Met Phe Thr Cys Arg Val Asp His Arg Gly Leu Thr Phe Gln
        195                 200                 205
```

```
Gln Asn Ala Ser Ser Met Cys Val Pro Asp Gln Asp Thr Ala Ile Arg
            210                 215                 220

Val Phe Ala Ile Pro Pro Ser Phe Ala Ser Ile Phe Leu Thr Lys Ser
225                 230                 235                 240

Thr Lys Leu Thr Cys Leu Val Thr Asp Leu Thr Thr Tyr Asp Ser Val
                245                 250                 255

Thr Ile Ser Trp Thr Arg Gln Asn Gly Glu Ala Val Lys Thr His Thr
                260                 265                 270

Asn Ile Ser Glu Ser His Pro Asn Ala Thr Phe Ser Ala Val Gly Glu
                275                 280                 285

Ala Ser Ile Cys Glu Asp Asp Trp Asn Ser Gly Glu Arg Phe Thr Cys
            290                 295                 300

Thr Val Thr His Thr Asp Leu Pro Ser Pro Leu Lys Gln Thr Ile Ser
305                 310                 315                 320

Arg Pro Lys Gly Val Ala Leu His Arg Pro Asp Val Tyr Leu Leu Pro
                325                 330                 335

Pro Ala Arg Glu Gln Leu Asn Leu Arg Glu Ser Ala Thr Ile Thr Cys
                340                 345                 350

Leu Val Thr Gly Phe Ser Pro Ala Asp Val Phe Val Gln Trp Gln Met
            355                 360                 365

Gln Arg Gly Gln Pro Leu Ser Pro Glu Lys Tyr Val Thr Ser Ala Pro
            370                 375                 380

Met Pro Glu Pro Gln Ala Pro Gly Arg Tyr Phe Ala His Ser Ile Leu
385                 390                 395                 400

Thr Val Ser Glu Glu Glu Trp Asn Thr Gly Glu Thr Tyr Thr Cys Val
                405                 410                 415

Val Ala His Glu Ala Leu Pro Asn Arg Val Thr Glu Arg Thr Val Asp
                420                 425                 430

Lys Ser Thr Gly Lys Pro Thr Ser Ala Asp Glu Glu Gly Phe Glu Asn
                435                 440                 445

Leu Trp Ala Thr Ala Ser Thr Phe Ile Val Leu Tyr Asn Val Ser Leu
            450                 455                 460

Val Met Ser Asp Thr Ala Gly Thr Cys Tyr Val Lys
465                 470                 475

<210> SEQ ID NO 71
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Light chain kappa constant region (IgKc)

<400> SEQUENCE: 71

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

```
Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 72
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Light chain lambda constant region (IgLambda)

<400> SEQUENCE: 72

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Lys Ser Tyr Ser Cys Gln Val Thr His Glu Gly Ser Thr
                85                  90                  95

Val Glu Lys Thr Val Ala Pro Thr Glu Cys Ser
            100                 105

<210> SEQ ID NO 73
<211> LENGTH: 4
<212> TYPE: PRT
<213> ORGANISM: Artificial
<220> FEATURE:
<223> OTHER INFORMATION: synthetic peptide

<400> SEQUENCE: 73

Gly Gly Gly Ser
1

<210> SEQ ID NO 74
<211> LENGTH: 6
<212> TYPE: PRT
<213> ORGANISM: Artificial
<220> FEATURE:
<223> OTHER INFORMATION: synthetic peptide

<400> SEQUENCE: 74

Gly Ser Gly Gly Gly Ser
1               5

<210> SEQ ID NO 75
<211> LENGTH: 5
<212> TYPE: PRT
<213> ORGANISM: Artificial
<220> FEATURE:
<223> OTHER INFORMATION: synthetic peptide

<400> SEQUENCE: 75

Cys Pro Pro Cys Pro
1               5
```

<210> SEQ ID NO 76
<211> LENGTH: 110
<212> TYPE: PRT
<213> ORGANISM: Artificial
<220> FEATURE:
<223> OTHER INFORMATION: synthetic peptide

<400> SEQUENCE: 76

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 77
<211> LENGTH: 110
<212> TYPE: PRT
<213> ORGANISM: Artificial
<220> FEATURE:
<223> OTHER INFORMATION: synthetic peptide

<400> SEQUENCE: 77

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 78
<211> LENGTH: 107
<212> TYPE: PRT
<213> ORGANISM: Artificial
<220> FEATURE:
<223> OTHER INFORMATION: synthetic peptide

<400> SEQUENCE: 78

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

```
Asn Asn Tyr Lys Thr Thr Pro Val Leu Asp Ser Asp Gly Ser Phe
            50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105
```

<210> SEQ ID NO 79
<211> LENGTH: 110
<212> TYPE: PRT
<213> ORGANISM: Artificial
<220> FEATURE:
<223> OTHER INFORMATION: synthetic peptide

<400> SEQUENCE: 79

```
Ala Pro Glu Phe Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser Gln Glu Asp Pro Glu Val Gln Phe Asn Trp Tyr
             35                  40                  45

Val Asp Gly Val Glu Val His Asn Ala Lys Thr Lys Pro Arg Glu Glu
 50                  55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys
            100                 105                 110
```

<210> SEQ ID NO 80
<211> LENGTH: 110
<212> TYPE: PRT
<213> ORGANISM: Artificial
<220> FEATURE:
<223> OTHER INFORMATION: synthetic peptide

<400> SEQUENCE: 80

```
Ala Pro Glu Ala Ala Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser Gln Glu Asp Pro Glu Val Gln Phe Asn Trp Tyr
             35                  40                  45

Val Asp Gly Val Glu Val His Asn Ala Lys Thr Lys Pro Arg Glu Glu
 50                  55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys
            100                 105                 110
```

<210> SEQ ID NO 81
<211> LENGTH: 107
<212> TYPE: PRT

```
<213> ORGANISM: Artificial
<220> FEATURE:
<223> OTHER INFORMATION: synthetic peptide

<400> SEQUENCE: 81

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 82
<211> LENGTH: 247
<212> TYPE: PRT
<213> ORGANISM: Artificial
<220> FEATURE:
<223> OTHER INFORMATION: synthetic peptide

<400> SEQUENCE: 82

Gln Ile Gln Gly Gly Thr Tyr Ser Cys His Phe Gly Pro Leu Thr Trp
1               5                   10                  15

Val Cys Lys Pro Gln Gly Gly Ser Cys Pro Cys Pro Ala Pro
            20                  25                  30

Glu Leu Leu Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
        50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220
```

```
Cys Ser Val Met His Glu Ala Leu His Asn His Tyr Thr Gln Lys Ser
225                 230                 235                 240

Leu Ser Leu Ser Pro Gly Lys
            245
```

<210> SEQ ID NO 83
<211> LENGTH: 249
<212> TYPE: PRT
<213> ORGANISM: Artificial
<220> FEATURE:
<223> OTHER INFORMATION: synthetic peptide

<400> SEQUENCE: 83

```
Gln Ile Gln Gly Gly Thr Tyr Ser Cys His Phe Gly Pro Leu Thr Trp
1               5                   10                  15

Val Cys Lys Pro Gln Gly Gly Gly Gly Ser Cys Pro Pro Cys Pro
            20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Asp Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245
```

<210> SEQ ID NO 84
<211> LENGTH: 251
<212> TYPE: PRT
<213> ORGANISM: Artificial
<220> FEATURE:
<223> OTHER INFORMATION: synthetic peptide

<400> SEQUENCE: 84

```
Gln Ile Gln Gly Gly Thr Tyr Ser Cys His Phe Gly Pro Leu Thr Trp
1               5                   10                  15

Val Cys Lys Pro Gln Gly Gly Gly Ser Gly Gly Gly Ser Cys Pro Pro
            20                  25                  30
```

```
Cys Pro Ala Pro Glu Leu Leu Gly Gly Pro Ser Val Phe Leu Phe Pro
             35                  40                  45

Pro Lys Pro Lys Asp Thr Leu Met Ile Ser Arg Thr Pro Glu Val Thr
 50                  55                  60

Cys Val Val Val Asp Val Ser His Glu Asp Pro Glu Val Lys Phe Asn
 65                  70                  75                  80

Trp Tyr Val Asp Gly Val Glu Val His Asn Ala Lys Thr Lys Pro Arg
                 85                  90                  95

Glu Glu Gln Tyr Asn Ser Thr Tyr Arg Val Val Ser Val Leu Thr Val
                100                 105                 110

Leu His Gln Asp Trp Leu Asn Gly Lys Glu Tyr Lys Cys Lys Val Ser
            115                 120                 125

Asn Lys Ala Leu Pro Ala Pro Ile Glu Lys Thr Ile Ser Lys Ala Lys
130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
            195                 200                 205

Phe Leu Tyr Ser Lys Leu Thr Val Asp Lys Ser Arg Trp Gln Gln Gly
            210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250

<210> SEQ ID NO 85
<211> LENGTH: 247
<212> TYPE: PRT
<213> ORGANISM: Artificial
<220> FEATURE:
<223> OTHER INFORMATION: synthetic peptide

<400> SEQUENCE: 85

Gln Ile Gln Gly Gly Thr Tyr Ser Cys His Phe Gly Pro Leu Thr Trp
 1               5                  10                  15

Val Cys Lys Pro Gln Gly Gly Ser Cys Pro Cys Pro Ala Pro
             20                  25                  30

Glu Ala Ala Gly Gly Pro Ser Val Phe Leu Phe Pro Lys Pro Lys
             35                  40                  45

Asp Thr Leu Met Ile Ser Arg Thr Pro Glu Val Thr Cys Val Val Val
 50                  55                  60

Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Asn Ser Thr Tyr Arg Val Val Ser Val Leu Thr Val Leu His Gln Asp
                100                 105                 110

Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
130                 135                 140
```

```
Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
            165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
            195                 200                 205

Lys Leu Thr Val Asp Lys Ser Arg Trp Gln Gln Gly Asn Val Phe Ser
            210                 215                 220

Cys Ser Val Met His Glu Ala Leu His Asn His Tyr Thr Gln Lys Ser
225                 230                 235                 240

Leu Ser Leu Ser Pro Gly Lys
                245

<210> SEQ ID NO 86
<211> LENGTH: 249
<212> TYPE: PRT
<213> ORGANISM: Artificial
<220> FEATURE:
<223> OTHER INFORMATION: synthetic peptide

<400> SEQUENCE: 86

Gln Ile Gln Gly Gly Thr Tyr Ser Cys His Phe Gly Pro Leu Thr Trp
1               5                   10                  15

Val Cys Lys Pro Gln Gly Gly Gly Gly Ser Cys Pro Pro Cys Pro
            20                  25                  30

Ala Pro Glu Ala Ala Gly Gly Pro Ser Val Phe Leu Phe Pro Pro Lys
            35                  40                  45

Pro Lys Asp Thr Leu Met Ile Ser Arg Thr Pro Glu Val Thr Cys Val
        50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Asp Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245
```

<210> SEQ ID NO 87
<211> LENGTH: 247
<212> TYPE: PRT
<213> ORGANISM: Artificial
<220> FEATURE:
<223> OTHER INFORMATION: synthetic peptide

<400> SEQUENCE: 87

```
Gln Ile Gln Gly Gly Thr Tyr Ser Cys His Phe Gly Pro Leu Thr Trp
1               5                   10                  15

Val Cys Lys Pro Gln Gly Gly Ser Cys Pro Cys Pro Ala Pro
            20                  25                  30

Glu Phe Leu Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
        50                  55                  60

Asp Val Ser Gln Glu Asp Pro Glu Val Gln Phe Asn Trp Tyr Val Asp
65                  70                  75                  80

Gly Val Glu Val His Asn Ala Lys Thr Lys Pro Arg Glu Glu Gln Phe
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Gly Leu
        115                 120                 125

Pro Ser Ser Ile Glu Lys Thr Ile Ser Lys Ala Lys Gly Gln Pro Arg
    130                 135                 140

Glu Pro Gln Val Tyr Thr Leu Pro Pro Ser Gln Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Arg Leu Thr Val Asp Lys Ser Arg Trp Gln Glu Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Leu Gly Lys
                245
```

<210> SEQ ID NO 88
<211> LENGTH: 247
<212> TYPE: PRT
<213> ORGANISM: Artificial
<220> FEATURE:
<223> OTHER INFORMATION: synthetic peptide

<400> SEQUENCE: 88

```
Gln Ile Gln Gly Gly Thr Tyr Ser Cys His Phe Gly Pro Leu Thr Trp
1               5                   10                  15

Val Cys Lys Pro Gln Gly Gly Ser Cys Pro Cys Pro Ala Pro
            20                  25                  30

Glu Ala Ala Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
```

-continued

```
                50                  55                  60
Asp Val Ser Gln Glu Asp Pro Glu Val Gln Phe Asn Trp Tyr Val Asp
 65                  70                  75                  80

Gly Val Glu Val His Asn Ala Lys Thr Lys Pro Arg Glu Glu Gln Phe
                 85                  90                  95

Asn Ser Thr Tyr Arg Val Val Ser Val Leu Thr Val Leu His Gln Asp
                100                 105                 110

Trp Leu Asn Gly Lys Glu Tyr Lys Cys Lys Val Ser Asn Lys Gly Leu
                115                 120                 125

Pro Ser Ser Ile Glu Lys Thr Ile Ser Lys Ala Lys Gly Gln Pro Arg
130                 135                 140

Glu Pro Gln Val Tyr Thr Leu Pro Pro Ser Gln Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
                180                 185                 190

Thr Thr Pro Pro Val Leu Asp Ser Asp Gly Ser Phe Phe Leu Tyr Ser
                195                 200                 205

Arg Leu Thr Val Asp Lys Ser Arg Trp Gln Glu Gly Asn Val Phe Ser
210                 215                 220

Cys Ser Val Met His Glu Ala Leu His Asn His Tyr Thr Gln Lys Ser
225                 230                 235                 240

Leu Ser Leu Ser Leu Gly Lys
                245

<210> SEQ ID NO 89
<211> LENGTH: 249
<212> TYPE: PRT
<213> ORGANISM: Artificial
<220> FEATURE:
<223> OTHER INFORMATION: synthetic peptide

<400> SEQUENCE: 89

Gln Ile Gln Gly Gly Thr Tyr Ser Cys His Phe Gly Pro Leu Thr Trp
  1               5                  10                  15

Val Cys Lys Pro Gln Gly Gly Gly Gly Ser Cys Pro Pro Cys Pro
                 20                  25                  30

Ala Pro Glu Ala Ala Gly Gly Pro Ser Val Phe Leu Phe Pro Pro Lys
                 35                  40                  45

Pro Lys Asp Thr Leu Met Ile Ser Arg Thr Pro Glu Val Thr Cys Val
 50                  55                  60

Val Val Asp Val Ser Gln Glu Asp Pro Glu Val Gln Phe Asn Trp Tyr
 65                  70                  75                  80

Val Asp Gly Val Glu Val His Asn Ala Lys Thr Lys Pro Arg Glu Glu
                 85                  90                  95

Gln Phe Asn Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
                115                 120                 125

Gly Leu Pro Ser Ser Ile Glu Lys Thr Ile Ser Lys Ala Lys Gly Gln
            130                 135                 140

Pro Arg Glu Pro Gln Val Tyr Thr Leu Pro Pro Ser Gln Glu Glu Met
145                 150                 155                 160

Thr Lys Asn Gln Val Ser Leu Thr Cys Leu Val Lys Gly Phe Tyr Pro
```

```
                    165                 170                 175
Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Arg Leu Thr Val Asp Lys Ser Arg Trp Gln Glu Gly Asn Val
        210                 215                 220

Phe Ser Cys Ser Val Met His Glu Ala Leu His Asn His Tyr Thr Gln
225                 230                 235                 240

Lys Ser Leu Ser Leu Ser Leu Gly Lys
                245
```